US008871706B2

(12) United States Patent
Dong et al.

(10) Patent No.: US 8,871,706 B2
(45) Date of Patent: Oct. 28, 2014

(54) METHOD FOR INHIBITING INFLAMMATION AND PRE-INFLAMMATORY CYTOKINE/CHEMOKINE EXPRESSION USING A GHRELIN ANALOGUE

(75) Inventors: Zheng Xin Dong, Holliston, MA (US); Michael DeWitt Culler, Hopkinton, MA (US); Rakesh Datta, Brookline, MA (US); John E. Taylor, Somerville, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 1102 days.

(21) Appl. No.: 12/672,681

(22) PCT Filed: Aug. 7, 2008

(86) PCT No.: PCT/US2008/009494
§ 371 (c)(1),
(2), (4) Date: Feb. 8, 2010

(87) PCT Pub. No.: WO2009/020643
PCT Pub. Date: Feb. 12, 2009

(65) Prior Publication Data
US 2011/0160133 A1 Jun. 30, 2011

Related U.S. Application Data

(60) Provisional application No. 60/963,951, filed on Aug. 8, 2007.

(51) Int. Cl.
*A61K 38/22* (2006.01)
*A61K 38/05* (2006.01)
*A61K 38/25* (2006.01)

(52) U.S. Cl.
CPC ............... *A61K 38/05* (2013.01); *A61K 38/25* (2013.01)
USPC ............. 514/1.1; 514/4.9; 514/5.3; 514/21.8; 514/9.7; 530/330

(58) Field of Classification Search
CPC ....... A61K 38/08; A61K 38/16; A61K 38/18; A61K 38/19; A61K 38/22; A61K 38/25; A61K 38/195; A61K 38/1709; C07K 7/06; C07K 7/04; C07K 7/00

USPC .......................................................... 514/1.1
See application file for complete search history.

(56) References Cited

U.S. PATENT DOCUMENTS

| | | |
|---|---|---|
| 2004/0224408 A1 | 11/2004 | Girad et al. |
| 2005/0148515 A1 | 7/2005 | Dong |
| 2005/0261201 A1 | 11/2005 | Polvino et al. |
| 2005/0272648 A1 | 12/2005 | Dong et al. |
| 2006/0229250 A1 | 10/2006 | Zhang et al. |
| 2007/0025991 A1 | 2/2007 | Pothoulakis et al. |
| 2007/0037857 A1 | 2/2007 | Perrissoud et al. |
| 2008/0269116 A1* | 10/2008 | Taub et al. ...................... 514/12 |

FOREIGN PATENT DOCUMENTS

| | | |
|---|---|---|
| CA | 2566703 | 11/2005 |
| WO | WO2004/009616 | 1/2004 |
| WO | WO2005/110463 | 11/2005 |
| WO | 2006/045314 | 5/2006 |
| WO | WO2007/038678 | 4/2007 |
| WO | WO2007/041278 | 4/2007 |

OTHER PUBLICATIONS

Whitcomb, Am. J. Physiol. Gastrointest. Liver Physiol. (2004) 287, G315-G319. Downloaded from http://ajpgi.physiology.org/ at US Patent & Trademark Office on Nov. 5, 2012.*
Guneli et al., Medical Hypotheses (2007, Epub Mar. 2, 2007) 69(2), 356-360).*
Guneli et al., Medical Hypotheses (2007, Epub Mar. 2, 2007) 69(2), 356-360.*
Whitcomb, Am. J. Physiol. Gastrointest. Liver Physiol (2004) 287, G315-G319. Downloaded from http://ajpgi.physiology.org/ at US Patent & Trademark Office on Nov. 5, 2012.*
Leite-Moreira, A.F., et al., "Physiological, Pathological and Potential Therapeutic Roles of Ghrelin", Drug Discovery Today, vol. 12, No. 7/8, pp. 276-288 (Apr. 2007).
Gonzalez-Rey, E., et al., "Therapeutic Action of Ghrelin in a Mouse Model of Colitis", Gastroenterology, 130:1707-1720 (2006).

* cited by examiner

*Primary Examiner* — Karlheinz R Skowronek
*Assistant Examiner* — Catherine Mader
(74) *Attorney, Agent, or Firm* — Janice M. Klunder

(57) ABSTRACT

The present invention provides a method of ameliorating inflammation, inhibiting proinflammatory cytokine and/or chemokine expression and treating various diseases and/or conditions incidental to the onset of inflammation, in a subject in need of treatment for such conditions, by administering select analogous of native hGhrelin.

6 Claims, 33 Drawing Sheets

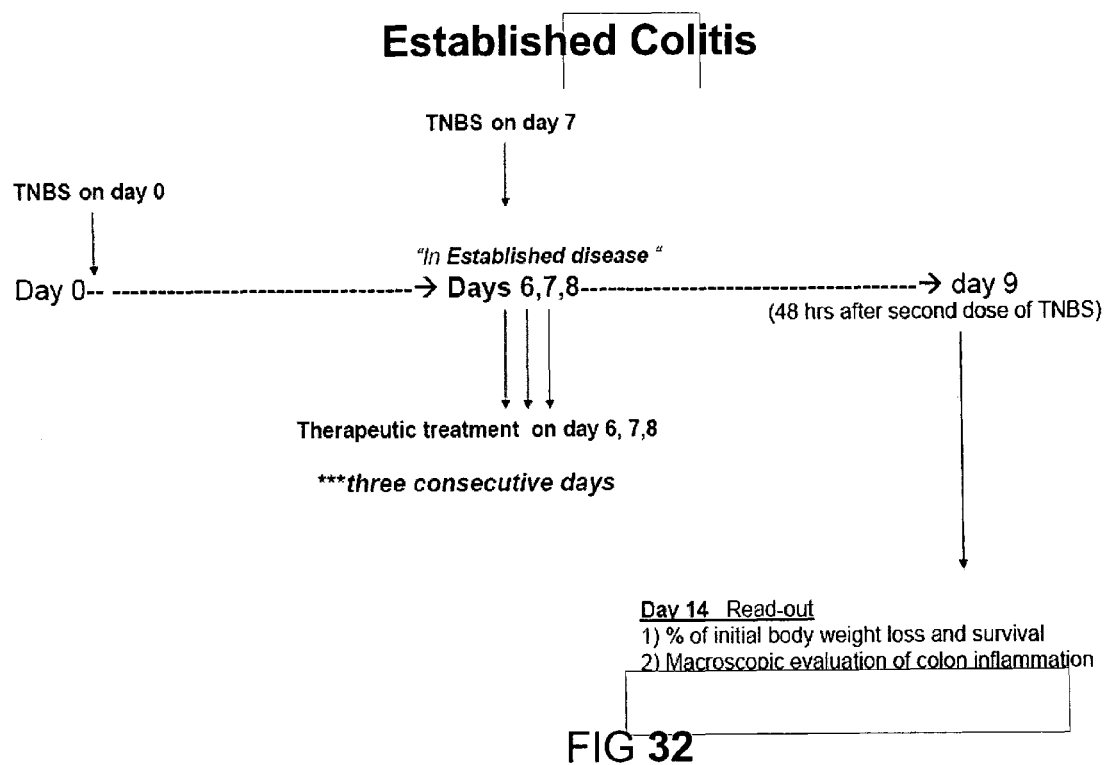

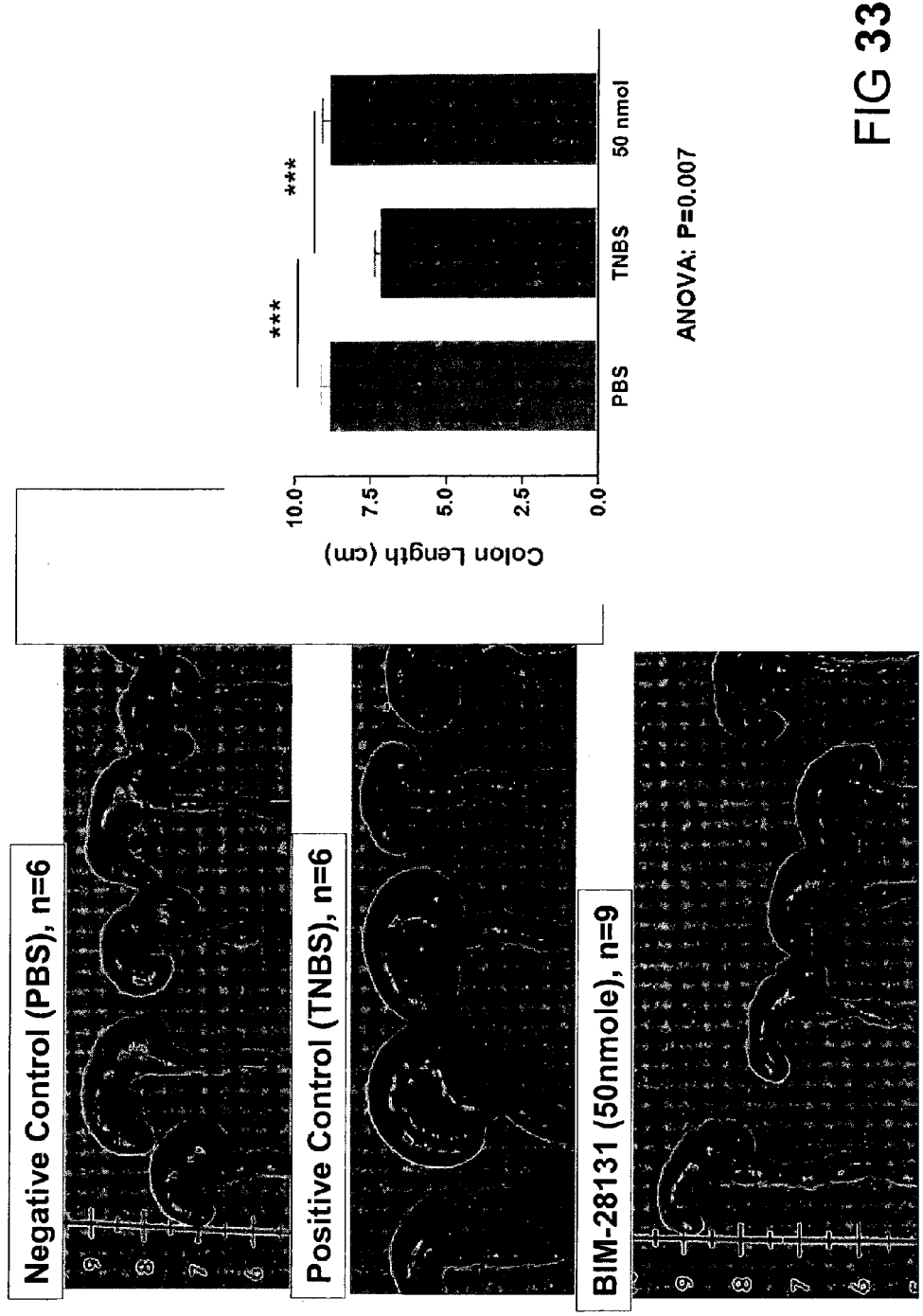

METHOD FOR INHIBITING INFLAMMATION AND PRE-INFLAMMATORY CYTOKINE/CHEMOKINE EXPRESSION USING A GHRELIN ANALOGUE

This application is a United States national stage filing under 35 U.S.C. §371 of international (PCT) application no. PCT/US2008/009494, filed Aug. 7, 2008, and designating the US, which claims priority to U.S. provisional application No. 60/963,951, filed Aug. 8, 2007.

FIELD OF THE INVENTION

The present invention is directed to methods for attenuating inflammation in a patient which comprises administering peptidyl analogues that possess agonistic ghrelin activity, a prodrug thereof, or a pharmaceutically acceptable salt of said analogues or prodrug.

BACKGROUND OF THE INVENTION

Inflammation is a complex of sequential changes expressing the response to damage of cells and vascularized tissues. When tissue injury occurs, whether it be caused by bacteria, trauma, chemicals, heat, or any other phenomenon, the substance histamine, along with other humoral substances, is liberated by the damaged tissue into the surrounding fluids. It is a protective attempt by the organism to remove the injurious stimuli as well as initiating the healing process.

The main features of the inflammatory response are vasodilation, i.e. widening of the blood vessels to increase the blood flow to the infected area; increased vascular permeability which allows diffusible components to enter the site; cellular infiltration by chemotaxis; or the directed movement of inflammatory cells through the walls of blood vessels into the site of injury; changes in biosynthetic, metabolic, and catabolic profiles of many organs; and activation of cells of the immune system as well as of complex enzymatic systems of blood plasma. Inflammation which runs unchecked can, however, lead to a host of diseases, such as hay fever, atherosclerosis and rheumatoid arthritis.

There are two forms of inflammation, commonly referred to as acute inflammation and chronic inflammation. Acute inflammation is the initial response of the body to harmful stimuli and is achieved by the increased movement of plasma and leukocytes from the blood into the injured tissues. Acute inflammation can be divided into several phases. The earliest, gross event of an inflammatory response is temporary vasoconstriction, i.e., narrowing of blood vessels caused by contraction of smooth muscle in the vessel walls which can be seen as blanching (whitening) of the skin. This is followed by several phases that occur minutes, hours and days later. The first is the acute vascular response which follows within seconds of the tissue injury and lasts for several minutes. This results from vasodilation and increased capillary permeability due to alterations in the vascular endothelium which leads to increased blood flow (hyperemia) that causes redness (erythema) and the entry of fluid into the tissues (edema).

The acute vascular response can be followed by an acute cellular response which takes place over the next few hours. The hallmark of this phase is the appearance of granulocytes, particularly neutrophils, in the tissues. These cells first attach themselves to the endothelial cells within the blood vessels (margination) and then cross into the surrounding tissue (diapedesis). During this phase erythrocytes may also leak into the tissues and a hemorrhage can occur. If the vessel is damaged, fibrinogen and fibronectin are deposited at the site of injury, platelets aggregate and become activated, and the red cells stack together in what are called "rouleau" to help stop bleeding and aid clot formation. The dead and dying cells contribute to pus formation. If the damage is sufficiently severe, a chronic cellular response may follow over the next few days. A characteristic of this phase of inflammation is the appearance of a mononuclear cell infiltrate composed of macrophages and lymphocytes. The macrophages are involved in microbial killing, in clearing up cellular and tissue debris, and in remodeling of tissues.

Chronic inflammation is an inflammatory response of prolonged duration—weeks, months or indefinitely—whose extended time course is provoked by persistence of the causative stimulus to inflammation in the tissue. The inflammatory process inevitably causes tissue damage and is accompanied by simultaneous attempts at healing and repair. The exact nature, extent and time course of chronic inflammation is variable depending on a balance between the causative agent and the attempts of the body to remove it.

Etiological agents producing chronic inflammation include:

(i) infectious organisms that can avoid or resist host defenses and so persist in the tissue for a prolonged period, including *Mycobacterium tuberculosis, Actinomycetes*, and numerous fungi, protozoa and metazoal parasites. Such organisms are in general able to avoid phagocytosis or survive within phagocytic cells, and tend not to produce toxins causing acute tissue damage;

(ii) infectious organisms that are not innately resistant but persist in damaged regions where they are protected from host defenses. An example is bacteria which grow in the pus within an un-drained abscess cavity where they are protected both from host immunity and from blood-borne therapeutic agents, e.g. antibiotics. Some locations are particularly prone to chronic abscess formation, e.g. bone and pleural cavities;

(iii) irritant non-living foreign material that cannot be removed by enzymatic breakdown or phagocytosis. Examples include a wide range of materials implanted into wounds (wood splinters, grit, metals and plastics), inhaled (silica dust and other particles or fibers) or deliberately introduced (surgical prostheses, sutures, etc.), including transplants. Dead tissue components that cannot be broken down may have similar effects, e.g. keratin squames from a ruptured epidermoid cyst or fragments of dead bone (sequestrum) in osteomyelitis.

(iv) in some cases the stimulus to chronic inflammation may be a normal tissue component. This occurs in inflammatory diseases where the disease process is initiated and maintained because of an abnormality in the regulation of the body's immune response to its own tissues—the so-called auto-immune diseases. This response is seen in elderly and aging subjects; and (v) for many diseases characterized by a chronic inflammatory pathological process the underlying cause remains unknown. An example is Crohn's disease.

Although the production of pro-inflammatory cytokines by cells of the innate immune system plays an important role in mediating the initial host defense against invading pathogens (O'Neill, L. A. et al., *Immunol. Today*, (2000), 21 (5):206-9), an inability to regulate the nature or duration of the host's inflammatory response can often mediate detrimental host effects as observed in chronic inflammatory diseases. Additionally, in the early stages of sepsis, the host's inflammatory response is believed to be in a hyperactive state with a predominant increase in the production of pro-inflammatory cytokines that mediate host tissue injury and lethal shock (Cohen, J., *Nature*, (2002), 420 (6917):885-91). In this regard, the ability to suppress pro-inflammatory cytokines and/or enhance anti-inflammatory cytokines, i.e. IL-10, has been shown to severely reduce the toxic effects of endotoxin (Berg, D. J. et al., *J. Clin. Invest.*, (1995), 96 (5):2339-47; and Howard, M. et al., *J. Exp. Med.*, (1993), 177 (4):1205-8).

Inflammatory cytokines released by immune cells have been shown to act on the central nervous system (CNS) to control food intake and energy homeostasis (Hart, B. L., *Neurosci. Biobehav. Rev.*, (1988), 12 (2):123-37). Decrease in food intake or anorexia is one of the most common symptoms of illness, injury or inflammation (Kotler, D. P., *Ann. Intern. Med.*, (2000), 133 (8):622-34). Cytokines, such as IL-1β, IL-6 and TNF-α, have been implicated in wasting associated with inflammation (Ershler, W. B. et al., *Annu. Rev. Med.*, (2000), 51:245-70), chronic low-grade inflammation in aging (Bruunsgaard, H. et al., *Curr. Opin. Hematol.*, (2001), 8 (3):131-6) and atherosclerosis (Bochkov, V. N. et al., *Nature*, (2002), 419 (6902):77-81).

What is need in the art is the regulation if inflammatory cytokine production by endogenous factors such as ghrelin analogues to ameliorate a wide variety of ailments and disease conditions.

Human ghrelin, an orexigenic hormone, is synthesized as a preprohormone and proteolytically processed to yield a 28-amino acid peptide of the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (SEQ ID: 1) (Kojima, M. et al., *Nature*, (1999), 402 (6762):656-60). Ghrelin is produced predominantly by epithelial cells lining the fundus of the stomach, however, smaller amounts are produced in the placenta, kidney, pituitary and hypothalamus. A core region present in ghrelin, responsible for observed activity, comprises the four N-terminal amino acids wherein the serine in the third position is normally modified with n-octanoic acid. In addition to acylation by n-octanoic acid, native ghrelin may also be acylated with n-decanoic acid (Kaiya, H. et al., *J. of Biol. Chem.*, (2001), 276 (44):40441-8).

The ghrelin receptor was known well before the peptide was discovered. Cells within the anterior pituitary gland bear a receptor that, when activated, powerfully stimulates GH secretion, mainly at the hypothalamic level (Kojima, M. et al., *Nature*, (1999), 402 (6762):656-60). That receptor was named the growth hormone secretagogue receptor ("GHS-R") (Ukkola, O. and Pöykkö, S., 2002 *Ann. Med.*, (2002), 34 (2):102-8; and Kojima, M. et al., *Nature*, (1999), 402 (6762): 656-60). It is postulated that ghrelin enhances the activity of growth hormone releasing hormone (GHRH)-secreting neurons and, concomitantly, acting as a functional somatostatin antagonist (Ghigo, E. et al., *Euro. J. Endocrinol.*, (1997), 136 (5):445-60).

The GHS-R and its subtypes are not restricted to the hypothalamus-pituitary unit, but are present in other central and peripheral tissues, such as heart and adipose tissues (Papotti, M. et al., *J. Clin. Endocrinol. Metab.*, (2000), 85 (10):3803-7). GHS-R is also expressed in the pancreas (Guan, X. M. et al., *Brain Res.*, (1997), 48 (1)-23-9; and Volante, M. et al., *J. Clin. Endocrinol. Metab.*, (2002), 87 (3):1300-8). The physiological actions of ghrelin, as well as those of synthetic GHS, are not restricted to GH secretion. Ghrelin has been shown to stimulate lactotroph and corticotroph hormone secretion has orexigenic and cardiovascular actions, shows anti-proliferative effects on thyroid and breast tumors, as well as regulating gastric motility and acid secretions through vagal mediation (Ukkola, O. and Pöykkö, S., *Ann. Med.*, (2000), 34 (2):102-8). Most importantly, expression of the GH and GH secretagogue receptors and ghrelin has been detected in all immune cells, including human T and β cells as well as neutrophils (Hattori, N. et al., *J. Clin. Endocrinol. Metab.*, (2001), 86 (9):4284-91).

Ghrelin is a physiological ligand for the growth hormone secretagogue receptor (GHS-R) and as such, powerfully stimulates secretion of growth hormone. Ghrelin acts by increasing intracellular Ca$^{2+}$ concentration. The ghrelin signal is integrated with that of growth hormone releasing hormone and somatostatin to control the timing and magnitude of growth hormone secretion. In both humans and rodents, ghrelin functions to increase hunger through its action on hypothalamic feeding centers (Cummings, D. E. et al., *Diabetes*, (2001), 50 (8):1714-9). Ghrelin also functions in energy metabolism and gastric acid secretion and motility (Date, Y. et al., *Diabetes*, (2002), 51 (1):124-9). Ghrelin has been found to have a variety of positive effects in cardiovascular function, such as increased cardiac output, however, it is not totally clear whether the cardiovascular effects are a directed effect of ghrelin or represent an indirect effect of ghrelin's ability to stimulate growth hormone secretion. In addition, the wide tissue distribution of GHS-R in the lymphoid system suggests that ghrelin and GHS-R ligands can function as signal modulators between the endocrine, nervous and immune systems.

Ghrelin, via functional cell surface GHS-R, exerts both specific and selective inhibitory effects on the expression and production of inflammatory cytokines such as IL-1β, IL-6 and TNF-a, by human PBMCs and T cells. The GHS-R on primary and cultured human T cells, similar to other classical GPCRs, elicits a potent intracellular calcium release upon ligation with its natural ligand, ghrelin, and is preferentially associated with GM1 lipid rafts upon cellular activation. Consistent with expression of functional GHS-R on T cells, ghrelin actively induces actin polymerization within T cells. Similar to chemokines (SDF-1), ghrelin treatment led to the cellular polarization of leukocytes and actin distribution changes from a linear cortical pattern in resting lymphocytes to more concentrated patterns at the leading edge and contact zones in polarized and activated T cells (Taub, D. D. et al. *Science*, (1993), 260 (5106):355-8; and Inui, A., *Cancer Res.*, (1999), 59 (18):4493-501). These GPCR-like redistribution patterns show an important role for GHS-R in immune cell signaling and trafficking.

Through a number of analytical techniques, it has been demonstrated that ghrelin is endogenously produced and secreted by both T cells and PBMCs in a fashion similar to many immune-derived cytokines. The majority of T cells examined from human donors were found to constitutively express low levels of endogenous ghrelin, which is significantly increased upon cellular activation. Activated T cells express and secrete the ghrelin protein, exhibiting that prepro peptide must be actively cleaved in T cells to yield the active ghrelin peptide. Similar to several cytokines (e.g., TGF-p) and hormones (e.g., TSH), these precursor proteins are synthesized and subsequently stored for immediate cleavage and use when needed. Furthermore, the expression and secretion of a mature form of ghrelin from T cells post activation via T cell receptor ligation has been demonstrated. Given that gastrectomy results in only a 35 to 50% decline in circulating ghrelin and that ghrelin levels increase to two thirds of pre-gastrectomy levels in human subjects, it has been shown that other tissues compensate for maintaining the circulating ghrelin (Hosoda, H. et al., *J. Biol. Chem.*, (2003), 278 (1):64-70). Secretion of ghrelin from T cells shows that immune cell-derived ghrelin makes up part of the residual concentration of circulating ghrelin. In addition, ghrelin is also regarded as the only known hormone where the hydroxyl group of its third serine residue is acylated by n-octanoic acid and this acylation is critical for some of the biological activities of this polypeptide (Kojima, M. et al., *Nature*, (1999), 402 (6762):656-60). N-terminal acylated peptides are known to preferentially aggregate in cholesterol rich micro-domains (Basa, N. R. et al., *Neurosci. Lett.*, (2003), 343 (1):25-8), and ghrelin is immunoreactive in activated T cells and is highly co-localized within cholesterol-rich GM1+ domains. These results show that ghrelin is selectively targeted to the plasma membrane to facilitate interaction with its own transmembrane receptor to optimally mediate receptor-ligand interactions. Such a pathway shows the role of ghrelin in the control of immune responses. In addition, localized production of ghrelin plays a critical role in the immediate control of ongoing and leptin-mediated responses within the local microenvironment.

Ghrelin has been effective in treating inflammation in a mammalian subject (International Patent Application No. PCT/US2005/016565 [WO 2005/110463]). In particular, the inflammation can be associated with a viral, bacterial, parasitic or fungal infection. Viral infections treatable with ghrelin may include Herpes simplex virus type-1, Herpes simplex virus type-2, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1 and Human Immunodeficiency virus type-2. (International Patent Application No. PCT/US2005/016565 [WO 2005/110463]).

Bacterial infections that cause inflammation that can be treated with ghrelin (International Patent Application No. PCT/US2005/016565 [WO 2005/110463]) include *M. tuberculosis, M bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsia* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica* and other *Yersinia* species (International Patent Application No. PCT/US2005/016565 [WO 2005/110463]).

Inflammation treatable with ghrelin (International Patent Application No. PCT/US2005/016565 [WO 2005/110463]) can also be caused by parasites including *Toxoplasma gondii, Plasmodium, Trypanosoma brucei, Trypanosoma cruzi, Leishmania, Schistosoma* and *Entamoeba histolytica* or fungi such as *Candida albicans, Cryptococcus neoformans, Histoplasma capsulatum, Aspergillus fumigatus, Coccidiodes immitis, Paracoccidiodes brasiliensis, Blastomyces dermitidis, Pneumocystis carinii, Penicillium marneffi* and *Alternaria alternate* (International Patent Application No. PCT/US2005/016565 [WO 2005/110463]).

Inflammation caused by liver toxicity or transplant rejection is also treatable by ghrelin (International Patent Application No. PCT/US2005/016565 [WO 2005/110463]). The liver toxicity may be associated with cancer therapy. In some instances, the cancer therapy, such as chemotherapy, may bring about liver toxicity. Liver toxicity brought about by both chemotherapy and apoptosis may be treatable by administration of ghrelin, ghrelin agonists or ghrelin antagonists (International Patent Application No. PCT/US2005/016565 [WO 2005/110463]).

Inflammation associated with cancer is also treatable with ghrelin (International Patent Application No. PCT/US2005/016565 [WO 2005/110463]). Such cancers include lymphoma, leukemia, mycosis fungoide, carcinoma, adenocarcinoma, sarcoma, glioma, blastoma, neuroblastoma, plasmacytoma, histiocytoma, melanoma, adenoma, hypoxic tumor, myeloma, AIDS-related lymphoma or AIDS-related sarcoma, metastatic cancer, bladder cancer, brain cancer, nervous system cancer, glioblastoma, ovarian cancer (International Patent Application No. PCT/AU02/00582 [WO 02/090387]; and Gaytan, F. et al., *J. Clin. Endocri. Metab.*, (2005), 90 (3):1798-804), skin cancer, liver cancer, squamous cell carcinomas of the mouth, throat, larynx, and lung, colon cancer, cervical cancer (International Patent Application No. PCT/AU02/00582 [WO 02/090387]), breast cancer (International Patent Application No. PCT/AU02/00582 [WO 02/090387]; and Cassoni, P. et al., *J. Clin. Endocri. Metab.*, (2001), 86 (4):1738-45), epithelial cancer, renal cancer (Jungwirth, A. et al., *Proc. Natl. Acad. Sci. U.S.A.*, (1997), 94 (11):5810-3), genitourinary cancer, pulmonary cancer (Ghé, C. et al., *Endocrinology*, (2002), 143 (2):484-91), esophageal carcinoma (Nwokolo, C. U. et al., *Gut*, (2003), 52 (5):637-40), head and neck carcinoma (Jozkow, P. et al., *Head Neck*, (2005), 27 (3):243-7), hematopoietic cancer, testicular cancer (Gaytan, F. et al., *J. Clin. Endocri Metab.*, (2004), 89 (1):400-9), colo-rectal cancer (Dagnaes-Hansen, H. et al., *Anticancer Res.*, (2004), 24 (6):3735), prostatic cancer (Jeffery, P. L. et al., *Endocrinology*, (2002), 172:R7-11), and pancreatic cancer (Volante, M. et al., *J. Clin. Endocri. Metab.*, (2002), 87 (3):1300-8); and International Patent Application No. PCT/US2005/016565 [WO 2005/110463]).

Ghrelin has been shown to treat inflammatory diseases (International Patent Application No. PCT/US2005/016565 [WO 2005/110463]) such as asthma, reactive arthritis (Granado, M. et al., *Am. J. Physiol. Endocrinol. Metab.*, (2005), 288 (3):E-486-92), hepatitis (Wallace, J. D. et al., *J. Clin. Endocri. Metab.*, (2002), 87 (6):2751-9), spondyarthritis, Sjogren's syndrome, Alzheimer's disease (U.S. Pat. Nos. 6,686,359 and 6,566,337; and Obermayr, R. P. et al., *Gerontology*, (2003), 49 (3):191-5), and atopic dermatitis or inflammatory diseases associated with an autoimmune disease such as systemic lupus erythematosus, rheumatoid arthritis (Otero, M. et al., *Rheumatology* (Oxford), (2004), 43 (3):306-10), systemic vasculitis, insulin dependent diabetes mellitus (Nieves-Riviera, F. et al., *Growth Regul.*, (1993), 3:235-44), multiple sclerosis and muscular dystrophy (U.S. Patent Publication No. 2003/0139348), experimental allergic encephalomyelitis (Ikushima, H. et al., *J. Immunol.*, (2003), 171: 2769-72), psoriasis (Edmondson, S. R. et al., *Endocri. Rev.*, (2003), 24 (6):737-64), Crohn's disease (Slonim, A. E. et al., *N. Engl. J. Med.*, (2000), 342 (22):1633-7), inflammatory bowel disease (Chen, K. et al., *Surgery*, (1997), 121 (2):212-8), ulcerative colitis, Addison's disease (Arvat, E. et al., *Neuroendocrinology*, (1999), 70 (3):200-6), alopecia areeta, celiac disease (Peracchi, M. et al., *Am. J. Gastroenterol.*, (2003), 98 (11):2474-8; and Capristo, E. et al., *Scand. J. Gastroenterol.*, (2005), 40 (4):430-6), thyroid disease (Riis, A. L. et al., *J. Clin. Endocrin. Metab.*, (2003), 88 (2):853-7), and scleroderma. Inflammation as a result of a burn may also benefit from treatment with ghrelin as may inflammation of the lung (International Patent Application No. PCT/US2005/016565 [WO 2005/110463]). Inflammation may also cause a subject to lose appetite, particularly when the inflammation is low grade and/or in an aging subject (International Patent Application No. PCT/US2005/016565 [WO 2005/110463]).

Inflammatory cytokines released by immune cells have been shown to act on the central nervous system (CNS) to control food intake and energy homeostasis (Hart, B. L., *Neurosci. Biobehay. Rev.*, (1988), 12 (2):123-37). Decrease in food intake or anorexia is one of the most common symptoms of illness, injury or inflammation (Kotler, D. P., *Ann. Internal Med.*, (2000), 133 (8):622-34). Cytokines such as IL-1β, IL-6 and TNF-α have been implicated in wasting associated with inflammation (Ershler, W. B. and Keller, E. T., *Annu. Rev. Med.*, (2000), 51:245-70), chronic low-grade inflammation in aging (Bruunsgaard, H. et al., *Curr. Opin. Hematol.*, (2001), 8 (3):131-6), and atherosclerosis (Bochkov, V. N. et al., *Nature*, (2002), 419 (6902):77-81).

SUMMARY OF THE INVENTION

Applicants have discovered that certain analogues of native human ghrelin are capable of ameliorating inflammation in a patient as well as inhibiting the chemical agents produced in the body that cause inflammation. In particular, the present invention relates to a method of inhibiting proinflammatory cytokine and/or chemokine production in a patient (e.g., a mammal such as a human). The method includes the step of administering a therapeutically effective amount of an analogue of ghrelin to said patient experiencing, or at risk of experiencing, acute or chronic inflammation.

In one aspect, the present invention provides a method of treating chronic inflammation by administering a therapeutically effective amount of a peptidyl analogue of ghrelin or prodrug thereof suitable for regulating inflammatory cytokine production where the analogue or prodrug comprises a compound according to Formula (I), Formula (II), Formula (III), Formula (IV), as well as the non-conforming compounds as indicated herein, or a pharmaceutically acceptable salt thereof. The method of the invention is useful for attenuating chronic inflammation in a patient (e.g., a mammal such as a human) and as such, is useful for treating conditions associated with prolonged inflammation, including tissue loss due to an inflammatory response of prolonged duration.

In a second aspect, the present invention provides a method of treating acute inflammation by administering a therapeutically effective amount of a peptidyl analogue of ghrelin or prodrug thereof suitable for regulating inflammatory cytokine production where the analogue or prodrug comprises a compound according to Formula (I), Formula (II), Formula (III), Formula (IV), as well as the non-conforming compounds as indicated herein, or a pharmaceutically acceptable salt thereof. The method of the invention is useful for attenuating acute inflammation in a patient (e.g., a mammal such as a human) and as such, is useful for treating conditions associated with short-term inflammation.

In another aspect, the present invention provides a method of treating inflammation, whether chronic or acute, wherein the etiological agent responsible for said inflammation is an infectious organism that can avoid or resist host defenses so as to persist in host tissue for a prolonged period, such as bacterium, actinomycetes, fungi, protazoa and metazoal parasites, by administering a therapeutically effective amount of a peptidyl analogue of ghrelin or prodrug thereof according to Formula (I), Formula (II), Formula (III), Formula (IV), as well as the non-conforming compounds as indicated herein, or a pharmaceutically acceptable salt thereof.

In another aspect, the invention features a method of treating inflammation associated with an infection in a patient. The infection may be viral, bacterial, parasitic or fungal. The method includes identifying a patient suffering from a viral, bacterial, parasitic or fungal infection and administering to the patient a pharmaceutical composition comprising an effective amount of a peptidyl analogue of ghrelin effective to ameliorate the inflammation resulting from said infection in the patient. The inflammation may be present in any part of the body, whether external, such as skin mast cells, or internal, including any organ(s) or tissue(s) in the abdomen, e.g., urogenital system (e.g., kidneys, urethra, and/or bladder; reproductive system (e.g., uterus, ovaries, and/or fallopian tubes)); digestive system (e.g., the stomach, small intestine, large intestine (e.g., the colon), appendix, gallbladder, liver, spleen, and/or pancreas); lymphatic system; respiratory system (e.g., the lungs); and/or muscular/skeletal system (diaphragm, joints, pelvis). The pharmaceutical composition can be administered to the patient via any route described herein, e.g., via inhalation (of gaseous compositions); orally; and/or by direct administration to the abdominal cavity of the patient. Particularly preferred peptidyl analogues of ghrelin are those compounds of Formula (I) or Formula (II) or Formula (III), or Formula (IV), as well as the non-conforming compounds as indicated herein, or a pharmaceutically acceptable salt thereof.

In another aspect, the present invention provides a method of treating inflammation, whether chronic or acute, wherein the etiological agent responsible for said inflammation is an irritant non-living foreign object, by administering a therapeutically effective amount of a peptidyl analogue of ghrelin or prodrug thereof according to Formula (I), Formula (II), Formula (III), Formula (IV), as well as the non-conforming compounds as indicated herein, or a pharmaceutically acceptable salt thereof. Said foreign object may be introduced by blunt force, such as a wood splinter or shard of glass, metal or plastic, or by inhalation, such as silica dust, or deliberately injected into subject such as surgical prostheses and sutures or a transplanted organ.

In another aspect, the present invention provides a method of treating chronic inflammation resulting from an abnormality in the regulation of the body's immune response to its own tissues, i.e. auto-immune disease, by administering a therapeutically effective amount of a peptidyl analogue of ghrelin or prodrug thereof according to Formula (I), Formula (II), Formula (III), Formula (IV), as well as the non-conforming compounds as indicated herein, or a pharmaceutically acceptable salt thereof. In particular, said treatment may be used to treat such unexplained inflammatory response in elderly and aging subjects.

In yet a further feature, the instant invention provides a method of treating diseases characterized by a chronic inflammatory pathological process by administering a therapeutically effective amount of a peptidyl analogue of ghrelin or prodrug thereof according to Formula (I), Formula (II), Formula (III), Formula (IV), as well as the non-conforming compounds as indicated herein, or a pharmaceutically acceptable salt thereof. In particular, the instant application provides a method of treating pancreatitis.

In a further aspect, the present invention provides a method of treating an inflammatory response, whether acute or chronic, incidental to the onset of any form of cancer, by administering a therapeutically effective amount of a peptidyl analogue of ghrelin or prodrug according to Formula (I), Formula (II), Formula (III), Formula (IV), as well as the non-conforming compounds as indicated herein, or a pharmaceutically acceptable salt thereof.

In yet another aspect, the present invention provides a method of treating sepsis caused by a bacterial infection that originated anywhere in the body, by administering a therapeutically effective amount of a peptidyl analogue of ghrelin or prodrug according to Formula (I), Formula (II), Formula (III), Formula (IV), as well as the non-conforming compounds as indicated herein, or a pharmaceutically acceptable salt thereof.

In a further aspect, the present invention provides a method of treating proinflammatory neuropathic pain incidental to an inflammatory response, whether acute or chronic, by administering a therapeutically effective amount of a peptidyl analogue of ghrelin or prodrug according to Formula (I), Formula (II), Formula (III), Formula (IV), as well as the non-conforming compounds as indicated herein, or a pharmaceutically acceptable salt thereof.

Accordingly, in one aspect, the invention features a method of treating inflammation in a patient, which includes identifying a patient suffering from or at risk for chronic inflammation and administering to the patient a pharmaceutical composition comprising an effective amount of a peptidyl analogue of ghrelin. Particularly preferred peptidyl analogues of ghrelin are those compounds of Formula (I) or Formula (II) or Formula (III), Formula (IV), as well as the non-conforming compounds as indicated herein, or a pharmaceutically acceptable salt thereof.

In yet another aspect, the invention provides a method of performing surgery on a patient. The method includes identifying a patient in need of surgery, and before, during, and/or after the surgery, administering to the patient an effective amount of a peptidyl analogue of ghrelin sufficient to prevent inflammation, sepsis and/or proinflammatory neuropathic pain. The surgery can be any surgery that causes and/or puts the patient at risk for inflammation, but is specifically preferred for transplant surgery or non-transplant surgery, e.g., surgery involving any organ(s) or tissue(s) in the abdomen, e.g., surgery of the urogenital system (e.g., kidneys, urethra, and/or bladder; and reproductive organs (e.g., uterus, ovaries, and/or fallopian tubes)); the digestive system (e.g., the stomach, small intestine, large intestine (e.g., the colon), appendix, gallbladder, liver, spleen, and/or pancreas); the lymphatic system; the respiratory system (e.g., the lungs); the diaphragm; surgery to treat cancer of any organ or tissue within the abdomen; endometrial surgery; and orthopedic surgeries, e.g., hip surgery. Particularly preferred peptidyl analogues of ghrelin are those compounds of Formula (I) or Formula (II) or Formula III, or Formula (IV), as well as each of the compounds that are specifically enumerated herein and below in the Examples section of the present disclosure, or a pharmaceutically acceptable salt thereof.

In a further aspect, the present invention provides the use of a therapeutically effective amount of a peptidyl ghrelin analogue compound according Formula (I) or Formula (II) or Formula (III), or Formula (IV), as defined hereinabove, as well as the non-specifically enumerated herein and below, or pharmaceutically acceptable salts thereof, for the manufacture of a medicament useful to treat inflammation and the diseases and/or conditions associated therewith, including, but not limited to, asthma, systemic lupus erythematosus, rheumatoid arthritis, reactive arthritis, spondyarthritis, systemic vasculitis, insulin dependent diabetes mellitus, multiple sclerosis, experimental allergic encephalomyelitis, Sjogren's syndrome, graft versus host disease, inflammatory bowel disease including Crohn's disease, ulcerative colitis, and scleroderma. Inflammatory diseases also includes autoimmune diseases such as myasthenia gravis, Guillain-Barre disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, multiple sclerosis, vitiligo, ankylosing spondylitis, Pemphigus vulgaris, psoriasis, dermatitis herpetiformis, Addison's disease, Goodpasture's syndrome, Basedow's disease, thrombopenia purpura, allergy, and cardiomyopathy. In yet another embodiment, the inflammation is associated with the onset of cancer and/or the administration of anti-cancer chemotherapeutic agents. This aspect also encompasses such medicaments to treat proinflammatory neuropathic pain.

In yet another aspect, the present invention provides a method of eliciting an agonist or an antagonist effect from a ghrelin receptor in a subject in need thereof which comprises administering to said subject an effective amount of a compound of Formula (I) or Formula (II) or Formula (III), or Formula (IV), as defined hereinabove, as well as the non-conforming compounds specifically enumerated herein and below or pharmaceutically acceptable salts thereof.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 32: shows the timeline for the protocol used to study the ghrelin analogue H-Inp-D-Bal-D-Trp-Phe-Apc-NH$_2$ (SEQ ID: 2) in the established colitis model; and FIG. 33: shows the colon length in centimeters of inflamed colons dissected from the established colon model after 8 days of treatment with a positive control, a negative control and the ghrelin analogue H-Inp-D-Bal-D-Trp-Phe-Apc-NH$_2$ (SEQ ID: 2).

LEGEND FOR FIGS. 1-33

Figure 1:
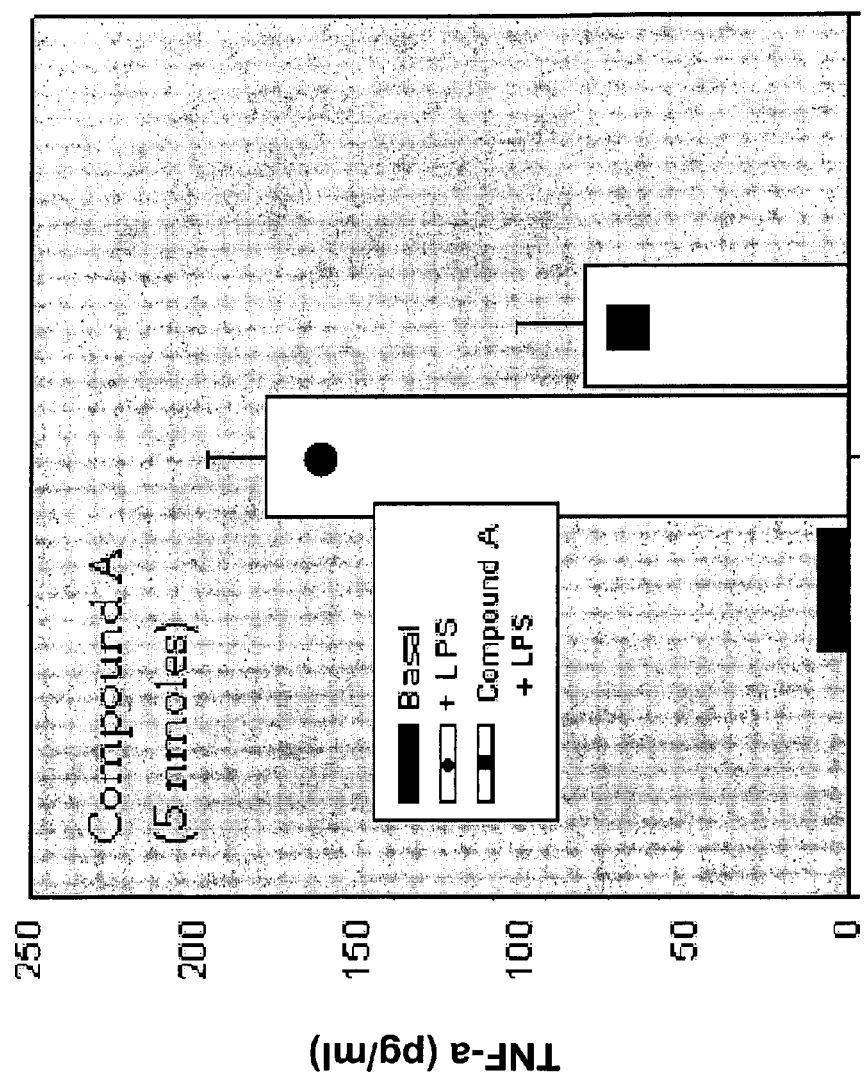
FIG. 1: shows the amount of TNF-α after an LPS challenge before and after injection of 5 nmoles of the ghrelin analogue H-Inp-D-Bal-D-Trp-Phe-Apc-$NH_2$; (SEQ ID: 2)
Figure 2:
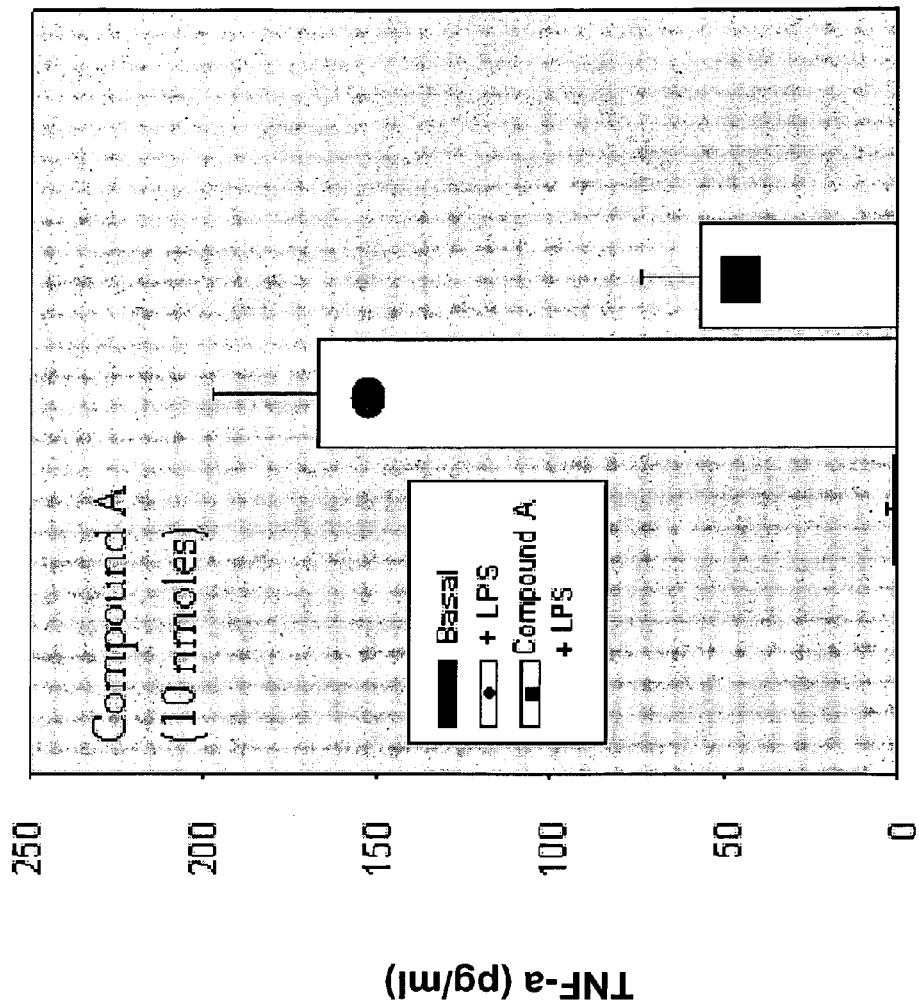
FIG. 2: shows the amount of TNF-α after an LPS challenge before and after injection of 10 nmoles of the ghrelin analogue H-Inp-D-Bal-D-Trp-Phe-Apc-$NH_2$; (SEQ ID: 2)

| Compound | Peptide Sequence |
| --- | --- |
| A | H-Inp-D-Bal-D-Trp-Phe-Apc-NH$_2$ (SEQ ID: 2) |
| B | (Ac-Gly$^1$, Aib$^{2,10}$, Glu$^3$ (NH-hexyl))hGhrelin(1-28)-NH$_2$ (SEQ ID: 3) |
| C | (Aib$^2$, Glu$^3$ (NH-hexyl)hGhrelin(1-28)-NH$_2$ (SEQ ID: 92) |

DETAILED DESCRIPTION OF THE INVENTION

The present invention may be understood more readily by reference to the following detailed description of preferred embodiments of the invention and the Examples included therein and to the Figures and their previous and following description. Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following description of the preferred embodiments and from the claims. Certain amino acids present in compounds of the invention can be and are represented herein as follows:

A. Definitions

1. Chemical Abbreviations and Definitions

The following are definitions of terms used in this specification. The initial definition provided for a group or term herein applies to that group or term throughout the present specification, individually or as part of another group, unless otherwise indicated. Unless defined otherwise, all technical and scientific terms used herein have the same meaning as commonly understood by one of ordinary skill in the art to which this invention belongs.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When a subscript is used with reference to an alkyl or other group, the subscript refers to the number of carbon atoms that the group may contain.

The term "substituted alkyl" refers to an alkyl group as defined above having one, two or three substituents selected from the group consisting of halo, amino, cyano, keto (=O), —$OR_a$, —$SR_a$, $NR_aR_b$, —(C=O)$R_a$, —$CO_2R_a$, —C(=O)$NR_aR_b$, —$NR_aC$(=O)$R_b$, $NR_aCO_2R_b$, —OC(=O)$R_a$, —OC(=O)$NR_aR_b$, —$NR_cC$(=O)$NR_aR_b$, $NR_aSO_2R_d$, $SO_2R_d$, $SO_3R_d$, cycloalkyl, aryl, heteroaryl, or heterocycle, wherein the groups $R_a$, $R_b$, and $R_c$ are selected from hydrogen, ($C_1$-$C_6$)alkyl, aryl, heteroaryl, heterocycle, cycloalkyl, or ($C_1$-$C_6$)alkyl substituted with halogen, hydroxy, methoxy, nitro, amino, cyano, —(C=O)H, —$CO_2$H, —(C=O)alkyl, —$CO_2$alkyl, —NH(alkyl), —NH(cycloalkyl), —N(alkyl)$_2$, carboxy, acyl, —C(=O)H, —C(=O)phenyl, —$CO_2$-alkyl, cycloalkyl, —(C=O)$NH_2$, —(C=O)NH(alkyl), —(C=O)NH(cycloalkyl), —(C=O)N(alkyl)$_2$, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, —NH—CH$_2$-carboxy, —NH—CH$_2$—CO$_2$-alkyl, phenyl, benzyl, phenylethyl, or phenyloxy. The group $R_d$ may be selected from the same groups as $R_a$, $R_b$ and $R_c$ but is not hydrogen. Alternatively, the groups $R_a$ and $R_b$ may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the definitions for these terms.

When the term "alkyl" is used as a suffix following another specifically named group, e.g., arylalkyl or heteroarylalkyl, the term defines, with more specificity, at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred. A substituted alkenyl or alkynyl will contain one, two, or three substituents as defined above for alkyl groups.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1 to 8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above. Substituted alkylene, alkenylene, and alkynylene groups may have substituents as defined above for substituted alkyl groups.

The term "alkoxy" refers to the group $OR_e$ wherein $R_e$ is alkyl, substituted alkyl, alkenyl, substituted alkenyl, alkynyl, substituted alkynyl, heterocycle or cycloalkyl. Thus, an alkoxy includes such groups as methoxy, ethoxy, cyclopropyloxy, pyrrolidinyloxy, and so forth. The term "aryloxy" refers to the groups O(aryl) or O(heteroaryl), wherein aryl and heteroaryl are as defined below.

The term "alkylthio" refers to an alkyl or substituted alkyl group as defined above bonded through one or more sulfur (—S—) atoms, e.g., —S(alkyl) or —S(alkyl-$R_a$).

The term "alkylamino" refers to an alkyl or substituted alkyl group as defined above bonded through one or more nitrogen (—$NR_f$—) groups, wherein $R_f$ is hydrogen, alkyl, substituted alkyl, or cycloalkyl.

The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O)} linked to the second named group. Thus, acylamino refers to —C(=O)NH$_2$, substituted acylamino refers to the group —C(=O)NRR, and acylaryl refers to —C(=O)(aryl).

The term "aminoacyl" refers to the group —$NR_f$C(=O)$R_g$, wherein $R_g$ is hydrogen, alkyl, or substituted alkyl, and $R_f$ is as defined above for alkylamino groups.

The term "halo" or "halogen" refers to chloro, bromo, fluoro and iodo. Unless otherwise indicated, any haloalkyl, haloalkoxy or haloalkylthio group contains one or more halo atoms which halo atoms may be the same or different.

The term "carboxy" when used alone refers to the group CO$_2$H. Carboxyalkyl refers to the group CO$_2$R, wherein R is alkyl or substituted alkyl.

The term "sulphonyl" refers to a sulphoxide group (i.e., —$S(O)_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —SO$_2$-alkyl), or bivalent (e.g., —SO$_2$-alkylene, etc.)

The term "cycloalkyl" refers to substituted and unsubstituted monocyclic or bicyclic hydrocarbon groups of 3 to 9 carbon atoms which are, respectively, fully saturated or partially unsaturated, including a fused aryl ring, for example, an indan. A cycloalkyl group may be substituted by one or more (such as one to three) substituents selected from alkyl, substituted alkyl, aminoalkyl, halogen, cyano, nitro, trifluoromethyl, hydroxy, alkoxy, alkylamino, sulphonyl, —SO$_2$(aryl), —CO$_2$H, —CO$_2$-alkyl, —C(=O)H, keto, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, acyl, aryl, heterocycle, heteroaryl, or another cycloalkyl ring of 3 to 7 carbon atoms. The term "cycloalkylene" refers to a cycloalkyl forming a link or spacer between two other groups, i.e., a cycloalkylene is a cycloalkyl that is bonded to at least two other groups. The term cycloalkyl includes saturated or partially unsaturated carbocyclic rings having a carbon-carbon bridge of three to four carbon atoms or having a benzene ring joined thereto. When the cycloalkyl group is substituted with a further ring, said further ring may have one to two substituents selected from Rk, wherein Rk is lower alkyl, hydroxy, lower alkoxy, amino, halogen, cyano, trifluoromethyl, trifluoromethoxy, nitro, and lower alkyl substituted with one to two hydroxy, lower alkoxy, amino, halogen, cyano, trifluoromethyl, trifluoromethoxy and/or nitro.

The term "aryl" refers to substituted and unsubstituted phenyl, 1-naphthyl and 2-naphthyl, with phenyl being preferred. The aryl may have zero, one, two or three substituents selected from the group consisting of alkyl, substituted alkyl, alkoxy, alkylthio, halo, hydroxy, nitro, cyano, amino, trifluoromethyl, trifluoromethoxy, sulphonyl, —SO$_2$(aryl), —NH(alkyl), —NH(cycloalkyl), —N(alkyl)$_2$, carboxy, acyl, —C(=O)H, —C(=O)phenyl, —CO$_2$-alkyl, cycloalkyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, phenyl, benzyl, phenylethyl, phenyloxy, phenylthio, heterocyclo, heteroaryl or a (C$_3$-C$_7$)cycloalkyl ring. The term "arylene" refers to an aryl as defined above forming a link or spacer between two other groups, i.e., an arylene is an aryl that is bonded to at least two other groups. When the aryl group is substituted with a further ring, said further ring may have one to two substituents selected from R$_k$, wherein R$_k$ is defined as above.

The term "heterocyclo" or "heterocycle" refers to substituted and unsubstituted non-aromatic 3- to 7-membered monocyclic groups, 7- to 11-membered bicyclic groups, and 10- to 15-membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less and further provided that the ring contains at least one carbon atom. The fused rings completing the bicyclic and tricyclic groups may contain only carbon atoms and may be saturated, partially saturated or unsaturated. The nitrogen and sulfur atoms may optionally be oxidized and the nitrogen atoms may optionally be quaternized. The heterocyclo group may be attached at any available nitrogen or carbon atom. The heterocyclo ring may contain one, two or three substituents selected from the group consisting of halo, amino, cyano, alkyl, substituted alkyl, trifluoromethyl, trifluoromethoxy, sulphonyl, —SO$_2$(aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, —C(=O)H, acyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, heterocyclo, heteroaryl, a (C$_3$-C$_7$)cycloalkyl ring, keto, =N—OH, =N—O-lower alkyl, or a five or six-membered ketal, i.e., 1,3-dioxolane or 1,3-dioxane. When the heterocyclo group is substituted with a further ring, said further ring may have one to two substituents selected from R$_k$, wherein R$_k$ is defined as above. Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, trifluoromethyl, trifluoromethoxy, sulphonyl, —SO$_2$(aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, —C(=O)H, acyl, —(C=O)NH$_2$, —(C=O)NH(alkyl), —(C=O)NH(cycloalkyl), —(C=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, heterocyclo, heteroaryl or a (C$_3$-C$_7$)cycloalkyl ring. The heterocyclo ring may have a sulfur heteroatom that is substituted with one or more oxygen (=O) atoms. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like. Exemplary tricyclic heteroaryl groups include carbazolyl, benzidolyl, phenanthrollinyl, acridinyl, phenanthridinyl, xanthenyl and the like.

When reference is made herein to a particularly-named heterocyclic or heteroaryl group, such as azetidinyl, imidazolyl, piperazinyl, and so forth, the named ring may optionally contain one or more (preferably one to three) substituents selected from the substituents recited above for heteroaryl and heterocyclo groups, as appropriate.

When reference is made to a particularly-named group having at least one heterocyclo, heteroaryl, or carbocyclic ring "joined" thereto, it is meant that two substituents attached to the same, adjacent, or non-adjacent atoms of the particularly-named group may join to form a second or third ring (i.e., the further ring may be fused, bridged or attached in a spiro fashion). Each ring of these bicyclic or tricyclic groups may be optionally substituted, wherein the substituents are selected from those recited above for cycloalkyl, aryl, heterocyclo and heteroaryl groups. Thus, an imidazole having at least one ring joined thereto may include an aryl-fused imidazole such as benzimidazole having one or more (preferably one to three substituents), to an heteroaryl-fused imidazole such as a pyridoimidazole having one or more (preferably one to three) substituents, and so forth.

Additionally, one skilled in the field may make appropriate substitutions for the various groups of compounds of Formula (I), (II), (III) or (IV), as well as the non-conforming compounds, herein without departing from the spirit and scope of the invention. Throughout the specification, groups and substituents thereof may be chosen to provide stable moieties and compounds.

Prodrugs and solvates of the compounds of this invention are also contemplated herein. The term "prodrug", as employed herein, denotes a compound which, upon administration to a subject, undergoes chemical conversion by metabolic or chemical processes to yield a compound of any one of Formula (I), (II), (III) or (IV) or the non-conforming compounds, and/or a salt and/or solvate thereof. Solvates of the compounds of Formula (I), (II), (III) or (IV) or the non-conforming compounds, are preferably hydrates.

Compounds of any one of Formula (I), (II), (III) or (IV), or the non-conforming compounds, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally-occurring amino acid polymers and non-naturally-occurring amino acid polymers. The nomenclature used to define the peptides is that typically used in the art wherein the amino group at the N-terminus appears to the left and the carboxyl group at the C-terminus appears to the right.

The term "amino acid" refers to naturally occurring and synthetic amino acids, as well as amino acid analogs and amino acid mimetics that function in a manner similar to the naturally occurring amino acids. Unless otherwise indicated, with the exception of the N-terminal amino acid, all abbreviations (e.g. Ala) of amino acids in this disclosure stand for the structure of —NH—C(R)(R')—CO— wherein R and R' each is, independently, hydrogen or the side chain of an amino acid (e.g., R=CH₃ and R'=H for Ala), or R and R' may be joined to form a ring system. For the N-terminal amino acid, the abbreviation stands for the structure of:

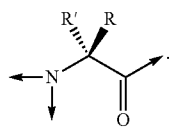

Naturally occurring amino acids are those encoded by the genetic code, as well as those amino acids that are later modified. The term "amino acid analog" refers to a compound that has the same basic chemical structure as a naturally-occurring amino acid, i.e., an α-carbon that is bound to a hydrogen, a carboxyl group, an amino group, and an R group, e.g., homoserine and norleucine. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission.

Nomenclature and Abbreviations

| Symbol | Meaning |
| --- | --- |
| Abu | α-aminobutyric acid |
| Acc | 1-amino-1-cyclo(C₃—C₉)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | 4-amino-4-carboxytetrahydropyran having the structure: |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | alanine |
| β-Ala | beta-alanine |
| Apn | 5-aminopentanoic acid (HN—(CH₂)₄—C(O)) |
| Arg or R | arginine |
| hArg | homoarginine |
| Asn or N | asparagine |
| Asp or D | aspartic acid |
| Ava | 5-amino-n-valeric acid |
| Bal | 3-benzothienylalanine |

-continued

| | |
|---|---|
| D-Bal | D-3-benzothienylalanine having the structure: 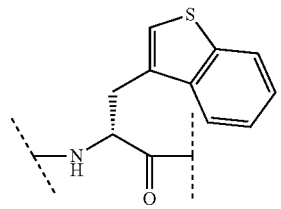 |
| Bip | 4,4'-biphenylalanine, represented by the structure: 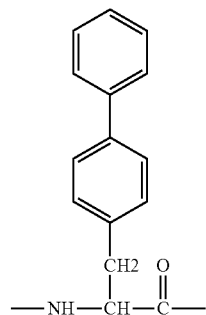 [SMILES: CNC(Cc1ccc(-c2ccccc2)cc1)C(C)=O] |
| D-Bip | D-4,4'-biphenylalanine having the structure: 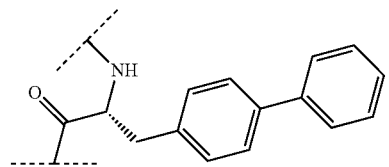 |
| Bpa | 4-benzoylphenylalanine |
| D-Bpa | D-4-benzoylphenylalanine having the structure: 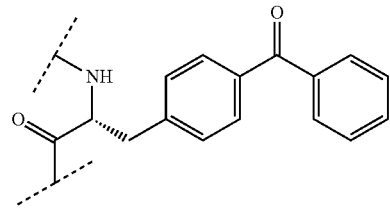 |
| Cha | β-cyclohexylalanine |
| hCha | homo-cyclohexylalanine |
| Chg | cyclohexylglycine |
| Cys or C | cysteine |
| hCys | L-homocysteine |
| Dab | 2,4-diaminobutyric acid |
| Dap | 2,3-diaminopropionic acid |
| Dap(octanoyl) | denotes the structure: 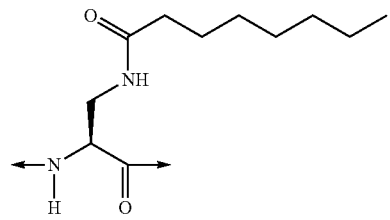 |

-continued

| | |
|---|---|
| Dhp | 3,4-dehydroproline |
| Dip | β,β-diphenylalanine having the structure: 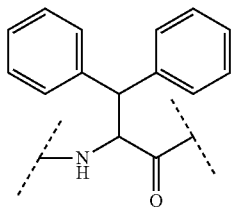 |
| Dmt | 5,5-dimethylthiazolidine-4-carboxylic acid |
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S, 3S)-3-hydroxypyrrolidine-carboxylic acid |
| 4-Hyp | 4-hydroxyproline, i.e., (2S, 4R)-4-hydroxypyrrolidine-2-carboxylic acid |
| Ile or I | isoleucine |
| Inc | indoline-2-carboxylic acid |
| Ktp | 4-ketoproline |
| Leu or L | leucine |
| hLeu | homoleucine |
| Lys or K | lysine |
| Lys (biotinyl) | lysine biotinyl having the structure: 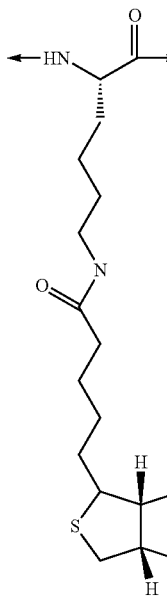 |
| Met or M | methionine |
| β-hMet | β-homomethionine |
| 1-Nal | β-(1-naphthyl)-L-alanine |
| 2-Nal | β-(2-naphthyl)-L-alanine |
| Nip | nipecotic acid |
| Nle | norleucine |
| Nva | norvaline |
| Oic | octahydroindole-2-carboxylic acid |
| Orn | ornithine |
| 2-Pal | β-(2-pyridiyl)alanine |
| 3-Pal | β-(3-pyridiyl)alanine |
| 4-Pal | β-(4-pyridiyl)alanine |
| Pen | penicillamine |
| Phe or F | phenylalanine |
| hPhe | homophenylalanine |

| | |
|---|---|
| Pff | pentafluorophenylalanine having the structure: |

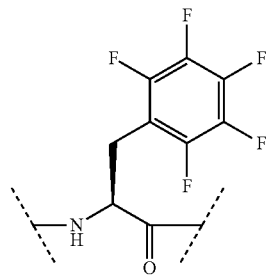

| | |
|---|---|
| Pip | pipecolic acid |
| Pim | 2'-(4-phenyl)imidazolyl having the structure: |

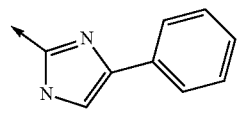

| | |
|---|---|
| Pro or P | proline |
| hPro | homoproline |
| Ser or S | serine |
| Ser(Bzl) | O-bezyl-serine |
| Taz | β-(4-thiazolyl)alanine having the structure: |

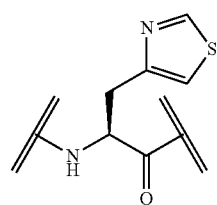

| | |
|---|---|
| 2-Thi | β-(2-thienyl)alanine |
| 3-Thi | β-(3-thienyl)alanine |
| Thr or T | threonine |
| Thr(Bzl) | O-bezyl-threonine |
| Thz | thiazolidine-4-carboxylic acid |
| Tic | 1,2,3,4-tetrahydroisoquinoline-3-carboxylic acid |
| Tle | tert-leucine |
| Trp or W | tryptophan |
| Tyr or Y | tyrosine |
| Val or V | valine |

What is meant by Asp(1-heptanol) is

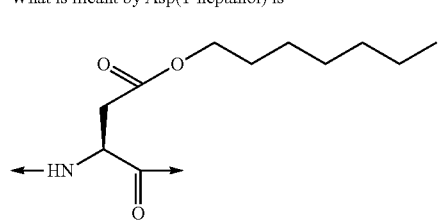

What is meant by Asp(NH-hexyl) is

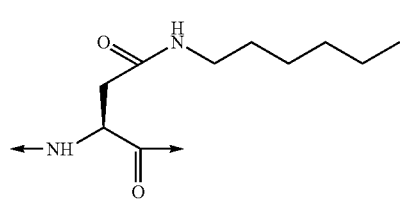

What is meant by Asp(NH-heptyl) is

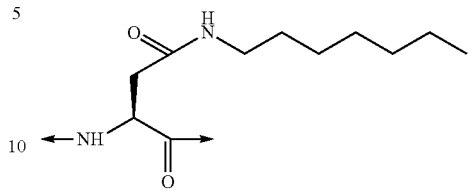

What is meant by Asp(O-hexyl) is

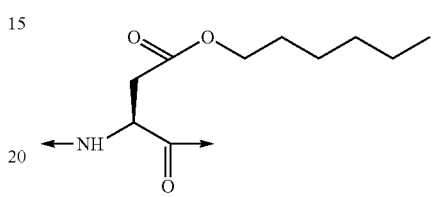

What is meant by Cys($R^{15}$) is:

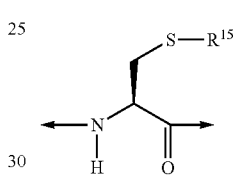

What is meant by Cys(S-heptyl) is

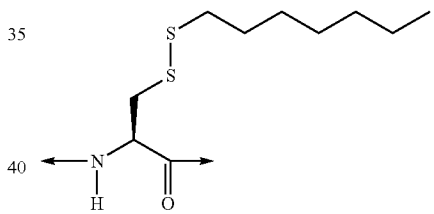

What is meant by Dap(octanoyl) is

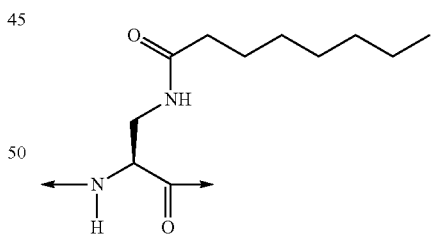

What is meant by Dap(octanesulfonyl) is

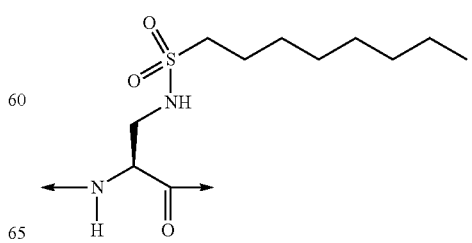

What is meant by Glu(NH-hexyl) is
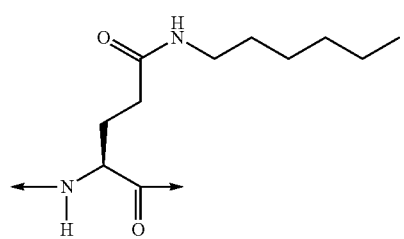
What is meant by Glu(O-hexyl) is
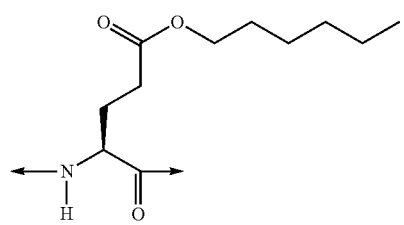
What is meant by Glu(1-heptanol) is
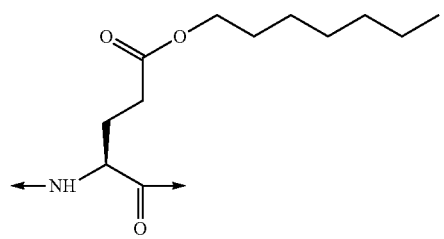
What is meant by Ser(n-octanoyl) or Ser(C(O)-heptyl) is
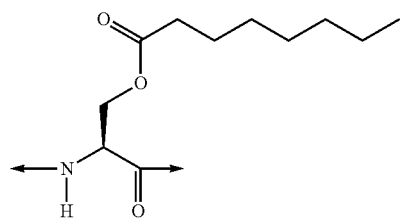
What is meant by biotinyl is
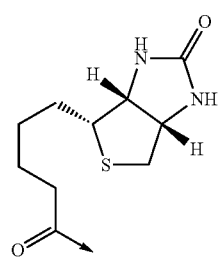
What is meant by myristyl is
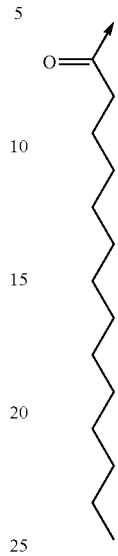
What is meant by Lys(biotinyl) is
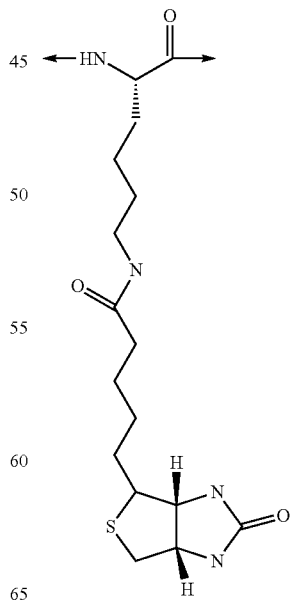

What is meant by Lys(myristyl) is

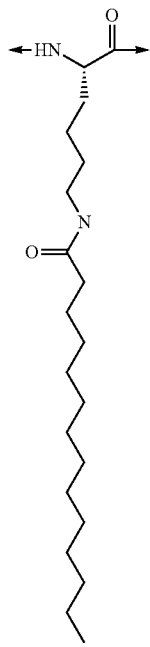

What is meant by Gly(myristyl) is

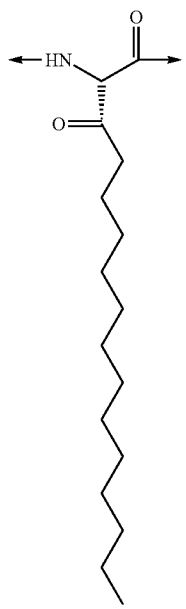

The N-terminal amino acids Inp and Apc have the structures of:

Inp:

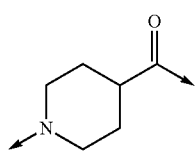

1-Apc:

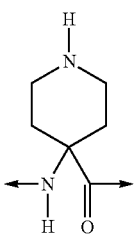

4-Apc:

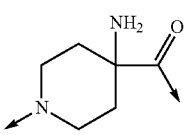

The letter "D" preceding the above three-letter abbreviations, e.g. as in "D-Nal" or "D-Phe", denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to the L-form. Where the common single-letter abbreviation is used, capitalization refers to the L-form and small letter designation refers to the D-form, unless otherwise indicated.

The designation "NH$_2$" in e.g., Ac-Nle-c(Cys-D-Ala-His-D-Phe-Arg-Trp-Cys)-NH$_2$ (SEQ ID: 4), indicates that the C-terminus of the peptide is amidated. Ac-Nle-c(Cys-D-Ala-His-D-Phe-Arg-Trp-Cys), or alternatively Ac-Nle-c(Cys-D-Ala-His-D-Phe-Arg-Trp-Cys)-OH (SEQ ID: 5), indicates that the C-terminus is the free acid. "-c(Cys-Cys)-" or "-cyclo(Cys-Cys)-" denotes the structure:

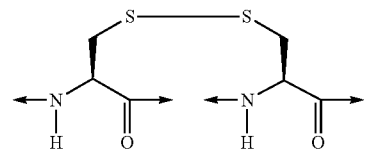

"-c(Cys-Pen)-" or "-cyclo(Cys-Pen)-" denotes the structure:

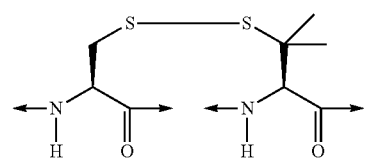

"-c(Asp-Lys)-" or "-cyclo(Asp-Lys)-" denotes the structure:

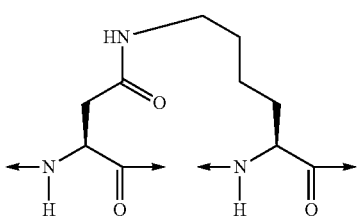

When a non-amino acid imidazole moiety (e.g., Pim, defined above), is present at the C-terminus of a compound of the invention it is understood that the imidazole moiety is attached to the adjacent amino acid via a pseudo-peptide bond wherein a bond is formed between the $2^{nd}$ carbon of the imidazole ring and the α-carbon of the amino acid. For example, in the case where the adjacent amino acid is D-Tryptophan (D-Trp) and the imidazole moiety is Pim, the C-terminus of the peptide would appear as follows:

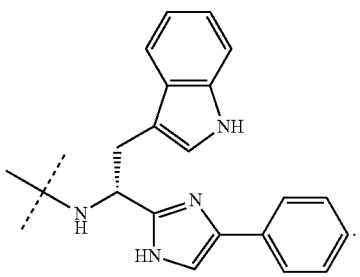

For clarity, in the written formula for such a compound the presence of this bond is indicated by the Greek letter "Ψ" alone in parentheses. For example, the written formula H-Inp-D-Trp-D-2Nal(Ψ)-Pim (SEQ ID: 127) denotes the structure:

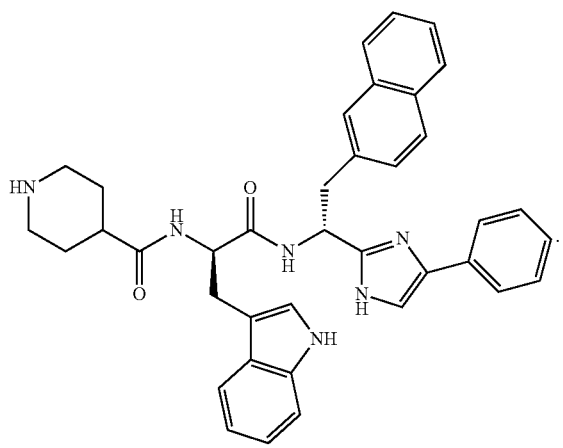 [SMILES: O=C(N[C@H](Cc1c[nH]c2ccccc12)C(=O)N[C@H](Cc1ccc2ccccc2c1)c1nc(-c2ccccc2)c[nH]1)C1CCNCC1]

As used herein, Acc encompasses an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c).

For avoidance of doubt, unless otherwise indicated, the term "substituted" means substituted by one or more defined groups. In the case where the groups may be selected from a number of alternative groups, the selected groups may be the same or different. For the avoidance of doubt, the term independently means that where more than one substituent is selected from a number of possible substituents, those substituents may be the same or different.

The compounds of the invention may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

2. Biological and Other Definitions

Before the present methods and compositions are disclosed and described, it is to be understood that this invention is not limited to specific methods or specific substances unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substance" includes one or more substances, and the like.

Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates" or "elevation" refer to increases above basal levels, or as compared to a control. The terms "low," "lower," "inhibits," "inhibition," "reduces" or "reduction" refer to decreases below basal levels or as compared to a control. For example, basal levels are normal in vivo levels prior to, or in the absence of, inflammation or the addition of an agent which causes inflammation.

As used herein, "measurable" means the biologic effect is both reproducible and significantly different from the baseline variability of the assay.

The terms "mediate" or "mediation" and "modulate" or "modulation" mean to regulate, or control, in particular to increase, enhance, elevate, or alternatively, to lower, inhibit or reduce. The terms "mediate" and "modulate" are used interchangeably throughout.

"Inflammation" or "inflammatory" is defined as the reaction of living tissues to injury, infection or irritation. Anything that stimulates an inflammatory response is said to be inflammatory. "Low-grade inflammation" refers to mild inflammation (or in the event that a range is provided, the lower end of the range).

"Inflammatory disease" is defined as any disease state associated with inflammation.

"Infection" or "infectious process" is defined as one organism being invaded by any type of foreign material or another organism. The results of an infection can include growth of the foreign organism, the production of toxins, and damage to the host organism. Infection includes viral, bacterial, parasitic and fungal infections, for example.

"β-cells" are a type of white blood cell or lymphocyte involved in generating antibodies and fighting infection. "T-cells" are white blood cells which play a central role in cell-mediated immunity.

"Liver toxicity" is defined as an abnormal accumulation of toxic substances in the liver. A number of criteria can be used to assess the clinical significance of toxicity data: (a) type/severity of injury, (b) reversibility, (c) mechanism of toxicity, (d) interspecies differences, (e) availability of sensitive biomarkers of toxicity, (e) safety margin (non toxic dose/pharmacologically active dose) and (f) therapeutic potential.

"Cancer therapy" is defined as any treatment or therapy useful in preventing, treating or ameliorating the symptoms associated with cancer. Cancer therapy can include, but is not limited to, apoptosis induction, radiation therapy and chemotherapy.

"Transplant" is defined as the transplantation of an organ or body part from one organism to another.

"Transplant rejection" is defined as an immune response triggered by the presence of foreign blood or tissue in the body of a subject. In one example of transplant rejection, antibodies are formed against foreign antigens on the transplanted material.

"Apoptosis" is defined as the orderly program of biochemical reactions leading to cell death and degradation.

"Autoimmune disease" or "autoimmune disorder" refers to any of a large group of diseases characterized by abnormal functioning of the immune system that causes the immune system to produce antibodies against the body's own tissues.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The terms "control levels" or "control cells" are defined as the standard by which a change is measured, for example, the controls are not subjected to the experiment, but are instead subjected to a defined set of parameters, or the controls are based on pre- or post-treatment levels.

By "treating" is meant that an improvement in the disease state, i.e., the inflammatory response, is observed and/or detected upon administration of a substance of the present invention to a subject. Treatment can range from a positive change in a symptom or symptoms of the disease to complete amelioration of the inflammatory response (e.g., reduction in severity or intensity of disease, alteration of clinical parameters indicative of the subject's condition, relief of discomfort or increased or enhanced function), as detected by art-known techniques.

An "effective amount" is that amount of the claimed compound which produces a noticeable improvement in the diseased state.

By "preventing" is meant that after administration of a substance of the present invention to a subject, the subject does not develop the symptoms of inflammation.

As used herein, a "cytokine" is a molecule which is released by cells in response to infection or injury that stimulates an inflammatory or healing response. Types of cytokines discussed in the instant application are as follows:

IL-1α interleukin-1α
IL-1β interleukin-1β
IL-2 interleukin-2
IL-4 interleukin-4
IL-6 interleukin-6
IL-10 interleukin-10
GM-CSF granulocyte-macrophage colony stimulating factor
TNF-α tumor-necrosis factor-α
INF-γ interferon-γ
P40 a glycoprotein of 126 amino acids which supports the growth of a number of T-helper cell lines in the absence of IL-2, IL-4 and antigens which is homologous with hIL-9.

As used herein, a "chemokine" is a type of cytokine (a soluble molecule that a cell produces to control reactions between other cells) that specifically alters the behavior of leukocytes (white blood cells), such as, but not limited to, interleukin-8, platelet factor-4 and melanoma growth stimulatory protein. Types of chemokines discussed in the instant application are as follows:

MCP-1 (otherwise known in the art as CCL2) monocyte chemotactic protein-1
MIP-α (otherwise known as CCL3) macrophage inflammatory protein-α
RANTES (otherwise known as CCL5) Regulated Upon Activation Normal T-cell Expression and Secreted
KC Keratinocyte-derived chemokine.

As used herein, "hematopoietic" refers to an agent that affects or promotes the formation of blood cells.

A "prodrug" is a compound that upon administration to subject must undergo chemical conversion by metabolic processes before becoming an active pharmacologic agent.

The abbreviation "hGhrelin(1-28)-NH$_2$" refers to native or naturally-occurring peptide having the following sequence: a 28-amino acid peptide of the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$." (SEQ ID: 1)

As used herein, a "peptidyl analogue of ghrelin", "analogue of ghrelin" and "ghrelin analogue" refer to peptide ligands for at least one ghrelin receptor which can be used to practice the therapeutic method of the present invention.

B. Compositions

Disclosed are the components to be used to prepare the disclosed compositions as well as the compositions themselves. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the amino acids within the peptide and the modifications that are possible unless specifically indicated to the contrary.

This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The present invention includes a method of treating inflammation in a subject comprising administering to the subject an effective amount of an analogue of native ghrelin and fragments thereof of any length that are functional ghrelin molecules according to the following Formula (I):

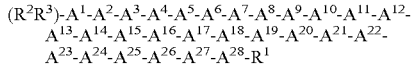

(R²R³)-A¹-A²-A³-A⁴-A⁵-A⁶-A⁷-A⁸-A⁹-A¹⁰-A¹¹-A¹²-A¹³-A¹⁴-A¹⁵-A¹⁶-A¹⁷-A¹⁸-A¹⁹-A²⁰-A²¹-A²²-A²³-A²⁴-A²⁵-A²⁶-A²⁷-A²⁸-R¹ wherein:

A¹ is Gly, Aib, Ala, β-Ala or Acc;

A² is Ser, Aib, Act, Ala, Acc, Abu, Ava, Thr or Val;

A³ is Ser, Ser(C(O)—R⁴), Asp(O—R⁸), Asp(NH—R⁹), Cys(S—R¹⁴), Dap(S(O)₂—R¹⁰), Dab(S(O)₂—R¹¹), Glu (O—R⁶), Glu(NH—R⁷), Thr, Thr(C(O)—R⁵) or HN—CH ((CH₂)$_n$—N(R¹²R¹³))—C(O);

A⁴ is Phe, Acc, Aic, Cha, 2-Fua, 1-Nal, 2-Nal, 2-Pal, 3-Pal, 4-Pal, hPhe, (X¹,X²,X³,X⁴,X⁵)Phe, Taz, 2-Thi, 3-Thi, Trp or Tyr;

A⁵ is Leu, Abu, Acc, Aib, Ala, Cha, Ile, hLeu, Nle, Nva, Phe, Tle or Val;

A⁶ is Ser, Abu, Acc, Act, Aib, Ala, Gly, Thr or Val;

A⁷ is Pro, Dhp, Dmt, 3-Hyp, 4-Hyp, Inc, Ktp, Oic, Pip, Thz, Tic or deleted;

A⁸ is Glu, Acc, Aib, Arg, Asn, Asp, Dab, Dap, Gln, Lys, Orn, HN—CH((CH₂)$_n$—N(R¹²R¹³))—C(O) or deleted;

A⁹ is His, Apc, Aib, Acc, 2-Fua, 2-Pal, 3-Pal, 4-Pal, Taz, 2-Thi, 3-Thi, (X¹,X²,X³,X⁴,X⁵-)Phe or deleted;

A¹⁰ is Gln, Acc, Aib, Asn, Asp, Glu or deleted;

A¹¹ is Arg, Apc, hArg, Dab, Dap, Lys, Orn, HN—CH ((CH₂)$_n$—N(R¹²R¹³))—C(O) or deleted;

A¹² is Val, Abu, Acc, Aib, Ala, Cha, Nva, Gly, Ile, Leu, Nle, Tle or deleted;

A¹³ is Gln, Acc, Aib, Asn, Asp, Glu or deleted;

A¹⁴ is Gln, Acc, Aib, Asn, Asp, Glu or deleted;

A¹⁵ is Arg, hArg, Acc, Aib, Apc, Dab, Dap, Lys, Orn, HN—CH((CH₂)$_n$—N(R¹²R¹³))—C(O) or deleted;

A¹⁶ is Lys, Acc, Aib, Apc, Arg, hArg, Dab, Dap, Orn, HN—CH((CH₂)$_n$—N(R¹²R¹³))—C(O) or deleted;

A¹⁷ is Glu, Arg, Asn, Asp, Dab, Dap, Gln, Lys, Orn, HN—CH((CH₂)$_n$—N(R¹²R¹³))—C(O) or deleted;

A¹⁸ is Ser, Abu, Acc, Act, Aib, Ala, Thr, Val or deleted;

A¹⁹ is Lys, Acc, Aib, Apc, Arg, hArg, Dab, Dap, Orn, HN—CH((CH₂)$_n$—N(R¹²R¹³))—C(O) or deleted;

A²⁰ is Lys, Acc, Aib, Apc, Arg, hArg, Dab, Dap, Orn, HN—CH((CH₂)$_n$—N(R¹²R¹³))—C(O) or deleted;

A²¹ is Pro, Dhp, Dmt, 3-Hyp, 4-Hyp, Inc, Ktp, Oic, Pip, Thz, Tic or deleted;

A²² is Pro, Dhp, Dmt, 3-Hyp, 4-Hyp, Inc, Ktp, Oic, Pip, Thz, Tic or deleted;

A²³ is Abu, Acc, Act, Aib, Ala, Apc, Gly, Nva, Val or deleted;

A²⁴ is Lys, Acc, Aib, Apc, Arg, hArg, Dab, Dap, Orn, HN—CH((CH₂)$_n$—N(R¹²R¹³))—C(O) or deleted;

A²⁵ is Leu, Abu, Acc, Aib, Ala, Cha, Ile, hLeu, Nle, Nva, Phe, Tle, Val or deleted;

A²⁶ is Gln, Aib, Asn, Asp, Glu or deleted;

A²⁷ is Pro, Dhp, Dmt, 3-Hyp, 4-Hyp, Inc, Ktp, Oic, Pip, Thz, Tic or deleted;

A²⁸ is Acc, Aib, Apc, Arg, hArg, Dab, Dap, Lys, Orn, HN—CH((CH₂)$_n$—N(R¹²R¹³))—C(O) or deleted;

R¹ is —OH, —NH₂, —(C₁-C₃₀)alkoxy or NH—X⁶—CH₂—Z⁰, wherein X⁶ is a (C₁-C₁₂)alkyl, (C₂-C₁₂)alkenyl and Z⁰ is —H, —OH, —CO₂H or —C(O)—NH₂;

R² and R³ each is, independently for each occurrence, H, (C₁-C₂₀)alkyl or (C₁-C₂₀)acyl;

R⁴, R⁵, R⁶, R⁷, R⁸, R⁹, R¹⁰, R¹¹ and R¹⁴ each is, independently for each occurrence, (C₁-C₄₀)alkyl, (C₂-C₄₀)alkenyl, substituted (C₁-C₄₀)alkyl, substituted (C₂-C₄₀)alkenyl, alkylaryl, substituted alklyaryl, aryl or substituted aryl;

R¹² and R¹³ each is, independently for each occurrence, H, (C₁-C₄₀)alkyl, (C₁-C₄₀)acyl, (C₁-C₃₀)alkylsulfonyl or —C(NH)—NH₂, wherein when R¹² is (C₁-C₄₀)acyl, (C₁-C₃₀)alkylsulfonyl or —C(NH)—NH₂, then R¹³ is H or (C₁-C₄₀)alkyl;

n is, independently for each occurrence, 1, 2, 3, 4 or 5;

X¹, X², X³, X⁴, and X⁵ each is, independently for each occurrence, H, F, Cl, Br, I, (C₁₋₁₀)alkyl, substituted (C₁₋₁₀) alkyl, aryl, substituted aryl, OH, NH₂, NO₂ or CN;

provided that the peptide contains at least one amino acid selected from the groups consisting of:

A² is Aib, Acc or Act;

A³ is Dap(S(O)₂—R¹⁰), Dab(S(O)₂—R¹¹), Glu(NH-hexyl) or Cys(S-decyl);

A⁵ is Abu, Acc, Aib, Ala, Cha, Ile, hLeu, Nle, Nva, Phe, Tle or Val;

A⁶ is Abu, Acc, Act, Aib, Ala, Gly, Thr or Val;

A⁷ is Dhp, Dmt, 3-Hyp, 4-Hyp, Inc, Ktp, Oic, Pip, Thz or Tic;

A⁸ is Acc, Aib, Arg, Asn, Asp, Dab, Dap, Gln, Lys, Orn or HN—CH((CH₂)$_n$—N(R¹²R¹³))—C(O);

A⁹ is Aib, Acc, Apc, 2-Fua, 2-Pal, 3-Pal, 4-Pal, Taz, 2-TN, 3-Thi or (X¹,X²,X³,X⁴,X⁵-)Phe; and A¹⁰ is Acc, Aib, Asn, Asp or Glu;

and further provided that the peptide is not (Lys⁸)hGhrelin (1-8)-NH₂ or (Arg⁸)hGhrelin(1-8)-NH₂; or a pharmaceutically acceptable salt thereof.

In yet another aspect, the invention provides a preferred group of compounds according to Formula (I), where the compound is:

| | |
|---|---|
| (Dap³(octanesulfonyl))hGhrelin(1-28)-NH₂; | Example #84 (SEQ ID: 6) |
| (Aib²,A6c⁵)hGhrelin(1-28)-NH₂; | Example #105 (SEQ ID: 7) |
| (A6c⁵)hGhrelin(1-28)-NH₂; | (SEQ ID: 8) |
| (Aib²,⁶)hGhrelin(1-28)-NH₂; | Example #117 (SEQ ID: 9) |
| (Aib²,A5c¹²)hGhrelin(1-28)-NH₂; | (SEQ ID: 10) |
| (Aib²,A5c¹²,Orn¹⁵)hGhrelin(1-28)-NH₂; | (SEQ ID: 11) |
| (Aib²,A5c¹²,Apc¹⁶)hGhrelin(1-28)-NH₂; | (SEQ ID: 12) |
| (Aib²,Act⁶)hGhrelin(1-28)-NH₂; | (SEQ ID: 9) |

| | |
|---|---|
| (Aib², 3-Pal⁹)hGhrelin(1-28)-NH₂; | Example #38 (SEQ ID: 13) |
| (Aib², Dmt⁷)hGhrelin(1-28)-NH₂; | (SEQ ID: 14) |
| (Aib², Thz⁷)hGhrelin(1-28)-NH₂; | (SEQ ID: 14) |
| (A5c²)hGhrelin(1-28)-NH₂; | Example #61 (SEQ ID: 15) |
| (Act²)hGhrelin(1-28)-NH₂; | Example #103 (SEQ ID: 15) |
| (Aib², A5c⁵)hGhrelin(1-28)-NH₂; | (SEQ ID: 7) |
| (Aib², A6c⁵)hGhrelin(1-28)-NH₂; | (SEQ ID: 7) |
| (Aib²,⁵)hGhrelin(1-28)-NH₂; | (SEQ ID: 7) |
| (Aib², hLeu⁵)hGhrelin(1-28)-NH₂; | (SEQ ID: 7) |
| (Aib², Cha⁵)hGhrelin(1-28)-NH₂; | (SEQ ID: 7) |
| (Aib²,⁶)hGhrelin(1-28)-NH₂; | (SEQ ID: 9) |
| (Aib², Act⁶)hGhrelin(1-28)-NH₂; | Example #123 (SEQ ID: 9) |
| (Aib², Thr⁶)hGhrelin(1-28)-NH₂; | (SEQ ID: 9) |
| (Aib², Abu⁶)hGhrelin(1-28)-NH₂; | Example #97 (SEQ ID: 9) |
| (Aib², 4-Hyp⁷)hGhrelin(1-28)-NH₂; | Example #45 (SEQ ID: 14) |
| (Aib², Thz⁷)hGhrelin(1-28)-NH₂; | Example #63 (SEQ ID: 14) |
| (Aib², Pip⁷)hGhrelin(1-28)-NH₂; | Example #74 (SEQ ID: 14) |
| (Aib², Dhp⁷)hGhrelin(1-28)-NH₂; | Example #53 (SEQ ID: 14) |
| (Aib², Ktp⁷)hGhrelin(1-28)-NH₂; | (SEQ ID: 14) |
| (Aib²,⁸)hGhrelin(1-28)-NH₂; | Example #58 (SEQ ID: 16) |
| (Aib², 2-Pal⁹)hGhrelin(1-28)-NH₂; | (SEQ ID: 13) |
| (Aib², 3-Pal⁹)hGhrelin(1-28)-NH₂; | (SEQ ID: 13) |
| (Aib², 4-Pal⁹)hGhrelin(1-28)-NH₂; | Example #64 (SEQ ID: 13) |
| (Aib², Taz⁹)hGhrelin(1-28)-NH₂; | Example #36 (SEQ ID: 13) |
| (Aib², 2-Thi⁹)hGhrelin(1-28)-NH₂; | (SEQ ID: 13) |
| (Aib², 2-Fua⁹)hGhrelin(1-28)-NH₂; | (SEQ ID: 13) |
| (Aib², Apc⁹)hGhrelin(1-28)-NH₂; | (SEQ ID: 13) |
| (Aib²,⁹)hGhrelin(1-28)-NH₂; | (SEQ ID: 13) |
| (Aib²,¹⁰)hGhrelin(1-28)-NH₂; | Example #57 (SEQ ID: 17) |
| (Aib², Tic⁷)hGhrelin(1-28)-NH₂; | Example #62 (SEQ ID: 14) |
| (Aib⁶)hGhrelin(1-28)-NH₂; | (SEQ ID: 18) |
| (A5c⁵)hGhrelin(1-28)-NH₂; | (SEQ ID: 8) |
| (A6c⁵)hGhrelin(1-28)-NH₂; | Example #111 (SEQ ID: 8) |
| (Act⁶)hGhrelin(1-28)-NH₂; | (SEQ ID: 18) |
| (3-Pal⁹)hGhrelin(1-28)-NH₂; | Example #41 (SEQ ID: 19) |
| (Dmt⁷)hGhrelin(1-28)-NH₂; | (SEQ ID: 20) |
| (Thz⁷)hGhrelin(1-28)-NH₂; | (SEQ ID: 20) |
| (Aib⁵)hGhrelin(1-28)-NH₂; | (SEQ ID: 8) |
| (hLeu⁵)hGhrelin(1-28)-NH₂; | (SEQ ID: 8) |
| (Cha⁵)hGhrelin(1-28)-NH₂; | (SEQ ID: 8) |

-continued

| | |
|---|---|
| (Thr⁶)hGhrelin(1-28)-NH₂; | (SEQ ID: 18) |
| (Abu⁹)hGhrelin(1-28)-NH₂; | (SEQ ID: 18) |
| (4-Hyp⁷)hGhrelin(1-28)-NH₂; | (SEQ ID: 20) |
| (Pip⁷)hGhrelin(1-28)-NH₂; | (SEQ ID: 20) |
| (Dhp⁷)hGhrelin(1-28)-NH₂; | (SEQ ID: 20) |
| (Ktp⁷)hGhrelin(1-28)-NH₂; | (SEQ ID: 20) |
| (Aib⁸)hGhrelin(1-28)-NH₂; | Example #17 (SEQ ID: 21) |
| (2-Pal⁹)hGhrelin(1-28)-NH₂; | (SEQ ID: 19) |
| (3-Pal⁹)hGhrelin(1-28)-NH₂; | (SEQ ID: 19) |
| (4-Pal⁹)hGhrelin(1-28)-NH₂; | (SEQ ID: 19) |
| (Taz⁹)hGhrelin(1-28)-NH₂; | (SEQ ID: 19) |
| (2-Thi⁹)hGhrelin(1-28)-NH₂; | Example #35 (SEQ ID: 19) |
| (2-Fua⁹)hGhrelin(1-28)-NH₂; | (SEQ ID: 19) |
| (Apc⁹)hGhrelin(1-28)-NH₂; | (SEQ ID: 19) |
| (Aib⁹)hGhrelin(1-28)-NH₂; | (SEQ ID: 19) |
| (Aib¹⁰)hGhrelin(1-28)-NH₂; | (SEQ ID: 22) |
| (Aib²,Dap³(octanesulfonyl),A6c⁵)hGhrelin(1-28)-NH₂; | (SEQ ID: 23) |
| (Dap³(octanesulfonyl),A6c⁵)hGhrelin(1-28)-NH₂; | (SEQ ID: 24) |
| (Aib²,⁶,Dap³(octanesulfonyl))hGhrelin(1-28)-NH₂; | (SEQ ID: 25) |
| (Aib²,Dap³(octanesulfonyl),A5c¹²)hGhrelin(1-28)-NH₂; | (SEQ ID: 26) |
| (Aib²,Dap³(octanesulfonyl),A5c¹²,Orn¹⁵)hGhrelin(1-28)-NH₂; | (SEQ ID: 27) |
| (Aib²,Dap³(octanesulfonyl),A5c¹²,Apc¹⁶)hGhrelin(1-28)-NH₂; | (SEQ ID: 28) |
| (Aib²,Dap³(octanesulfonyl),Act⁶)hGhrelin(1-28)-NH₂; | (SEQ ID: 25) |
| (Aib²,Dap³(octanesulfonyl),3-Pal⁹)hGhrelin(1-28)-NH₂; | (SEQ ID: 29) |
| (Aib²,Dap³(octanesulfonyl),Dmt⁷)hGhrelin(1-28)-NH₂; | (SEQ ID: 30) |
| (Aib²,Dap³(octanesulfonyl),Thz⁷)hGhrelin(1-28)-NH₂; | (SEQ ID: 30) |
| (A5c²,Dap³(octanesulfonyl))hGhrelin(1-28)-NH₂; | (SEQ ID: 31) |
| (Act²,Dap³(octanesulfonyl))hGhrelin(1-28)-NH₂; | (SEQ ID: 31) |
| (Aib²,Dap³(octanesulfonyl),A5c⁵)hGhrelin(1-28)-NH₂; | (SEQ ID: 32) |
| (Aib²,⁵,Dap³(octanesulfonyl))hGhrelin(1-28)-NH₂; | (SEQ ID: 32) |
| (Aib²,Dap³(octanesulfonyl),hLeu⁵)hGhrelin(1-28)-NH₂; | (SEQ ID: 32) |
| (Aib²,Dap³(octanesulfonyl),Cha⁵)hGhrelin(1-28)-NH₂; | (SEQ ID: 32) |
| (Aib²,⁶,Dap³(octanesulfonyl))hGhrelin(1-28)-NH₂; | (SEQ ID: 25) |
| (Aib²,Dap³(octanesulfonyl),Thr⁶)hGhrelin(1-28)-NH₂; | (SEQ ID: 25) |
| (Aib²,Dap³(octanesulfonyl),Abu⁶)hGhrelin(1-28)-NH₂; | (SEQ ID: 25) |
| (Aib²,Dap³(octanesulfonyl),4-Hyp⁷)hGhrelin(1-28)-NH₂; | (SEQ ID: 30) |
| (Aib²,Dap³(octanesulfonyl),Pip⁷)hGhrelin(1-28)-NH₂; | (SEQ ID: 30) |
| (Aib²,Dap³(octanesulfonyl),Dhp⁷)hGhrelin(1-28)-NH₂; | (SEQ ID: 30) |
| (Aib²,Dap³(octanesulfonyl),Ktp⁷)hGhrelin(1-28)-NH₂; | (SEQ ID: 30) |
| (Aib²,⁸,Dap³(octanesulfonyl))hGhrelin(1-28)-NH₂; | (SEQ ID: 33) |
| (Aib²,Dap³(octanesulfonyl),2-Pal⁹)hGhrelin(1-28)-NH₂; | (SEQ ID: 29) |

-continued

| | |
|---|---|
| (Aib$^2$,Dap$^3$(octanesulfonyl),3-Pal$^9$)hGhrelin(1-28)-NH$_2$; | (SEQ ID: 29) |
| (Aib$^2$,Dap$^3$(octanesulfonyl),4-Pal$^9$)hGhrelin(1-28)-NH$_2$; | (SEQ ID: 29) |
| (Aib$^2$,Dap$^3$(octanesulfonyl),Taz$^9$)hGhrelin(1-28)-NH$_2$; | (SEQ ID: 29) |
| (Aib$^2$,Dap$^3$(octanesulfonyl),2-Thi$^9$)hGhrelin(1-28)-NH$_2$; | (SEQ ID: 29) |
| (Aib$^2$,Dap$^3$(octanesulfonyl),2-Fua$^9$)hGhrelin(1-28)-NH$_2$; | (SEQ ID: 29) |
| (Aib$^2$,Dap$^3$(octanesulfonyl),Apc$^9$)hGhrelin(1-28)-NH$_2$; | (SEQ ID: 29) |
| (Aib$^{2,9}$,Dap$^3$(octanesulfonyl))hGhrelin(1-28)-NH$_2$; | (SEQ ID: 29) |
| (Aib$^{2,10}$,Dap$^3$(octanesulfonyl))hGhrelin(1-28)-NH$_2$; | (SEQ ID: 34) |
| (Dap$^3$(octanesulfonyl),A6c$^5$)hGhrelin(1-28)-NH$_2$; | (SEQ ID: 24) |
| (Dap$^3$(octanesulfonyl),Aib$^6$)hGhrelin(1-28)-NH$_2$; | (SEQ ID: 35) |
| (Dap$^3$(octanesulfonyl),A5c$^{12}$)hGhrelin(1-28)-NH$_2$; | (SEQ ID: 36) |
| (Dap$^3$(octanesulfonyl),A5c$^{12}$,Orn$^{15}$)hGhrelin(1-28)-NH$_2$; | (SEQ ID: 37) |
| (Dap$^3$(octanesulfonyl),A5c$^{12}$,Apc$^{16}$)hGhrelin(1-28)-NH$_2$; | (SEQ ID: 38) |
| (Dap$^3$(octanesulfonyl),Act$^6$)hGhrelin(1-28)-NH$_2$; | (SEQ ID: 35) |
| (Dap$^3$(octanesulfonyl),3-Pal$^9$)hGhrelin(1-28)-NH$_2$; | (SEQ ID: 39) |
| (Dap$^3$(octanesulfonyl),Dmt$^7$)hGhrelin(1-28)-NH$_2$; | (SEQ ID: 40) |
| (Dap$^3$(octanesulfonyl),Thz$^7$)hGhrelin(1-28)-NH$_2$; | (SEQ ID: 40) |
| (Dap$^3$(octanesulfonyl),A5c$^5$)hGhrelin(1-28)-NH$_2$; | (SEQ ID: 24) |
| (Dap$^3$(octanesulfonyl),Aib$^5$)hGhrelin(1-28)-NH$_2$; | (SEQ ID: 24) |
| (Dap$^3$(octanesulfonyl),hLeu$^5$)hGhrelin(1-28)-NH$_2$; | (SEQ ID: 24) |
| (Dap$^3$(octanesulfonyl),Cha$^5$)hGhrelin(1-28)-NH$_2$; | (SEQ ID: 24) |
| (Dap$^3$(octanesulfonyl),Thr$^6$)hGhrelin(1-28)-NH$_2$; | (SEQ ID: 35) |
| (Dap$^3$(octanesulfonyl),Abu$^6$)hGhrelin(1-28)-NH$_2$; | (SEQ ID: 35) |
| (Dap$^3$(octanesulfonyl),4-Hyp$^7$)hGhrelin(1-28)-NH$_2$; | (SEQ ID: 40) |
| (Dap$^3$(octanesulfonyl),Pip$^7$)hGhrelin(1-28)-NH$_2$; | (SEQ ID: 40) |
| (Dap$^3$(octanesulfonyl),Dhp$^7$)hGhrelin(1-28)-NH$_2$; | (SEQ ID: 40) |
| (Dap$^3$(octanesulfonyl),Ktp$^7$)hGhrelin(1-28)-NH$_2$; | (SEQ ID: 40) |
| (Dap$^3$(octanesulfonyl),Aib$^8$)hGhrelin(1-28)-NH$_2$; | (SEQ ID: 41) |
| (Dap$^3$(octanesulfonyl),2-Pal$^9$)hGhrelin(1-28)-NH$_2$; | (SEQ ID: 39) |
| (Dap$^3$(octanesulfonyl),3-Pal$^9$)hGhrelin(1-28)-NH$_2$; | (SEQ ID: 39) |
| (Dap$^3$(octanesulfonyl),4-Pal$^9$)hGhrelin(1-28)-NH$_2$; | (SEQ ID: 39) |
| (Dap$^3$(octanesulfonyl),Taz$^9$)hGhrelin(1-28)-NH$_2$; | (SEQ ID: 39) |
| (Dap$^3$(octanesulfonyl),2-Thi$^9$)hGhrelin(1-28)-NH$_2$; | (SEQ ID: 39) |
| (Dap$^3$(octanesulfonyl),2-Fua$^9$)hGhrelin(1-28)-NH$_2$; | (SEQ ID: 39) |
| (Dap$^3$(octanesulfonyl),Apc$^9$)hGhrelin(1-28)-NH$_2$; | (SEQ ID: 39) |
| (Dap$^3$(octanesulfonyl),Aib$^9$)hGhrelin(1-28)-NH$_2$; | (SEQ ID: 39) |
| (Dap$^3$(octanesulfonyl),Aib$^{10}$)hGhrelin(1-28)-NH$_2$; | (SEQ ID: 42) |
| (Dap$^3$(octanesulfonyl),A5c$^{12}$,Orn$^{15}$)hGhrelin(1-28)-NH$_2$; | (SEQ ID: 37) |
| (Dab$^3$(octanesulfonyl),A5c$^{12}$,Orn$^{15}$)hGhrelin(1-28)-NH$_2$; | (SEQ ID: 37) |
| (Aib$^2$,A6c$^5$,A5c$^{12}$,Orn$^{15}$)hGhrelin(1-28)-NH$_2$; | (SEQ ID: 43) |

-continued

| | |
|---|---|
| (A6c⁵,A5c¹²,Orn¹⁵)hGhrelin(1-28)-NH₂; | (SEQ ID: 44) |
| (Aib²,⁶,A5c¹²,Orn¹⁵)hGhrelin(1-28)-NH₂; | (SEQ ID: 45) |
| (Aib²,Act⁶,A5c¹²,Orn¹⁵)hGhrelin(1-28)-NH₂; | (SEQ ID: 45) |
| (Aib²,3-Pal⁹,A5c¹²,Orn¹⁵)hGhrelin(1-28)-NH₂; | (SEQ ID: 46) |
| (Aib²,Dmt⁷,A5c¹²,Orn¹⁵)hGhrelin(1-28)-NH₂; | (SEQ ID: 47) |
| (Aib²,Thz⁷,A5c¹²,Orn¹⁵)hGhrelin(1-28)-NH₂; | (SEQ ID: 47) |
| (Aib²,A5c⁵,A5c¹²,Orn¹⁵)hGhrelin(1-28)-NH₂; | (SEQ ID: 43) |
| (Aib²,⁵,A5c¹²,Orn¹⁵)hGhrelin(1-28)-NH₂; | (SEQ ID: 43) |
| (Aib²,hLeu⁵,A5c¹²,Orn¹⁵)hGhrelin(1-28)-NH₂; | (SEQ ID: 43) |
| (Aib²,Cha⁵,A5c¹²,Orn¹⁵)hGhrelin(1-28)-NH₂; | (SEQ ID: 43) |
| (Aib²,⁶,A5c¹²,Orn¹⁵)hGhrelin(1-28)-NH₂; | (SEQ ID: 45) |
| (Aib²,Thr⁶,A5c¹²,Orn¹⁵)hGhrelin(1-28)-NH₂; | (SEQ ID: 45) |
| (Aib²,Abu⁶,A5c¹²,Orn¹⁵)hGhrelin(1-28)-NH₂; | (SEQ ID: 45) |
| (Aib²,4-Hyp⁷,A5c¹²,Orn¹⁵)hGhrelin(1-28)-NH₂; | (SEQ ID: 47) |
| (Aib²,Pip⁷,A5c¹²,Orn¹⁵)hGhrelin(1-28)-NH₂; | (SEQ ID: 47) |
| (Aib²,Dhp⁷,A5c¹²,Orn¹⁵)hGhrelin(1-28)-NH₂; | (SEQ ID: 47) |
| (Aib²,Ktp⁷,A5c¹²,Orn¹⁵)hGhrelin(1-28)-NH₂; | (SEQ ID: 47) |
| (Aib²,⁸,A5c¹²,Orn¹⁵)hGhrelin(1-28)-NH₂; | (SEQ ID: 48) |
| (Aib²,2-Pal⁹,A5c¹²,Orn¹⁵)hGhrelin(1-28)-NH₂; | (SEQ ID: 46) |
| (Aib²,3-Pal⁹,A5c¹²,Orn¹⁵)hGhrelin(1-28)-NH₂; | (SEQ ID: 46) |
| (Aib²,4-Pal⁹,A5c¹²,Orn¹⁵)hGhrelin(1-28)-NH₂; | (SEQ ID: 46) |
| (Aib²,Taz⁹,A5c¹²,Orn¹⁵)hGhrelin(1-28)-NH₂; | (SEQ ID: 46) |
| (Aib²,2-Thi⁹,A5c¹²,Orn¹⁵)hGhrelin(1-28)-NH₂; | (SEQ ID: 46) |
| (Aib²,2-Fua⁹,A5c¹²,Orn¹⁵)hGhrelin(1-28)-NH₂; | (SEQ ID: 46) |
| (Aib²,Apc⁹,A5c¹²,Orn¹⁵)hGhrelin(1-28)-NH₂; | (SEQ ID: 46) |
| (Aib²,⁹,A5c¹²,Orn¹⁵)hGhrelin(1-28)-NH₂; | (SEQ ID: 46) |
| (Aib²,¹⁰,A5c¹²,Orn¹⁵)hGhrelin(1-28)-NH₂; | (SEQ ID: 49) |
| (Dap³(octanesulfonyl),A5c¹²,Apc¹⁶)hGhrelin(1-28)-NH₂; | (SEQ ID: 38) |
| (Dab³(octanesulfonyl),A5c¹²,Apc¹⁶)hGhrelin(1-28)-NH₂; | (SEQ ID: 38) |
| (Aib²,A6c⁵,A5c¹²,Apc¹⁶)hGhrelin(1-28)-NH₂; | (SEQ ID: 50) |
| (A6c⁵,A5c¹²,Apc¹⁶)hGhrelin(1-28)-NH₂; | (SEQ ID: 51) |
| (Aib²,⁶,A5c¹²,Apc¹⁶)hGhrelin(1-28)-NH₂; | (SEQ ID: 52) |
| (Aib²,Act⁶,A5c¹²,Apc¹⁶)hGhrelin(1-28)-NH₂; | (SEQ ID: 52) |
| (Aib²,3-Pal⁹,A5c¹²,Apc¹⁶)hGhrelin(1-28)-NH₂; | (SEQ ID: 53) |
| (Aib²,Dmt⁷,A5c¹²,Apc¹⁶)hGhrelin(1-28)-NH₂; | (SEQ ID: 54) |
| (Aib²,Thz⁷,A5c¹²,Apc¹⁶)hGhrelin(1-28)-NH₂; | (SEQ ID: 54) |
| (Aib²,A5c⁵,¹²,Apc¹⁶)hGhrelin(1-28)-NH₂; | (SEQ ID: 50) |
| (Aib²,⁵,A5c¹²,Apc¹⁶)hGhrelin(1-28)-NH₂; | (SEQ ID: 50) |
| (Aib²,hLeu⁵,A5c¹²,Apc¹⁶)hGhrelin(1-28)-NH₂; | (SEQ ID: 50) |
| (Aib²,Cha⁵,A5c¹²,Apc¹⁶)hGhrelin(1-28)-NH₂; | (SEQ ID: 50) |
| (Aib²,⁶,A5c¹²,Apc¹⁶)hGhrelin(1-28)-NH₂; | (SEQ ID: 52) |

-continued (Aib², Thr⁶, A5c¹², Apc¹⁶)hGhrelin(1-28)-NH₂;  (SEQ ID: 52)

(Aib², Abu⁶, A5c¹², Apc¹⁶)hGhrelin(1-28)-NH₂;  (SEQ ID: 52)

(Aib², 4-Hyp⁷, A5c¹², Apc¹⁶)hGhrelin(1-28)-NH₂;  (SEQ ID: 54)

(Aib², Pip⁷, A5c¹², Apc¹⁶)hGhrelin(1-28)-NH₂;  (SEQ ID: 54)

(Aib², Dhp⁷, A5c¹², Apc¹⁶)hGhrelin(1-28)-NH₂;  (SEQ ID: 54)

(Aib², Ktp⁷, A5c¹², Apc¹⁶)hGhrelin(1-28)-NH₂;  (SEQ ID: 54)

(Aib²,⁸, A5c¹², Apc¹⁶)hGhrelin(1-28)-NH₂;  (SEQ ID: 55)

(Aib², 2-Pal⁹, A5c¹², Apc¹⁶)hGhrelin(1-28)-NH₂;  (SEQ ID: 53)

(Aib², 3-Pal⁹, A5c¹², Apc¹⁶)hGhrelin(1-28)-NH₂;  (SEQ ID: 53)

(Aib², 4-Pal⁹, A5c¹², Apc¹⁶)hGhrelin(1-28)-NH₂;  (SEQ ID: 53)

(Aib², Taz⁹, A5c¹², Apc¹⁶)hGhrelin(1-28)-NH₂;  (SEQ ID: 53)

(Aib², 2-Thi⁹, A5c¹², Apc¹⁶)hGhrelin(1-28)-NH₂;  (SEQ ID: 53)

(Aib², 2-Fua⁹, A5c¹², Apc¹⁶)hGhrelin(1-28)-NH₂;  (SEQ ID: 53)

(Aib², Apc⁹, A5c¹², Apc¹⁶)hGhrelin(1-28)-NH₂;  (SEQ ID: 53)

(Aib²,⁹, A5c¹², Apc¹⁶)hGhrelin(1-28)-NH₂;  (SEQ ID: 53)

(Aib²,¹⁰, A5c¹², Apc¹⁶)hGhrelin(1-28)-NH₂;  (SEQ ID: 56)

(A6c⁵, A5c¹², Orn¹⁵)hGhrelin(1-28)-NH₂;  (SEQ ID: 44)

(Aib⁶, A5c¹², Orn¹⁵)hGhrelin(1-28)-NH₂;  (SEQ ID: 57)

(Act⁶, A5c¹², Orn¹⁵)hGhrelin(1-28)-NH₂;  (SEQ ID: 57)

(3-Pal⁹, A5c¹², Orn¹⁵)hGhrelin(1-28)-NH₂;  (SEQ ID: 58)

(Dmt⁷, A5c¹², Orn¹⁵)hGhrelin(1-28)-NH₂;  (SEQ ID: 59)

(Thz⁷, A5c¹², Orn¹⁵)hGhrelin(1-28)-NH₂;  (SEQ ID: 59)

(A5c⁵, A5c¹², Orn¹⁵)hGhrelin(1-28)-NH₂;  (SEQ ID: 49)

(Aib⁵, A5c¹², Orn¹⁵)hGhrelin(1-28)-NH₂;  (SEQ ID: 49)

(hLeu⁵, A5c¹², Orn¹⁵)hGhrelin(1-28)-NH₂;  (SEQ ID: 49)

(Cha⁵, A5c¹², Orn¹⁵)hGhrelin(1-28)-NH₂;  (SEQ ID: 49)

(Aib⁶, A5c¹², Orn¹⁵)hGhrelin(1-28)-NH₂;  (SEQ ID: 57)

(Thr⁶, A5c¹², Orn¹⁵)hGhrelin(1-28)-NH₂;  (SEQ ID: 57)

(Abu⁶, A5c¹², Orn¹⁵)hGhrelin(1-28)-NH₂;  (SEQ ID: 57)

(4-Hyp⁷, A5c¹², Orn¹⁵)hGhrelin(1-28)-NH₂;  (SEQ ID: 59)

(Pip⁷, A5c¹², Orn¹⁵)hGhrelin(1-28)-NH₂;  (SEQ ID: 59)

(Dhp⁷, A5c¹², Orn¹⁵)hGhrelin(1-28)-NH₂;  (SEQ ID: 59)

(Ktp⁷, A5c¹², Orn¹⁵)hGhrelin(1-28)-NH₂;  (SEQ ID: 59)

(Aib⁸, A5c¹², Orn¹⁵)hGhrelin(1-28)-NH₂;  (SEQ ID: 60)

(2-Pal⁹, A5c¹², Orn¹⁵)hGhrelin(1-28)-NH₂;  (SEQ ID: 58)

(3-Pal⁹, A5c¹², Orn¹⁵)hGhrelin(1-28)-NH₂;  (SEQ ID: 58)

(4-Pal⁹, A5c¹², Orn¹⁵)hGhrelin(1-28)-NH₂;  (SEQ ID: 58)

(Taz⁹, A5c¹², Orn¹⁵)hGhrelin(1-28)-NH₂;  (SEQ ID: 58)

(2-Thi⁹, A5c¹², Orn¹⁵)hGhrelin(1-28)-NH₂;  (SEQ ID: 58)

(2-Fua⁹, A5c¹², Orn¹⁵)hGhrelin(1-28)-NH₂;  (SEQ ID: 58)

-continued

| | |
|---|---|
| (Apc⁹,A5c¹²,Orn¹⁵)hGhrelin(1-28)-NH₂; | (SEQ ID: 58) |
| (Aib⁹,A5c¹²,Orn¹⁵)hGhrelin(1-28)-NH₂; | (SEQ ID: 58) |
| (Aib¹⁰,A5c¹²,Orn¹⁵)hGhrelin(1-28)-NH₂; | (SEQ ID: 61) |
| (Aib⁶,A5c¹²,Apc¹⁶)hGhrelin(1-28)-NH₂; | (SEQ ID: 62) |
| (A5c⁵,A5c¹²,Apc¹⁶)hGhrelin(1-28)-NH₂; | (SEQ ID: 51) |
| (Act⁶,A5c¹²,Apc¹⁶)hGhrelin(1-28)-NH₂; | (SEQ ID: 62) |
| (3-Pal⁹,A5c¹²,Apc¹⁶)hGhrelin(1-28)-NH₂; | (SEQ ID: 63) |
| (Dmt⁷,A5c¹²,Apc¹⁶)hGhrelin(1-28)-NH₂; | (SEQ ID: 64) |
| (Thz⁷,A5c¹²,Apc¹⁶)hGhrelin(1-28)-NH₂; | (SEQ ID: 64) |
| (Aib⁵,A5c¹²,Apc¹⁶)hGhrelin(1-28)-NH₂; | (SEQ ID: 51) |
| (hLeu⁵,A5c¹²,Apc¹⁶)hGhrelin(1-28)-NH₂; | (SEQ ID: 51) |
| (Cha⁵,A5c¹²,Apc¹⁶)hGhrelin(1-28)-NH₂; | (SEQ ID: 51) |
| (Thr⁶,A5c¹²,Apc¹⁶)hGhrelin(1-28)-NH₂; | (SEQ ID: 62) |
| (Abu⁶,A5c¹²,Apc¹⁶)hGhrelin(1-28)-NH₂; | (SEQ ID: 62) |
| (4-Hyp⁷,A5c¹²,Apc¹⁶)hGhrelin(1-28)-NH₂; | (SEQ ID: 64) |
| (Pip⁷,A5c¹²,Apc¹⁶)hGhrelin(1-28)-NH₂; | (SEQ ID: 64) |
| (Dhp⁷,A5c¹²,Apc¹⁶)hGhrelin(1-28)-NH₂; | (SEQ ID: 64) |
| (Ktp⁷,A5c¹²,Apc¹⁶)hGhrelin(1-28)-NH₂; | (SEQ ID: 64) |
| (Aib⁸,A5c¹²,Apc¹⁶)hGhrelin(1-28)-NH₂; | (SEQ ID: 65) |
| (2-Pal⁹,A5c¹²,Apc¹⁶)hGhrelin(1-28)-NH₂; | (SEQ ID: 63) |
| (3-Pal⁹,A5c¹²,Apc¹⁶)hGhrelin(1-28)-NH₂; | (SEQ ID: 63) |
| (4-Pal⁹,A5c¹²,Apc¹⁶)hGhrelin(1-28)-NH₂; | (SEQ ID: 63) |
| (Taz⁹,A5c¹²,Apc¹⁶)hGhrelin(1-28)-NH₂; | (SEQ ID: 63) |
| (2-Thi⁹,A5c¹²,Apc¹⁶)hGhrelin(1-28)-NH₂; | (SEQ ID: 63) |
| (2-Fua⁹,A5c¹²,Apc¹⁶)hGhrelin(1-28)-NH₂; | (SEQ ID: 63) |
| (Apc⁹,A5c¹²,Apc¹⁶)hGhrelin(1-28)-NH₂; | (SEQ ID: 63) |
| (Aib⁹,A5c¹²,Apc¹⁶)hGhrelin(1-28)-NH₂; | (SEQ ID: 63) |
| (Aib¹⁰,A5c¹²,Apc¹⁶)hGhrelin(1-28)-NH₂; | (SEQ ID: 66) |
| (Aib²,Glu³(NH-hexyl),A6c⁵)hGhrelin(1-28)-NH₂; | (SEQ ID: 67) |
| (Glu³(NH-hexyl),A6c⁵)hGhrelin(1-28)-NH₂; | (SEQ ID: 68) |
| (Aib²,⁶,Glu³(NH-hexyl))hGhrelin(1-28)-NH₂; | (SEQ ID: 69) |
| (Aib²,Glu³(NH-hexyl),Act⁶)hGhrelin(1-28)-NH₂; | (SEQ ID: 69) |
| (Aib²,Glu³(NH-hexyl),3-Pal⁹)hGhrelin(1-28)-NH₂; | (SEQ ID: 70) |
| (Aib²,Glu³(NH-hexyl),Dmt⁷)hGhrelin(1-28)-NH₂; | (SEQ ID: 71) |
| (Aib²,Glu³(NH-hexyl),Thz⁷)hGhrelin(1-28)-NH₂; | (SEQ ID: 71) |
| (Aib²,Glu³(NH-hexyl),A5c⁵)hGhrelin(1-28)-NH₂; | (SEQ ID: 67) |
| (Aib²,⁵,Glu³(NH-hexyl))hGhrelin(1-28)-NH₂; | (SEQ ID: 67) |
| (Aib²,Glu³(NH-hexyl),hLeu⁵)hGhrelin(1-28)-NH₂; | (SEQ ID: 67) |
| (Aib²,Cha⁵)hGhrelin(1-28)-NH₂; | Example #90 (SEQ ID: 7) |
| (Aib²,⁶,Glu³(NH-hexyl))hGhrelin(1-28)-NH₂; | (SEQ ID: 69) |
| (Aib²,Glu³(NH-hexyl),Thr⁶)hGhrelin(1-28)-NH₂; | (SEQ ID: 69) |

-continued

| | |
|---|---|
| (Aib², Glu³(NH-hexyl), Abu⁶)hGhrelin(1-28)-NH₂; | (SEQ ID: 69) |
| (Aib², Glu³(NH-hexyl), 4-Hyp⁷)hGhrelin(1-28)-NH₂; | Example #88 (SEQ ID: 71) |
| (Aib², Glu³(NH-hexyl), Pip⁷)hGhrelin(1-28)-NH₂; | (SEQ ID: 71) |
| (Aib², Glu³(NH-hexyl), Dhp⁷)hGhrelin(1-28)-NH₂; | (SEQ ID: 71) |
| (Aib², Glu³(NH-hexyl), Ktp⁷)hGhrelin(1-28)-NH₂; | (SEQ ID: 71) |
| (Aib²,⁸, Glu³(NH-hexyl))hGhrelin(1-28)-NH₂; | Example #65 (SEQ ID: 72) |
| (Aib², Glu³(NH-hexyl), 2-Pal⁹)hGhrelin(1-28)-NH₂; | (SEQ ID: 70) |
| (Aib², Glu³(NH-hexyl), 3-Pal⁹)hGhrelin(1-28)-NH₂; | Example #89 (SEQ ID: 70) |
| (Aib², Glu³(NH-hexyl), 4-Pal⁹)hGhrelin(1-28)-NH₂; | Example #94 (SEQ ID: 70) |
| (Aib², Glu³(NH-hexyl), Taz⁹)hGhrelin(1-28)-NH₂; | Example #52 (SEQ ID: 70) |
| (Aib², Glu³(NH-hexyl), 2-Thi⁹)hGhrelin(1-28)-NH₂; | Example #60 (SEQ ID: 70) |
| (Aib², Glu³(NH-hexyl), 2-Fua⁹)hGhrelin(1-28)-NH₂; | (SEQ ID: 70) |
| (Aib², Glu³(NH-hexyl), Apc⁹)hGhrelin(1-28)-NH₂; | (SEQ ID: 70) |
| (Aib²,⁹, Glu³(NH-hexyl))hGhrelin(1-28)-NH₂; | (SEQ ID: 70) |
| (Aib²,¹⁰, Glu³(NH-hexyl))hGhrelin(1-28)-NH₂; | Example #68 (SEQ ID: 73) |
| (Glu³(NH-hexyl), Aib⁶)hGhrelin(1-28)-NH₂; | (SEQ ID: 74) |
| (Glu³(NH-hexyl), A5c⁵)hGhrelin(1-28)-NH₂; | (SEQ ID: 68) |
| (Glu³(NH-hexyl), Act⁶)hGhrelin(1-28)-NH₂; | (SEQ ID: 74) |
| (Glu³(NH-hexyl), 3-Pal⁹)hGhrelin(1-28)-NH₂; | (SEQ ID: 75) |
| (Glu³(NH-hexyl), Dmt⁷)hGhrelin(1-28)-NH₂; | (SEQ ID: 76) |
| (Glu³(NH-hexyl), Thz⁷)hGhrelin(1-28)-NH₂; | (SEQ ID: 76) |
| (Glu³(NH-hexyl), Aib⁵)hGhrelin(1-28)-NH₂; | (SEQ ID: 68) |
| (Glu³(NH-hexyl), hLeu⁵)hGhrelin(1-28)-NH₂; | (SEQ ID: 68) |
| (Glu³(NH-hexyl), Cha⁵)hGhrelin(1-28)-NH₂; | (SEQ ID: 68) |
| (Glu³(NH-hexyl), Thr⁶)hGhrelin(1-28)-NH₂; | (SEQ ID: 74) |
| (Glu³(NH-hexyl), Abu⁶)hGhrelin(1-28)-NH₂; | (SEQ ID: 74) |
| (Glu³(NH-hexyl), 4-Hyp⁷)hGhrelin(1-28)-NH₂; | Example #91 (SEQ ID: 76) |
| (Glu³(NH-hexyl), Pip⁷)hGhrelin(1-28)-NH₂; | (SEQ ID: 76) |
| (Glu³(NH-hexyl), Dhp⁷)hGhrelin(1-28)-NH₂; | (SEQ ID: 76) |
| (Glu³(NH-hexyl), Ktp⁷)hGhrelin(1-28)-NH₂; | (SEQ ID: 76) |
| (Glu³(NH-hexyl), Aib⁸)hGhrelin(1-28)-NH₂; | Example #44 (SEQ ID: 41) |
| (Glu³(NH-hexyl), 2-Pal⁹)hGhrelin(1-28)-NH₂; | (SEQ ID: 75) |
| (Glu³(NH-hexyl), 3-Pal⁹)hGhrelin(1-28)-NH₂; | (SEQ ID: 75) |
| (Glu³(NH-hexyl), 4-Pal⁹)hGhrelin(1-28)-NH₂; | (SEQ ID: 75) |
| (Glu³(NH-hexyl), Taz⁹)hGhrelin(1-28)-NH₂; | (SEQ ID: 75) |
| (Glu³(NH-hexyl), 2-Thi⁹)hGhrelin(1-28)-NH₂; | (SEQ ID: 75) |
| (Glu³(NH-hexyl), 2-Fua⁹)hGhrelin(1-28)-NH₂; | (SEQ ID: 75) |
| (Glu³(NH-hexyl), Apc⁹)hGhrelin(1-28)-NH₂; | (SEQ ID: 75) |
| (Glu³(NH-hexyl), Aib⁹)hGhrelin(1-28)-NH₂; | (SEQ ID: 75) |
| (Glu³(NH-hexyl), Aib¹⁰)hGhrelin(1-28)-NH₂; | (SEQ ID: 42) |

-continued (Aib², Glu³(NH-hexyl), A6c⁵, A5c¹², Orn¹⁵)hGhrelin(1-28)-NH₂; (SEQ ID: 77)

(Glu³(NH-hexyl), A6c⁵, A5c¹², Orn¹⁵)hGhrelin(1-28)-NH₂; (SEQ ID: 78)

(Aib²,⁶, Glu³(NH-hexyl), A5c¹², Orn¹⁵)hGhrelin(1-28)-NH₂; (SEQ ID: 79)

(Aib², Glu³(NH-hexyl), Act⁶, A5c¹², Orn¹⁵)hGhrelin(1-28)-NH₂; (SEQ ID: 79)

(Aib², Glu³(NH-hexyl), 3-Pal⁹, A5c¹², Orn¹⁵)hGhrelin(1-28)-NH₂; (SEQ ID: 80)

(Aib², Glu³(NH-hexyl), Dmt⁷, A5c¹², Orn¹⁵)hGhrelin(1-28)-NH₂; (SEQ ID: 81)

(Aib², Glu³(NH-hexyl), Thz⁷, A5c¹², Orn¹⁵)hGhrelin(1-28)-NH₂; (SEQ ID: 81)

(Aib², Glu³(NH-hexyl), A5c⁵,¹², Orn¹⁵)hGhrelin(1-28)-NH₂; (SEQ ID: 77)

(Aib²,⁵, Glu³(NH-hexyl), A5c¹², Orn¹⁵)hGhrelin(1-28)-NH₂; (SEQ ID: 77)

(Aib², hLeu⁵, A5c¹², Orn¹⁵)hGhrelin(1-28)-NH₂; (SEQ ID: 43)

(Aib², Glu³(NH-hexyl), Cha⁵, A5c¹², Orn¹⁵)hGhrelin(1-28)-NH₂; (SEQ ID: 77)

(Aib²,⁶, Glu³(NH-hexyl), A5c¹², Orn¹⁵)hGhrelin(1-28)-NH₂; (SEQ ID: 79)

(Aib², Glu³(NH-hexyl), Thr⁶, A5c¹², Orn¹⁵)hGhrelin(1-28)-NH₂; (SEQ ID: 79)

(Aib², Glu³(NH-hexyl), Abu⁶, A5c¹², Orn¹⁵)hGhrelin(1-28)-NH₂; (SEQ ID: 79)

(Aib², Glu³(NH-hexyl), 4-Hyp⁷, A5c¹², Orn¹⁵)hGhrelin(1-28)-NH₂; (SEQ ID: 81)

(Aib², Glu³(NH-hexyl), Pip⁷, A5c¹², Orn¹⁵)hGhrelin(1-28)-NH₂; (SEQ ID: 81)

(Aib², Glu³(NH-hexyl), Dhp⁷, A5c¹², Orn¹⁵)hGhrelin(1-28)-NH₂; (SEQ ID: 81)

(Aib², Glu³(NH-hexyl), Ktp⁷, A5c¹², Orn¹⁵)hGhrelin(1-28)-NH₂; (SEQ ID: 81)

(Aib²,⁸, Glu³(NH-hexyl), A5c¹², Orn¹⁵)hGhrelin(1-28)-NH₂; (SEQ ID: 82)

(Aib², Glu³(NH-hexyl), 2-Pal⁹, A5c¹², Orn¹⁵)hGhrelin(1-28)-NH₂; (SEQ ID: 80)

(Aib², Glu³(NH-hexyl), 3-Pal⁹, A5c¹², Orn¹⁵)hGhrelin(1-28)-NH₂; (SEQ ID: 80)

(Aib², Glu³(NH-hexyl), 4-Pal⁹, A5c¹², Orn¹⁵)hGhrelin(1-28)-NH₂; (SEQ ID: 80)

(Aib², Glu³(NH-hexyl), Taz⁹, A5c¹², Orn¹⁵)hGhrelin(1-28)-NH₂; (SEQ ID: 80)

(Aib², Glu³(NH-hexyl), 2-Thi⁹, A5c¹², Orn¹⁵)hGhrelin(1-28)-NH₂; (SEQ ID: 80)

(Aib², Glu³(NH-hexyl), 2-Fua⁹, A5c¹², Orn¹⁵)hGhrelin(1-28)-NH₂; (SEQ ID: 80)

(Aib², Glu³(NH-hexyl), Apc⁹, A5c¹², Orn¹⁵)hGhrelin(1-28)-NH₂; (SEQ ID: 80)

(Aib²,⁹, Glu³(NH-hexyl), A5c¹², Orn¹⁵)hGhrelin(1-28)-NH₂; (SEQ ID: 80)

(Aib²,¹², Glu³(NH-hexyl), 4-Pal⁹, Orn¹⁵)hGhrelin(1-28)-NH₂; Example #98 (SEQ ID: 125)

(Aib²,¹⁰, Glu³(NH-hexyl), A5c¹², Orn¹⁵)hGhrelin(1-28)-NH₂; (SEQ ID: 83)

(Aib², Glu³(NH-hexyl), A6c⁵, A5c¹², Apc¹⁶)hGhrelin(1-28)-NH₂; (SEQ ID: 84)

(Glu³(NH-hexyl), A6c⁵, A5c¹², Apc¹⁶)hGhrelin(1-28)-NH₂; (SEQ ID: 85)

(Aib²,⁶, Glu³(NH-hexyl), A5c¹², Apc¹⁶)hGhrelin(1-28)-NH₂; (SEQ ID: 86)

(Aib², Glu³(NH-hexyl), Act⁶, A5c¹², Apc¹⁶)hGhrelin(1-28)-NH₂; (SEQ ID: 86)

(Aib², Glu³(NH-hexyl), 3-Pal⁹, A5c¹², Apc¹⁶)hGhrelin(1-28)-NH₂; (SEQ ID: 87)

(Aib², Glu³(NH-hexyl), Dmt⁷, A5c¹², Apc¹⁶)hGhrelin(1-28)-NH₂; (SEQ ID: 88)

(Aib², Glu³(NH-hexyl), Thz⁷, A5c¹², Apc¹⁶)hGhrelin(1-28)-NH₂; (SEQ ID: 88)

(Aib², Glu³(NH-hexyl), A5c⁵,¹², Apc¹⁶)hGhrelin(1-28)-NH₂; (SEQ ID: 84)

(Aib²,⁵, Glu³(NH-hexyl), A5c¹², Apc¹⁶)hGhrelin(1-28)-NH₂; (SEQ ID: 84)

(Aib², Glu³(NH-hexyl), hLeu⁵, A5c¹², Apc¹⁶)hGhrelin(1-28)-NH₂; (SEQ ID: 84)

(Aib², Glu³(NH-hexyl), Cha⁵, A5c¹², Apc¹⁶)hGhrelin(1-28)-NH₂; (SEQ ID: 84)

(Aib²,⁶, Glu³(NH-hexyl), A5c¹², Apc¹⁶)hGhrelin(1-28)-NH₂; (SEQ ID: 86)

| | |
|---|---|
| (Aib², Glu³(NH-hexyl), Thr⁶, A5c¹², Apc¹⁶)hGhrelin(1-28)-NH₂; | (SEQ ID: 86) |
| (Aib², Glu³(NH-hexyl), Abu⁶, A5c¹², Apc¹⁶)hGhrelin(1-28)-NH₂; | (SEQ ID: 86) |
| (Aib², Glu³(NH-hexyl), 4-Hyp⁷, A5c¹², Apc¹⁶)hGhrelin(1-28)-NH₂; | (SEQ ID: 88) |
| (Aib², Glu³(NH-hexyl), Pip⁷, A5c¹², Apc¹⁶)hGhrelin(1-28)-NH₂; | (SEQ ID: 88) |
| (Aib², Glu³(NH-hexyl), Dhp⁷, A5c¹², Apc¹⁶)hGhrelin(1-28)-NH₂; | (SEQ ID: 88) |
| (Aib², Glu³(NH-hexyl), Ktp⁷, A5c¹², Apc¹⁶)hGhrelin(1-28)-NH₂; | (SEQ ID: 88) |
| (Aib²,⁸, Glu³(NH-hexyl), A5c¹², Apc¹⁶)hGhrelin(1-28)-NH₂; | (SEQ ID: 89) |
| (Aib², Glu³(NH-hexyl), 2-Pal⁹, A5c¹², Apc¹⁶)hGhrelin(1-28)-NH₂; | (SEQ ID: 87) |
| (Aib², Glu³(NH-hexyl), 3-Pal⁹, A5c¹², Apc¹⁶)hGhrelin(1-28)-NH₂; | (SEQ ID: 87) |
| (Aib², Glu³(NH-hexyl), 4-Pal⁹, A5c¹², Apc¹⁶)hGhrelin(1-28)-NH₂; | (SEQ ID: 87) |
| (Aib², Glu³(NH-hexyl), Taz⁹, A5c¹², Apc¹⁶)hGhrelin(1-28)-NH₂; | (SEQ ID: 87) |
| (Aib², Glu³(NH-hexyl), 2-Thi⁹, A5c¹², Apc¹⁶)hGhrelin(1-28)-NH₂; | (SEQ ID: 87) |
| (Aib², Glu³(NH-hexyl), 2-Fua⁹, A5c¹², Apc¹⁶)hGhrelin(1-28)-NH₂; | (SEQ ID: 87) |
| Aib², Glu³(NH-hexyl), Apc⁹, A5c¹², Apc¹⁶)hGhrelin(1-28)-NH₂; | (SEQ ID: 87) |
| (Aib²,⁹, Glu³(NH-hexyl), A5c¹², Apc¹⁶)hGhrelin(1-28)-NH₂; | (SEQ ID: 87) |
| (Aib²,¹⁰, Glu³(NH-hexyl), A5c¹², Apc¹⁶)hGhrelin(1-28)-NH₂; | (SEQ ID: 89) |
| (Glu³(O-hexyl))hGhrelin(1-28)-NH₂; | Example #30 (SEQ ID: 91) |
| (Aib²)hGhrelin(1-28)-NH₂; | Example #34 (SEQ ID: 15) |
| (Glu³(NH-hexyl))hGhrelin(1-28)-NH₂; | Example #85 (SEQ ID: 91) |
| (Aib², Glu³(O-hexyl))hGhrelin(1-28)-NH₂; | (SEQ ID: 92) |
| (Aib¹, Glu³(O-hexyl))hGhrelin(1-28)-NH₂; | (SEQ ID: 93) |
| (Aib², Glu³(NH-hexyl))hGhrelin(1-28)-NH₂; | Example #13 (SEQ ID: 92) |
| (Dap³(octanesulfonyl))hGhrelin(1-28)-NH₂; | (SEQ ID: 6) |
| (Aib², Dap³(octanesulfonyl))hGhrelin(1-28)-NH₂; | (SEQ ID: 94) |
| (Aib¹, Dap³(octanesulfonyl))hGhrelin(1-28)-NH₂; | (SEQ ID: 93) |
| (Ava², Dap³(octanesulfonyl))hGhrelin(2-28)-NH₂; | (SEQ ID: 126) |
| (Ac-Gly¹)hGhrelin(1-5)-NH₂; | (SEQ ID: 95) |
| (Ac-Gly¹)hGhrelin(1-6)-NH₂; | (SEQ ID: 96) |
| (Ac-Gly¹)hGhrelin(1-7)-NH₂; | (SEQ ID: 97) |
| (Ac-Gly¹, Aib²)hGhrelin(1-28)-NH₂; | Example #72 (SEQ ID: 98) |
| (Ac-Gly¹, Aib², Glu³(NH-hexyl))hGhrelin(1-5)-NH₂; | (SEQ ID: 99) |
| (Ac-Gly¹, Aib², Glu³(NH-hexyl))hGhrelin(1-6)-NH₂; | (SEQ ID: 100) |
| (Ac-Gly¹, Aib², Glu³(NH-hexyl))hGhrelin(1-7)-NH₂; | (SEQ ID: 101) |
| (Ac-Gly¹, Aib², Glu³(NH-hexyl), Arg⁸)hGhrelin(1-8)-NH₂; | (SEQ ID: 103) |
| (Ac-Gly¹, Aib², Glu³(NH-hexyl), Lys⁸)hGhrelin(1-8)-NH₂; | (SEQ ID: 103) |
| (n-butyryl-Gly¹)hGhrelin(1-28)-NH₂; | Example #104 (SEQ ID: 104) |
| (isobutyryl-Gly¹)hGhrelin(1-28)-NH₂; | Example #108 (SEQ ID: 104) |
| (n-octanoyl-Gly¹)hGhrelin(1-28)-NH2, | Example #101 (SEQ ID: 104) |
| Cys³(S(CH₂)₉CH₃)hGhrelin(1-28)-NH₂; | Example #70 (SEQ ID: 106) |
| (Lys⁵)hGhrelin(1-28)-NH₂ | Example #51 (SEQ ID: 406) |

-continued

| | |
|---|---|
| (Aib², Ser³)hGhrelin(1-28)-NH₂; | (SEQ ID: 15) |
| (Aib²,⁶, Ser³)hGhrelin(1-28)-NH₂ | (SEQ ID: 9) |
| (Aib², Ser³, 3-Pal⁹)hGhrelin(1-28)-NH₂; | (SEQ ID: 13) |
| (Aib², Ser³, Thz⁷)hGhrelin(1-28)-NH₂; | (SEQ ID: 14) |
| (Aib², Ser³, Cha⁵)hGhrelin(1-28)-NH₂; | (SEQ ID: 7) |
| (Aib², Ser³, Abu⁶)hGhrelin(1-28)-NH₂; | (SEQ ID: 9) |
| (Aib², Ser³, 4-Hyp⁷)hGhrelin(1-28)-NH₂; | (SEQ ID: 14) |
| (Aib², Ser³, Taz⁹)hGhrelin(1-28)-NH₂; | (SEQ ID: 13) |
| (Aib², Ser³, Dhp⁷)hGhrelin(1-28)-NH₂; | (SEQ ID: 14) |
| (Aib²,⁸, Ser³)hGhrelin(1-28)-NH₂; | (SEQ ID: 16) |
| (Aib², Ser³, Pip⁷)hGhrelin(1-28)-NH₂; | (SEQ ID: 14) |
| (Ac-Gly¹, Aib²,¹⁰, Ser³)hGhrelin(1-28)-NH₂; | (SEQ ID: 107) |
| (Aib²,¹⁰, Ser³)hGhrelin(1-28)-NH₂; | (SEQ ID: 17) |
| (n-butyryl-Gly¹, Aib², Ser³)hGhrelin(1-28)-NH₂; | (SEQ ID: 108) |
| (Ac-Gly¹, Aib², Ser³)hGhrelin(1-28)-NH₂; | (SEQ ID: 98) |
| (Aib², Ser³, Tic⁷)hGhrelin(1-28)-NH₂; | (SEQ ID: 14) |
| (Ac-Gly¹, Aib², Ser³, Arg⁸)hGhrelin(1-28)-NH₂; | (SEQ ID: 109) |
| (Ser³, Aib⁸)hGhrelin(1-28)-NH₂; | (SEQ ID: 110) |
| (Ser³, Taz⁹)hGhrelin(1-28)-NH₂; | (SEQ ID: 19) |
| (Ser³, 3-Pal⁹)hGhrelin(1-28)-NH₂; | (SEQ ID: 19) |
| (Ser³, 4-Pal⁹)hGhrelin(1-28)-NH₂; | (SEQ ID: 19) |
| (Aib², Ser³, 2-Thi⁹)hGhrelin(1-28)-NH₂; | (SEQ ID: 13) |
| (Ser³, 2-Thi⁹)hGhrelin(1-28)-NH₂; | (SEQ ID: 19) |
| (Ser³, 4-Hyp⁷)hGhrelin(1-28)-NH₂; | (SEQ ID: 20) |
| (Aib², Ser³, Tic⁷)hGhrelin(1-28)-NH₂; | (SEQ ID: 14) |
| (Aib², Thr³)hGhrelin(1-28)-NH₂; | (SEQ ID: 111) |
| (Aib²,⁶, Thr³)hGhrelin(1-28)-NH₂; | (SEQ ID: 112) |
| (A5c⁵, Thr³)hGhrelin(1-28)-NH₂; | (SEQ ID: 113) |
| (Aib², Thr³, 3-Pal⁹)hGhrelin(1-28)-NH₂; | (SEQ ID: 114) |
| (Aib², Thr³, Thz⁷)hGhrelin(1-28)-NH₂; | (SEQ ID: 115) |
| (Aib², Thr³, Cha⁵)hGhrelin(1-28)-NH₂; | (SEQ ID: 116) |
| (Aib², Thr³, Abu⁶)hGhrelin(1-28)-NH₂; | (SEQ ID: 112) |
| (Aib², Thr³, 4-Hyp⁷)hGhrelin(1-28)-NH₂; | (SEQ ID: 115) |
| (Aib², Thr³, Taz⁹)hGhrelin(1-28)-NH₂; | (SEQ ID: 114) |
| (Aib², Thr³, Dhp⁷)hGhrelin(1-28)-NH₂; | (SEQ ID: 115) |
| (Aib²,⁸, Thr³)hGhrelin(1-28)-NH₂; | (SEQ ID: 117) |
| (Aib², Thr³, Pip⁷)hGhrelin(1-28)-NH₂; | (SEQ ID: 115) |
| (Ac-Gly¹, Aib²,¹⁰, Thr³)hGhrelin(1-28)-NH₂; | (SEQ ID: 118) |
| (Aib²,¹⁰, Thr³)hGhrelin(1-28)-NH₂; | (SEQ ID: 118) |
| (n-butyryl-Gly¹, Aib², Thr³)hGhrelin(1-28)-NH₂; | (SEQ ID: 119) |
| (Ac-Gly¹, Aib², Thr³)hGhrelin(1-28)-NH₂; | (SEQ ID: 119) |

(Aib², Thr³, Tic⁷)hGhrelin(1-28)-NH₂; (SEQ ID: 115)

(Ac-Gly¹, Aib², Thr³, Arg⁸)hGhrelin(1-28)-NH₂; (SEQ ID: 120)

(Thr³, Aib⁸)hGhrelin(1-28)-NH₂; (SEQ ID: 121)

(Thr³, Taz⁹)hGhrelin(1-28)-NH₂; (SEQ ID: 122)

(Thr³, 3-Pal⁹)hGhrelin(1-28)-NH₂; (SEQ ID: 122)

(Thr³, 4-Pal⁹)hGhrelin(1-28)-NH₂; (SEQ ID: 122)

(Aib², Thr³, 2-Thi⁹)hGhrelin(1-28)-NH₂; (SEQ ID: 114)

(Thr³, 2-Thi⁹)hGhrelin(1-28)-NH₂; (SEQ ID: 122)

(Thr³, 4-Hyp⁷)hGhrelin(1-28)-NH₂; (SEQ ID: 123)

(Aib², Thr³, Tic⁷)hGhrelin(1-28)-NH₂; and (SEQ ID: 115)

(Ac-Gly¹, Glu³(NH-hexyl))hGhrelin(1-28)-NH₂; (SEQ ID: 124)

or pharmaceutically acceptable salts thereof.

The present invention includes a method of treating inflammation in a subject comprising administering to the subject an effective amount of an analogue of native ghrelin and fragments thereof of any length that are functional ghrelin molecules according to the following Formula (II):

$$R^1\text{-}A^1\text{-}A^2\text{-}A^3\text{-}A^4\text{-}A^5\text{-}R^2$$

wherein:
$A^1$ is Aib, Apc or Inp;
$A^2$ is D-Bal, D-Bip, D-Bpa, D-Dip, D-1-Nal, D-2-Nal, D-Ser(Bzl) or D-Trp;
$A^3$ is D-Bal, D-Bip, D-Bpa, D-Dip, D-1-Nal, D-2-Nal, D-Ser(Bzl) or D-Trp;
$A^4$ is 2-Fua, Orn, 2-Pal, 3-Pal, 4-Pal, Pff, Phe, Pim, Taz, 2-Thi, 3-Thi or Thr(Bzl);
$A^5$ is Apc, Dab, Dap, Lys, Orn or deleted;
$R^1$ is hydrogen, $(C_{1-6})$alkyl, $(C_{5-14})$aryl, $(C_{1-6})$alkyl$(C_{5-14})$aryl, $(C_{3-8})$cycloakyl or $(C_{2-10})$acyl; and
$R^2$ is OH or NH₂;
provided that
when $A^5$ is Dab, Dap, Lys or Orn, then:
$A^2$ is D-Bip, D-Bpa, D-Dip or D-Bal; or
$A^3$ is D-Bip, D-Bpa, D-Dip or D-Bal; or
$A^4$ is 2-Thi, 3-Thi, Taz, 2-Fua, 2-Pal, 3-Pal, 4-Pal, Orn, Thr(Bzl) or Pff;
when $A^5$ is deleted, then:
$A^3$ is D-Bip, D-Bpa or D-Dip; or
$A^4$ is 2-Fua, Pff, Taz or Thr(Bzl); or
$A^1$ is Apc when
$A^2$ is D-Bip, D-Bpa, D-Dip or D-Bal; or
$A^3$ is D-Bip, D-Bpa, D-Dip or D-Bal; or
$A^4$ is 2-Thi, 3-Thi, Orn, 2-Pal, 3-Pal or 4-Pal;
or a pharmaceutically acceptable salt thereof.

In yet another aspect, the invention provides a preferred group of compounds according to Formula (II), where the compound is:

| Compound | Example | SEQ ID |
|---|---|---|
| Inp-D-2-Nal-D-Trp-Phe-Lys-NH₂; | Example #4 | |
| H-Inp-D-1-Nal-D-Trp-3-Pal-Lys-NH₂; | Example #59 | (SEQ ID: 128) |
| H-Inp-D-2-Nal-D-Trp-4-Pal-Lys-NH₂; | | (SEQ ID: 129) |
| H-Inp-D-2-Nal-D-Trp-Orn-Lys-NH₂; | Example #125 | (SEQ ID: 129) |
| H-Inp-D-Bip-D-Trp-Phe-Lys-NH₂; | Example #75 | (SEQ ID: 130) |
| H-Inp-D-2-Nal-D-Trp-Thr(Bzl)-Lys-NH₂; | | (SEQ ID: 131) |
| H-Inp-D-2-Nal-D-Trp-Pff-Lys-NH₂; | Example #109 | (SEQ ID: 131) |
| H-Inp-D-2-Nal-D-Trp-2-Thi-Lys-NH₂; | Example #23 | (SEQ ID: 132) |
| H-Inp-D-2-Nal-D-Trp-Taz-Lys-NH₂; | Example #46 | (SEQ ID: 132) |
| H-Inp-D-Dip-D-Trp-Phe-Lys-NH₂; | Example #114 | (SEQ ID: 133) |
| H-Inp-D-Bpa-D-Trp-Phe-Lys-NH₂; | Example #118 | (SEQ ID: 133) |
| H-Inp-D-2-Nal-D-Bpa-Phe-Lys-NH₂; | Example #127 | (SEQ ID: 134) |
| H-Inp-D-2-Nal-D-Trp-3-Pal-NH₂; | Example #102 | (SEQ ID: 135) |
| H-Inp-D-2-Nal-D-Trp-4-Pal-NH₂; | Example #121 | (SEQ ID: 135) |
| H-Inp-D-1-Nal-D-Trp-3-Pal-NH₂; | Example #106 | (SEQ ID: 136) |
| H-Inp-D-Bip-D-Trp-Phe-NH₂; | Example #107 | (SEQ ID: 137) |

-continued

```
H-Inp-D-2-Nal-D-Trp-Thr(Bzl)-NH₂;       Example #96   (SEQ ID: 138)
H-Inp-D-2-Nal-D-Trp-Pff-NH₂;            Example #112  (SEQ ID: 138)
H-Inp-D-2-Nal-D-Trp-2-Thi-NH₂;          Example #93   (SEQ ID: 138)
H-Inp-D-2-Nal-D-Trp-Taz-NH₂;            Example #99   (SEQ ID: 138)
H-Inp-D-Dip-D-Trp-Phe-NH₂;              Example #120  (SEQ ID: 139)
H-Inp-D-2-Nal-D-Dip-Phe-NH₂;            Example #119  (SEQ ID: 140)
H-Inp-D-Bal-D-Trp-Phe-NH₂;              Example #87   (SEQ ID: 141)
H-Inp-D-2-Nal-D-Bal-Phe-NH₂;            Example #110  (SEQ ID: 142)
H-Inp-D-2-Nal-D-Trp-3-Pal-Lys-NH₂;      Example #80   (SEQ ID: 143)
H-Inp-D-Trp-D-2-Nal(Ψ)-Pim;             Example #124  (SEQ ID: 127)
H-Inp-D-Bal-D-Trp-2-Thi-Lys-NH₂;        Example #19   (SEQ ID: 144)
H-Inp-D-Bal-D-Trp-Phe-Lys-NH₂;          Example #8    (SEQ ID: 144)
H-Inp-D-1-Nal-D-Trp-2-Thi-Lys-NH₂;      Example #5    (SEQ ID: 128)
H-Inp-D-2-Nal-D-Trp-Phe-Apc-NH₂;        Example #37   (SEQ ID: 2)
H-Inp-D-1-Nal-D-Trp-Phe-Apc-NH₂;        Example #10   (SEQ ID: 2)
H-Inp-D-Bal-D-Trp-Phe-Apc-NH₂;          Example #27   (SEQ ID: 2)
H-Apc-D-2-Nal-D-Trp-Phe-Lys-NH₂;        Example #18   (SEQ ID: 145)
H-Apc-D-1-Nal-D-Trp-2-Thi-Lys-NH₂;      Example #3    (SEQ ID: 146)
H-Inp-D-1-Nal-D-Trp-2-Thi-NH₂;          Example #48   (SEQ ID: 147)
H-Apc-D-1-Nal-D-Trp-Phe-NH₂;            Example #40   (SEQ ID: 148)
H-Inp-D-2-Nal-D-Trp(Ψ)-Pim;             Example #122  (SEQ ID: 149)
H-Inp-D-1-Nal-D-Trp(Ψ)-Pim;             Example #116  (SEQ ID: 149)
H-Inp-D-Bal-D-Trp(Ψ)-Pim;               Example #115  (SEQ ID: 149)
H-Aib-D-Ser(Bzl)-D-Trp(Ψ)-Pim;          Example #128  (SEQ ID: 150)
H-Inp-D-1-Nal-D-Trp-Taz-Lys-NH₂;        Example #66   (SEQ ID: 151)
H-Inp-D-Bal-D-Trp-Taz-Lys-NH₂;          Example #32   (SEQ ID: 151)
H-Apc-D-1-Nal-D-Trp-Taz-Lys-NH₂;        Example #22   (SEQ ID: 152)
H-Apc-D-Bal-D-Trp-Taz-Lys-NH₂;          Example #29   (SEQ ID: 152)
H-Apc-D-Bal-D-Trp-2-Thi-Lys-NH₂;        Example #11   (SEQ ID: 153)
H-Apc-D-Bal-D-Trp-Phe-Lys-NH₂;          Example #6    (SEQ ID: 153)
H-Apc-D-1-Nal-D-Trp-Phe-Apc-NH₂;        Example #26   (SEQ ID: 154)
H-Apc-D-Bal-D-Trp-Phe-Apc-NH₂;          Example #42   (SEQ ID: 154)
H-Apc-D-1-Nal-D-1-Nal-Phe-Apc-NH₂;      Example #83   (SEQ ID: 155)
H-Apc-D-1-Nal-D-2-Nal-Phe-Apc-NH₂;      Example #82   (SEQ ID: 155)
H-Apc-D-1-Nal-D-1-Nal-Phe-Lys-NH₂;      Example #73   (SEQ ID: 156)
H-Apc-D-Bal-D-1-Nal-Phe-Apc-NH₂;        Example #92   (SEQ ID: 157)
H-Apc-D-Bal-D-2-Nal-Phe-Apc-NH₂;        Example #78   (SEQ ID: 157)
H-Apc-D-Bal-D-1-Nal-Phe-Lys-NH₂;                      (SEQ ID: 158)
H-Apc-D-Bal-D-2-Nal-Phe-Lys-NH₂;        Example #39   (SEQ ID: 158)
H-Apc-D-1-Nal-D-Trp-2-Thi-NH₂;          Example #43   (SEQ ID: 159)
```

-continued

```
H-Apc-D-Bal-D-Trp-Phe-NH2;           Example #50   (SEQ ID: 160)
H-Apc-D-1-Nal-D-Trp-Taz-NH2;         Example #76   (SEQ ID: 159)
H-Apc-D-Bal-D-Trp-2-Thi-NH2;         Example #56   (SEQ ID: 161)
H-Apc-D-Bal-D-Trp-Taz-NH2;           Example #81   (SEQ ID: 161)
H-Apc-D-2-Nal-D-Trp-2-Thi-NH2;       Example #54   (SEQ ID: 162)
H-Apc-D-2-Nal-D-Trp-Taz-NH2;         Example #86   (SEQ ID: 162)
H-Inp-D-1-Nal-D-Trp-Taz-Apc-NH2;     Example #69   (SEQ ID: 163)
H-Inp-D-Bal-D-Trp-Taz-Apc-NH2;       Example #47   (SEQ ID: 163)
H-Apc-D-1-Nal-D-Trp-Taz-Apc-NH2;     Example #55   (SEQ ID: 164)
H-Apc-D-Bal-D-Trp-Taz-Apc-NH2;       Example #67   (SEQ ID: 164)
H-Apc-D-1-Nal-D-Trp-2-Fua-Apc-NH2;                 (SEQ ID: 165)
H-Apc-D-1-Nal-D-Trp-2-Fua-Lys-NH2;                 (SEQ ID: 165)
H-Apc-D-1-Nal-D-Trp-2-Fua-NH2;                     (SEQ ID: 165)
H-Apc-D-1-Nal-D-Trp-2-Pal-NH2;                     (SEQ ID: 166)
H-Apc-D-1-Nal-D-Trp-3-Pal-NH2;                     (SEQ ID: 166)
H-Apc-D-1-Nal-D-Trp-3-Thi-Apc-NH2;                 (SEQ ID: 167)
H-Apc-D-1-Nal-D-Trp-3-Thi-Lys-NH2;                 (SEQ ID: 167)
H-Apc-D-1-Nal-D-Trp-3-Thi-NH2;                     (SEQ ID: 168)
H-Apc-D-1-Nal-D-Trp-4-Pal-NH2;                     (SEQ ID: 168)
H-Apc-D-1-Nal-D-Trp-Pff-Apc-NH2;                   (SEQ ID: 169)
H-Apc-D-1-Nal-D-Trp-Pff-Lys-NH2;                   (SEQ ID: 169)
H-Apc-D-1-Nal-D-Trp-Pff-NH2;                       (SEQ ID: 168)
H-Apc-D-2-Nal-D-Trp-2-Fua-Apc-NH2;                 (SEQ ID: 170)
H-Apc-D-2-Nal-D-Trp-2-Fua-Lys-NH2;                 (SEQ ID: 170)
H-Apc-D-2-Nal-D-Trp-2-Fua-NH2;                     (SEQ ID: 171)
H-Apc-D-2-Nal-D-Trp-2-Pal-NH2;                     (SEQ ID: 171)
H-Apc-D-2-Nal-D-Trp-2-Thi-Apc-NH2;                 (SEQ ID: 172)
H-Apc-D-2-Nal-D-Trp-2-Thi-Lys-NH2;                 (SEQ ID: 172)
H-Apc-D-2-Nal-D-Trp-3-Pal-NH2;                     (SEQ ID: 171)
H-Apc-D-2-Nal-D-Trp-3-Thi-Apc-NH2;                 (SEQ ID: 173)
H-Apc-D-2-Nal-D-Trp-3-Thi-Lys-NH2;                 (SEQ ID: 173)
H-Apc-D-2-Nal-D-Trp-3-Thi-NH2;                     (SEQ ID: 171)
H-Apc-D-2-Nal-D-Trp-4-Pal-NH2;                     (SEQ ID: 171)
H-Apc-D-2-Nal-D-Trp-Pff-Apc-NH2;                   (SEQ ID: 174)
H-Apc-D-2-Nal-D-Trp-Pff-Lys-NH2;                   (SEQ ID: 174)
H-Apc-D-2-Nal-D-Trp-Pff-NH2;                       (SEQ ID: 171)
H-Apc-D-2-Nal-D-Trp-Taz-Apc-NH2;                   (SEQ ID: 175)
H-Apc-D-2-Nal-D-Trp-Taz-Lys-NH2;                   (SEQ ID: 175)
H-Apc-D-Bal-D-Bal-2-Fua-Apc-NH2;                   (SEQ ID: 176)
H-Apc-D-Bal-D-Bal-2-Fua-Lys-NH2;                   (SEQ ID: 176)
H-Apc-D-Bal-D-Bal-2-Fua-NH2;                       (SEQ ID: 177)
```

-continued

```
H-Apc-D-Bal-D-Bal-2-Pal-NH₂;                    (SEQ ID: 177)
H-Apc-D-Bal-D-Bal-2-Thi-Apc-NH₂;                (SEQ ID: 178)
H-Apc-D-Bal-D-Bal-2-Thi-Lys-NH₂;                (SEQ ID: 178)
H-Apc-D-Bal-D-Bal-2-Thi-NH₂;                    (SEQ ID: 177)
H-Apc-D-Bal-D-Bal-3-Pal-NH₂;                    (SEQ ID: 177)
H-Apc-D-Bal-D-Bal-3-Thi-Apc-NH₂;                (SEQ ID: 179)
H-Apc-D-Bal-D-Bal-3-Thi-Lys-NH₂;                (SEQ ID: 179)
H-Apc-D-Bal-D-Bal-3-Thi-NH₂;                    (SEQ ID: 177)
H-Apc-D-Bal-D-Bal-4-Pal-NH₂;                    (SEQ ID: 177)
H-Apc-D-Bal-D-Bal-Pff-Apc-NH₂;                  (SEQ ID: 180)
H-Apc-D-Bal-D-Bal-Pff-Lys-NH₂;                  (SEQ ID: 180)
H-Apc-D-Bal-D-Bal-Pff-NH₂;                      (SEQ ID: 177)
H-Apc-D-Bal-D-Bal-Phe-Apc-NH₂;                  (SEQ ID: 181)
H-Apc-D-Bal-D-Bal-Phe-Lys-NH₂;                  (SEQ ID: 181)
H-Apc-D-Bal-D-Bal-Phe-NH₂;                      (SEQ ID: 177)
H-Apc-D-Bal-D-Bal-Taz-Apc-NH₂;                  (SEQ ID: 182)
H-Apc-D-Bal-D-Bal-Taz-Lys-NH₂;                  (SEQ ID: 182)
H-Apc-D-Bal-D-Bal-Taz-NH₂;                      (SEQ ID: 177)
H-Apc-D-Bal-D-Trp-2-Fua-Apc-NH₂;                (SEQ ID: 183)
H-Apc-D-Bal-D-Trp-2-Fua-Lys-NH₂;                (SEQ ID: 183)
H-Apc-D-Bal-D-Trp-2-Fua-NH₂;                    (SEQ ID: 184)
H-Apc-D-Bal-D-Trp-2-Pal-NH₂;                    (SEQ ID: 184)
H-Apc-D-Bal-D-Trp-3-Pal-NH₂;                    (SEQ ID: 184)
H-Apc-D-Bal-D-Trp-3-Thi-Apc-NH₂;                (SEQ ID: 185)
H-Apc-D-Bal-D-Trp-3-Thi-Lys-NH₂;                (SEQ ID: 185)
H-Apc-D-Bal-D-Trp-3-Thi-NH₂;                    (SEQ ID: 184)
H-Apc-D-Bal-D-Trp-4-Pal-NH₂;                    (SEQ ID: 184)
H-Apc-D-Bal-D-Trp-Pff-Apc-NH₂;                  (SEQ ID: 186)
H-Apc-D-Bal-D-Trp-Pff-Lys-NH₂;                  (SEQ ID: 186)
H-Apc-D-Bal-D-Trp-Pff-NH₂;                      (SEQ ID: 184)
H-Inp-D-1-Nal-D-Bal-2-Fua-Lys-NH₂;              (SEQ ID: 187)
H-Inp-D-1-Nal-D-Bal-2-Fua-NH₂;                  (SEQ ID: 188)
H-Inp-D-1-Nal-D-Bal-2-Thi-Lys-NH₂;              (SEQ ID: 187)
H-Inp-D-1-Nal-D-Bal-3-Thi-Lys-NH₂;              (SEQ ID: 187)
H-Inp-D-1-Nal-D-Bal-Pff-Lys-NH₂;                (SEQ ID: 187)
H-Inp-D-1-Nal-D-Bal-Pff-NH₂;                    (SEQ ID: 188)
H-Inp-D-1-Nal-D-Bal-Phe-Lys-NH₂;                (SEQ ID: 187)
H-Inp-D-1-Nal-D-Bal-Taz-Lys-NH₂;                (SEQ ID: 187)
H-Inp-D-1-Nal-D-Bal-Taz-NH₂;                    (SEQ ID: 188)
H-Inp-D-1-Nal-D-Trp-2-Fua-Apc-NH₂;              (SEQ ID: 189)
```

-continued

| | |
|---|---|
| H-Inp-D-1-Nal-D-Trp-2-Fua-Lys-NH$_2$; | (SEQ ID: 189) |
| H-Inp-D-1-Nal-D-Trp-2-Fua-NH$_2$; | (SEQ ID: 189) |
| H-Inp-D-1-Nal-D-Trp-3-Thi-Apc-NH$_2$; | (SEQ ID: 190) |
| H-Inp-D-1-Nal-D-Trp-3-Thi-Lys-NH$_2$; | (SEQ ID: 190) |
| H-Inp-D-1-Nal-D-Trp-Pff-Apc-NH$_2$; | (SEQ ID: 191) |
| H-Inp-D-1-Nal-D-Trp-Pff-Lys-NH$_2$; | (SEQ ID: 191) |
| H-Inp-D-1-Nal-D-Trp-Pff-NH$_2$; | (SEQ ID: 192) |
| H-Inp-D-1-Nal-D-Trp-Taz-NH$_2$; | (SEQ ID: 192) |
| H-Inp-D-2-Nal-D-Trp-2-Fua-Apc-NH$_2$; | (SEQ ID: 193) |
| H-Inp-D-2-Nal-D-Trp-2-Fua-NH$_2$; | (SEQ ID: 194) |
| H-Inp-D-2-Nal-D-Trp-2-Thi-Apc-NH$_2$; | (SEQ ID: 193) |
| H-Inp-D-2-Nal-D-Trp-3-Thi-Apc-NH$_2$; | (SEQ ID: 193) |
| H-Inp-D-2-Nal-D-Trp-3-Thi-Lys-NH$_2$; | (SEQ ID: 195) |
| H-Inp-D-2-Nal-D-Trp-3-Thi-NH$_2$; | (SEQ ID: 194) |
| H-Inp-D-2-Nal-D-Trp-Pff-Apc-NH$_2$; | (SEQ ID: 193) |
| H-Inp-D-2-Nal-D-Trp-Pff-NH$_2$; | (SEQ ID: 194) |
| H-Inp-D-2-Nal-D-Trp-Taz-Apc-NH$_2$; | (SEQ ID: 193) |
| H-Inp-D-2-Nal-D-Trp-Taz-NH$_2$; | (SEQ ID: 194) |
| H-Inp-D-Bal-D-Bal-2-Fua-Lys-NH$_2$; | (SEQ ID: 196) |
| H-Inp-D-Bal-D-Bal-2-Fua-NH$_2$; | (SEQ ID: 197) |
| H-Inp-D-Bal-D-Bal-2-Thi-Lys-NH$_2$; | (SEQ ID: 196) |
| H-Inp-D-Bal-D-Bal-3-Thi-Lys-NH$_2$; | (SEQ ID: 196) |
| H-Inp-D-Bal-D-Bal-Pff-Lys-NH$_2$; | (SEQ ID: 196) |
| H-Inp-D-Bal-D-Bal-Pff-NH$_2$; | (SEQ ID: 197) |
| H-Inp-D-Bal-D-Bal-Phe-Lys-NH$_2$; | (SEQ ID: 196) |
| H-Inp-D-Bal-D-Bal-Taz-Lys-NH$_2$; | (SEQ ID: 196) |
| H-Inp-D-Bal-D-Bal-Taz-NH$_2$; | (SEQ ID: 197) |
| H-Inp-D-Bal-D-Trp-2-Fua-Apc-NH$_2$; | (SEQ ID: 198) |
| H-Inp-D-Bal-D-Trp-2-Fua-Lys-NH$_2$; | (SEQ ID: 198) |
| H-Inp-D-Bal-D-Trp-2-Fua-NH$_2$; | (SEQ ID: 199) |
| H-Inp-D-Bal-D-Trp-3-Thi-Apc-NH$_2$; | (SEQ ID: 200) |
| H-Inp-D-Bal-D-Trp-3-Thi-Lys-NH$_2$; | (SEQ ID: 200) |
| H-Inp-D-Bal-D-Trp-Pff-Apc-NH$_2$; | (SEQ ID: 201) |
| H-Inp-D-Bal-D-Trp-Pff-Lys-NH$_2$; | (SEQ ID: 201) |
| H-Inp-D-Bal-D-Trp-Pff-NH$_2$; | (SEQ ID: 199) |
| H-Inp-D-Bal-D-Trp-Taz-NH$_2$; | (SEQ ID: 199) |
| H-Inp-D-Bip-D-Bal-2-Fua-Lys-NH$_2$; | (SEQ ID: 202) |
| H-Inp-D-Bip-D-Bal-2-Fua-NH$_2$; | (SEQ ID: 203) |
| H-Inp-D-Bip-D-Bal-2-Thi-Lys-NH$_2$; | (SEQ ID: 202) |
| H-Inp-D-Bip-D-Bal-3-Thi-Lys-NH$_2$; | (SEQ ID: 202) |
| H-Inp-D-Bip-D-Bal-Pff-Lys-NH$_2$; | (SEQ ID: 202) |

```
H-Inp-D-Bip-D-Bal-Pff-NH2;              (SEQ ID: 203)
  or
H-Inp-D-Bip-D-Bal-Taz-Lys-NH2;          (SEQ ID: 204)
H-Inp-D-Bip-D-Bal-Taz-NH2;              (SEQ ID: 205)
H-Inp-D-Bip-D-Trp-2-Fua-Lys-NH2;        (SEQ ID: 206)
H-Inp-D-Bip-D-Trp-2-Fua-NH2;            (SEQ ID: 207)
H-Inp-D-Bip-D-Trp-2-Thi-Lys-NH2;        (SEQ ID: 206)
H-Inp-D-Bip-D-Trp-3-Thi-Lys-NH2;        (SEQ ID: 206)
H-Inp-D-Bip-D-Trp-Pff-Lys-NH2;          (SEQ ID: 206)
H-Inp-D-Bip-D-Trp-Pff-NH2;              (SEQ ID: 207)
H-Inp-D-Bip-D-Trp-Taz-Lys-NH2;          (SEQ ID: 206)
  or
H-Inp-D-Bip-D-Trp-Taz-NH2;              (SEQ ID: 207)
H-Inp-D-1-Nal-D-Trp-3-Pal-Lys-NH2;      (SEQ ID: 128)
H-Inp-D-2-Nal-D-Trp-4-Pal-Lys-NH2;   Example #100   (SEQ ID: 129)
H-Inp-D-2-Nal-D-Trp-Orn-Lys-NH2;        (SEQ ID: 129)
H-Inp-D-Bip-D-Trp-Phe-Lys-NH2;          (SEQ ID: 130)
H-Inp-D-2-Nal-D-Trp-Thr(Bzl)-Lys-NH2;  Example #79   (SEQ ID: 131)
H-Inp-D-2-Nal-D-Trp-Pff-Lys-NH2;        (SEQ ID: 131)
H-Inp-D-2-Nal-D-Trp-2-Thi-Lys-NH2;      (SEQ ID: 132)
H-Inp-D-2-Nal-D-Trp-Taz-Lys-NH2;        (SEQ ID: 132)
H-Inp-D-Dip-D-Trp-Phe-Lys-NH2;          (SEQ ID: 133)
H-Inp-D-Bpa-D-Trp-Phe-Lys-NH2;          (SEQ ID: 133)
H-Inp-D-2-Nal-D-Bpa-Phe-Lys-NH2;        (SEQ ID: 134)
H-Inp-D-2-Nal-D-Trp-Thr(Bzl)-NH2;       (SEQ ID: 138)
H-Inp-D-2-Nal-D-Trp-Pff-NH2;            (SEQ ID: 138)
H-Inp-D-2-Nal-D-Trp-Taz-NH2;            (SEQ ID: 138)
H-Inp-D-2-Nal-D-Dip-Phe-NH2;            (SEQ ID: 140)
H-Inp-D-2-Nal-D-Trp-3-Pal-Lys-NH2;      (SEQ ID: 143)
H-Inp-D-Trp-D-2-Nal(Ψ)-Pim;             (SEQ ID: 127)
H-Inp-D-Bal-D-Trp-2-Thi-Lys-NH2;        (SEQ ID: 144)
H-Inp-D-Bal-D-Trp-Phe-Lys-NH2;          (SEQ ID: 144)
H-Inp-D-1-Nal-D-Trp-2-Thi-Lys-NH2;      (SEQ ID: 128)
H-Inp-D-2-Nal-D-Trp-Phe-Apc-NH2;        (SEQ ID: 2)
H-Inp-D-1-Nal-D-Trp-Phe-Apc-NH2;        (SEQ ID: 2)
H-Inp-D-Bal-D-Trp-Phe-Apc-NH2;          (SEQ ID: 2)
H-Apc-D-2-Nal-D-Trp-Phe-Lys-NH2;        (SEQ ID: 145)
H-Apc-D-1-Nal-D-Trp-2-Thi-Lys-NH2;      (SEQ ID: 146)
H-Inp-D-2-Nal-D-Trp(Ψ)-Pim;             (SEQ ID: 149)
H-Inp-D-1-Nal-D-Trp(Ψ)-Pim;             (SEQ ID: 149)
H-Inp-D-Bal-D-Trp(Ψ)-Pim;               (SEQ ID: 149)
```

-continued

| | | |
|---|---|---|
| H-Aib-D-Ser(Bzl)-D-Trp(Ψ)-Pim; | | (SEQ ID: 150) |
| H-Inp-D-1-Nal-D-Trp-Taz-Lys-NH$_2$; | | (SEQ ID: 151) |
| H-Inp-D-Bal-D-Trp-Taz-Lys-NH$_2$; | | (SEQ ID: 151) |
| H-Apc-D-1-Nal-D-Trp-Taz-Lys-NH$_2$; | | (SEQ ID: 152) |
| H-Apc-D-Bal-D-Trp-Taz-Lys-NH$_2$; | | (SEQ ID: 152) |
| H-Apc-D-Bal-D-Trp-2-Thi-Lys-NH$_2$; | | (SEQ ID: 153) |
| H-Apc-D-Bal-D-Trp-Phe-Lys-NH$_2$; | | (SEQ ID: 153) |
| H-Apc-D-1-Nal-D-Trp-Phe-Apc-NH$_2$; | | (SEQ ID: 154) |
| H-Apc-D-Bal-D-Trp-Phe-Apc-NH$_2$; | | (SEQ ID: 154) |
| H-Apc-D-1-Nal-D-1-Nal-Phe-Apc-NH$_2$; | | (SEQ ID: 155) |
| H-Apc-D-1-Nal-D-2-Nal-Phe-Apc-NH$_2$; | | (SEQ ID: 155) |
| H-Apc-D-1-Nal-D-1-Nal-Phe-Lys-NH$_2$; | | (SEQ ID: 156) |
| H-Apc-D-Bal-D-1-Nal-Phe-Apc-NH$_2$; | | (SEQ ID: 157) |
| H-Apc-D-Bal-D-2-Nal-Phe-Apc-NH$_2$; | | (SEQ ID: 157) |
| H-Apc-D-Bal-D-1-Nal-Phe-Lys-NH$_2$; | Example #77 | (SEQ ID: 158) |
| H-Apc-D-Bal-D-2-Nal-Phe-Lys-NH$_2$; | | (SEQ ID: 158) |
| H-Apc-D-1-Nal-D-Trp-2-Thi-NH$_2$; | | (SEQ ID: 159) |
| H-Apc-D-Bal-D-Trp-Phe-NH$_2$; | | (SEQ ID: 160) |
| H-Apc-D-1-Nal-D-Trp-Taz-NH$_2$; | | (SEQ ID: 159) |
| H-Apc-D-Bal-D-Trp-2-Thi-NH$_2$; | | (SEQ ID: 161) |
| H-Apc-D-Bal-D-Trp-Taz-NH$_2$; | | (SEQ ID: 161) |
| H-Apc-D-2-Nal-D-Trp-2-Thi-NH$_2$; | | (SEQ ID: 162) |
| H-Apc-D-2-Nal-D-Trp-Taz-NH$_2$; | | (SEQ ID: 162) |
| H-Inp-D-1-Nal-D-Trp-Taz-Apc-NH$_2$; | | (SEQ ID: 163) |
| H-Inp-D-Bal-D-Trp-Taz-Apc-NH$_2$; | | (SEQ ID: 163) |
| H-Apc-D-1-Nal-D-Trp-Taz-Apc-NH$_2$; | | (SEQ ID: 164) |
| H-Apc-D-Bal-D-Trp-Taz-Apc-NH$_2$; | | (SEQ ID: 164) |
| H-Inp-D-2-Nal-D-Trp-3-Thi-Lys-NH$_2$; | | (SEQ ID: 195) |
| H-Inp-D-Bal-D-Trp-3-Thi-Lys-NH$_2$; | | (SEQ ID: 200) |
| H-Inp-D-Bal-D-Trp-2-Fua-Lys-NH$_2$; | | (SEQ ID: 198) |
| H-Inp-D-Bal-D-Trp-Pff-Lys-NH$_2$; | | (SEQ ID: 201) |
| H-Inp-D-Bal-D-Trp-3-Thi-Apc-NH$_2$; | | (SEQ ID: 200) |
| H-Inp-D-Bal-D-Trp-2-Fua-Apc-NH$_2$; | | (SEQ ID: 198) |
| H-Inp-D-Bal-D-Trp-Pff-Apc-NH$_2$; | | (SEQ ID: 201) |
| H-Apc-D-Bal-D-Trp-3-Thi-Lys-NH$_2$; | | (SEQ ID: 185) |
| H-Apc-D-Bal-D-Trp-2-Fua-Lys-NH$_2$; | | (SEQ ID: 183) |
| H-Apc-D-Bal-D-Trp-Pff-Lys-NH$_2$; | | (SEQ ID: 186) |
| H-Inp-D-Bal-D-Bal-Phe-Lys-NH$_2$; | | (SEQ ID: 196) |
| H-Inp-D-Bal-D-Bal-2-Thi-Lys-NH$_2$; | | (SEQ ID: 196) |
| H-Inp-D-Bal-D-Bal-3-Thi-Lys-NH$_2$; | | (SEQ ID: 196) |
| H-Inp-D-Bal-D-Bal-Taz-Lys-NH$_2$; | | (SEQ ID: 196) |

-continued

| | |
|---|---|
| H-Inp-D-Bal-D-Bal-2-Fua-Lys-NH₂; | (SEQ ID: 196) |
| H-Inp-D-Bal-D-Bal-Pff-Lys-NH₂; | (SEQ ID: 196) |
| H-Apc-D-Bal-D-Bal-Phe-Lys-NH₂; | (SEQ ID: 181) |
| H-Apc-D-Bal-D-Bal-2-Thi-Lys-NH₂; | (SEQ ID: 178) |
| H-Apc-D-Bal-D-Bal-3-Thi-Lys-NH₂; | (SEQ ID: 179) |
| H-Apc-D-Bal-D-Bal-Taz-Lys-NH₂; | (SEQ ID: 182) |
| H-Apc-D-Bal-D-Bal-2-Fua-Lys-NH₂; | (SEQ ID: 176) |
| H-Apc-D-Bal-D-Bal-Pff-Lys-NH₂; | (SEQ ID: 180) |
| H-Inp-D-1-Nal-D-Trp-3-Thi-Lys-NH₂; | (SEQ ID: 190) |
| H-Inp-D-1-Nal-D-Trp-2-Fua-Lys-NH₂; | (SEQ ID: 189) |
| H-Inp-D-1-Nal-D-Trp-Pff-Lys-NH₂; | (SEQ ID: 191) |
| H-Inp-D-1-Nal-D-Bal-Phe-Lys-NH₂; | (SEQ ID: 187) |
| H-Inp-D-1-Nal-D-Bal-2-Thi-Lys-NH₂; | (SEQ ID: 187) |
| H-Inp-D-1-Nal-D-Bal-3-Thi-Lys-NH₂; | (SEQ ID: 187) |
| H-Inp-D-1-Nal-D-Bal-Taz-Lys-NH₂; | (SEQ ID: 187) |
| H-Inp-D-1-Nal-D-Bal-2-Fua-Lys-NH₂; | (SEQ ID: 187) |
| H-Inp-D-1-Nal-D-Bal-Pff-Lys-NH₂; | (SEQ ID: 187) |
| H-Inp-D-2-Nal-D-Trp-2-Thi-Apc-NH₂; | (SEQ ID: 193) |
| H-Inp-D-2-Nal-D-Trp-3-Thi-Apc-NH₂; | (SEQ ID: 193) |
| H-Inp-D-2-Nal-D-Trp-Taz-Apc-NH₂; | (SEQ ID: 193) |
| H-Inp-D-2-Nal-D-Trp-2-Fua-Apc-NH₂; | (SEQ ID: 193) |
| H-Inp-D-2-Nal-D-Trp-Pff-Apc-NH₂; | (SEQ ID: 193) |
| H-Inp-D-1-Nal-D-Trp-3-Thi-Apc-NH₂; | (SEQ ID: 190) |
| H-Inp-D-1-Nal-D-Trp-2-Fua-Apc-NH₂; | (SEQ ID: 189) |
| H-Inp-D-1-Nal-D-Trp-Pff-Apc-NH₂; | (SEQ ID: 191) |
| H-Apc-D-1-Nal-D-Trp-3-Thi-Lys-NH₂; | (SEQ ID: 167) |
| H-Apc-D-1-Nal-D-Trp-2-Fua-Lys-NH₂; | (SEQ ID: 165) |
| H-Apc-D-1-Nal-D-Trp-Pff-Lys-NH₂; | (SEQ ID: 169) |
| H-Apc-D-2-Nal-D-Trp-2-Thi-Lys-NH₂; | (SEQ ID: 172) |
| H-Apc-D-2-Nal-D-Trp-3-Thi-Lys-NH₂; | (SEQ ID: 173) |
| H-Apc-D-2-Nal-D-Trp-Taz-Lys-NH₂; | (SEQ ID: 175) |
| H-Apc-D-2-Nal-D-Trp-2-Fua-Lys-NH₂; | (SEQ ID: 170) |
| H-Apc-D-2-Nal-D-Trp-Pff-Lys-NH₂; | (SEQ ID: 174) |
| H-Inp-D-Bip-D-Trp-2-Thi-Lys-NH₂; | (SEQ ID: 206) |
| H-Inp-D-Bip-D-Trp-3-Thi-Lys-NH₂; | (SEQ ID: 206) |
| H-Inp-D-Bip-D-Trp-Taz-Lys-NH₂; | (SEQ ID: 206) |
| H-Inp-D-Bip-D-Trp-2-Fua-Lys-NH₂; | (SEQ ID: 206) |
| H-Inp-D-Bip-D-Trp-Pff-Lys-NH₂; | (SEQ ID: 206) |
| H-Inp-D-Bip-D-Bal-2-Thi-Lys-NH₂; | (SEQ ID: 202) |
| H-Inp-D-Bip-D-Bal-3-Thi-Lys-NH₂; | (SEQ ID: 202) |

-continued

| | |
|---|---|
| H-Inp-D-Bip-D-Bal-Taz-Lys-NH$_2$; | (SEQ ID: 204) |
| H-Inp-D-Bip-D-Bal-2-Fua-Lys-NH$_2$; | (SEQ ID: 202) |
| H-Inp-D-Bip-D-Bal-Pff-Lys-NH$_2$; | (SEQ ID: 202) |
| H-Apc-D-Bal-D-Trp-3-Thi-Apc-NH$_2$; | (SEQ ID: 185) |
| H-Apc-D-Bal-D-Trp-2-Fua-Apc-NH$_2$; | (SEQ ID: 183) |
| H-Apc-D-Bal-D-Trp-Pff-Apc-NH$_2$; | (SEQ ID: 186) |
| H-Apc-D-Bal-D-Bal-Phe-Apc-NH$_2$; | (SEQ ID: 181) |
| H-Apc-D-Bal-D-Bal-2-Thi-Apc-NH$_2$; | (SEQ ID: 178) |
| H-Apc-D-Bal-D-Bal-3-Thi-Apc-NH$_2$; | (SEQ ID: 179) |
| H-Apc-D-Bal-D-Bal-Taz-Apc-NH$_2$; | (SEQ ID: 182) |
| H-Apc-D-Bal-D-Bal-2-Fua-Apc-NH$_2$; | (SEQ ID: 176) |
| H-Apc-D-Bal-D-Bal-Pff-Apc-NH$_2$; | (SEQ ID: 180) |
| H-Apc-D-1-Nal-D-Trp-3-Thi-Apc-NH$_2$; | (SEQ ID: 167) |
| H-Apc-D-1-Nal-D-Trp-2-Fua-Apc-NH$_2$; | (SEQ ID: 165) |
| H-Apc-D-1-Nal-D-Trp-Pff-Apc-NH$_2$; | (SEQ ID: 169) |
| H-Apc-D-2-Nal-D-Trp-2-Thi-Apc-NH$_2$; | (SEQ ID: 172) |
| H-Apc-D-2-Nal-D-Trp-3-Thi-Apc-NH$_2$; | (SEQ ID: 173) |
| H-Apc-D-2-Nal-D-Trp-Taz-Apc-NH$_2$; | (SEQ ID: 175) |
| H-Apc-D-2-Nal-D-Trp-2-Fua-Apc-NH$_2$; | (SEQ ID: 170) |
| H-Apc-D-2-Nal-D-Trp-Pff-Apc-NH$_2$; | (SEQ ID: 174) |
| H-Inp-D-Bal-D-Trp-Taz-NH$_2$; | (SEQ ID: 199) |
| H-Inp-D-Bal-D-Trp-2-Fua-NH$_2$; | (SEQ ID: 199) |
| H-Inp-D-Bal-D-Trp-Pff-NH$_2$; | (SEQ ID: 199) |
| H-Apc-D-Bal-D-Trp-3-Thi-NH$_2$; | (SEQ ID: 184) |
| H-Apc-D-Bal-D-Trp-2-Fua-NH$_2$; | (SEQ ID: 184) |
| H-Apc-D-Bal-D-Trp-Pff-NH$_2$; | (SEQ ID: 184) |
| H-Apc-D-Bal-D-Trp-4-Pal-NH$_2$; | (SEQ ID: 184) |
| H-Apc-D-Bal-D-Trp-3-Pal-NH$_2$; | (SEQ ID: 184) |
| H-Apc-D-Bal-D-Trp-2-Pal-NH$_2$; | (SEQ ID: 184) |
| H-Inp-D-Bal-D-Bal-Taz-NH$_2$; | (SEQ ID: 197) |
| H-Inp-D-Bal-D-Bal-2-Fua-NH$_2$; | (SEQ ID: 197) |
| H-Inp-D-Bal-D-Bal-Pff-NH$_2$; | (SEQ ID: 197) |
| H-Apc-D-Bal-D-Bal-Phe-NH$_2$; | (SEQ ID: 177) |
| H-Apc-D-Bal-D-Bal-2-Thi-NH$_2$; | (SEQ ID: 177) |
| H-Apc-D-Bal-D-Bal-3-Thi-NH$_2$; | (SEQ ID: 177) |
| H-Apc-D-Bal-D-Bal-Taz-NH$_2$; | (SEQ ID: 177) |
| H-Apc-D-Bal-D-Bal-2-Fua-NH$_2$; | (SEQ ID: 177) |
| H-Apc-D-Bal-D-Bal-Pff-NH$_2$; | (SEQ ID: 177) |
| H-Apc-D-Bal-D-Bal-4-Pal-NH$_2$; | (SEQ ID: 177) |
| H-Apc-D-Bal-D-Bal-3-Pal-NH$_2$; | (SEQ ID: 177) |
| H-Apc-D-Bal-D-Bal-2-Pal-NH$_2$; | (SEQ ID: 177) |

```
H-Inp-D-1-Nal-D-Trp-Taz-NH2;              (SEQ ID: 192)
H-Inp-D-1-Nal-D-Trp-2-Fua-NH2;            (SEQ ID: 189)
H-Inp-D-1-Nal-D-Trp-Pff-NH2;              (SEQ ID: 192)
H-Inp-D-1-Nal-D-Bal-Taz-NH2;              (SEQ ID: 188)
H-Inp-D-1-Nal-D-Bal-2-Fua-NH2;            (SEQ ID: 188)
H-Inp-D-1-Nal-D-Bal-Pff-NH2;              (SEQ ID: 188)
H-Inp-D-2-Nal-D-Trp-Taz-NH2;              (SEQ ID: 194)
H-Inp-D-2-Nal-D-Trp-2-Fua-NH2;            (SEQ ID: 194)
H-Inp-D-2-Nal-D-Trp-Pff-NH2;              (SEQ ID: 194)
H-Apc-D-1-Nal-D-Trp-3-Thi-NH2;            (SEQ ID: 168)
H-Apc-D-1-Nal-D-Trp-2-Fua-NH2;            (SEQ ID: 165)
H-Apc-D-1-Nal-D-Trp-Pff-NH2;              (SEQ ID: 168)
H-Apc-D-1-Nal-D-Trp-4-Pal-NH2;            (SEQ ID: 168)
H-Apc-D-1-Nal-D-Trp-3-Pal-NH2;            (SEQ ID: 166)
H-Apc-D-1-Nal-D-Trp-2-Pal-NH2;            (SEQ ID: 166)
H-Apc-D-2-Nal-D-Trp-3-Thi-NH2;            (SEQ ID: 171)
H-Apc-D-2-Nal-D-Trp-2-Fua-NH2;            (SEQ ID: 171)
H-Apc-D-2-Nal-D-Trp-Pff-NH2;              (SEQ ID: 171)
H-Apc-D-2-Nal-D-Trp-4-Pal-NH2;            (SEQ ID: 171)
H-Apc-D-2-Nal-D-Trp-3-Pal-NH2;            (SEQ ID: 171)
H-Apc-D-2-Nal-D-Trp-2-Pal-NH2;            (SEQ ID: 171)
H-Inp-D-Bip-D-Trp-Taz-NH2;                (SEQ ID: 207)
H-Inp-D-Bip-D-Trp-2-Fua-NH2;              (SEQ ID: 207)
H-Inp-D-Bip-D-Trp-Pff-NH2;                (SEQ ID: 207)
H-Inp-D-Bip-D-Bal-Taz-NH2;                (SEQ ID: 205)
H-Inp-D-Bip-D-Bal-2-Fua-NH2;              (SEQ ID: 203)
or
H-Inp-D-Bip-D-Bal-Pff-NH2;                (SEQ ID: 203)
H-Inp-D-1-Nal-D-Trp-2-Thi-Apc-NH2;   Example #33   (SEQ ID: 208)
H-Inp-D-Bal-D-Trp-2-Thi-Apc-NH2;     Example #15   (SEQ ID: 208)
H-Apc-D-1-Nal-D-Trp-2-Thi-Apc-NH2;   Example #25   (SEQ ID: 209)
H-Apc-D-Bal-D-Trp-2-Thi-Apc-NH2;     Example #31   (SEQ ID: 209)
and
H-Apc-D-1-Nal-D-Trp-Phe-Lys-NH2;     Example #20   (SEQ ID: 145)
``` or a pharmaceutically acceptable salts thereof.

The present invention includes a method of treating inflammation in a subject comprising administering to the subject an effective amount of an analogue of native ghrelin and fragments thereof of any length that are functional ghrelin molecules according to the following Formula (III):

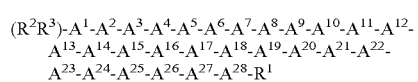

wherein:

$A^1$ is Gly, Aib, Ala, β-Ala, Acc or Gly(myristyl);

$A^2$ is Ser, Aib, Ala, Acc, Abu, Act, Ava, Thr or Val;

$A^3$ is Ser, Ser(C(O)—$R^4$), Asp(O—$R^8$), Asp(NH—$R^9$), Cys(S—$R^{14}$), Dap(S(O)$_2$—$R^{10}$), Dab(S(O)$_2$—$R^{11}$), Glu(O—$R^6$), Glu(NH—$R^7$), Thr(C(O)—$R^5$) or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

A⁶ is Ser, Abu, Acc, Act, Aib, Ala, Gly, Thr or Val;

A⁷ is Pro, Dhp, Dmt, 3-Hyp, 4-Hyp, Inc, Ktp, Oic, Pip, Thz or Tic;

A⁸ is Glu, Acc, Aib, Arg, Asn, Asp, Dab, Dap, Gln, Lys, Orn or HN—CH((CH$_2$)$_n$—N(R$^{12}$R$^{13}$))—C(O);

A⁹ is His, Apc, Aib, Acc, 2-Fua, 2-Pal, 3-Pal, 4-Pal, Taz, 2-Thi, 3-Thi or (X¹,X²,X³,X⁴,X⁵-)Phe;

A¹⁰ is Gln, Acc, Aib, Asn, Asp or Glu;

A¹¹ is Arg, Apc, hArg, Dab, Dap, Lys, Orn or HN—CH((CH$_2$)$_n$—N(R$^{12}$R$^{13}$))—C(O);

A¹² is Val, Abu, Acc, Aib, Ala, Cha, Nva, Gly, Ile, Leu, Nle, Tle or Cha;

A¹³ is Gln, Acc, Aib, Asn, Asp or Glu;

A¹⁴ is Gln, Acc, Aib, Asn, Asp or Glu;

A¹⁵ is Arg, hArg, Acc, Aib, Apc, Dab, Dap, Lys, Orn, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶) or hCys(R¹⁷);

A¹⁶ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶), hCys(R¹⁷) or deleted;

A¹⁷ is Glu, Arg, Asn, Asp, Dab, Dap, Gln, Lys, Orn, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶), hCys(R¹⁷), Lys(biotinyl) or deleted;

A¹⁸ is Ser, Abu, Acc, Act, Aib, Ala, Thr, Val, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶), hCys(R¹⁷) or deleted;

A¹⁹ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶), hCys(R¹⁷) or deleted;

A²⁰ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶), hCys(R¹⁷) or deleted;

A²¹ is Pro, Dhp, Dmt, Inc, 3-Hyp, 4-Hyp, Ktp, Oic, Pip, Thz, Tic or deleted;

A²² is Pro, Dhp, Dmt, 3-Hyp, 4-Hyp, Inc, Ktp, Oic, Pip, Thz, Tic or deleted;

A²³ is Abu, Acc, Act, Aib, Ala, Apc, Gly, Nva, Val or deleted;

A²⁴ is Lys, Acc, Aib, Apc, Arg, hArg, Dab, Dap, Orn, HN—CH((CH$_2$)$_n$—N(R$^{12}$R$^{13}$))—C(O) or deleted;

A²⁵ is Leu, Abu, Acc, Aib, Ala, Cha, Ile, hLeu, Nle, Nva, Phe, Tle, Val or deleted;

A²⁶ is Gln, Aib, Asn, Asp, Glu or deleted;

A²⁷ is Pro, Dhp, Dmt, 3-Hyp, 4-Hyp, Inc, Ktp, Oic, Pip, Thz, Tic or deleted;

A²⁸ is Acc, Aib, Apc, Arg, hArg, Dab, Dap, Lys, Orn, HN—CH((CH$_2$)$_n$—N(R$^{12}$R$^{13}$))—C(O) or deleted;

R¹ is —OH, —NH$_2$, —(C$_1$-C$_{30}$)alkoxy or NH—X⁶—CH$_2$—Z⁰, wherein X⁶ is a (C$_1$-C$_{12}$)alkyl, (C$_2$-C$_{12}$)alkenyl and Z⁰ is —H, —OH, —CO$_2$H or —C(O)—NH$_2$;

R² and R³ is, independently for each occurrence thereof, selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_2$-C$_{30}$)acyl, substituted (C$_2$-C$_{30}$)alkenyl, substituted aryl(C$_1$-C$_{30}$)alkyl and substituted aryl(C$_1$-C$_{30}$)acyl;

R⁴, R⁵, R⁶, R⁷, R⁸, R⁹, R¹⁰, R¹¹, R¹⁴, R¹⁵, R¹⁶ and R¹⁷ is, independently for each occurrence thereof, selected from the group consisting of (C$_1$-C$_{40}$)alkyl, (C$_2$-C$_{40}$)alkenyl, substituted (C$_1$-C$_{40}$)alkyl, substituted (C$_2$-C$_{40}$)alkenyl, alkylaryl, substituted alklyaryl, aryl and substituted aryl;

R¹² and R¹³ is, independently for each occurrence thereof, selected from the group consisting of H, (C$_1$-C$_{40}$)alkyl, (C$_1$-C$_{40}$)acyl, (C$_1$-C$_{30}$)alkylsulfonyl, biotinyl and —C(NH)—NH$_2$;

X¹, X², X³, X⁴, and X⁵ is, independently for each occurrence thereof, selected from the group consisting of H, F, Cl, Br, I, (C$_{1-10}$)alkyl, substituted (C$_{1-10}$)alkyl, aryl, substituted aryl, OH, NH$_2$, NO$_2$ and CN; and n is, independently for each occurrence thereof, 1, 2, 3, 4 or 5;

provided that:

(I). when R² is (C$_1$-C$_{30}$)acyl, aryl(C$_1$-C$_{30}$)acyl, substituted (C$_2$-C$_{30}$)acyl, or substituted aryl(C$_1$-C$_{30}$)acyl, R³ is H, (C$_1$-C$_{30}$)alkyl, (C$_1$-C$_{30}$)heteroalkyl, (C$_2$-C$_{30}$)alkenyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl or substituted aryl(C$_1$-C$_{30}$)alkyl;

(II). when R¹² is (C$_1$-C$_{40}$)acyl, (C$_1$-C$_{30}$)alkylsulfonyl, biotinyl or —C(NH)—NH$_2$, then R¹³ is H or (C$_1$-C$_{40}$)alkyl;

(III). at least one of A¹⁵, A¹⁶, A¹⁷, A¹⁸, A¹⁹ or A²⁰ must be selected from the group consisting of Ser(C(O)—R⁴), Thr(C(O)—R⁵), Glu(O—R⁶), Glu(NH—R⁷), Asp(O—R⁸), Asp(NH—R⁹), Dap(S(O)$_2$—R¹⁰), Dab(S(O)$_2$—R¹¹), HN—CH((CH$_2$)$_n$—N(R$^{12}$R$^{13}$))—C(O), Cys(S—R¹⁴), Cys(R¹⁵), hCys(S—R¹⁶) and hCys(R¹⁷); and (IV). when any of the group consisting of A¹⁵, A¹⁶, A¹⁷, A¹⁹ and A²⁰ is HN—CH((CH$_2$)$_n$—N(R$^{12}$R$^{13}$))—C(O), then R¹² must be biotinyl;

or a pharmaceutically acceptable salt thereof.

In yet another aspect, the invention provides a preferred group of compounds according to Formula (III), where the compound is:

(Ser(n-octanoyl)¹⁵)hGhrelin(1-28)-NH$_2$; (SEQ ID: 210)

(Glu(NH-hexyl)¹⁵)hGhrelin(1-28)-NH$_2$; (SEQ ID: 211)

(Glu(NH-hexyl)³,¹⁵)hGhrelin(1-28)-NH$_2$; (SEQ ID: 212)

(Glu(NH-hexyl)³, Ser(n-octanoyl)¹⁵)hGhrelin(1-28)-NH$_2$; (SEQ ID: 213)

(Aib², Glu(NH-hexyl)¹⁵)hGhrelin(1-28)-NH$_2$; (SEQ ID: 214)

(Aib², Glu(NH-hexyl)³,¹⁵)hGhrelin(1-28)-NH$_2$; (SEQ ID: 215)

(Aib²,⁸, Glu(NH-hexyl)¹⁵)hGhrelin(1-28)-NH$_2$; (SEQ ID: 216)

(Aib²,⁸, Glu(NH-hexyl)³,¹⁵)hGhrelin(1-28)-NH$_2$; (SEQ ID: 217)

(Aib²,¹⁰, Glu(NH-hexyl)¹⁵)hGhrelin(1-28)-NH$_2$; (SEQ ID: 218)

(Aib²,¹⁰, Glu(NH-hexyl)³,¹⁵)hGhrelin(1-28)-NH$_2$; (SEQ ID: 219)

(Ser(n-octanoyl)¹⁶)hGhrelin(1-28)-NH₂; (SEQ ID: 220)

(Glu(NH-hexyl)¹⁶)hGhrelin(1-28)-NH₂; (SEQ ID: 221)

(Glu(NH-hexyl)³,¹⁶)hGhrelin(1-28)-NH₂; (SEQ ID: 222)

(Glu(NH-hexyl)³, Ser(n-octanoyl)¹⁶)hGhrelin(1-28)-NH₂; (SEQ ID: 223)

(Aib², Glu(NH-hexyl)¹⁶)hGhrelin(1-28)-NH₂; (SEQ ID: 224)

(Aib², Glu(NH-hexyl)³,¹⁶)hGhrelin(1-28)-NH₂; (SEQ ID: 225)

(Aib²,⁸, Glu(NH-hexyl)¹⁶)hGhrelin(1-28)-NH₂; (SEQ ID: 226)

(Aib²,⁸, Glu(NH-hexyl)³,¹⁶)hGhrelin(1-28)-NH₂; (SEQ ID: 227)

(Aib²,¹⁰, Glu(NH-hexyl)¹⁶)hGhrelin(1-28)-NH₂; (SEQ ID: 228)

(Aib²,¹⁰, Glu(NH-hexyl)³,¹⁶)hGhrelin(1-28)-NH₂; (SEQ ID: 229)

(Ser(n-octanoyl)¹⁷)hGhrelin(1-28)-NH₂; (SEQ ID: 230)

(Glu(NH-hexyl)¹⁷)hGhrelin(1-28)-NH₂; (SEQ ID: 231)

(Glu(NH-hexyl)³,¹⁷)hGhrelin(1-28)-NH₂; (SEQ ID: 232)

(Glu(NH-hexyl)³, Ser(n-octanoyl)¹⁷)hGhrelin(1-28)-NH₂; (SEQ ID: 233)

(Dap(octanesulfonyl)¹⁷)hGhrelin(1-28)-NH₂; (SEQ ID: 234)

(Dap(octanesulfonyl)³,¹⁷)hGhrelin(1-28)-NH₂; (SEQ ID: 235)

(Dap(octanesulfonyl)³, Glu(NH-Hexyl)¹⁷)hGhrelin(1-28)-NH₂; (SEQ ID: 236)

(Dap(octanesulfonyl)³, Ser(n-octanoyl)¹⁷)hGhrelin(1-28)-NH₂; (SEQ ID: 237)

(Glu(NH-hexyl)³, Dap(octanesulfonyl)¹⁷)hGhrelin(1-28)-NH₂; (SEQ ID: 238)

(Cys(S-(CH₂)₉CH₃)¹⁷)hGhrelin(1-28)-NH₂; (SEQ ID: 239)

(Cys(S-(CH₂)₉CH₃)³,¹⁷)hGhrelin(1-28)-NH₂; (SEQ ID: 240)

(Glu(NH-hexyl)³, Cys(S-(CH₂)₉CH₃)¹⁷)hGhrelin(1-28)-NH₂; (SEQ ID: 241)

(Cys(S-(CH₂)₉CH₃)³, Glu(NH-hexyl)¹⁷)hGhrelin(1-28)-NH₂; (SEQ ID: 242)

(Cys(S-(CH₂)₉CH₃)³, Ser(n-octanoyl)¹⁷)hGhrelin(1-28)-NH₂; (SEQ ID: 243)

(Aib², Glu(NH-hexyl)¹⁷)hGhrelin(1-28)-NH₂; (SEQ ID: 244)

(Aib², Glu(NH-hexyl)³,¹⁷)hGhrelin(1-28)-NH₂; (SEQ ID: 245)

(Aib², Thz⁷, Glu(NH-hexyl)¹⁷)hGhrelin(1-28)-NH₂; (SEQ ID: 246)

(Aib², 4-Hyp⁷, Glu(NH-hexyl)¹⁷)hGhrelin(1-28)-NH₂; (SEQ ID: 246)

(Aib², Dhp⁷, Glu(NH-hexyl)¹⁷)hGhrelin(1-28)-NH₂; (SEQ ID: 246)

(Aib², Pip⁷, Glu(NH-hexyl)¹⁷)hGhrelin(1-28)-NH₂; (SEQ ID: 246)

(Aib², Tic⁷, Glu(NH-hexyl)¹⁷)hGhrelin(1-28)-NH₂; (SEQ ID: 246)

(Aib², Glu(NH-hexyl)³,¹⁷, Thz⁷)hGhrelin(1-28)-NH₂; (SEQ ID: 247)

(Aib², Glu(NH-hexyl)³,¹⁷, 4-Hyp⁷)hGhrelin(1-28)-NH₂; (SEQ ID: 247)

(Aib², Glu(NH-hexyl)³,¹⁷, Dhp⁷)hGhrelin(1-28)-NH₂; (SEQ ID: 247)

(Aib², Glu(NH-hexyl)³,¹⁷, Pip⁷)hGhrelin(1-28)-NH₂; (SEQ ID: 247)

(Aib², Glu(NH-hexyl)³,¹⁷, Tic⁷)hGhrelin(1-28)-NH₂; (SEQ ID: 247)

(Aib²,⁸, Glu(NH-hexyl)¹⁷)hGhrelin(1-28)-NH₂; (SEQ ID: 248)

(Aib²,⁸, Glu(NH-hexyl)³,¹⁷)hGhrelin(1-28)-NH₂; (SEQ ID: 249)

Example #24

(Aib², 3-Pal⁹, Glu(NH-hexyl)¹⁷)hGhrelin(1-28)-NH₂; (SEQ ID: 250)

(Aib², 4-Pal⁹, Glu(NH-hexyl)¹⁷)hGhrelin(1-28)-NH₂; (SEQ ID: 250)

(Aib², Taz⁹, Glu(NH-hexyl)¹⁷)hGhrelin(1-28)-NH₂; (SEQ ID: 250)

(Aib², 2-Thi⁹, Glu(NH-hexyl)¹⁷)hGhrelin(1-28)-NH₂; (SEQ ID: 250)

(Aib², Glu(NH-hexyl)³,¹⁷, 3-Pal⁹)hGhrelin(1-28)-NH₂; (SEQ ID: 251)

(Aib², Glu(NH-hexyl)³,¹⁷, 4-Pal⁹)hGhrelin(1-28)-NH₂; (SEQ ID: 251)

(Aib², Glu(NH-hexyl)³,¹⁷, Taz⁹)hGhrelin(1-28)-NH₂; (SEQ ID: 251)

(Aib², Glu(NH-hexyl)³,¹⁷, 2-Thi⁹)hGhrelin(1-28)-NH₂; (SEQ ID: 251)

(SEQ ID: 252)
(Aib$^{2,10}$, Glu(NH-hexyl)$^{17}$)hGhrelin(1-28)-NH$_2$;

(SEQ ID: 253)
(Aib$^{2,10}$, Glu(NH-hexyl)$^{3,17}$)hGhrelin(1-28)-NH$_2$;

(SEQ ID: 254)
(Aib$^8$, Glu(NH-hexyl)$^{17}$)hGhrelin(1-28)-NH$_2$;

(SEQ ID: 255)
(Taz$^9$, Glu(NH-hexyl)$^{17}$)hGhrelin(1-28)-NH$_2$;

(SEQ ID: 255)
(3-Pal$^9$, Glu(NH-hexyl)$^{17}$)hGhrelin(1-28)-NH$_2$;

(SEQ ID: 255)
(4-Pal$^9$, Glu(NH-hexyl)$^{17}$)hGhrelin(1-28)-NH$_2$;

(SEQ ID: 255)
(2-Thi$^9$, Glu(NH-hexyl)$^{17}$)hGhrelin(1-28)-NH$_2$;

(SEQ ID: 256)
(Glu(NH-hexyl)$^{3,17}$, Aib$^8$)hGhrelin(1-28)-NH$_2$;

(SEQ ID: 257)
(Glu(NH-hexyl)$^{3,17}$, Taz$^9$)hGhrelin(1-28)-NH$_2$;

(SEQ ID: 257)
(Glu(NH-hexyl)$^{3,17}$, 3-Pal$^9$)hGhrelin(1-28)-NH$_2$;

(SEQ ID: 257)
(Glu(NH-hexyl)$^{3,17}$, 4-Pal$^9$)hGhrelin(1-28)-NH$_2$;

(SEQ ID: 257)
(Glu(NH-hexyl)$^{3,17}$, 2-Thi$^9$)hGhrelin(1-28)-NH$_2$;

(SEQ ID: 258)
(Aib$^{1,2,10}$, Glu(NH-hexyl)$^{17}$)hGhrelin(1-28)-NH$_2$;

(SEQ ID: 259)
(Aib$^{1,2,10}$, Glu(NH-hexyl)$^{3,17}$)hGhrelin(1-28)-NH$_2$;

(SEQ ID: 260)
(A5c$^2$, Glu(NH-hexyl)$^{17}$)hGhrelin(1-28)-NH$_2$;

(SEQ ID: 261)
(A5c$^2$, Glu(NH-hexyl)$^{3,17}$)hGhrelin(1-28)-NH$_2$;

(SEQ ID: 262)
(Glu(1-heptanol)$^{3,17}$)hGhrelin(1-28)-NH$_2$;

(SEQ ID: 263)
(Asp(1-heptanol)$^{3,17}$)hGhrelin(1-28)-NH$_2$;

(SEQ ID: 264)
(Glu(NH-hexyl)$^{3,17}$)hGhrelin(1-28)-NH$_2$;

(SEQ ID: 265)
(Asp(NH-hexyl)$^{3,17}$)hGhrelin(1-28)-NH$_2$;

(SEQ ID: 266)
(Aib$^2$, Glu(NH-hexyl)$^{3,17}$)hGhrelin(1-28)-NH$_2$;

(SEQ ID: 267)
(Lys(biotinyl)$^{17}$)hGhrelin(1-28)-NH$_2$;

(SEQ ID: 268)
(Ser(n-octanoyl)$^{18}$)hGhrelin(1-28)-NH$_2$;

(SEQ ID: 269)
(Glu(NH-hexyl)$^{18}$)hGhrelin(1-28)-NH$_2$;

(SEQ ID: 270)
(Glu(NH-hexyl)$^{3,18}$)hGhrelin(1-28)-NH$_2$;

(SEQ ID: 271)
(Glu(NH-hexyl)$^3$, Ser(n-octanoyl)$^{18}$)hGhrelin(1-28)-NH$_2$;

(SEQ ID: 272)
(Aib$^2$, Glu(NH-hexyl)$^{18}$)hGhrelin(1-28)-NH$_2$;

(SEQ ID: 273)
(Aib$^2$, Glu(NH-hexyl)$^{3,18}$)hGhrelin(1-28)-NH$_2$;

(SEQ ID: 274)
(Aib$^{2,8}$, Glu(NH-hexyl)$^{18}$)hGhrelin(1-28)-NH$_2$;

(SEQ ID: 275)
(Aib$^{2,8}$, Glu(NH-hexyl)$^{3,18}$)hGhrelin(1-28)-NH$_2$;

(SEQ ID: 276)
(Aib$^{2,10}$, Glu(NH-hexyl)$^{18}$)hGhrelin(1-28)-NH$_2$;

(SEQ ID: 277)
(Aib$^{2,10}$, Glu(NH-hexyl)$^{3,18}$)hGhrelin(1-28)-NH$_2$;

(SEQ ID: 278)
(Ser(n-octanoyl)$^{19}$)hGhrelin(1-28)-NH$_2$;

(SEQ ID: 279)
(Glu(NH-hexyl)$^{19}$)hGhrelin(1-28)-NH$_2$;

(SEQ ID: 280)
(Glu(NH-hexyl)$^{3,19}$)hGhrelin(1-28)-NH$_2$;

(SEQ ID: 281)
(Glu(NH-hexyl)$^3$, Ser(n-octanoyl)$^{19}$)hGhrelin(1-28)-NH$_2$;

(SEQ ID: 282)
(Aib$^2$, Glu(NH-hexyl)$^{19}$)hGhrelin(1-28)-NH$_2$;

(SEQ ID: 283)
(Aib$^2$, Glu(NH-hexyl)$^{3,19}$)hGhrelin(1-28)-NH$_2$;

(SEQ ID: 284)
(Aib$^{2,8}$, Glu(NH-hexyl)$^{19}$)hGhrelin(1-28)-NH$_2$;

(SEQ ID: 285)
(Aib$^{2,8}$, Glu(NH-hexyl)$^{3,19}$)hGhrelin(1-28)-NH$_2$;

(SEQ ID: 286)
(Aib$^{2,10}$, Glu(NH-hexyl)$^{19}$)hGhrelin(1-28)-NH$_2$;

(SEQ ID: 287)
(Aib$^{2,10}$, Glu(NH-hexyl)$^{3,19}$)hGhrelin(1-28)-NH$_2$;

(SEQ ID: 288)
(Ser(n-octanoyl)$^{20}$)hGhrelin(1-28)-NH$_2$;

(SEQ ID: 289)
(Glu(NH-hexyl)$^{20}$)hGhrelin(1-28)-NH$_2$;

(SEQ ID: 290)
(Glu(NH-hexyl)$^{3,20}$)hGhrelin(1-28)-NH$_2$;

(SEQ ID: 291)
(Glu(NH-hexyl)$^3$, Ser(n-octanoyl)$^{20}$)hGhrelin(1-28)-NH$_2$;

(SEQ ID: 292)
(Aib$^2$, Glu(NH-hexyl)$^{20}$)hGhrelin(1-28)-NH$_2$;

(SEQ ID: 293)
(Aib$^2$, Glu(NH-hexyl)$^{3,20}$)hGhrelin(1-28)-NH$_2$;

(SEQ ID: 294)
(Aib$^{2,8}$, Glu(NH-hexyl)$^{20}$)hGhrelin(1-28)-NH$_2$;

(SEQ ID: 295)
(Aib$^{2,8}$, Glu(NH-hexyl)$^{3,20}$)hGhrelin(1-28)-NH$_2$;

(SEQ ID: 296)
(Aib$^{2,10}$, Glu(NH-hexyl)$^{20}$)hGhrelin(1-28)-NH$_2$;

(Aib$^{2,10}$, Glu(NH-hexyl)$^{3,20}$)hGhrelin(1-28)-NH$_2$; (SEQ ID: 297)

(Ac-Gly$^1$, Glu(NH-hexyl)$^{17}$)hGhrelin(1-28)-NH$_2$; (SEQ ID: 298)

(Ac-Gly$^1$, Ser(n-octanoyl)$^{17}$)hGhrelin(1-28)-NH$_2$; (SEQ ID: 299)

(Ac-Gly$^1$, Glu(NH-hexyl)$^{3,17}$)hGhrelin(1-28)-NH$_2$; (SEQ ID: 300)

(Ac-Gly$^1$, Glu(NH-hexyl)$^3$, Ser(n-octanoyl)$^{17}$)hGhrelin(1-28)-NH$_2$; (SEQ ID: 301)

(Ac-Gly$^1$, Dap(octanesulfonyl)$^{17}$)hGhrelin(1-28)-NH$_2$; (SEQ ID: 302)

(Ac-Gly$^1$, Dap(octanesulfonyl)$^{3,17}$)hGhrelin(1-28)-NH$_2$; (SEQ ID: 303)

(Ac-Gly$^1$, Dap(octanesulfonyl)$^3$, Glu(NH-hexyl)$^{17}$)hGhrelin(1-28)-NH$_2$; (SEQ ID: 304)

(Ac-Gly$^1$, Dap(octanesulfonyl)$^3$, Ser(n-octanoyl)$^{17}$)hGhrelin(1-28)-NH$_2$; (SEQ ID: 305)

(Ac-Gly$^1$, Glu(NH-hexyl)$^3$, Dap(octanesulfonyl)$^{17}$)hGhrelin(1-28)-NH$_2$; (SEQ ID: 306)

(Ac-Gly$^1$, Cys(S-(CH$_2$)$_9$CH$_3$)$^{17}$)hGhrelin(1-28)-NH$_2$; (SEQ ID: 307)

(Ac-Gly$^1$, Cys(S-(CH$_2$)$_9$CH$_3$)$^{3,17}$)hGhrelin(1-28)-NH$_2$; (SEQ ID: 308)

(Ac-Gly$^1$, Glu(NH-hexyl)$^3$, Cys(S-(CH$_2$)$_9$CH$_3$)$^{17}$)hGhrelin(1-28)-NH$_2$; (SEQ ID: 309)

(Ac-Gly$^1$, Cys(S-(CH$_2$)$_9$CH$_3$)$^3$, Glu(NH-hexyl)$^{17}$)hGhrelin(1-28)-NH$_2$; (SEQ ID: 310)

(Ac-Gly$^1$, Cys(S-(CH$_2$)$_9$CH$_3$)$^3$, Ser(n-octanoyl)$^{17}$)hGhrelin(1-28)-NH$_2$; (SEQ ID: 311)

(Ac-Gly$^1$, Aib$^2$, Glu(NH-hexyl)$^{17}$)hGhrelin(1-28)-NH$_2$; (SEQ ID: 312)

(Ac-Gly$^1$, Aib$^2$, Thz$^7$, Glu(NH-hexyl)$^{17}$)hGhrelin(1-28)-NH$_2$; (SEQ ID: 313)

(Ac-Gly$^1$, Aib$^2$, 4-Hyp$^7$, Glu(NH-hexyl)$^{17}$)hGhrelin(1-28)-NH$_2$; (SEQ ID: 313)

(Ac-Gly$^1$, Aib$^2$, Dhp$^7$, Glu(NH-hexyl)$^{17}$)hGhrelin(1-28)-NH$_2$; (SEQ ID: 313)

(Ac-Gly$^1$, Aib$^2$, Pip$^7$, Glu(NH-hexyl)$^{17}$)hGhrelin(1-28)-NH$_2$; (SEQ ID: 313)

(Ac-Gly$^1$, Aib$^2$, Tic$^7$, Glu(NH-hexyl)$^{17}$)hGhrelin(1-28)-NH$_2$; (SEQ ID: 313)

(Ac-Gly$^1$, Aib$^2$, Glu(NH-hexyl)$^{3,17}$, Thz$^7$)hGhrelin(1-28)-NH$_2$; (SEQ ID: 314)

(Ac-Gly$^1$, Aib$^2$, Glu(NH-hexyl)$^{3,17}$, 4-Hyp$^7$)hGhrelin(1-28)-NH$_2$; (SEQ ID: 314)

(Ac-Gly$^1$, Aib$^2$, Glu(NH-hexyl)$^{3,17}$, Dhp$^7$)hGhrelin(1-28)-NH$_2$; (SEQ ID: 314)

(Ac-Gly$^1$, Aib$^2$, Glu(NH-hexyl)$^{3,17}$, Pip$^7$)hGhrelin(1-28)-NH$_2$; (SEQ ID: 314)

(Ac-Gly$^1$, Aib$^2$, Glu(NH-hexyl)$^{3,17}$, Tic$^7$)hGhrelin(1-28)-NH$_2$; (SEQ ID: 314)

(Ac-Gly$^1$, Aib$^{2,8}$, Glu(NH-hexyl)$^{17}$)hGhrelin(1-28)-NH$_2$; (SEQ ID: 315)

(Ac-Gly$^1$, Aib$^2$, 3-Pal$^9$, Glu(NH-hexyl)$^{17}$)hGhrelin(1-28)-NH$_2$; (SEQ ID: 316)

(Ac-Gly$^1$, Aib$^2$, 4-Pal$^9$, Glu(NH-hexyl)$^{17}$)hGhrelin(1-28)-NH$_2$; (SEQ ID: 316)

(Ac-Gly$^1$, Aib$^2$, Taz$^9$, Glu(NH-hexyl)$^{17}$)hGhrelin(1-28)-NH$_2$; (SEQ ID: 316)

(Ac-Gly$^1$, Aib$^2$, 2-Thi$^9$, Glu(NH-hexyl)$^{17}$)hGhrelin(1-28)-NH$_2$; (SEQ ID: 316)

(Ac-Gly$^1$, Aib$^2$, Glu(NH-hexyl)$^{3,17}$, 3-Pal$^9$)hGhrelin(1-28)-NH$_2$; (SEQ ID: 317)

(Ac-Gly$^1$, Aib$^2$, Glu(NH-hexyl)$^{3,17}$, 4-Pal$^9$)hGhrelin(1-28)-NH$_2$; (SEQ ID: 317)

(Ac-Gly$^1$, Aib$^2$, Glu(NH-hexyl)$^{3,17}$, Taz$^9$)hGhrelin(1-28)-NH$_2$; (SEQ ID: 317)

(Ac-Gly¹, Aib², Glu(NH-hexyl)³,¹⁷, 2-Thi⁹) (SEQ ID: 317)
hGhrelin(1-28)-NH₂;

(Ac-Gly¹, Aib²,¹⁰, Glu(NH-hexyl)¹⁷) (SEQ ID: 318)
hGhrelin(1-28)-NH₂;

(Ac-Gly¹, Aib²,¹⁰, Glu(NH-hexyl)³,¹⁷) (SEQ ID: 319)
hGhrelin(1-28)-NH₂;

(Ac-Gly¹, Aib⁸, Glu(NH-hexyl)¹⁷) (SEQ ID: 320)
hGhrelin(1-28)-NH₂;

(Ac-Gly¹, Taz⁹, Glu(NH-hexyl)¹⁷) (SEQ ID: 321)
hGhrelin(1-28)-NH₂;

(Ac-Gly¹, 3-Pal⁹, Glu(NH-hexyl)¹⁷) (SEQ ID: 321)
hGhrelin(1-28)-NH₂;

(Ac-Gly¹, 4-Pal⁹, Glu(NH-hexyl)¹⁷) (SEQ ID: 321)
hGhrelin(1-28)-NH₂;

(Ac-Gly¹, 2-Thi⁹, Glu(NH-hexyl)¹⁷) (SEQ ID: 321)
hGhrelin(1-28)-NH₂;

(Ac-Gly¹, Glu(NH-hexyl)³,¹⁷, Aib⁸) (SEQ ID: 322)
hGhrelin(1-28)-NH₂;

(Ac-Gly¹, Glu(NH-hexyl)³,¹⁷, Taz⁹) (SEQ ID: 323)
hGhrelin(1-28)-NH₂;

(Ac-Gly¹, Glu(NH-hexyl)³,¹⁷, 3-Pal⁹) (SEQ ID: 323)
hGhrelin(1-28)-NH₂;

(Ac-Gly¹, Glu(NH-hexyl)³,¹⁷, 4-Pal⁹) (SEQ ID: 323)
hGhrelin(1-28)-NH₂;

(Ac-Gly¹, Glu(NH-hexyl)³,¹⁷, 2-Thi⁹) (SEQ ID: 323)
hGhrelin(1-28)-NH₂;

(Ac-Aib¹, Aib²,¹⁰, Glu(NH-hexyl)¹⁷) (SEQ ID: 324)
hGhrelin(1-28)-NH₂;

(Ac-Aib¹, Aib²,¹⁰, Glu(NH-hexyl)³,¹⁷) (SEQ ID: 325)
hGhrelin(1-28)-NH₂;

(Ac-Gly¹, A5c², Glu(NH-hexyl)¹⁷) (SEQ ID: 326)
hGhrelin(1-28)-NH₂;

(Ac-Gly¹, A5c², Glu(NH-hexyl)³,¹⁷) (SEQ ID: 327)
hGhrelin(1-28)-NH₂;

(Ac-Gly¹, Glu(1-heptanol)³,¹⁷) (SEQ ID: 328)
hGhrelin(1-28)-NH₂;

(Ac-Gly¹, Asp(1-heptanol)³,¹⁷) (SEQ ID: 329)
hGhrelin(1-28)-NH₂;

(Ac-Gly¹, Glu(NH-hexyl)³,¹⁷) (SEQ ID: 330)
hGhrelin(1-28)-NH₂;

(Ac-Gly¹, Asp(NH-hexyl)³,¹⁷) (SEQ ID: 331)
hGhrelin(1-28)-NH₂;

(Ac-Gly¹, Aib²,¹⁰, Glu(NH-hexyl)³, Lys (SEQ ID: 332)
(biotinyl)¹⁷)hGhrelin(1-28)-NH₂;

(Ac-Gly¹, Glu(NH-hexyl)¹⁵)hGhrelin(1-28)-NH₂; (SEQ ID: 333)

(Ac-Gly¹, Ser(n-octanoyl)¹⁵)hGhrelin(1-28)-NH₂; (SEQ ID: 334)

(Ac-Gly¹, Glu(NH-hexyl)³,¹⁵)hGhrelin(1-28)-NH₂; (SEQ ID: 335)

(Ac-Gly¹, Glu(NH-hexyl)³, Ser(n-octanoyl)¹⁵) (SEQ ID: 336)
hGhrelin(1-28)-NH₂;

(Ac-Gly¹, Aib², Glu(NH-hexyl)¹⁵)hGhrelin (SEQ ID: 337)
(1-28)-NH₂;

(Ac-Gly¹, Aib², Glu(NH-hexyl)³,¹⁵)hGhrelin (SEQ ID: 338)
(1-28)-NH₂;

(Ac-Gly¹, Aib²,⁸, Glu(NH-hexyl)¹⁵)hGhrelin (SEQ ID: 339)
(1-28)-NH₂;

(Ac-Gly¹, Aib²,⁸, Glu(NH-hexyl)³,¹⁵)hGhrelin (SEQ ID: 340)
(1-28)-NH₂;

(Ac-Gly¹, Aib²,¹⁰, Glu(NH-hexyl)¹⁵)hGhrelin (SEQ ID: 341)
(1-28)-NH₂;

(Ac-Gly¹, Aib²,¹⁰, Glu(NH-hexyl)3,15)hGhrelin (SEQ ID: 342)
(1-28)-NH₂;

(Ac-Gly¹, Glu(NH-hexyl)¹⁶)hGhrelin(1-28)-NH₂; (SEQ ID: 343)

(Ac-Gly¹, Ser(n-octanoyl)¹⁶)hGhrelin(1-28)-NH₂; (SEQ ID: 344)

(Ac-Gly¹, Glu(NH-hexyl)³,¹⁶)hGhrelin(1-28)-NH₂; (SEQ ID: 345)

(Ac-Gly¹, Glu(NH-hexyl)³, Ser(n-octanoyl)¹⁶)hGhrelin(1-28)-NH₂; (SEQ ID: 346)

(Ac-Gly¹, Aib², Glu(NH-hexyl)¹⁶)hGhrelin(1-28)-NH₂; (SEQ ID: 347)

(Ac-Gly¹, Aib², Glu(NH-hexyl)³,¹⁶)hGhrelin(1-28)-NH₂; (SEQ ID: 348)

(Ac-Gly¹, Aib²,⁸, Glu(NH-hexyl)¹⁶)hGhrelin(1-28)-NH₂; (SEQ ID: 349)

(Ac-Gly¹, Aib²,⁸, Glu(NH-hexyl)³,¹⁶)hGhrelin(1-28)-NH₂; (SEQ ID: 350)

(Ac-Gly¹, Aib²,¹⁰, Glu(NH-hexyl)¹⁶)hGhrelin(1-28)-NH₂; (SEQ ID: 351)

(Ac-Gly¹, Aib²,¹⁰, Glu(NH-hexyl)³,¹⁶)hGhrelin(1-28)-NH₂; (SEQ ID: 352)

(Ac-Gly¹, Glu(NH-hexyl)¹⁸)hGhrelin(1-28)-NH₂; (SEQ ID: 353)

(Ac-Gly¹, Ser(n-octanoyl)¹⁸)hGhrelin(1-28)-NH₂; (SEQ ID: 354)

(Ac-Gly¹, Glu(NH-hexyl)³,¹⁸)hGhrelin(1-28)-NH₂; (SEQ ID: 355)

(Ac-Gly¹, Glu(NH-hexyl)³, Ser(n-octanoyl)¹⁸)hGhrelin(1-28)-NH₂; (SEQ ID: 356)

(Ac-Gly¹, Aib², Glu(NH-hexyl)¹⁸)hGhrelin(1-28)-NH₂; (SEQ ID: 357)

(Ac-Gly¹, Aib², Glu(NH-hexyl)³,¹⁸)hGhrelin(1-28)-NH₂; (SEQ ID: 358)

(Ac-Gly¹, Aib²,⁸, Glu(NH-hexyl)¹⁸)hGhrelin(1-28)-NH₂; (SEQ ID: 359)

(Ac-Gly¹, Aib²,⁸, Glu(NH-hexyl)³,¹⁸)hGhrelin(1-28)-NH₂; (SEQ ID: 360)

(Ac-Gly¹, Aib²,¹⁰, Glu(NH-hexyl)¹⁸)hGhrelin(1-28)-NH₂; (SEQ ID: 361)

(Ac-Gly¹, Aib²,¹⁰, Glu(NH-hexyl)³,¹⁸)hGhrelin(1-28)-NH₂; (SEQ ID: 362)

(Ac-Gly¹, Glu(NH-hexyl)¹⁹)hGhrelin(1-28)-NH₂; (SEQ ID: 363)

(Ac-Gly¹, Ser(n-octanoyl)¹⁹)hGhrelin(1-28)-NH₂; (SEQ ID: 364)

(Ac-Gly¹, Glu(NH-hexyl)³,¹⁹)hGhrelin(1-28)-NH₂; (SEQ ID: 365)

(Ac-Gly¹, Glu(NH-hexyl)³, Ser(n-octanoyl)¹⁹)hGhrelin(1-28)-NH₂; (SEQ ID: 366)

(Ac-Gly¹, Aib², Glu(NH-hexyl)¹⁹)hGhrelin(1-28)-NH₂; (SEQ ID: 367)

(Ac-Gly¹, Aib², Glu(NH-hexyl)³,¹⁹)hGhrelin(1-28)-NH₂; (SEQ ID: 368)

(Ac-Gly¹, Aib²,⁸, Glu(NH-hexyl)¹⁹)hGhrelin(1-28)-NH₂; (SEQ ID: 369)

(Ac-Gly¹, Aib²,⁸, Glu(NH-hexyl)³,¹⁹)hGhrelin(1-28)-NH₂; (SEQ ID: 370)

(Ac-Gly¹, Aib²,¹⁰, Glu(NH-hexyl)¹⁹)hGhrelin(1-28)-NH₂; (SEQ ID: 371)

(Ac-Gly¹, Aib²,¹⁰, Glu(NH-hexyl)³,¹⁹)hGhrelin(1-28)-NH₂; (SEQ ID: 372)

(Ac-Gly¹, Glu(NH-hexyl)²⁰)hGhrelin(1-28)-NH₂; (SEQ ID: 373)

(Ac-Gly¹, Ser(n-octanoyl)²⁰)hGhrelin(1-28)-NH₂; (SEQ ID: 374)

(Ac-Gly¹, Glu(NH-hexyl)³,²⁰)hGhrelin(1-28)-NH₂; (SEQ ID: 375)

(Ac-Gly¹, Glu(NH-hexyl)³, Ser(n-octanoyl)²⁰)hGhrelin(1-28)-NH₂; (SEQ ID: 376)

(Ac-Gly¹, Aib², Glu(NH-hexyl)²⁰)hGhrelin(1-28)-NH₂; (SEQ ID: 377)

(Ac-Gly¹, Aib², Glu(NH-hexyl)³,²⁰)hGhrelin(1-28)-NH₂; (SEQ ID: 378)

(Ac-Gly¹, Aib²,⁸, Glu(NH-hexyl)²⁰)hGhrelin(1-28)-NH₂; (SEQ ID: 379)

(Ac-Gly¹, Aib²,⁸, Glu(NH-hexyl)³,²⁰)hGhrelin(1-28)-NH₂; (SEQ ID: 380)

-continued (Ac-Gly¹, Aib²,¹⁰, Glu(NH-hexyl)²⁰)hGhrelin (SEQ ID: 381)

(1-28)-NH₂; and (Ac-Gly¹, Aib²,¹⁰, Glu(NH-hexyl)³,²⁰)hGhrelin (SEQ ID: 382)

(1-28)-NH₂;

or pharmaceutically acceptable salts thereof.

The present invention includes a method of treating inflammation in a subject comprising administering to the subject an effective amount of an analogue of native ghrelin and fragments thereof of any length that are functional ghrelin molecules according to the following Formula (IV):

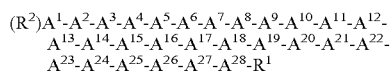

wherein:
$A^1$ is Inp, 1-Apc or 4-Apc;
$A^2$ is Ser, Abu, Acc, Act, Aib, Ala, Ava, Thr or Val;
$A^3$ is Ser, Asp(NH—$R^3$), Asp(O—$R^4$), Cys(S—$R^5$), Dab(S(O)₂—$R^6$), Dap(S(O)₂—$R^7$), Glu(NH—$R^8$), Glu(O—$R^9$), Ser(C(O)—$R^{10}$), Thr(C(O)—$R^{11}$) or HN—CH((CH₂)$_n$—N($R^{12}R^{13}$))—C(O);
$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;
$A^5$ is Leu, Abu, Acc, Aib, Ala, Cha, Ile, hLeu, Nle, Nva, Phe, Tle or Val;
$A^6$ is Ser, Abu, Acc, Act, Aib, Ala, Gly, Thr or Val;
$A^7$ is Pro, Dhp, Dmt, 3-Hyp, 4-Hyp, Inc, Ktp, Oic, Pip, Thz or Tic;
$A^8$ is Glu, Acc, Aib, Arg, Asn, Asp, Dab, Dap, Gln, Lys, Orn or HN—CH((CH₂)$_n$—N($R^{12}R^{13}$))—C(O);
$A^9$ is His, Acc, Apc, Aib, 2-Fua, 2-Pal, 3-Pal, 4-Pal, ($X^1,X^2,X^3,X^4,X^5$-)Phe, Taz, 2-Thi or 3-Thi;
$A^{10}$ is Gln, Acc, Aib, Asn, Asp or Glu;
$A^{11}$ is Arg, Apc, hArg, Dab, Dap, Lys, Orn or HN—CH((CH₂)$_n$—N($R^{12}R^{13}$))—C(O);
$A^{12}$ is Val, Abu, Acc, Aib, Ala, Cha, Gly, Ile, Leu, Nle, Nva or Tle;
$A^{13}$ is Gln, Acc, Aib, Asn, Asp or Glu;
$A^{14}$ is Gln, Acc, Aib, Asn, Asp or Glu;
$A^{15}$ is Arg, Acc, Aib, Apc, hArg, Dab, Dap, Lys or Orn;
$A^{16}$ is Lys, Acc, Aib, Apc, Arg, hArg, Dab, Dap, Orn or deleted;
$A^{17}$ is Glu, Arg, Asn, Asp, Dab, Dap, Gln, Lys, Orn, Asp(NH—$R^3$), Asp(O—$R^4$), Cys(S—$R^5$), Dab(S(O)₂—$R^6$), Dap(S(O)₂—$R^7$), Glu(NH—$R^8$), Glu(O—$R^9$), Ser(C(O)—$R^{10}$), Thr(C(O)—$R^{11}$), HN—CH((CH₂)$_n$—N($R^{12}R^{13}$))—C(O) or deleted;
$A^{18}$ is Ser, Abu, Acc, Act, Aib, Ala, Thr, Val or deleted;
$A^{19}$ is Lys, Acc, Aib, Apc, Arg, hArg, Dab, Dap, Orn or deleted;
$A^{20}$ is Lys, Acc, Aib, Apc, Arg, hArg, Dab, Dap, Orn or deleted;
$A^{21}$ is Pro, Dhp, Dmt, 3-Hyp, 4-Hyp, Inc, Ktp, Oic, Pip, Thz, Tic or deleted;
$A^{22}$ is Pro, Dhp, Dmt, 3-Hyp, 4-Hyp, Inc, Ktp, Oic, Pip, Thz, Tic or deleted;
$A^{23}$ is Ala, Abu, Acc, Act, Aib, Apc, Gly, Nva, Val or deleted;
$A^{24}$ is Lys, Acc, Aib, Apc, Arg, hArg, Dab, Dap, Orn, HN—CH((CH₂)$_n$—N($R^{12}R^{13}$))—C(O) or deleted;
$A^{25}$ is Leu, Abu, Acc, Aib, Ala, Cha, Ile, hLeu, Nle, Nva, Phe, Tle, Val or deleted;
$A^{26}$ is Gln, Aib, Asn, Asp, Glu or deleted;
$A^{27}$ is Pro, Dhp, Dmt, 3-Hyp, 4-Hyp, Inc, Ktp, Oic, Pip, Thz, Tic or deleted;
$A^{28}$ is Arg, Acc, Aib, Apc, hArg, Dab, Dap, Lys, Orn, HN—CH((CH₂)$_n$—N($R^{12}R^{13}$))—C(O) or deleted;
$R^1$ is —OH, —NH₂, —(C₁-C₃₀)alkoxy or NH—$X^6$—CH₂—$Z^0$, wherein $X^6$ is a (C₁-C₁₂)alkyl or (C₂-C₁₂)alkenyl and $Z^0$ is —H, —OH, —CO₂H or —C(O)—NH₂;
$R^2$ is, H, (C₁-C₃₀)alkyl, (C₁-C₃₀)heteroalkyl, (C₁-C₃₀)acyl, (C₂-C₃₀)alkenyl, (C₂-C₃₀)alkynyl, aryl(C₁-C₃₀)alkyl, aryl(C₁-C₃₀)acyl, substituted (C₁-C₃₀)alkyl, substituted (C₁-C₃₀)heteroalkyl, substituted (C₂-C₃₀)acyl, substituted (C₂-C₃₀)alkenyl, substituted aryl(C₁-C₃₀)alkyl, substituted (C₁-C₃₀)alkynyl or substituted aryl(C₁-C₃₀)acyl;
each of $R^3$, $R^4$, $R^5$, $R^6$, $R^7$, $R^8$, $R^9$, $R^{10}$ and $R^{11}$ is, independently for each occurrence thereof, selected from the group consisting of (C₁-C₄₀)alkyl, (C₂-C₄₀)alkenyl, substituted (C₁-C₄₀)alkyl, substituted (C₂-C₄₀)alkenyl, alkylaryl, substituted alkylaryl, aryl and substituted aryl;
each of $R^{12}$ and $R^{13}$ is, independently for each occurrence thereof, selected from the group consisting of H, (C₁-C₄₀)alkyl, (C₁-C₄₀)heteroalkyl, (C₁-C₄₀)acyl, (C₂-C₄₀)alkenyl, (C₂-C₄₀)alkynyl, aryl(C₁-C₄₀)alkyl, aryl(C₁-C₄₀)acyl, substituted (C₁-C₄₀)alkyl, substituted (C₁-C₄₀)heteroalkyl, substituted (C₁-C₄₀)acyl, substituted (C₂-C₄₀)alkenyl, substituted (C₂-C₄₀)alkynyl, substituted aryl(C₁-C₄₀)alkyl, substituted aryl(C₁-C₄₀)acyl, (C₁-C₄₀)alkylsulfonyl or —C(NH)—NH₂;
n is, independently for each occurrence thereof, 1, 2, 3, 4 or 5;
each of $X^1$, $X^2$, $X^3$, $X^4$, and $X^5$ is, independently for each occurrence thereof, selected from the group consisting of H, F, Cl, Br, I, (C₁₋₁₀)alkyl, substituted (C₁₋₁₀)alkyl, aryl, substituted aryl, OH, NH₂, NO₂ and CN; provided that when $R^{12}$ is (C₁-C₄₀)acyl, aryl(C₁-C₄₀)acyl, substituted (C₁-C₄₀)acyl, substituted aryl(C₁-C₄₀)acyl, (C₁-C₄₀)alkylsulfonyl, or —C(NH)—NH₂, then $R^{13}$ is H or (C₁-C₄₀)alkyl, (C₁-C₄₀)heteroalkyl, (C₂-C₄₀)alkenyl, (C₂-C₄₀)alkynyl, aryl(C₁-C₄₀)alkyl, substituted (C₁-C₄₀)alkyl, substituted (C₁-C₄₀)heteroalkyl, substituted (C₂-C₄₀)alkenyl, substituted (C₂-C₄₀)alkynyl, or substituted aryl(C₁-C₄₀)alkyl;

or a pharmaceutically acceptable salt thereof.

In yet another aspect, the invention provides a preferred group of compounds according to formula (IV), where the compound is:

(Inp¹, Aib²,¹⁰, Glu(NH-hexyl)³)hGhrelin (SEQ ID: 385)

(1-28)-NH₂; Example #1

(I-Ape¹, Aib²,¹⁰, Glu(NH-hexyl)³)- (SEQ ID: 385)

hGhrelin(1-28)NH₂; Example #2

(Inp¹)hGhrelin(1-28)-NH₂; (SEQ ID: 386)

Example #9

(Inp¹, Aib²)hGhrelin(1-28)-NH₂; (SEQ ID: 386)

Example #16

(SEQ ID: 387)
(Inp¹, Aib², Glu(NH-hexyl)³)hGhrelin
(1-28)-NH₂; Example #7

(SEQ ID: 388)
(Inp¹, Aib²,¹⁰)hGhrelin(1-28)-NH₂;
Example #14

(SEQ ID: 389)
(Inp¹, Aib²,⁸)hGhrelin(1-28)-NH₂;
Example #12

(SEQ ID: 390)
(Inp¹, Aib², Ser(n-octanoyl)¹⁷)hGhrelin
(1-28)-NH₂; Example #21

(SEQ ID: 390)
(Inp¹, Ser(n-octanoyl)¹⁷)hGhrelin(1-28)-
NH₂; Example #28

(SEQ ID: 389)
(Inp¹, Aib²,⁸, Ser(n-octanoyl)¹⁷)hGhrelin
(1-28)-NH₂;

(SEQ ID: 385)
Ac-(Inp¹, Aib²,¹⁰, Glu(NH-hexyl)³)hGhrelin
(1-28)-NH₂
and (SEQ ID: 385)
Ac-(1-Apc¹, Aib²,¹⁰, Glu(NH-hexyl)³)hGhrelin
(1-28)-NH₂;

or a pharmaceutically acceptable salt thereof.

The present invention includes a method of treating inflammation in a subject comprising administering to the subject an effective amount of anyone one of the following analogues of native ghrelin and fragments thereof of any length that are functional ghrelin molecules which are inconsistent with Formulae (I), (II), (III) or (IV) (referred to as the "non-conforming compounds"):

(SEQ ID: 391)
(Asp³(NH-heptyl))hGhrelin(1-28)-NH₂;
Example #95

(SEQ ID: 392)
(des-Ser²)hGhrelin(1-28)-NH₂;
Example #113

(SEQ ID: 392)
(des-Gly¹, des-Ser²)hGhrelin(1-28)-NH₂;
Example #126

(SEQ ID: 393)
(Aib¹)hGhrelin(1-28)-NH₂;
Example #71

(SEQ ID: 394)
(Asp³(O-hexyl))hGhrelin(1-28)-NH₂;

Example #49

(SEQ ID: 395)
(Aib¹, Ser³)hGhrelin(1-28)-NH₂;

(SEQ ID: 396)
(A5c⁵, Ser³)hGhrelin(1-28)-NH₂;

(SEQ ID: 397)
(Aib²,⁴, Ser³, 4-Pal⁹)hGhrelin(1-28)-NH₂;

(SEQ ID: 398)
(n-octanoyl-Gly¹, Ser³)hGhrelin(1-28)-NH₂;

(SEQ ID: 398)
(isobutyryl-Gly¹, Ser³)hGhrelin(1-28)-NH₂;

(SEQ ID: 398)
(n-butyryl-Gly¹, Ser³)hGhrelin(1-28)-NH₂;

(SEQ ID: 395)
(Aib¹, Thr³)hGhrelin(1-28)-NH₂;

(SEQ ID: 397)
(Aib²,⁴, Thr³, 4-Pal⁹)hGhrelin(1-28)-NH₂;

(SEQ ID: 399)
(n-octanoyl-Gly¹, Thr³)hGhrelin(1-28)-NH₂;

(SEQ ID: 399)
(isobutyryl-Gly¹, Thr³)hGhrelin(1-28)-NH₂;

(SEQ ID: 399)
(n-butyryl-Gly¹, Thr³)hGhrelin(1-28)-NH₂;

(SEQ ID: 400)
(Ac-Gly¹)hGhrelin(1-28)-NH₂;

(SEQ ID: 400)
(Ac-Gly¹, Ser³)hGhrelin(1-28)-NH₂, (SEQ ID: 383)
(Aib², Lys(myristyl)¹⁷)hGhrelin-(1-28)-NH₂;
or (SEQ ID: 384)
[Gly(myristyl)¹, Aib², Lys(myristyl)¹⁷]
hGhrelin-(1-28)-NH₂;

or pharmaceutically acceptable salts thereof.

The present invention includes diastereomers as well as their racemic and resolved enantiomerically pure forms. Ghrelin analogues can contain D-amino acids, L-amino acids or a combination thereof. Preferably, amino acids present in a ghrelin analogue are the L-enantiomers.

Preferred derivatives of analogues of the invention comprise D-amino acids, N-alkyl-amino acids, β-amino acids and/or one or more labeled amino acids (including a labeled version of a D-amino acid, N-alkyl-amino acids, or a β-amino acid). A labeled derivative indicates the alteration of an amino acid or amino acid derivative with a detectable label. Examples of detectable labels include luminescent, enzymatic and radioactive labels. Both the type of label and the position of the label can affect analogue activity. Labels should be selected and positioned so as not to substantially alter the activity of the ghrelin analogue at the GHS receptor. The effect of a particular label and position on ghrelin activity can be determined using assays measuring ghrelin activity and/or binding.

C. Methods of Treatment and Prevention

The peptidyl analogue of ghrelin or prodrug thereof may be administered parenterally, e.g., administered intravenously, subcutaneously, or by implantation of a sustained release formulation. The peptidyl analogue of ghrelin may also be administered intracerebroventricular (icy) injection. In another embodiment, the peptidyl analogue of ghrelin is administered via oral administration. Particularly preferred peptidyl analogues of ghrelin are those compounds of formula (I) or formula (II) or formula (III), or formula (IV), as well as the non-conforming compounds indicated above, as well as each of the compounds that are specifically enumerated herein and below in the Examples section of the present disclosure, or a pharmaceutically acceptable salt thereof.

1. Inflammation

The present invention provides a method of treating inflammation in a subject comprising administering to the subject an effective amount of ghrelin. Inflammation can be associated with a number of different diseases and disorders. Examples of inflammation include, but are not limited to, inflammation associated with hepatitis, inflammation associated with the lungs, inflammation associated with bums, and inflammation associated with an infectious process. Inflammation can also be associated with liver toxicity, which can be associated in turn with cancer therapy, such as apoptosis induction or chemotherapy, or a combination of the two, for example.

Inhibition of the NFkB pathway has been identified as one of the major mediators of ghrelin's protective effects. NFkB regulatory genes regulated by ghrelin were identified as TRCP, TOM1, AP2, GAB1 and TANK, therefore, disclosed are methods of treating inflammation comprising targeting TRCP, TOM1, AP2, GAB 1 and TANK with ghrelin.

a. Disease

The inflammation can be associated with an inflammatory disease. Examples of inflammatory disease include, but are not limited to, asthma, systemic lupus erythematosus, rheumatoid arthritis, reactive arthritis, spondyarthritis, systemic vasculitis, insulin dependent diabetes mellitus, multiple sclerosis, experimental allergic encephalomyelitis, Sjogren's syndrome, graft versus host disease and scleroderma. Inflammatory diseases also include autoimmune diseases such as myasthenia gravis, Guillain-Barre disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, multiple sclerosis, vitiligo, ankylosing spondylitis, Pemphigus vulgaris, psoriasis, dermatitis herpetiformis, Addison's disease, Goodpasture's syndrome, Basedow's disease, thrombopenia purpura, allergy and cardiomyopathy.

b. Cancer

The inflammation can also be associated with cancer. Examples of types of cancer include, but are not limited to, lymphoma (Hodgkins and non-Hodgkins) B-cell lymphoma, T-cell lymphoma, leukemia such as myeloid leukemia and other types of leukemia, mycosis fungoide, carcinoma, adenocarcinoma, sarcoma, glioma, blastoma, neuroblastoma, plasmacytoma, histiocytoma, melanoma, adenoma, hypoxic tumor, myeloma, AIDS-related lymphoma or AIDS-related sarcoma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, head and neck carcinoma, hematopoietic cancer, testicular cancer, colo-rectal cancer, prostatic cancer and pancreatic cancer.

Activated cells can also be treated at the site of inflammation defined as cells that participate in the inflammatory response. Examples of such cells include, but are not limited to, T-cells and B-cells, macrophages, NK cells, mast cells, eosinophils, neutrophils, Kupffer cells, antigen presenting cells, as well as vascular endothelial cells.

c. Infection

Inflammation can be caused by an infectious process in a subject. When the inflammation is associated with an infectious process, the infectious process can be associated with a viral infection. Examples of viral infections include, but are not limited to, Herpes simplex virus type-1, Herpes simplex virus type-2, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian Immunodeficiency virus, Human Immunodeficiency virus type-1 and Human Immunodeficiency virus type-2.

When the inflammation is associated with an infectious process, the infectious process can be associated with a bacterial infection. The bacterial infection can be caused by either gram positive or gram negative bacterium. The gram positive bacterium can be selected from the group consisting of: *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Nocardia asteroides*, and other *Nocardia* species, *Listeria monocytogenes, Listeria ivanovii, Staphylococcus aureus, Staphylococcus epidermidis, Staphylococcus equi, Streptococcus pyogenes, Streptococcus agalactiae, Streptococcus viridans* group, *Bacillus anthracis, B. subtilis, Peptostreptococcus* species, *Peptostreptococcus* species, *Actinomyces israelii* and other *Actinomyces* species, and *Propionibacterium acnes*.

The gram negative bacterium can be selected from the group consisting of: *Clostridium tetani, Clostridium perfringens, Clostridium botulinum*, other *Clostridium* species, *Pseudomonas aeruginosa*, other *Pseudomonas* species, *Campylobacter* species, *Vibrio cholerae, Ehrlichia* species, *Actinobacillus pleuropneumoniae, Pasteurella haemolytica, Pasteurella multocida*, other *Pasteurella* species, *Legionella pneumophila*, other *Legionella species, Salmonella typhi*, other *Salmonella* species, *Shigella* species *Brucella abortus*, other *Brucella* species, *Chlamydia trachomatis, Chlamydia psittaci, Chlamydia pneumoniae, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species as well as other *Enterobacteriaceae, Brucella abortus* and other *Brucella* species, *Burkholderia cepacia*,

*Burkholderia pseudomallei, Francisella tularensis, Bacteroides fragilis, Fusobacterium nucleatum, Provetella* species and *Cowdria ruminantium.*

The above examples of gram positive and gram negative bacteria are not intended to be limiting, but are intended to be representative of a larger population including all gram positive and gram negative bacteria, as well as non-gram test responsive bacteria. Examples of other species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobiospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chryseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Halococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oerskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyromonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas* and other *Rickettsia* species, *Rothia, Ruminococcus, Salmonella, Selenomonas, Serpulina, Serratia, Shewanella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsukamurella, Turicella, Ureaplasma, Vagococcus, Veillonella, Vibrio, Weeksella, Wolinella, Xanthomonas, Xenorhabdus, Yersinia* and *Yokenella.*

When the inflammation is associated with an infectious process, the infectious process can be associated with a parasitic infection. Examples of parasitic infections include, but are not limited to, *Toxoplasma gondii, Plasmodium* species such as *Plasmodium falciparum, Plasmodium vivax, Plasmodium malariae,* and other *Plasmodium species, Trypanosoma brucei, Trypanosoma cruzi, Leishmania* species such as *Leishmania major, Schistosoma* such as *Schistosoma mansoni* and other *Schistosoma* species, and *Entamoeba histolytica.*

When the inflammation is associated with an infectious process, the infectious process can be associated with a fungal infection. Examples of fungal infections include, but are not limited to, *Candida albicans, Cryptococcus neoformans, Histoplasma capsulatum, Aspergillus fumigatus, Coccidiodes immitis, Paracoccidiodes brasiliensis, Blastomyces dermitidis, Pneumocystis carinii, Penicillium marneffi* and *Alternaria alternata.*

2. Sepsis

Furthermore, the infection can be associated with sepsis, also known as systemic inflammatory response syndrome (SIRS), a severe illness caused by overwhelming infection of the bloodstream by toxin-producing bacteria. Sepsis occurs in 2 of every 100 hospital admissions. It is caused by bacterial infection that can originate anywhere in the body. Common sites include, but are not limited to, the kidneys (upper urinary tract infection), the liver or the gall bladder, the bowel (usually seen with peritonitis), the skin (cellulitis) and the lungs (bacterial pneumonia).

LPS-induced endotoxemia in mice is a well recognized model for inducing septic shock and is also associated with anorexia due to excessive production of pro-inflammatory mediators. In spite of a large body of data, the causes of systemic inflammatory response syndrome (SIRS) remain unknown and various therapeutic approaches have yielded minimally beneficial results (Riedemann, N. C. et al., *J. Clin. Invest.,* (2003), 112(4):460-7; and Luheshi, G. N. et al., *Proc. Natl. Acad. Sci. U.S.A.,* (1999), 96(12):7047-52).

LPS directly acts on mononuclear cells, but the resultant endotoxemia also affects a wide variety of cells and systems and is associated with a refractory catabolic state.

It was demonstrated that ghrelin infusions in LPS challenged mice led to a significant inhibition of pro-inflammatory cytokines IL-1α and -1β, IL-6 and TNF-α in circulation as well as in liver, spleen, lungs and mesenteric lymph nodes. In addition, LPS-induced endotoxemia resulted in inhibition of ghrelin secretion (Hataya, Y. et al., *Endocrinology,* (2003), 144 (12):5365-71) and ghrelin infusion increases body weight in septic animals (Murray, C. D. et al., *Gastroenterology,* (2003), 125 (5):1492-502). Inhibition of ghrelin secretion, post-LPS challenge, exacerbates the ongoing inflammatory insult and promotes development of a catabolic state. Furthermore, it was demonstrated that LPS induced inflammatory anorexia is also significantly reduced in ghrelin treated mice. The inclusion of ghrelin and synthetic GHS are therefore candidates in treatment of SIRS. Ghrelin also plays a regulatory role in chronic conditions such as *Helicobacter pylori* infection where persisting gastric inflammation is associated with lower ghrelin levels and correction of infection leads to up regulation of ghrelin secretion.

Meningitis may also be accompanied by sepsis. In children, sepsis may accompany infection of the bone (osteomyelitis). In hospitalized patients, common sites of infection include intravenous lines, surgical wounds, surgical drains and sites of skin breakdown known as decubitus ulcers or bedsores. The infection is often confirmed by a positive blood culture though blood cultures may be negative in individuals who have been receiving antibiotics. In sepsis, blood pressure drops resulting in shock. Major organs and systems, including the kidneys, liver, lungs and central nervous system, stop functioning normally. Sepsis is often life-threatening especially in people with a weakened immune system or other medical illnesses.

3. Transplantation

Inflammation can be associated with transplant rejection in a transplant or implant recipient. As disclosed above, "transplant rejection" is defined as an immune response triggered by the presence of foreign blood or tissue in the body of a subject. In one example of transplant rejection, antibodies are formed against foreign antigens on the transplanted material. The transplantation can be, for example, tissue, cell or organ transplantation, such as liver, kidney, skin, corneal, pancreas, pancreatic islet cells, eyes, heart, or any other transplantable organ of the body.

Transplantation immunology refers to an extensive sequence of events that occurs after an allograft or a xenograft is removed from a donor and then transplanted into a recipient. Tissue is damaged at both the graft and the transplantation sites. An inflammatory reaction follows immediately, as does activation of biochemical cascades.

Such an inflammatory reaction can be reduced using the methods taught herein. In the inflammatory reaction, a series of specific and nonspecific cellular responses ensues as antigens are recognized. Antigen-independent causes of tissue damage (i. e., ischemia, hypothermia, reperfusion injury) are the result of mechanical trauma as well as disruption of the blood supply as the graft is harvested. In contrast, antigen-dependent causes of tissue damage involve immune-mediated damage.

Macrophages release cytokines (e. g., tumor necrosis factor, interleukin-1), which heighten the intensity of inflammation by stimulating inflammatory endothelial responses; these endothelial changes help recruit large numbers of T cells to the transplantation site.

Damaged tissues release pro-inflammatory mediators (e. g., Hageman factor [factor XII]) that trigger several biochemical cascades. The clotting cascade induces fibrin and several related fibrinopeptides which promote local vascular permeability and attract neutrophils and macrophages. The kinin cascade principally produces bradykinin which promotes vasodilation, smooth muscle contraction, and increased vascular permeability.

Rejection is the consequence of the recipient's alloimmune response to the nonself antigens expressed by donor tissues. In hyper-acute rejection, transplant subjects are serologically pre-sensitized to alloantigen (i. e., graft antigens are recognized as nonself).

Histologically, numerous polymorphonuclear leukocytes (PMNs) exist within the graft vasculature and are associated with widespread microthrombin formation and platelet accumulation. Little or no leukocyte infiltration occurs. Hyper-acute rejection manifests within minutes to hours of graft implantation. Hyper-acute rejection has become relatively rare since the introduction of routine pre-transplantation screening of graft recipients for anti-donor antibodies.

In acute rejection, graft antigens are recognized by T cells; the resulting cytokine release eventually leads to tissue distortion, vascular insufficiency and cell destruction.

Histologically, leukocytes are present, dominated by equivalent numbers of macrophages and T cells within the interstitium. These processes can occur within 24 hours of transplantation and occur over a period of days to weeks.

In chronic rejection, pathologic tissue remodeling results from peri-transplant and post-transplant trauma. Cytokines and tissue growth factor induce smooth muscle cells to proliferate, to migrate, and to produce new matrix material. Interstitial fibroblasts are also induced to produce collagen. Histologically, progressive neointimal formation occurs within large and medium arteries and, to a lesser extent, within veins of the graft.

Leukocyte infiltration usually is mild or even absent. All these result in reduced blood flow, with subsequent regional tissue ischemia, fibrosis, and cell death (Prescilla et al. emedicine website, Immunology of Transplant Rejection, updated Jun. 20, 2003).

Transplant rejection may occur within 1-10 minutes of transplantation, or within 10 minutes to 1 hour of transplantation, or within 1 hour to 10 hours of transplantation, or within 10 hours to 24 hours of transplantation, within 24 hours to 48 hours of transplantation, within 48 hours to 1 month of transplantation, within 1 month to 1 year of transplantation, within 1 year to 5 years of transplantation, or even longer after transplantation.

4. Pancreatitis

Pancreatic inflammatory disease may be classified as follows: 1). acute pancreatitis and 2). chronic pancreatitis. This classification is based primarily on clinical criteria with the obvious difference between the acute and chronic varieties being restoration of normal function in the former and permanent residual damage in the latter (Steer, M. L. et al., *N. Engl. J. Med.*, (1995), 332 (22):1482-90; and Klöppel, G. and Maillet, B., *Virchows Arch. A Pathol. Anat. Histopathol.*, (1992), 420 (1):1-4).

The pathologic spectrum of acute pancreatitis varies from edematous pancreatitis, which is usually a mild and self-limited disorder, to necrotizing pancreatitis, in which the degree of pancreatic necrosis correlates with the severity of the attack and its systematic manifestations.

The incidence of pancreatitis varies in different countries and depends upon etiologic factors, e.g., alcohol (Ranson, J. H. et al., *Surg. Gynecol. Obstet.*, (1976), 143 (2):209-19), gallstones (Steinberg, W. and Tenner, S., *N. Engl. J. Med.*, (1994), 330 (17):1198-210), metabolic factors (Toskes, P. P., *Gastroenterol. Clin. North Am.*, (1990), 19 (4):783-91; Izsak, E. M. et al., *Gastroenterology*, (1980), 79 (3):555-8; Gafter, U. et al., JAMA, (1976), 235 (18):2004-5; and Cope, O. et al., *Ann. Surg.* (1957), 145 (6):857-63), and drugs (Banerjee, A. K. et al., Med. *Toxicol. Adverse Drug Exp.*, (1989), 4 (3):186-98; Steinberg, W. M., *Hosp. Pract.* (Off. Ed.), (1985), 20 (5):95-102; Mallory, A. and Kern, F., *Gastroenterology*, (1980), 78 (4):813-20; and Wilson, R. H. and Moorehead, R. J., *Br. J. Surg.*, (1991), 78 (10):1196-202). In the United States, for example, acute pancreatitis is related to alcohol ingestion more commonly than to gallstones (Agarwal, N. and Pitchumoni, C. S., *Pancreas*, (1986), 1 (1):69-73); in England the opposite is true (Blarney, S. L. et al., *Gut*, (1984), 25 (12) 1340-6). There are many causative factors in the pathogenesis of acute pancreatitis (Leach, S. D. et al., *Scand. J. Gastroenterol. Suppl.*, (1992), 192:29-38). Auto-digestion is one pathogenic theory which proposes that proteolytic enzymes, such a trypsinogen, chymotrypsinogen, proelastase, phospholipase and the like, are activated in the pancreas rather than in the intestinal lumen (Figarella, C. et al., *Biochem. Biophys. Res. Commun.*, (1984), 118 (1):154-61). A variety of factors, such as endotoxins, exotoxins, viral infections (Feldstein, J. D. et al., *Ann. Surg.*, (1974), 180 (1):85-8; Imrie, C. W. et al., *Gut*, (1977), 18 (1):53-6; Lopez-Morante, A. et al., *Postgrad. Med. J.*, (1986), 62 (727):407-8; Joe, L. et al., *South Med. J.*, (1989), 82 (11):1444-5; and Dowell, S. F. et al., *Mod. Pathol.*, (1990), 3 (1):49-53), ischemia, anoxia, direct trauma (Wilson, R. H. and Moorehead, R. J., *Br. J. Surg.*, (1991), 78 (10):1196-202) and the like, are believed to activate these pro-enzymes. Activated proteolytic enzymes, especially trypsin, not only digest pancreatic and peripancreatic tissues, but also activate other enzymes such as elastase and phospholipase. The active enzymes then digest cellular membranes and cause proteolysis, edema, interstitial hemorrhage, vascular damage, coagulation necrosis, fat necrosis and parenchymal cell necrosis.

Cellular injury and death result in the liberation of activated enzymes. In addition, activation and release of bradykinin peptides and vasoactive substances, such as histamine, are believed to produce vasodilation, to increase vascular permeability and to create an edema.

Chronic inflammatory disease of the pancreas may present as episodes of acute inflammation superimposed upon a previously injured pancreas or as chronic damage with persistent pain or malabsorption. The causes of relapsing chronic pancreatitis are similar to those of acute pancreatitis, except that frequently there is an appreciable incidence of cases of undetermined origin. In addition, pancreatitis associated with gallstones is predominantly acute or relapsing acute in nature. A cholecystectomy is almost always performed in patients after the first or second attack of gallstone-associated pancreatitis. Patients with chronic pancreatitis may present with persistent abdominal pain, with or without steatorrhea, and some may present with steatorrhea and no pain.

Patients with chronic pancreatitis who develop extensive destruction of the pancreas (i.e., less than ten percent of exocrine function remaining) will demonstrate steatorrhea and azotorrhea. In the adult patient from the United States, alcoholism is the most common cause of clinically apparent pancreatic exocrine insufficiency, while cystic fibrosis is the most frequent cause in patients who are children. In up to twenty-five percent of adults in the United States with chronic pancreatitis, the cause is not known, i.e. they have idiopathic chronic pancreatitis (Steer, M. L. et al., *N. Engl. J. Med.*, (1995), 332 (22):1482-90). In other parts of the world, severe protein calorie malnutrition is a common etiology.

Unfortunately, the events that initiate an inflammatory process within the pancreas are still not well understood (Steinberg, W. and Tenner, S., *N. Engl. J. Med.*, (1994), 330 (17): 1198-210). In the case of alcohol-induced pancreatitis, however, it has been suggested that the primary defect may be the precipitation of protein (inspissated enzymes) within the ducts. The resulting ductal obstruction can lead to duct dilation, diffuse atrophy of the acinar cells, fibrosis, and eventual calcification of some of the protein plugs (Nakamura, K. et al., *Gastroenterology*, (1972), 62 (5):942-9).

Patients with relapsing chronic pancreatitis may present with symptoms identical with those found in acute pancreatitis, but their pain may be continuous, intermittent or altogether absent. The pathogenesis of this pain is poorly understood. Although the classic description is that of epigastric pain radiating through the back, the pain pattern is often atypical. Characteristically, the pain is persistent, deep-seated, and unresponsive to antacids. It is often increased with by alcohol and ingestion of heavy meals. Often the pain is so severe as to require the frequent use of narcotics.

In contrast to patients with relapsing acute pancreatitis, the serum amylase and lipase levels are usually not elevated. Elevations of the serum bilirubin and alkaline phosphate may indicate cholestasis secondary to chronic inflammation around the common bile duct. Many patients demonstrate impaired glucose tolerance and some may have an elevated fasting blood glucose level.

The complications of chronic pancreatitis are protean. Cobalamin (vitamin $B_{12}$) malabsorption occurs in 40 percent of the patients with alcohol-induced chronic pancreatitis and in virtually all with cystic fibrosis (Steer, M. L. et al., *N. Engl. J. Med.*, (1995), 332 (22) 1482-90). The cobalamin malabsorption is consistently corrected by the administration of pancreatic enzymes (containing proteases). The cobalamin malabsorption may be due to excessive binding cobalamin by nonintrinsic factor cobalamin-binding proteins. The latter are ordinarily destroyed by pancreatic proteases, but with pancreatic insufficiency, the nonspecific binding proteins escape degradation and compete with intrinsic factors for cobalamin binding.

Therapy for patients with chronic pancreatitis is directed to two major problems: 1). pain and 2). malabsorption. Patients with intermittent attacks of pain are essentially treated like those with acute pancreatitis. Since the pain is often severe enough to require the frequent use of narcotics (and hence addiction), a number of surgical procedures have been developed for pain relief. Short-term pain relief may be achieved in up to 80 percent of patients, while long-term pain relief occurs in approximately 50 percent. In some of these patients, however, pain relief can be achieved only by re-secting 50 to 95 percent of the gland. Although pain relief is achieved in three-quarters of these patients, they tend to develop pancreatic endocrine and exocrine insufficiency and must undergo pancreatic enzyme replacement therapy.

The treatment of malabsorption rests upon the use of pancreatic enzyme replacement therapy. Although diarrhea and steatorrhea are usually improved, the results are frequently less than satisfactory. The major problem is delivery of enough active enzyme into the duodenum. Steatorrhea can be abolished if 10 percent of the normal amount of lipase could be delivered into the duodenum at the proper time. This concentration of lipase can not be achieved with the presently available preparation of pancreatic enzymes, even if the latter are given in large doses. These poor results may be due to inactivation of lipase by gastric acid, food emptying from the stomach more rapidly than the exogenously administered pancreatic enzymes, and variation in the enzyme activity of various batches of commercially available pancreatic extracts.

Hereditary pancreatitis is a rare disease similar to chronic pancreatitis except for an early age of onset and evidence of hereditary factors involving an autosomal dominant gene with incomplete penetrance (Perrault, J., *Gastroenterol. Clin. North Am.*, (1994), 23 (4):743-52). These patients have recurring attacks of severe abdominal pain which may last from a few days to a few weeks. Serum amylase and lipase levels may be elevated during acute attacks, but are usually normal. Patients frequently develop pancreatic calcification, diabetes mellitus and steatorrhea and, in addition, have an increased incidence of pancreatic carcinoma. Such patients often require ductal decompression to obtain pain relief.

Ghrelin has been shown to attenuate the development of acute pancreatitis by reducing inflammatory infiltrates in the pancreas and by reducing IL-β levels (Debinski, A. et al., *J. Physio. Pharmacol.*, (2003), 54:561-73) and to ameliorate pancreaticobiliary inflammation in rats (Kasimay, O. et al., *Hepatol. Res.*, (2006), 36 (1):11-9).

5. Inflammatory Bowel Disease

Inflammatory bowel disease (IBD) is a general term for a group of chronic inflammatory disorders of unknown etiology involving the gastrointestinal tract. Chronic IBD may be divided into two major groups, chronic non-specific ulcerative colitis and Crohn's disease. Crohn's disease of the small bowel is also known as regional enteritis. In addition, a similar inflammatory picture may occur in the colon, either alone, or with accompanying small-intestine involvement. In most instances, this form of colitis can be distinguished clinically and pathologically from ulcerative colitis and is also referred to as Crohn's disease of the colon. Clinically these disorders are characterized by recurrent inflammatory involvement of intestinal segments with diverse and clinical manifestations often resulting in a chronic, unpredictable course.

Ulcerative colitis (including ulcerative proctitis) has an incidence of approximately 6 to 8 cases per a population of 100,000 and an estimated prevalence of approximately 70 to 150 cases per 100,000 population. Estimates of the incidence of Crohn's disease (colonic plus small bowel) are approximately 2 cases per 100,000 population; the prevalence is estimated at 20 to 40 per 100,000 population. Many believe the incidence of Crohn's disease (especially colonic) to be increasing.

The major symptoms of ulcerative colitis are bloody diarrhea and abdominal pain, often with fever and weight loss in more severe cases. With mild disease, there may be one or two semi-formed stools containing little blood and with no systemic manifestations. In contrast, the patient with severe disease may also have frequent liquid stools containing blood and pus, complain of severe cramps and demonstrate symptoms and signs of dehydration anemia, fever and weight loss.

The clinical course of ulcerative colitis is variable. The majority of patients will suffer a relapse within 1 year of the initial attack, reflecting the recurrent nature of the disease. There may, however, be prolonged periods of remission with only minimal symptoms. In general, the severity of symptoms reflects the extent of colonic involvement and the intensity of the inflammation. Most patients (estimated at 85%) will have mild to moderate disease of intermittent nature and can be managed without hospitalization. In approximately 15% of the patients, the disease assumes a more fulminant course, involves the entire colon, and presents with severe bloody diarrhea and systemic signs and symptoms. The patients are at risk to develop toxic dilatation and perforation of the colon and represent a medical emergency.

The major clinical features of Crohn's disease are fever, abdominal pain, diarrhea often without blood, and general fatigability. There may be associated weight loss. With colonic involvement, diarrhea and pain are the most frequent symptoms. With recurrent pen-rectal inflammation, the anal canal may thicken and pen-anal fistulas or scarring may be present. With extensive colonic involvement, dilatation of the colon may occur. Extra-colonic manifestations, particularly arthritis, are seen more commonly with colonic than with small bowel Crohn's disease. On occasion, often in the setting of extensive small-bowel involvement, features of malabsorption may be prominent. These features, along with anorexia and the catabolic effects of the chronic inflammatory process, may combine to produce striking degrees of weight loss.

The complications of the disease are often local, resulting from intestinal inflammation and involvement of adjacent structures.

Intestinal obstruction is a frequent complication, occurring in 20 to 30 percent of patients during the course of the disease. In the initial stages, the obstruction usually is due to the acute inflammation and edema of the involved intestinal segment, usually the terminal ileum, however, as the disease progresses and fibrosis develops, obstruction may be due to a fixed narrowing of the bowel.

Fistula formation is a frequent complication of chronic regional enteritis as well as Crohn's disease of the colon. Fistulas may occur between contiguous segments of intestine; they may also burrow into the retroperitoneal spaces and present as cutaneous fistulas or indolent abscesses. Ina a significant number of patients, the first indication of the disease may be the presence of persistent rectal fissures, a pen-rectal abscess or a rectal fistula. Although uncommon, pneumaturia should raise the suspicion of enterovesical fistula and is often associated with a persistent urinary tract infection.

Crohn's disease may also involve the stomach and duodenum. The involvement is usually of the antrum and/or the first and second portions of the duodenum. Symptoms may include pain mimicking peptic ulcer disease. Later in the course of the disease, chronic scarring may produce gastric outlet or duodenal obstruction.

The diagnosis of IBD should be entertained in all patients presenting with diarrhea or bloody diarrhea, persistent pen-anal sepsis and abdominal pain. There may be atypical presentations such as fever of unexplained origin in the absence of bowel symptoms or with extra-colonic manifestations such as arthritis or liver disease antedating or overshadowing the bowel involvement. Since Crohn's disease may also involve the small intestine, it should be considered in the differential diagnosis of all types of malabsorption syndromes, intermittent intestinal obstruction and abdominal fistulas. Sigmoidoscopy and radiological studies of the bowel are most important in establishing the diagnosis of inflammatory bowel disease. Sigmoidoscopy must be performed in all patients presenting with chronic diarrhea and in all instances of rectal bleeding. Endoscopic examination of the colon is also of value in the in the diagnosis of colonic Crohn's diseases. The radiological evaluation of the bowel provides essential information in the diagnosis of IBD. Barium enema, in ulcerative colitis, may reveal the extent of the disease and held define associated features such as stricture, pseudopolyposis, or carcinoma. Fiberoptic colonoscopy has added greatly to the diagnosis of colonic inflammatory bowel disease.

Acute colitis may be caused by a variety of infectious agents. Often presenting with bloody diarrhea, infectious colitis may be difficult to distinguish from IBD at initial presentation. Rectal biopsy in infectious colitis shows marked polymorphonuclear infiltration with pronounced edema and relative sparing of the crypts, features which may distinguish it from idiopathic inflammatory bowel disease. Microbiologic causes of acute colitis, include, but are not limited to, *Shigella, Salmonella, Amebiasis, Yersinia, Campylobacter, Lymphogranuloma venereum* (LGV), "Non-LGV" *Chlamydia*, Gonorrhea, Psuedomembranous colitis (*Clostridium difficile* toxin) and Tuberculosis.

Inflammatory bowel disease may be difficult to distinguish from functional diarrhea early in the course of disease. The presence of constitutional symptoms such as fatigue, fever, and weight loss, coupled with laboratory features of anemia, elevated erythrocyte sedimentation rate, or occult blood in the stool should alert the clinician to the possibility of IBD. Similarly, finding leukocytes in a stained stool specimen suggests an inflammatory basis for the diarrhea. In all cases, stool cultures and parasitologic examination of the stool are required to rule out enteric bacterial pathogens or amebiasis.

With small-intestinal involvement (regional enteritis) the differential diagnosis should include disorders presenting with intra-abdominal abscesses, fistulas, intestinal obstruction, and malabsorption. The finding of associated colonic involvement in patients with ileal disease will often serve to distinguish Crohn's disease from other ileal disorders.

The complications of IBD may be classified as local, which are a direct reflection of mucosal inflammation and its extension, or systemic complications. Local complications of IBD include fistulas, abscesses and structures. In addition, perforation, toxic dilatation and the development of carcinoma may complicate both ulcerative colitis and Crohn's disease. Intestinal perforation can occur in severe ulcerative colitis since with extensive ulceration the bowel wall may become extremely thin. Toxic dilation of the colon may occur in Crohn's colitis, but is more common in ulcerative colitis. This complication can best be considered as a severe form of ulcerative colitis with the additional feature of colonic dilatation. It is thought that the neuromuscular tone of the bowel is affected by the severe inflammation resulting in dilatation.

There is an increases incidence of carcinoma in patients with chronic IBD when compared to the general population, especially in patients who have more extensive mucosal involvement, i.e. pancolitis, and those who have had their disease for extended period of time. Cumulative risk of cancer rises steadily with the duration of the disease. Malignancy developing in Crohn's disease of the colon or small bowel is less well-documented, but the incidences of both small- and large-bowel malignancies are increased compared to the general population. The incidence is, however, less than in ulcerative colitis.

The development of colon carcinoma arising in the setting of IBD demonstrates important differences when compared to carcinoma arising in a noncolitic population. Clinically, many of the earlier warning signs of a colonic neoplasm, i.e., rectal bleeding, change in bowel habits, will be difficult to interpret in the setting of colitis. In colitic patients, the distribution of carcinomas is more uniform throughout the colon than in noncolitic patients; in the latter the majority of carcinomas are in the rectosigmoid within reach of the sigmoidoscope. In colitis patients, the tumors are more often multiple, flat, and infiltrating and appear to have a higher grade malignancy. There is some evidence to suggest that these features may reflect the younger age at which they occur rather than the associated colitis.

There are a variety of non-intestinal symptoms and signs which may be associated with IBD and occur in both ulcerative colitis and Crohn's disease. Joint manifestations are common in patients with IBD; ranging from arthralgia only to an acute arthritis with painful, swollen joints. Skin manifestations are also common with colonic disease, such as Erythema nodosum, Pyoderma gangrenosum, an ulcerating lesion, Aphthous ulcers, resembling canker sores of the mouth. Ocular manifestations, such as episcleritis, recurrent iritis and uveitis occur in approximately 5 to 10 percent of patients suffering from IBD. Abnormalities of liver function are possible, including non-specific focal hepatitis and fatty infiltration. *Pericholangitis* characterized histologically by portal tract inflammation, some bile ductular proliferation and concentric fibrosis around bile ductules. Uncommonly, patients with IBD may develop sclerosing cholangitis, a chronic inflammation of unknown etiology involving the extrahepatic and intrahepatic bile ducts which may produce varying degrees of extrahepatic biliary obstruction. Corticosteriods and immunosuppressive therapy are not beneficial. Cholangiocarcinoma, arising in the extrahepatic biliary tree, has an increased incidence in patients with chronic ulcerative colitis. Finally, chronic active hepatitis which may progress to cirrhosis may be seen in IBD, although the exact relationship between these disorders is unknown.

In general, the treatment of ulcerative colitis and Crohn's disease shares certain common principles. Initial treatment of all forms of uncomplicated IBD is primarily medical, and the principles of medical therapy are similar. Surgery is reserved for (1) specific complications and (2) intractability of disease. There are certain important differences, however, between ulcerative colitis and Crohn's disease, namely the response to drug therapy may differ, complications often differ and the prognosis after surgical therapy is not the same. Mild ulcerative colitis, including ulcerative proctitis, can usually be treated on an ambulatory basis. More severe cases are best treated in a hospital setting due to the unpredictability of the course of a given attack. The principal drugs used in the therapy of ulcerative colitis are anti-inflammatory agents, sulfasalazine (Azulfidine) and adrenal gluccocorticoids or ACTH.

Approximately 20 to 25 percent of patients with ulcerative colitis will require colectomy during the course of their disease. A major indication for colectomy is failure to respond to intensive medical management. Such patients, although not showing colonic dilatation, may fail to improve over 7 to 10 days of optimal medical therapy. Fever, persistent bloody diarrhea and severe fatigue may persist. Elective colectomy may be performed in patients whose disease remains chronically active and who may require continuous corticosteroid administration.

The medical management of colonic Crohn's disease is similar in most respects to those of ulcerative colitis. Sulfasalazine and glucocoticoids have been found to be effective, however, since intra-abdominal sepsis can result from fistula or abscess formation, corticosteroids must be used with caution and constant attention is required to detect evidence of sepsis. Because of the indolent nature of the disease, the response to therapy is often less complete than in ulcerative colitis and the disease tends to progress despite apparent clinical inactivity. Frequency of reoccurrence is not altered by prophylactic steroid therapy. Sulfasalazine does not decrease reoccurrence rates in Crohn's disease. While response to therapy of the initial attack of Crohn's colitis may be satisfactory, many patients continue to have persistently active diseases. This may express itself as progressive weight loss, diarrhea and deterioration of general health. Pen-anal disease with predominantly left-sided colonic involvement (fistula formation and pen-rectal abscesses) may constitute a recurrent problem.

The management of Crohn's disease of the small intestine (regional enteritis) is similar to that for colonic Crohn's disease and many patients have concomitant small- and large-bowel disease. Intestinal obstruction is not uncommonly a presenting feature with ileal involvement. Initially, this may be secondary to acute inflammation and will respond to corticosteroids. With recurrent involvement and the development of fibrosis, steroid therapy is less effective and surgical decompression is required. Nutritional problems often are more severe with involvement of the small intestine that with colonic involvement alone. Added to the general catabolic nature of the disease may be loss of absorptive surface which may result from progressive involvement or because of surgical resection.

Surgical therapy is generally reserved for the complications of Crohn's disease rather than as a primary form of therapy. In contrast to ulcerative colitis, more patients with Crohn's disease will require surgery in the chronic management of the disease. Approximately 70% of patients will require at least one operation during the course of their disease. Although each case and situation must be individualized, surgery may be required (1) for persistent or fixed bowel narrowing or obstruction; (2) for symptomatic fistula formation to the bladder, vagina or skin; (3) for persistent anal fistulas or abscesses; and (4) for intra-abdominal abscesses, toxic dilatation of the colon, or perforation. In contrast to ulcerative colitis where colectomy is curative, Crohn's disease surgical resection of the small or large intestine is followed by a high rate of recurrence. Faced with the possibility of recurrent diseases, many physicians are reluctant to advise surgery in Crohn's disease. Alternatively, patients with persistently active disease may require chronic maintenance on unacceptably high levels of corticosteroids with the appreciable risk of steroid side effects.

The therapy for Crohn's disease in children presents special problems since normal growth and development may be retarded in the presence of active disease.

6. Myocardial Damage

Approximately 1.1 million Americans have an acute myocardial infarction each year. The size of the infarction is a major determinant of both the risk of death and the likelihood of subsequent heart failure. A robust inflammatory response is an integral component of the response to tissue injury during a myocardial infarction (Suleiman, M. et al., *J. Am. Coll. Cardiol.*, (2006), 47 (5):962-8). Complement-mediated inflammation exacerbates the tissue injury of ischemic necrosis in heart attacks and strokes. Large infarct size increases immediate morbidity and mortality and, in survivors of the acute event, larger non-functional scars adversely affect long-term prognosis (Pepy, M. B. et al., *Nature*, (2006), 440 (7088):1217-21).

A goal of therapy is to reduce the size of the infarct.

CRP is an acute-phase serum protein that is synthesized by hepatocytes. It has been shown that human CRP binds to ligands exposed in damaged tissue and then activates complement, increases myocardial infarct size (Pepys, M. B. et al., *Nature*, 92006), 21 (10:2718-20). During infarction, inflammation and tissue injury, the serum levels of CRP rises by a factor of up to several thousand. The physiologic roles of CRP are not known, but it may contribute to innate immunity and suppression of autoimmunity. CRP levels increase dramatically in patients with myocardial infarction beginning 6 hours after the onset of ischemia and peaking at approximately 50 hours. CRP values after acute myocardial infarction predict outcome, including death and heart failure (Suleiman, M. et al., *J. Am. Coll. Cardiol.*, (2006), 47 (5):962-8). The binding of CRP to phosphocholine groups in damaged cell membranes leads to complement activation which may cause further tissue damage. CRP and complement are found in infarcted human myocardial tissue (Lagrand, W. K. et al., *Circulation*, (1997), 95 (1):97-103). Human CRP was shown to increase the size of myocardial infarctions in rats in a complement-dependent way (Griselli, M. et al., *J. Exp. Med.*, (1999), 190 (12):1733-40).

Therapeutic inhibition of CRP is a promising new approach to cardio-protection in acute myocardial infarction and may provide neuroprotection during a stroke.

7. Aging

Low-grade inflammation can be associated with aging. as aging is associated with an increase in inflammatory cytokines including IL-6. The increase in inflammatory mediators with age is related to 'anorexia of aging' and frailty (Ershler, W. B. and Keller, T. E., *Annu. Rev. Med.*, (2000), 51:245-70). Ghrelin supplementation therapy of frail and aging subjects can reduce the ongoing inflammatory insult, increase food intake and promote the anabolic processes.

8. Proinflammatory Neuropathic Pain

Neuropathic pain is a kind of chronic pain as a result of injury to the peripheral nervous system, i.e., post-therapeutic neuralgia or diabetic neuropathy, or to the central nervous system, i.e., spinal cord injury or stroke. Such pain is often associated with abnormal sensory signs, such as spontaneous pain (pain independent of stimulus), hyperalgesia (an increased response to normally painful stimuli) and allodynia (a painful response to normally innocuous stimuli (Zimmermann, M., *Eur. J. Pharmacol.*, (2001), 429:23-37; and Gilron, I. et al., *CMAJ*, (2006), 175 (3):265-75).

The precise mechanisms of neuropathic pain are unknown and multiple mechanisms can co-exist in individual patients. When a peripheral nerve, however, is damaged, a variety of inflammatory cells are recruited to the site of injury from the blood stream. Under these conditions, neuroinflammatory and immune responses contribute as much to the development and maintenance of pain as does the initial damage itself. Studies indicate that inflammatory response often accompany the onset of neuropathic pain (Myers, R. R. et al, *DDT*, (2006), 11:8-20; Pace, M. C. et al., *J. Cell Physiol.*, (2006), 209:8-12; and Watkins, L. R. and Maier, S. F., *Physiol. Rev.*, (2002), 82:981-1011). Previous studies have also shown that proinflammatory cytokines, the primary molecular agents responsible for an inflammatory response, contribute to injury-induced peripheral nerve pathology and to the development of neuropathic pain (Watkins, L. R. and Maier, S. F., *Physiol. Rev.*, (2002), 82:981-1011; Verri, W. A. et al., *Pharmacol. & Therapeut.*, (2006), 112:116-38; and Stoll, G. et al., *J. Peripher. Nerv. Syst.*, (2002), 7:13-27).

TNF-α is strongly implicated in neuropathic pain. It induces axonal damage, macrophage recruitment and ectopic activity in peripheral nerve fibers (Wagner, R. and Myers, R. R., *Neuroreport*, (1996), 7 (18):2897-901; Redford, E. J. et al., *Brain*, (1995), 118:869-78; and Sorkin, L. S. et al., *Neuroscience*, (1997), 81:255-62). TNF-α also plays a key role in hyperalgesia (Cui, J. G., et al., *Pain*, (2000), 88:239-48). In a clinical study, TNF-α were upregulated in patients with neuropathic pain (Empl, M. et al., *Neurology*, (2001), 56 (10): 1371-7). In addition, intraneural injection of IL-1β into rat sciatic nerve produced neuropathic pain behavior (Zelenka, M. et al., *Pain*, (2005), 116 (3):257-63). Plasma levels of IL-6 have been shown to increase following nerve injury (Wells, M. R., et al., *J. Neuroimmunol.*, (1992), 39:261-8) and IL-6 mRNA upregulation was found to occur following chronic constriction injury in animal models (Murphy, P. G. et al., *Eur. J. Neurosci.*, (199), 11:2243-53).

Treatment of neuropathic pain still remains as a difficult issue because neuropathic pain has a complex pathophysiology. The most widely utilized pharmacotherapical options include anticonvulsants, antidepressants, topical treatments, i.e., 5% lidocaine patches and capsaicin, and opioids. Although conventional analgesics are clinically used in the treatment of neuropathic pain, they are not satisfactory due to incomplete efficacy and dose-limiting side effects (Jackson, K. C., *Pain Pract.*, (2006), 6 (1):27-33; and Stacey, B. R., *Am. J. Phys. Med, Rehabil.*, (2005), 84 (3):4-16).

Ghrelin receptors were found to be particularly expressed in various brain areas such as the hypothalamus and the pons medulla oblongata, the regions of the brain responsible for controlling pain transmission (Guan, X. M. et al., *Brain Res. Mol. Brain Res.*, (1997), 48:23-9; and Zigman, J. M. et al., *J. Comp. Neurol.*, (2006), 548:528-48). Studies have shown that ghrelin produces excitatory effects on neurons of the ventromedial arcuate nucleus (Riediger, T. et al., *Neurosci. Lett.*, (2003), 341:151-5) where endogenous opioid containing neurons are located (Bloom, F. et al., *Proc. Nat'l. Acad. Sci. U.S.A.*, (1978), 75:1591-5). The localization of ghrelin suggests a role in modulating pain (Guneli, E. et al., *Med. Hypoth.*, (2007), 69:356-60).

Studies have shown that ghrelin reduced pain threshold on acute pain in mice (Kutlu, S. et al., *Firat Tip Dergisi*, (2005), 10 (3):89-91). In other studies, ghrelin's relationship with antinociceptive mechanism through its interaction with central opioid systems decreases inflammatory in rats was proven (Sibilia, V. et al., *Neuropharmacol.*, (2006), 51 (3):497-505). Ghrelin potently inhibits the expression of TNF-α, IL-1β and IL-6 by lymphocytes and monocytes (Dixit, V. D. et al., *J. Clin. Invest.*, (2004), 114:57-66) and inhibits TNF-α induced activation of NF-κB (Li, W. G. et al., *Circulation*, (2004), 109:2221-6). Recent studies demonstrate that ghrelin exerted beneficial effects to inflammatory diseases due to its anti-inflammatory activity. Ghrelin has been shown to exert potent anti-inflammatory activity in a murine model of endotoxemia by inhibiting levels of TNF-α, IL-1β and IL-6 after LPS challenge (Dixit, V. D., et al., *J. Clin. Invest.*, (2004), 114:57-66). Finally, ghrelin agonist growth hormone-releasing peptide-2 (GHRP-2) administration was shown to exert an anti-inflammatory effect in arthritic rats (Granado, M. et al., *Am. J. Physiol. Endocrinol. Metab.*, (2005), 288 (3):486-92). Ghrelin is considered an important mediator in the regulation of inflammation capable of diminishing the proinflammatory cytokines thus regulating neuropathic pain.

9. Cytokines

Also disclosed are methods of inhibiting secretion of cytokines, comprising administering an effective amount of a ghrelin analogue. For example, the cytokines can be inhibited at the site of inflammation. The cytokine can be expressed by cells selected from the group consisting of T-cells, B-cells, dendritic cells and mononuclear cells.

Examples of cytokines and immunomodulatory agents that can be employed in the methods of this invention include, but are not limited to, those participating in humoral inflammation, such as IL-3, IL-4, IL-5, IL-6, IL-7, IL-9, IL-10, IL-13, and transforming growth factor-3 (TGF-p), and those contributing to cellular inflammation such as IL-1, IL-2, IL-3, IL-4, IL-7, IL-9, IL-10, IL-12, interferons (IFNs), IFN-γ inducing factor (IGIF), TGF-p and TNF-α and TNF-β. Ghrelin can be used to modulate cytokines and/or immunomodulators according to the methods of this invention both to treat an acute episode of disease and/or to maintain the subject's condition in a non-inflammatory state.

Cytokines are proteins made by cells that affect the behavior of other cells.

Cytokines made by lymphocytes are often called lymphokines or interleukins (IL).

Cytokines act on specific cytokine receptors on the cells they affect. Binding of the receptor induces activity in the cell such as growth, differentiation or death. Several cytokines play key roles in mediating acute inflammatory reactions, namely IL-1, TNF-α, IL-6, IL-11, IL-8 and other chemokines, GCSF and GM-CSF. Of these, IL-1 (α and β) and TNF are extremely potent inflammatory molecules; they are the primary cytokines that mediate acute inflammation induced in animals by intradermal injection of bacterial lipopolysaccharide and two of the primary mediators of septic shock.

Chronic inflammation may develop following acute inflammation and may last for weeks or months, and in some instances, for years. During this phase of inflammation, cytokine interactions result in monocyte chemotaxis to the site of inflammation where macrophage activating factors (MAF), such as IFN-γ MCP-1 and other molecules then activate the macrophages while migration inhibition factors (MIF), such as GM-CSF and IFN-γ retain them at the inflammatory site. The macrophages contribute to the inflammatory process by chronically elaborating low levels of IL-1 and TNF which are responsible for some of the resulting clinical symptoms such as anorexia, cachexia, fever, sleepiness and leukocytosis. The cytokines known to mediate chronic inflammatory processes can be divided into those participating in humoral inflammation, such as IL-3, IL-4, IL-5, IL-6, IL-7, IL-9, IL-10, IL-13, and transforming growth factor-P (TGF-P), and those contributing to cellular inflammation such as IL-1, IL-2, IL-3, IL-4, IL-7, IL-9, IL-10, IL-12, interferons (IFNs), IFN-γ inducing factor (IGIF), TGF-p and TNF-α and -@ (Feghali, C. A. and Wright, T. M., *Front. Biosci.*, (1997 Jan. 1), d12-26).

The production of pro-inflammatory cytokines by cells of the innate immune system plays an important role in mediating the initial host defense against invading pathogens. Furthermore, the inability to regulate the nature or duration of the host's inflammatory response can often mediate detrimental host effects as observed in chronic inflammatory diseases. For example, in the early stages of sepsis, the host's inflammatory response is believed to be in a hyperactive state with a predominant increase in the production of pro-inflammatory cytokines that mediate host tissue injury and lethal shock. Thus, the ability of the innate immune system to dictate the levels of pro- and anti-inflammatory cytokine production is critical in limiting or modulating the nature of the host inflammatory response.

The immune system, in particular the production of inflammatory cytokines by leukocytes, plays an important role in the development of anorexia-cachexia syndrome (Hart, B. L. et al., *Neurosci. Biobehav. Rev.*, (1988), 12 (2):123-37; Kotler, D. P., *Cachexia 2000 Ann. Internal. Med.*, (2000), 133 (8): 622-34; and Ershler, W. B. and Keller, E. T., *Ann. Rev. Med.*, (2000), 51:245-70). Examples of cytokines considered to be relevant to inflammatory anorexia include IL-1p, IL-6 and TNF-α.

Peripherally administered ghrelin is shown herein to block IL-1 p-induced anorexia and produces positive energy balance by promoting food intake and decreasing energy expenditure. The inhibitory effect of ghrelin on pro-inflammatory cytokine expression shows a regulatory role for ghrelin and GHS-R in controlling cytokine-induced anorexia. Moreover, the combination of IL-1β and leptin has also been shown to inhibit ghrelin expression in stomach (Cohen, J., *Nature*, (2002), 420 (6917):885-91) and stomach ghrelin expression is increased in leptin deficient mice. Leptin and ghrelin are considered to exert mutually antagonistic effects on the food intake at the hypothalamic level (Nakazato, M. et al., *Nature*, (2001), 409 (6817):194-8; and Inui, A., *Nature Rev. Neurosci.*, (2001), 2 (8):551-60). Leptin, a member of gp130 family of cytokines, induces a strong Th1 response (Hosoda, H. et al., *J. Biol. Chem.*, (2003), 278 (1):64-70) and is regarded as a pro-inflammatory inducer (Loffreda, S. et al., FASEB J., (1998), 12(1):57-65; Zarkesh-Esfahani, H. et al., *J. Immunol.*, (2001), 167 (8):4593-9; Lord, G. M. et al., *Nature*, (1988), 394(6696):897-901; Hosoda, H. et al., *J. Biol. Chem.*, (2003), 278 (1):64-70; and Dixit, V. D. et al., *Endocrinology*, (2003), 144 (12):5595-603). Leptin's actions on food intake are controlled, in part, by an increase in the level of IL-1β; in the hypothalamus (Janik, J. E. et al., *J. Clin. Endocrinol. Metab.*, (1997), 82 (9):3084-6). Similarly, anorectic effects of IL-1 are mediated via increasing leptin levels (Lambert, P. D. et al., *Proc. Natl. Acad. Sci. U.S.A.*, (2001), 98 (8):4652-7).

It has been demonstrated that leptin can directly induce the mRNA expression and secretion of IL-1β; IL-6 and TNF-α by human T cells and PBMCs. Leptin and several other gp 130 ligands including LIF, CNTF and IL-6 exert similar effects on host metabolism (Beretta, E. et al., *Peptides*, (2002), 23 (5):975-84; and Wallenius, V. et al., *Nat. Med.*, (2002), 8(1):75-9). Moreover, IL-6'@' deficient mice in a fashion similar to leptin deficient mice develop obesity (Laviano, A. et al., *Nutrition*, (2002), 18 (1):100-5). While leptin has been shown to be associated with cachexia, leptin levels are not elevated in many cancer-associated wasting conditions (Doehner, W. et al., *Eur. J. Endocrinol.*, (2001), 145(6): 727-35), most likely due to a systemic decline in adipose tissue. Cachexia seen in chronic heart failure patients, however, is associated with hyperleptinemia (Nagaya, N. et al., *Circulation*, (2001), 104 (12):1430-5). In contrast, ghrelin attenuates cachexia associated with chronic heart failure in rats (Van den Berghe, G. et al., *J. Clin. Endocrinol. Metab.*, (1999), 84 (4):1311-23) and the GHS-R analogue, GHRP-2, counteracts protein hypercatabolism, skeletal muscle proteolysis, and osteoporosis in critically ill patients with wasting condition (Sarna, V. et al., *J. Clin. Invest.*, (2003), 111

(2):241-50). Furthermore, increased levels of circulating leptin within a murine multiple sclerosis (MS) model regulate inflammatory anorexia and disease susceptibility (Sun, Y. et al. *Mol. Cell. Biol.*, (2003), 23:7973-81). Fasting induced suppression of leptin levels dramatically attenuates the onset of EAE in this model (Sun, Y. et al., *Mol. Cell Biol.*, (2003), 23 (22):7973-81). Not only is fasting associated with a decrease in serum leptin and a strong increase in circulating ghrelin levels (Cummings, D. E. et al., N. E. *J. Med.*, (2002), 346 (21):1623-30; and Inui, A., *Nat. Rev. Neurosci.*, (2001), 2(8): 551-60), the observed anti-inflammatory effects of fasting in this murine MS model are also mediated by ghrelin. Given that regulation of hunger is most critical for the survival of species, a complex circuitry of compensatory mechanisms has evolved to protect against lack of one or more of these regulators.

Ghrelin inhibits pro-inflammatory cytokine production, mononuclear cell binding and nuclear factor-κβ activation in human endothelial cells in vitro and endotoxin-induced cytokine production in vivo (Li, W. G. et al., *Circulation*, (2004), 109(18):2221-6). Ghrelin functions as a vital counter-regulatory signal in the immune system controlling not only activation-induced cytokine expression, but also leptin-induced expression of these same inflammatory mediators. The reciprocal regulatory effects of these hormones on expression of IL-1β; IL-6 and TNF-α by immune cells has widespread implications in the development of wasting diseases, aging and frailty.

Proposed interventions to lower ghrelin levels or blocking GHS-R for treatment of obesity can result in a potentiation of ongoing inflammatory insults or lead to immune disregulation. On the contrary, the novel anti-inflammatory actions of ghrelin within the immune system have benefits in management of anorexia-cachexia syndrome associated with a wide range of inflammatory conditions and cancer.

10. Chemokines

Many molecules have been identified that are necessary for the recruitment of monocytes and other inflammatory cell types to sites of injury or insult. These molecules represent targets for the inhibition of monocytes recruitment. One class of such molecules includes inflammatory mediators, chemokines, e.g., monocytes chemoattractant protein-1 (MCP-1). As a result, agents which modulate the activity of chemokines are likely to be useful to prevent and treat a wide range of diseases. Recent studies suggest that MCP-1(Δ2-8) exhibits a dominant negative effect, i.e., it forms heterodimers with wild-type MCP-1 that cannot elicit a biological effect (Zhang, Y. and Rollins, B. J., *Mol. Cell. Biol.*, (1995), 15 (9):4851-5). MCP-1(Δ2-8), thus, does not exhibit properties of a classic receptor antagonist. Moreover, MCP-1(Δ2-8) is unlikely to be widely useful for inhibition of MCP-1 activity in vivo, as MCP-1(Δ2-8) is a large polypeptide with undesirable pharmacodynamic properties. Furthermore, it is unknown whether MCP-1(Δ2-8) is active as dominant-negative inhibitor of other chemokines associated with inflammation. Therefore, there is a need to identify agents that inhibit chemokine-induced macrophage and/or monocyte recruitment and which have desirable pharmacodynamic properties. Moreover, there is a need to identify agents that inhibit chemokine-induced activities of other cell types, such as lymphocytes, neutrophils or eosinophils. Further, there is a need to identify agents that are pan-selective chemokine inhibitors.

D. Synthesis of the Selected Ghrelin Analogues

The ghrelin analogues and compounds of the invention can be produced using the techniques disclosed in the examples herein as well as techniques that are well known in the art. For example, a polypeptide region of a ghrelin analogue can be chemically or biochemically synthesized and modified. Examples of techniques for biochemical synthesis involving the introduction of a nucleic acid into a cell and expression of nucleic acids are provided in Ausubel, Current Protocols in Molecular Biology, John Wiley, 1987-1998 and Sambrook et al., in Molecular Cloning, A Laboratory Manual, $2^{nd}$ Edition, Cold Spring Harbor Laboratory Press, 1989. Techniques for chemical synthesis of polypeptides are also well known in the art (See e.g., Vincent in Peptide and Protein Drug Delivery, New York, N.Y., Dekker, 1990). For example, the peptides of this invention can be prepared by standard solid phase peptide synthesis (See, e.g., Stewart, J. M., et al., Solid Phase Synthesis, Pierce Chemical Co., 2d ed., 1984).

The substituents $R^2$ and $R^3$ of the above generic formula may be attached to the free amine of the N-terminal amino acid by standard methods known in the art. For example, alkyl groups, e.g., ($C_1$-$C_{30}$)alkyl, may be attached using reductive alkylation. Hydroxyalkyl groups, e.g., ($C_1$-$C_{30}$)hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for 1 hour. If the free acid contains a free hydroxy group, e.g., p-hydroxyphenylpropionic acid, then the coupling should be performed with an additional 3 molar equivalents of HOBT.

When $R^1$ is NH—$X^2$—$CH_2$—$CONH_2$, (i.e., $Z^0$=$CONH_2$), the synthesis of the peptide starts with Fmoc-HN—$X^2$—$CH_2$—COOH coupled to a Rink Amide-MBHA resin (Amide-4-methylbenzylhydryl amine obtained from Novabiochem®, San Diego, Calif., U.S.A.). If $R^1$ is NH—$X^2$—$CH_2$—COOH (i.e., $Z^0$—COOH) the synthesis of the peptide starts with Fmoc-HN—$X^2$—$CH_2$—COOH which is coupled to Wang resin. In the synthesis of a ghrelin analogue of this invention containing A5c, A6c and/or Aib, the coupling time is 2 hours for these residues and the residue immediately following them.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide and ethylamide.

Certain abbreviations used during the description of the synthesis of the representative examples that follow are defined as follows:

Ac: acyl group, i.e. $CH_3C(=O)$—
Boc: tert-butyloxycarbonyl
Bzl: benzyl
DCM: dichloromethane
DIC: N,N-diisopropylcarbodiimide
DIPEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF dimethylformamide
DNP: 2,4-dinitrophenyl
DTT: dithiothrietol
Fm: fluorenylmethyl
Fmoc: fluorenylmethyloxycarbonyl
For: formyl
HATU: O-(7-azabenzothiazol-1-yl)-N,N,N',N'-tetramethyluronium-hexafluorophosphate HBTU: 2-(1H-benzotriazole-1-yl)-1,1,3,3-tetramethyluronium Hexafluorophosphate
cHex: cyclohexyl
HOAT: O-(7-azabenzotriazol-1-yl)-1,1,3,3-tetramethyluronium hexafluorophosphate
HOBT: 1-hydroxy-benzotriazole hydrate
MBHA: 4-methylbenzhydrylamine
Mmt: 4-methoxytrityl
Mtt: N-e-4-methyltrityl
NMP: N-methylpyrrolidone
ODmab: 4{N-[1-(4,4-dimethyl-2,6-dioxo-cyclohexylidene)-3-methylbutyl]-amino}benzyloxy
O-tBu: oxy-tert-butyl
Pbf: 2,2,4,6,7-pentamethyldihydrobenzofuran-5-sulfonyl
PyAoP: 7-azabenzotriazol-1-yloxytris(pyrrolidino)phosphonium-hexafluorophosphate
PyBroP: bromo-tris-pyrrolidino-phosphonium hexafluorophosphate
tBu: tert-butyl
TIS: triisopropylsilane
TOS: tosyl
Trt: trityl
TFA: trifluoroacetic acid
TFFH: tramethylfluoroforamidinium hexafluorophosphate
Z: benzyloxycarbonyl Examples are provided below to further illustrate different features of the present invention. The examples also illustrate useful methodology for practicing the invention. These examples do not limit the claimed invention.

Synthesis of short amino acid sequences is well established in the peptide art. For example, synthesis of compounds according to formula I such as (Glu$^3$(O-hexyl))hGhrelin(1-28)-NH$_2$ (SEQ ID: 91), (Aib$^2$)hGhrelin(1-28)-NH$_2$ (SEQ ID: 15), (Glu$^3$(NH-hexyl))hGhrelin(1-28)-NH$_2$ (SEQ ID: 91) and (Cys$^3$(S-decyl))hGhrelin(1-28)-NH$_2$ (SEQ ID: 106) described above, can be achieved by following the protocol set forth in International Patent Publication WO04/009616 at pages 46 to 56 as follows:

1: (Glu$^3$(O-hexyl))hGhrelin(1-28)-NH$_2$ (Example #30) (SEQ ID: 91)

The titled peptide was synthesized on an model 433A peptide synthesizer (Applied Biosystems, Foster City, Calif., U.S.A.). 4-(2',4'-Dimethoxyphenyl-Fmoc-aminomethyl)-phenoxyacetamido-norleucyl-MBHA resin (Rink Amide MBHA® resin, Novabiochem, San Diego, Calif., U.S.A.) was used with a substitution of 0.72 mmol/g. The Fmoc amino acids (AnaSpec, San Jose, Calif., U.S.A.) were used with the following side chain protection: Fmoc-Arg(Pbf)-OH, Fmoc-Pro-OH, Fmoc-Gln-OH, Fmoc-Leu-OH, Fmoc-Lys(Boc)-OH, Fmoc-Ala-OH, Fmoc-Ser(tBu)-OH, Fmoc-Glu(OtBu)-OH, Fmoc-Val-OH, Fmoc-His(Trt)-OH, Fmoc-Phe-OH, and Fmoc-Asp(OtBu)-OH. Boc-Gly-OH (Midwest Bio-Tech, Fishers, Ind., U.S.A.) was used in the 1$^{st}$ position. N-α-Fmoc-L-glutamic acid γ-4-{N-(1-(4,4-dimethyl-2,6-dioxocyclohexylidene)-3-methylbutyl)-amino}benzyl ester (Fmoc-Glu(ODmab)-OH) (Chem-Inpex International, Wood Dale, Ill., U.S.A.) was used in the 3$^{rd}$ position. The synthesis was carried out on a 0.25 mmol scale. The Fmoc groups were removed by treatment with 20% piperidine in N-methylpyrrolidone (NMP) for 30 minutes. In each coupling step, the Fmoc amino acid (1 mmol) was first pre-activated with HBTU (0.9 mmol) and HOBt (0.9 mmol) in DMF and then added to the resin. The ABI 433A® peptide synthesizer was programmed to perform the following reaction cycle:

(1) washing with NMP;
(2) removing Fmoc protecting group with 20% piperidine in NMP for 30 minutes;
(3) washing with NMP; and
(4) coupling with pre-activated Fmoc amino acid for 1 hour.

At the end of assembly of the peptide chain on the Applied Biosystems (ABI) 433A® peptide synthesizer, the resin was transferred into a reaction vessel on a shaker for manual synthesis. The Dmab protecting group in the side chain of the Glu residue was removed with a solution of 2% hydrazine in DMF for two hours. After washing with DMF, the resin was treated with 2.5 mmol of tetramethylfluoroforamidinium hexafluorophosphate (TFFH) (Perspective Biosystems, Warrington, U.K.) in dichloromethane (DCM) for 25 minutes to convert the free carboxylic acid functional group in the side chain of the Glu residue to its acid fluoride. Thereafter, 5.0 mmol of hexanol, 2.5 mmol of O-(7-azabenzotriazol-1-yl)-1,1,3,3-tetramethyluronium hexafluorophosphate (HOAT) (Anaspec, San Jose, Calif., U.S.A.), 5.0 mmol of diisopropylethyl amine (DIEA) (Aldrich, Milwaukee, Wis., U.S.A.) and catalytic amount of 4-(dimethylamino)pyridine (DMAP) (Aldrich, Milwaukee, Wis., U.S.A.) were added sequentially, to the reaction vessel. The mixture was shaken at room temperature for 2 hours. The resin was washed with DMF and DCM and treated overnight with 2.5 mmol of N,N-diisopropylcarbodiimide (DIC)(Chem-Impex International, Wood Dale, Ill., U.S.A.), 2.5 mmol of 1-hexanol, 2.5 mmol of HOBt, and 0.025 mmol of DMAP. After washing and drying, the peptide was cleaved off from the resin by using a mixture of TFA (9.5 mL), H$_2$O (0.85 mL) and triisopropylsilane (TIS) (0.85 mL) for 2 hours. The resin was filtered off and the filtrate was poured into 70 mL of ether. The precipitate formed was filtered off and washed thoroughly with ether. This crude product was dissolved into 5% acetic acid and purified on a reverse-phase preparative HPLC using a column (4×43 cm) of C$_{18}$ DYNAMAX-100A°® (Varian, Walnut Creek, Calif., U.S.A.). The column was eluted with a linear gradient from 75% A and 25% B to 55% A and 45% B in an hour where A was 0.1% TFA in water and B was 0.1% TFA in acetonitrile. The fractions were checked by an analytical HPLC. Those containing pure product were combined and lyophilized to dryness.

The purity of the compound was 92.8%. Yield was 8.6%. Electro-spray ionization mass spectrometry (ESI MS) analysis gave a molecular weight for the product of 3369.4 (in agreement with the calculated molecular weight of 3369.9).

2: (Aib$^2$)hGhrelin(1-28)-NH$_2$ (Example #34) (SEQ ID: 15)

The titled peptide was synthesized according to the procedure described in Example 1 for the synthesis of (Glu$^3$(O-hexyl))hGhrelin(1-28)-NH$_2$, except as follows: Fmoc-Ser-OH was used at position 3, Fmoc-Aib-OH was used at the 2$^{nd}$ position and Boc-Gly-OH was used at the 1$^{st}$ position. After the peptide chain was assembled, the peptide-resin was treated with 25% piperidine in DMF three times with each treatment lasting 2 hours. The resin was then washed with DMF and treated with octanoic acid (2.5 mmol, 10 fold excess), HBTU (2.2 mmol), HOBt (2.2 mmol) and DIEA (7.5 mmol) in DMF for 2 hours. The resin was washed with DMF and then treated with octanoic acid (2.5 mmol), DIC (2.5 mmol), HOBt (2.5 mmol) and DMAP (0.025 mmol) in DMF for 2 hours. The final cleavage and purification procedures were the same as those in Example 1.

The product was found to be homogenous by analytical HPLC, with a purity of 99% in 18.5% yield. Electro-spray ionization mass spectrometry (ESI MS) analysis gave a molecular weight for the product of 3367.6 (in agreement with the calculated molecular weight of 3367.0).

3: (Glu$^3$(NH-hexyl))hGhrelin(1-28)-NH$_2$ (Example #85) (SEQ ID: 91)

The titled peptide was synthesized on a model 430A peptide synthesizer (Applied Biosystems, Foster City, Calif., U.S.A.) which was modified to do accelerated Boc-chemistry solid phase peptide synthesis (Schnolzer, M. et al., *Int. J. Peptide Protein Res.*, (1992), 40:180). 4-Methylbenzhydrylamine (MBHA) resin (Peninsula, Belmont, Calif., U.S.A.), with a substitution of 0.91 mmol/g was used. Boc amino acids (Midwest Bio-Tech, Fishers, Ind., U.S.A.; Novabiochem., San Diego, Calif., U.S.A.) were used with the following side chain protection: Boc-Ala-OH, Boc-Arg(Tos)-OH, Boc-His (DNP)-OH, Boc-Val-OH, Boc-Leu-OH, Boc-Gly-OH, Boc-Gln-OH, Boc-Lys(2ClZ)-OH, Boc-Ser(Bzl)-OH, Boc-Phe-OH, Boc-Glu(OcHex)-OH and Boc-Pro-OH. Fmoc-Glu (OtBu)-OH (Novabiochem, San Diego, Calif., U.S.A.) was used for the residue at the 3$^{rd}$ position in the sequence. The synthesis was carried out on a 0.25 mmol scale. The Boc groups were removed by two treatments with 100% TFA each lasting one minute. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 minutes. At the end of the assembly of the first 25 residues on the ABI 430A® peptide synthesizer and before the coupling of Fmoc-Glu (OtBu)-OH, the protected peptide-resin was transferred into a reaction vessel on a shaker for manual synthesis. After removing the Boc protecting group with two, one-minute treatments with 100% TFA and a washing with DMF, the resin was mixed with Fmoc-Glu(OtBu)-OH (2.5 mmol) which was pre-activated with HBTU (2.0 mmol), HOBt (2.0 mmol) and DIEA (1.0 mL) in 4 mL of DMF. The mixture was shaken for 2 hours. This coupling step was repeated. After washing with DMF, the resin was treated with a TFA solution containing 5% water and 5% TIS for 2 hours to remove the tBu protecting group in the side chain of the Glu residue. The resin was neutralized with 10% DIEA in DMF and washed with DMF and DCM. The resin was then treated twice with hexylamine (2.0 mmol), DIC (2.0 mmol), HOBt (2.0 mmol) in 5 ml of DCM for two hours per treatment. The resin was washed with DMF and treated with 25% piperidine in DMF for 30 minutes to remove the Fmoc protecting group. After washing with DMF and DCM, the resin was transferred into the reaction vessel on the ABI 430A peptide synthesizer for the assembly of the rest two residues.

At the end of the assembly of the whole peptide chain, the resin was treated with a solution of 20% mercaptoethanol/10% DIEA in DMF for 2×30 min to remove the DNP group on the His side chain. The N-terminal Boc group was then removed by two treatments of 100% TFA for 2 minutes. The peptide-resin was washed with DMF and DCM and dried under reduced pressure. The final cleavage was done by stirring the peptide-resin in 10 mL of HF containing 1 mL of anisole and dithiothreitol (50 mg) at 0° C. for 75 minutes. HF was removed by a flow of nitrogen. The residue was washed with ether (6×10 mL) and extracted with 4N HOAc (6×10 mL). This crude product was purified on a reverse-phase preparative HPLC using a column (4×43 cm) of C$_{18}$ DYNAMAX-100A°® (Varian, Walnut Creek, Calif., U.S.A.). The column was eluted with a linear gradient from 75% A and 25% B to 55% A and 45% B at flow rate of 10 mL/min in an hour where A was 0.1% TFA in water and B was 0.1% TFA in acetonitrile. Fractions were collected and checked on an analytical HPLC. Those containing pure product were combined and lyophilized to dryness. 31.8 mg of a white solid was obtained.

Purity was 89% based on analytical HPLC analysis. Electro-spray ionization mass spectrometry (ESI MS) analysis gave the molecular weight at 3368.4 (in agreement with the calculated molecular weight of 3368.9).

4: (Cys$^3$(S-decyl))hGhrelin(1-28)-NH$_2$ (Example #70) (SEQ ID: 106)

The titled peptide was synthesized according to the procedure described in Example 3 for the synthesis of (Glu$^3$(NH-Hexyl))hGhrelin(1-28)-NH$_2$ (SEQ ID: 91) with the following modifications: After the assembly of the first 25 residues using Boc chemistry, the last 3 residues were assembled by employing Fmoc chemistry. The following 3 Fmoc amino acids were used: N-α-Fmoc-S-(p-methoxytrityl)-L-cysteine (Fmoc-Cys(Mmt)-OH), Fmoc-Ser(Bzl)-OH and Fmoc-Gly-OH (Novabiochem, San Diego, Calif., U.S.A.). The Fmoc amino acid (1 mmol) was first pre-activated with HBTU (0.9 mmol) and HOBt (0.9 mmol) in DMF before it was coupled to the peptide-resin. The synthesis cycle for the Fmoc amino acids included:

(1) washing with NMP
(2) removing Fmoc protecting group with 20% piperidine in NMP for 30 minutes;
(3) washing with NMP; and
(4) coupling with pre-activated Fmoc amino acid for 1 hour.

At the end of the assembly of the entire peptide chain, the protected peptide-resin was treated twice with a solution of 20% mercaptoethanol and 10% DIEA in DMF for 30 minutes to remove the DNP group on the side-chain of the His residue. The Mmt protecting group in the side-chain of the Cys residue was then removed by using a solution of 1% TFA and 5% TIS in DCM for 30 minutes and the peptide-resin was washed with DMF.

A solution of 1-(2-pyridyldithio)decane was prepared by stirring 2,2'-dipyridyl disulfide (1.06 g, 4.8 mmol), 1-decanethiol (0.83 mL, 4 mmol) and triethylamine (2 mL) in propanol and acetonitrile (1/9, v/v) at room temperature for about 3 hours (Carlsson, J. et al., *Biochem. J.*, (1978), 173 (3):723-37). Purification of the crude 1-(2-pyridyldithio)decane was performed using flash chromatography, eluting with a mixed solvent system of DCM/MeOH (10:0.4).

The peptide-resin from 2$^{nd}$ step (i.e., removal of the DNP group on the side chain of His and the Mmt protecting group on the side chain of Cys) was treated with the 1-(2-pyridyldithio)decane from the 3$^{rd}$ step and DIEA (3 eq., 0.75 mmol) overnight in a mixed solvent system of DMF/1-propanol (7:3). The resin was then washed with DMF and the N-terminal Fmoc protecting group was removed by treatment with 25% piperidine in DMF for 30 minutes. The peptide-resin was then washed with DMF and DCM and dried under reduced pressure.

Final cleavage was performed by stirring the peptide-resin in 10 mL of HF containing 1 mL anisole at about 0° C. for about 70 minutes. The purification procedure was the same as that described in Example 3.

The target product (yield 10.2%) was found by analytical HPLC to have a purity of 99.9%. Electro-spray ionization mass spectrometry (ESI-MS) analysis gave the molecular weight at 3432.1 (in agreement with the calculated molecular weight of 3432.1).

Other peptides of the invention can be prepared by a person of ordinary skill in the art using synthetic procedures analogous to those disclosed generally hereinabove in using the protocols set forth in International Patent Publication WO04/

009616. Other peptides of the invention can be prepared by a person of ordinary skill in the art using synthetic procedures analogous to those disclosed generally hereinabove.

The synthesis of peptidyl analogues according to formula II, such as H-Inp-D-Bal-D-Trp-Phe-Apc-NH$_2$ (SEQ ID: 2), H-Inp-D-2-Nal-D-Trp(Ψ)-Pim (SEQ ID: 149) and H-Inp-D-Trp-D-2-Nal(Ψ)Pim (SEQ ID: 127) can be achieved by following the protocol set forth in International Patent Publication WO04/014415 at pages 33-44 as follows:

5: H-Apc-D-1-Nal-D-1-Nal-Phe-Apc-NH$_2$ (Example #83) (SEQ ID: 155)

Each of the reaction wells contained 0.0675 mmol of Rink Amide MBHA® resin (substitution=0.72 mmol/g, Novabiochem, San Diego, Calif., U.S.A.). The following Fmoc amino acids (Novabiochem, San Diego, Calif., U.S.A.; Chem-Impex International, Wood Dale, Ill., U.S.A.; SyntheTech, Albany, Oreg., U.S.A.; Pharma Core, High Point, N.C., U.S.A.) were used: Fmoc-Lys(Boc)-OH, Fmoc-Phe-OH, Fmoc-H-Inp-OH, Fmoc-D-1-Nal-OH, Fmoc-D-2-Nal-OH, Fmoc-D-Trp(Boc)-OH, Fmoc-3-Pal-OH, Fmoc-4-Pal-OH, Fmoc-Orn(Boc)-OH, Fmoc-D-Bip-OH, Fmoc-Thr(Bzl)-OH, Fmoc-Pff-OH, Fmoc-2-Thi-OH, Fmoc-Taz-OH, Fmoc-D-Dip-OH, Fmoc-D-Bpa-OH, Fmoc-D-Bal-OH, and Fmoc-Apc(Boc)-OH.

Each of the Fmoc amino acids was dissolved in a 0.3 N solution of HOBt in DMF wherein the concentration of the resulting Fmoc amino acid was 0.3 N. A four fold excess (0.27 mmol, 0.9 mL of the 0.3 N solution) of Fmoc amino acid was used for each coupling. DIC (0.27 mmol, 0.6 mL of 0.45N DIC solution in DMF) was used as the coupling reagent for each coupling. Deprotection was performed by using 20% piperidine in DMF (2×1.5 mL per residue).

The peptides were cleaved from the resin by treating the peptide-resins with 8% triisopropylsilane (TIP) in trifluoroacetic acid (TFA) (1.5 mL per reaction well) at room temperature for 2 hours. The resin was removed by filtration. Each filtrate was diluted to 25 mL with ether in a centrifuge tube. The resulting precipitate in each tube was centrifuged and the solvents were decanted from the precipitate. The precipitate in each tube was then dissolved in methanol (3 mL) and diluted with water (1 mL). The purification of the crude products was done on a reverse-phase preparative HPLC using a column (100×21.20 mm, 5μ) of LUNA 5μ C8(2)® (Phenomenex, Torrance, calif., U.S.A.). For each peptide, the column was eluted with a linear gradient from 85% A and 15% B to 25% A and 75% B in 15 minutes with a flow rate of 25 mL/min. A was 0.1% TFA in water and B was 0.1% TFA in acetonitrile/water (80/20, v/v). The fractions were checked by analytical HPLC and those containing the pure product were combined and lyophilized to dryness.

Yields ranged from 13% to 71% and purity of each of Examples 1-65 exceeded 94% based upon analytical HPLC analysis. Electro-spray ionization mass spectrometry (ES-MS) analysis was performed and observed molecular weights were in agreement with calculated molecular weights.

6: H-Inp-D-2-Nal-D-Trp(W)-Pim (Example #122) (SEQ ID: 149)

A solution of BOC-(D)-Trp-OH (4.0 g, 13.1 mmole) (Novabiochem, San Diego, Calif., U.S.A.) in methanol (36 ml) and a solution of Cs$_2$CO$_3$ (2.14 g, 6.57 mmole) in water (10 ml) were combined and the resulting mixture was swirled until a homogeneous mixture was obtained. Solvents were removed in vacuo and the residue was dissolved in DMF (45 ml). 2-bromoacetophenone (2.61 g, 13.1 mmole) in DMF (9 ml) was added to the solution and the solution was stirred for 30 minutes at room temperature. Cesium bromide was removed by filtration and the filtrate was concentrated in vacuo. The resulting concentrate was dissolved in xylenes (45 ml), NH$_4$OAc (17.1 g) was added and the solution was heated at reflux for one hour. The cooled solution was washed two times with saturated NaHCO$_3$ solution (45 ml) and then with saturated NaCl. The resulting organic layer was purified by flash chromatography to yield 4.1 g (77%) of intermediate 1A depicted in Scheme 1A, ("Compound 1A").

Scheme 1A

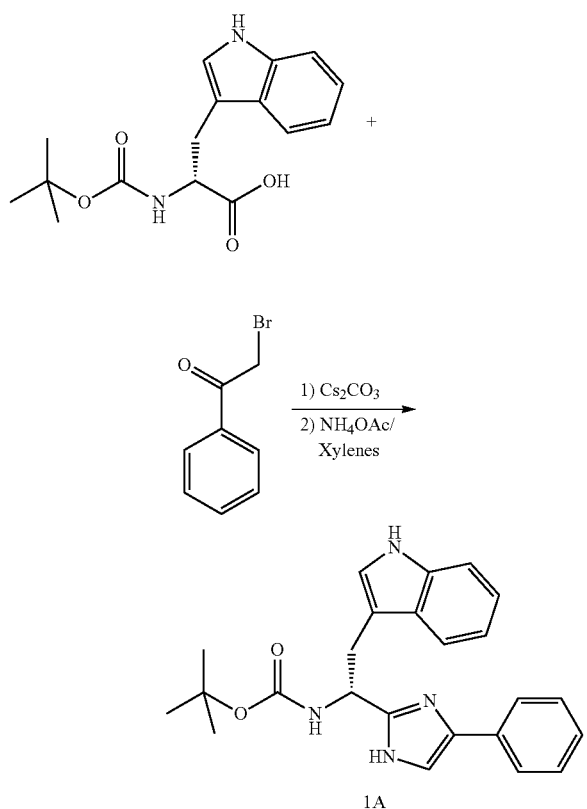

Compound 1A (403 mg) was de-blocked using a mixture of trifluoroacetic acid (TFA) (8 ml) dichloromethane (DCM) (8 ml) and triisopropylsilane (TIPS) (1.4 ml). After mixing for one hour the solution was concentrated under a stream of nitrogen. The residue was dissolved in DCM (40 ml), washed two times with a saturated solution of NaHCO$_3$ (40 ml) and then dried over Na$_2$SO$_4$ to yield a solution of the intermediate product 1B, depicted in Scheme 1B, below.

Scheme 1B

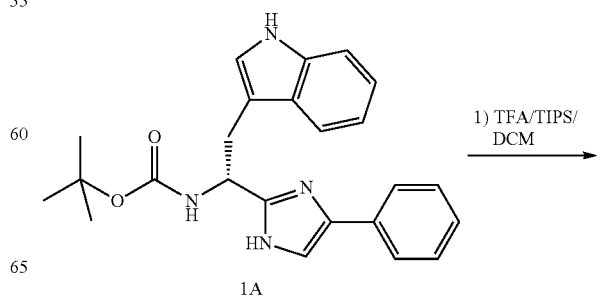

-continued

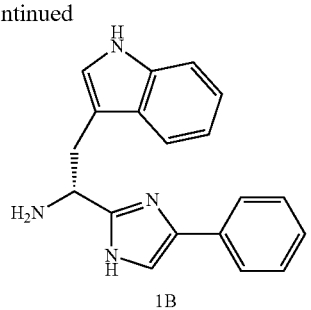

1B

The forgoing solution of the intermediate product 1B was divided into four equal portions and coupled with the pre-activated HOBT esters of FMOC protected amino acids, as summarized in reaction schemes 1C, 1D, 1E, and 1F, below. The amino acid used: FMOC-D-2Nal-OH (130 mg, 0.30 mmole) (Synthetech, Albany, Oreg., U.S.A.).

Each of the immediately foregoing amino acids was pre-activated with HOBT (46 mg, 0.30 mmole) and DIC (38 mg, 0.30 mmole) in DCM (5 ml) for ten minutes before addition to one of the four portions of the forgoing solution of the intermediate product 1B. The coupling reaction was then allowed to proceed for 30 minutes at room temperature.

Scheme 1C

Scheme 1D

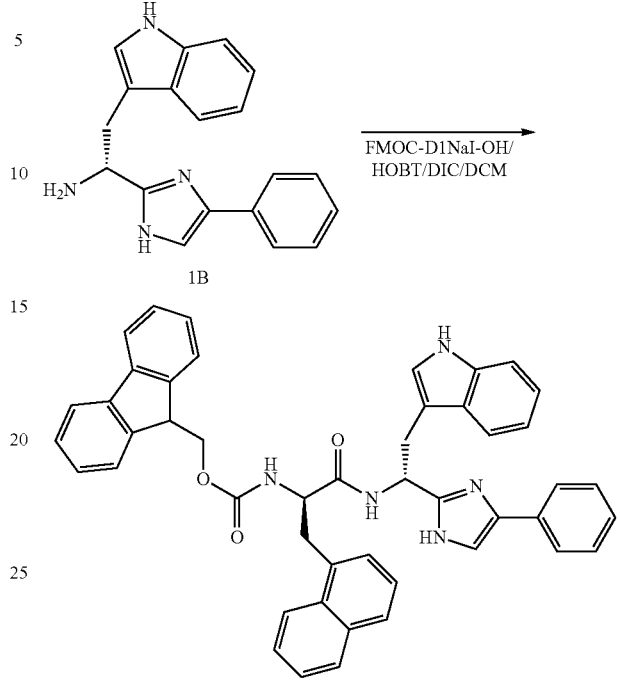

Scheme 1E

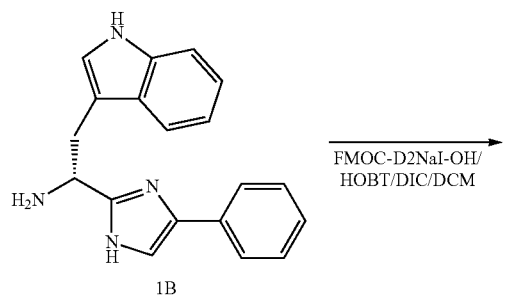

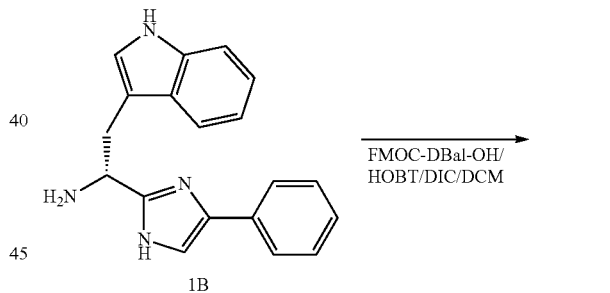

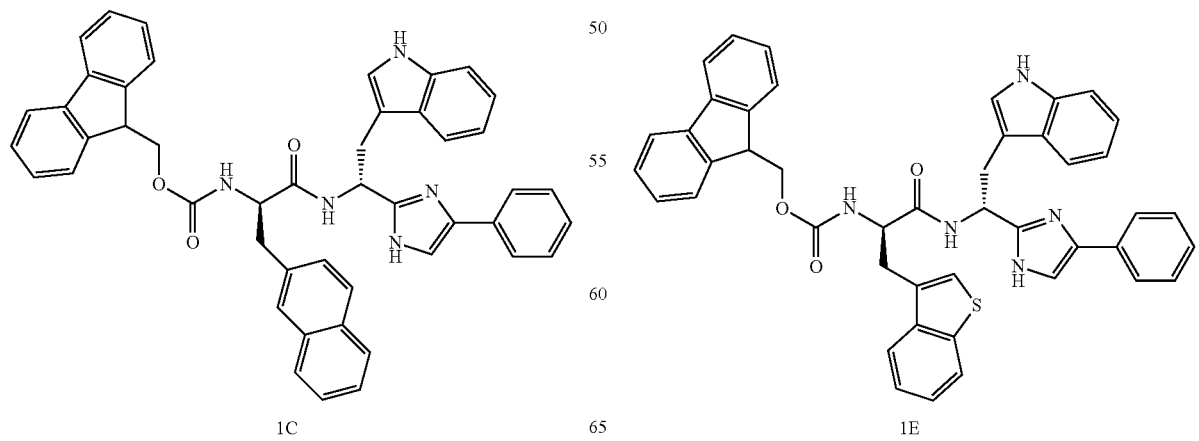

Scheme 1F

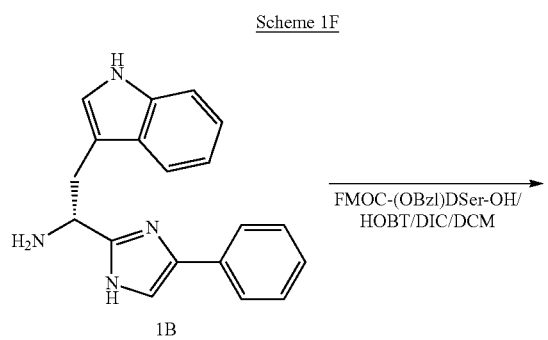

1B

FMOC-(OBzl)DSer-OH/
HOBT/DIC/DCM →

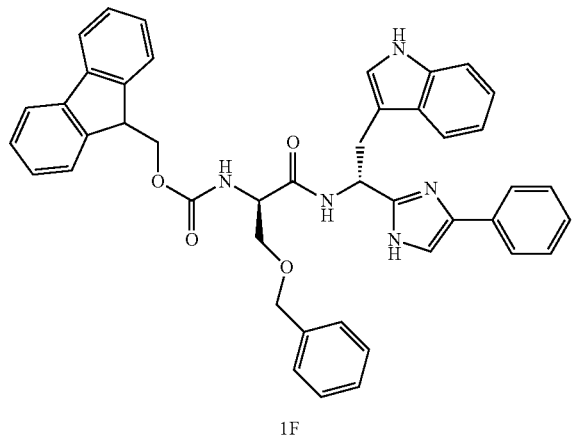

1F

The FMOC group is removed from each of the resulting compounds 1C, 1D, 1E and 1F by addition of tris(2-aminoethyl)amine (0.9 ml) to the respective reaction mixtures from the previous step and mixing for 30 minutes at room temperature. The reaction mixtures containing the de-blocked compounds were then washed three times with 10% pH 5.5 phosphate buffer (10 ml).

The resulting free amine solutions were coupled with pre-activated HOBT esters of FMOC-Inp-OH (105 mg, 0.30 mmole) (Chem Impex, Wood Dale, Ill., U.S.A.) and was pre-activated with HOBT (46 mg, 0.30 mmole) and DIC (38 mg, 0.30 mmole) in DCM (5 ml) for ten minutes before addition to the appropriate de-protected amine. The coupling reaction was then allowed to proceed for one hour at room temperature.

The FMOC group was removed from the resulting FMOC-protected compounds by addition of tris(2-aminoethyl)amine (0.9 ml) and mixing for 30 minutes. The de-blocked compounds were washed three times with 10% pH 5.5 phosphate buffer (10 ml) and the crude products were collected as a precipitate. The BOC-protected compounds were purified by flash chromatography and then de-blocked for one hour with TIPS (0.50 ml), TFA (0.50 ml), in DCM (2.75 ml). The crude products were then concentrated and dried under vacuum.

The foregoing de-protection, coupling, and de-protection steps are summarized in reaction schemes 1G, 1H, 1I and 1J, below

Scheme 1G

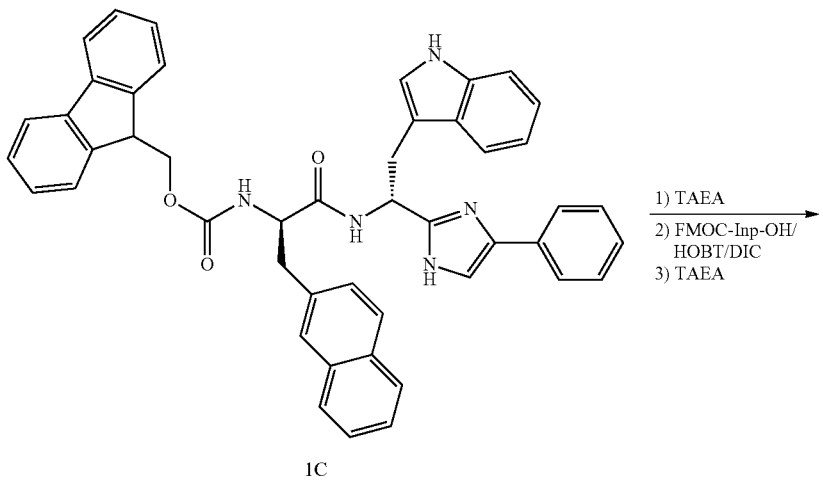

1C

1) TAEA
2) FMOC-Inp-OH/
   HOBT/DIC
3) TAEA

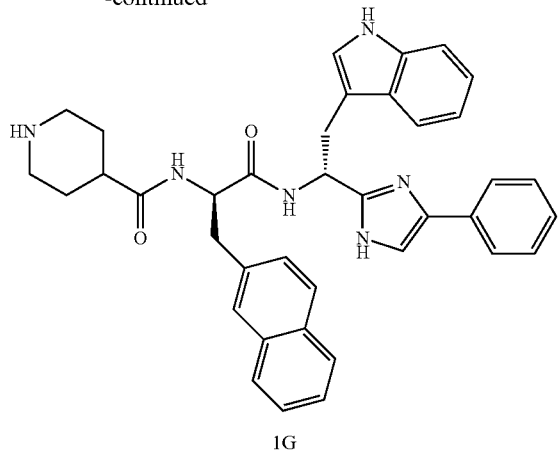
1G
Scheme 1H
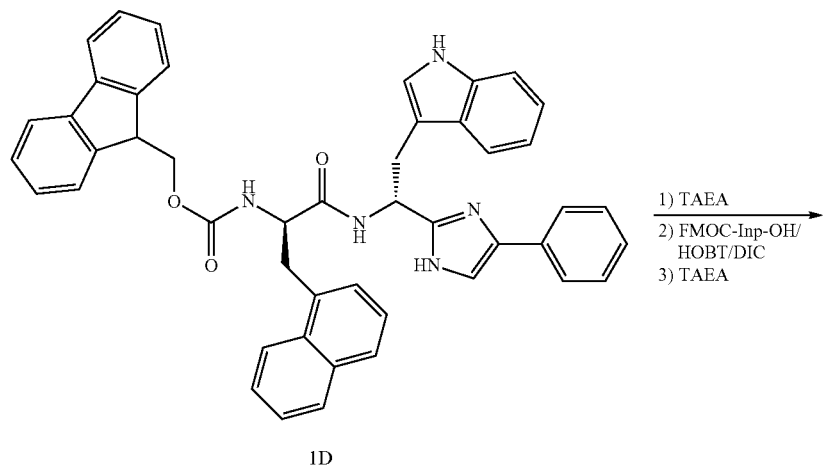
1D
1) TAEA
2) FMOC-Inp-OH/ HOBT/DIC
3) TAEA
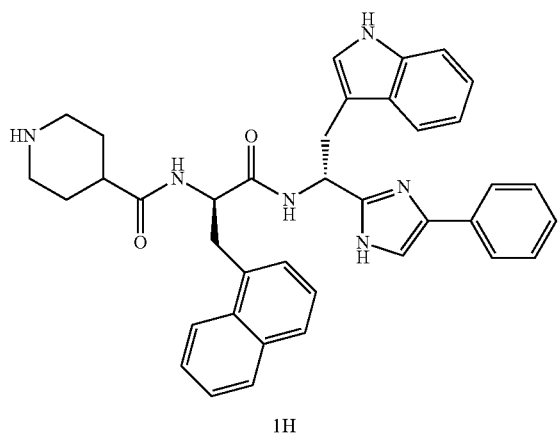
1H Scheme 1I
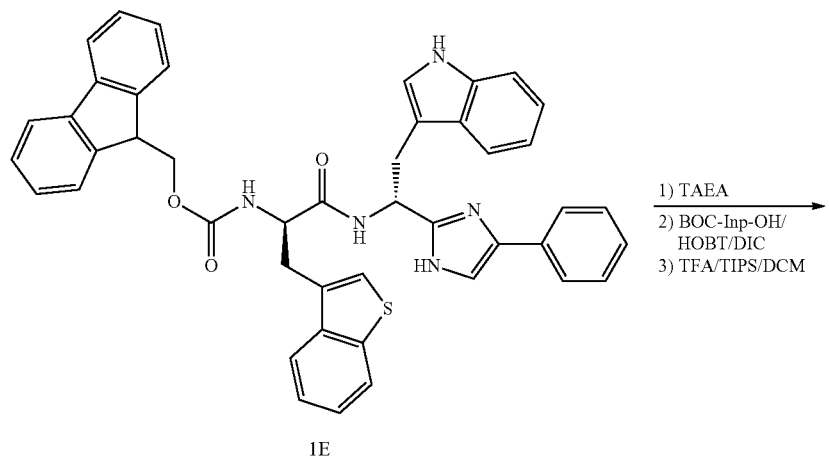
1E
1) TAEA
2) BOC-Inp-OH/ HOBT/DIC
3) TFA/TIPS/DCM
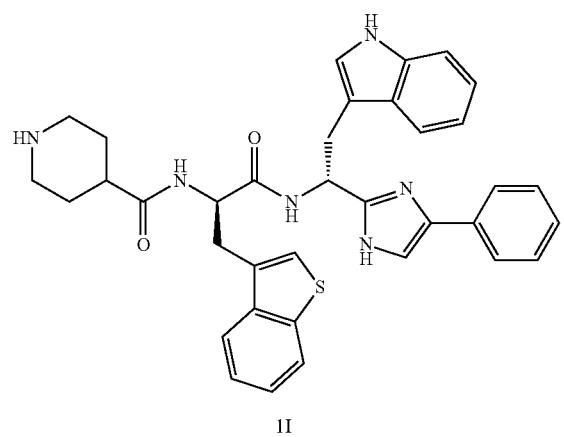
1I
Scheme 1J
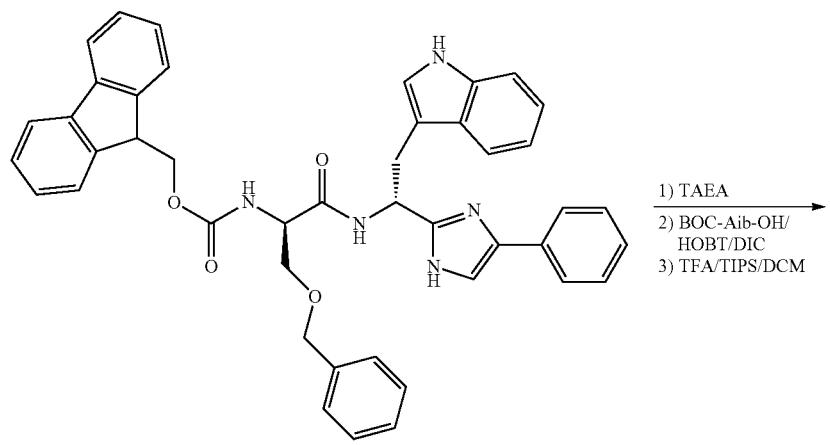
1F
1) TAEA
2) BOC-Aib-OH/ HOBT/DIC
3) TFA/TIPS/DCM

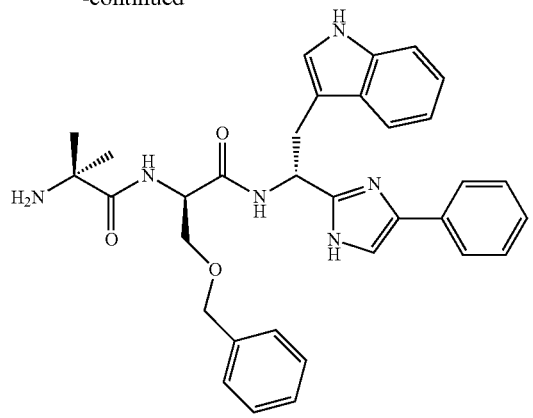

1J

7: H-Inp-D-Trp-D-2-Nal(Ψ)-Pim (Example #124) (SEQ ID: 127)

Compound 2A was made in an analogous manner as was Compound 1A, using BOC-D-2-Nal-OH and 2-bromoacetophenone as starting materials.

Steps 2.a.1. and 2.a.2. are summarized in Scheme 2A, below.

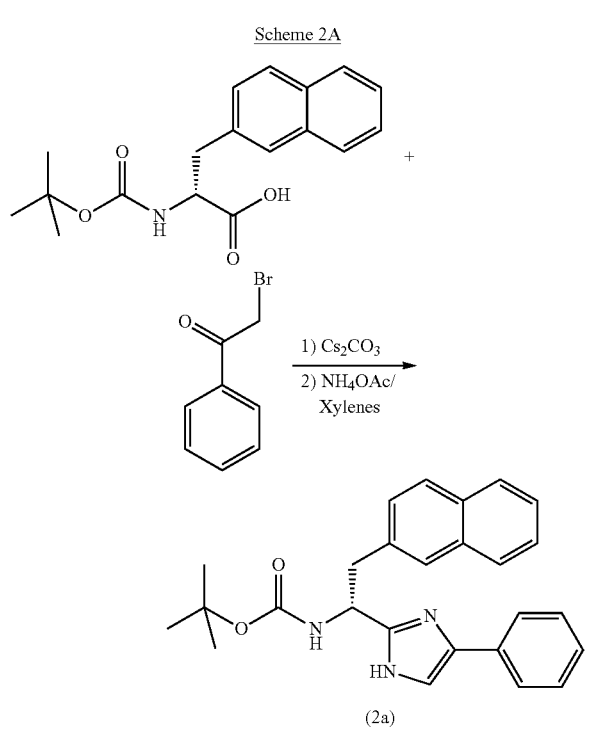

2.b.1. Compound 2A (100 mg, 0.242 mmole) was de-blocked in TFA (2 ml) and DCM (2 ml) for one hour. Volatiles were then removed under a stream of nitrogen and the residue was dissolved in DCM (10 ml). The resulting solution washed three times with saturated NaHCO₃ (10 ml) to yield a solution of Compound 2A in free amine form.

2.b.2. The active ester of FMOC-D-Trp-(BOC)-OH (153 mg, 0.290 mmole) was preformed with N-hydroxysuccinimide (HOSu; 33 mg, 0.290 mmole) and DIC (37 mg, 0.290 mmole) in DCM (1.5 ml). After one hour, diisopropylurea was removed by filtration and the filtrate was added to the Compound 2A (free amine) solution. The resulting solution was diluted with DCM to 4 ml and the coupling reaction allowed to proceed for 30 minutes.

Steps 2.b.1. and 2.b.2. are summarized in Scheme 2B, below.

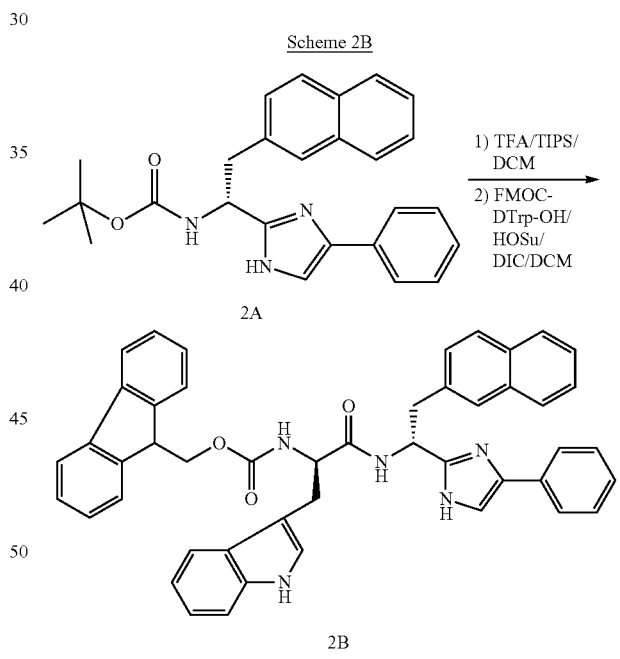

2.c.1 Compound 2B was de-blocked by addition of tris(2-aminoethyl)amine (TAEA) (0.9 ml) to the immediately foregoing coupling reaction solution and mixing for 30 minutes at room temperature. The reaction solution was then washed three times with saturated NaCl solution (10 ml) followed by three times with 10% pH 5.5 phosphate buffer (10 ml) to yield a solution of Compound 2B in free amine form.

2.c.2. The active ester of BOC-Inp-OH (66.5 mg, 0.290 mmole) was preformed with HOSu (33 mg, 0.290 mmole) and DIC (37 mg 0.290 mmole) in DCM (1.5 ml). After one hour diisopropylurea was removed by filtration and the filtrate was added to the Compound 2B (free amine) solution.

The resulting solution was diluted with DCM to 4 ml and the coupling reaction was allowed to proceed for 12 hours.

The reaction mixture was then washed three times with 10% pH 5.5 phosphate buffer (10 ml) and dried over $Na_2SO_4$. Solvent was removed under vacuum and the concentrate was purified by flash chromatography.

2.c.3. The intermediate was de-blocked using TFA (2.75 ml) and TIPS (0.5 ml) in DCM (2.75 ml) for 30 minutes. Volatiles were removed from the reaction mixture under a stream of nitrogen and the residue was triturated with ether (15 ml). After centrifugation the ether was decanted and the resulting solid was subjected to HPLC to yield purified Compound 70 in 39% yield.

Steps 2.c.1. and 2.c.2. and 2.c.3. are summarized in Scheme 2C, below.

OH, Fmoc-His(Trt)-OH, Fmoc-Leu-OH, Fmoc-Lys(Boc)-OH, Fmoc-Phe-OH, Fmoc-Pro-OH, Fmoc-Ser(tBu)-OH and Fmoc-Val-OH. In addition, Fmoc-Glu(O-2-PhiPr)-OH (Novabiochem, San Diego, Calif., U.S.A.) was used for the amino acids in $3^{rd}$ and $17^{th}$ positions. The synthesis was carried out on a 0.1 mmol scale. The Fmoc groups were removed by treating the resin with a solution of 20% piperidine in N-methylpyrrolidone (NMP) for a period of approximately 30 minutes. In each coupling step, the Fmoc amino acid (3 eq, 0.3 mmol) was first pre-activated in 2 mL solution of 0.45M 2-(1-H-benzotriazole-1-yl)-1,1,2,3-tetramethyluronium-hexafluorophosphate/1-hydroxy-benzotriazole (HBTU/HOBT) in NMP. A solution containing the activated amino acid ester together with 1 mL of diisopropylethylamine

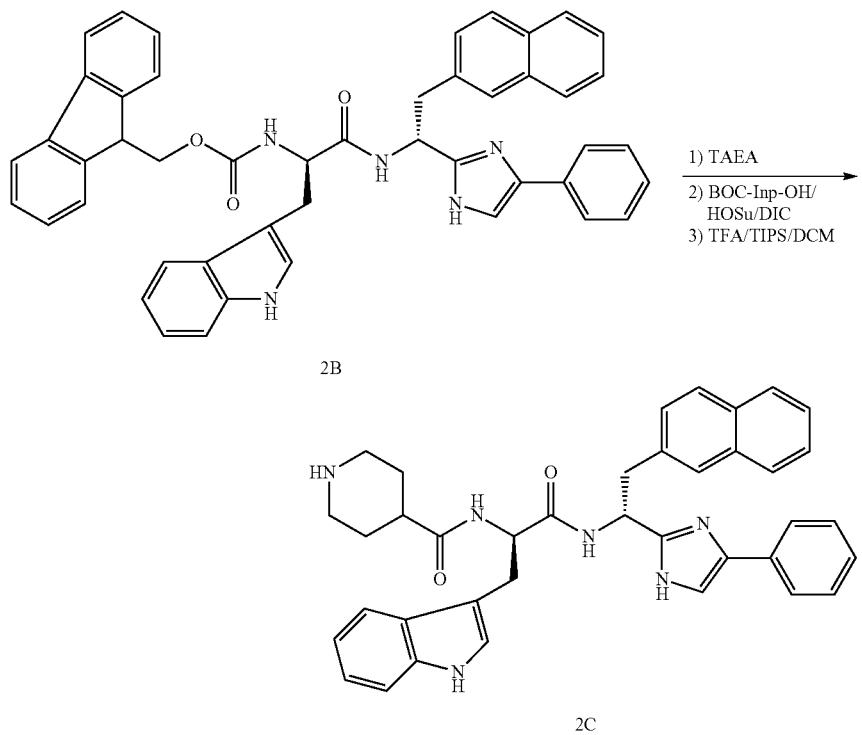

Scheme 2C (DIEA) and 1 mL of NMP was introduced to the resin. The ABI 433A® peptide synthesizer was programmed to perform the following reaction cycle:

(1) washing with NMP;
(2) removing Fmoc protecting group with 20% piperidine in NMP for 30 minutes;
(3) washing with NMP; and
(4) coupling with pre-activated Fmoc amino acid for approximately 1 or 3 hours.

The resin was coupled successively according to the sequence of the title peptide. After the peptide chain was assembled, the resin was washed completely with N,N-dimethylformamide (DMF) and dichloromethane (DCM).

At the end of the assembly of the peptide chain on the ABI 433A® peptide synthesizer (without the Fmoc-Aib residue in $A^1$), the peptide-resin was transferred to a reaction vessel on a shaker and the Fmoc was removed using 25% piperidine in DMF for 30 minutes. The resin was then washed with DMF. The Fmoc-Aib-OH (0.4 mmole) was coupled using TFFH Additional examples for synthesizing compounds according to formula III, such as (Ac-Aib$^1$, Aib$^{2,10}$, Glu(NH-hexyl)$^{3,17}$)hGhrelin(1-28)-NH$_2$ (SEQ ID: 325) and (Aib$^{1,2,10}$, Glu(NH-hexyl)$^{3,17}$)hGhrelin(1-28)NH$_2$(SEQ ID: 259), are provided below to further illustrate different features of the present invention. The examples also illustrate useful methodology for practicing the invention. These examples do not limit the claimed invention.

8: (Ac-Aib$^1$, Aib$^{2,10}$, Glu(NH-hexyl)$^{3,17}$)hGhrelin(1-28)-NH$_2$ (SEQ ID: 325)

The title peptide was synthesized on an Applied Biosystems model 433A® peptide synthesizer (Applied Biosystems, Foster City, Calif., U.S.A.) using Fluorenylmethyloxycarbonyl (Fmoc) chemistry. A Rink Amide-4-methylbenzylhydrylamine (MBHA) resin (Novabiochem, San Diego, Calif., U.S.A.) with substitution of 0.64 mmol/g was employed. The Fmoc amino acids (AnaSpec, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-

(Tetramethylfluoroformamidinium Hexafluorophosphate) (Perceptive Biosystems, Warrington, U.K.) (0.4 mmole), HOAt (0.4 mmol), DMAP (Dimethylaminopyridine) (0.1 g) and DIEA (1.2 mmole) once for 4 hours and once overnight.

The Fmoc group was removed as above and the peptide was capped using Ac$_2$O (acetic anhydride) (5 mmole) and DIEA (5 mmole) in DMF for approximately 30 minutes. The PhiPr (γ-2-phenylisopropyl ester) groups were removed from the Glu residues at A$^3$ and A$^{17}$ by washing with a solution of 3% TFA in DCM twice for a period of 10 minutes for each washing. The Boc that was partially removed from the side chain of Lysine was replaced by using Boc$_2$O (0.8 mmole) and DIEA (0.8 mmole) in DCM overnight. The resin was treated with PyAOP (7-Azabenzotriazol-1-yloxytris(pyrrolidino)phosphonium-hexafluorophosphate) (Applied Biosystems, Foster City, Calif., U.S.A.) (0.6 mmole), HOAt (0.6 mmole), DMAP (0.1 g) and DIEA (1.8 mmole) for 10 minutes. Hexyl-NH2(Hexylamine) (Sigma-Aldrich Chemicals, St. Louis, Mo., U.S.A.) (2.0 mmole) was then added to the resin solution which was then shaken and allowed to stand overnight.

To cleave the title peptide from the resin, the peptide-resin was treated with a mixture of TFA, H$_2$O and triisopropylsilane (TIS) (9.5 mL/0.85 mL/0.8 mL, respectively) for approximately 4 hours. The cleaved resin was filtered off and the remaining filtrate was poured into 200 mL of ether. A precipitate formed which was then collected by centrifugation. The crude product was dissolved in a mixture of acetonitrile and water which was purified on a reverse-phase preparative HPLC system with a column (4×43 cm) of C$_{18}$ DYNAMAX-100 A°® (Varian, Walnut Creek, Calif., U.S.A.). The column was eluted over approximately 1 hour using a linear gradient of 85% A:15% B to 60% A:40% B, where A was 0.1% TFA in water and B was 0.1% TFA in acetonitrile. The fractions were analyzed by HPLC and those fractions found to contain pure product were pooled and lyophilized to dryness.

Approximately 27.1 mg (6.3%) of a white solid was recovered which was assayed using HPLC and found to be approximately 97.5% pure. Electro-spray ionization mass spectrometry (ESI-MS) analysis determined the molecular weight to be 3477.4 which was in agreement with the calculated molecular weight of 3477.19.

9: (Aib$^{1,2,10}$, Glu(NH-hexyl)$^{3,17}$)hGhrelin(1-28)-NH$_2$ (SEQ ID: 259)

The titled peptide was synthesized according to the procedure described for Example 8, i.e., (Ac-Aib$^1$, Aib$^{2,10}$, Glu(NH-hexyl)$^{3,17}$)hGhrelin(1-28)-NH$_2$) (SEQ ID: 325), with the following exception: After coupling the last Fmoc-Aib-OH in the 1$^{st}$ position on a shaker, the PhiPr protecting groups were removed from the Glu residues at A$^3$ and A$^{17}$ by washing with a 3% TFA in DCM twice for intervals lasting approximately 10 minutes. The Boc that was partially removed from the side chain of Lysine was replaced using a solution of Boc$_2$O (0.8 mmole) and DIEA (0.8 mmole) in DCM. After being shaken and standing overnight, the resin was treated with a solution of PyAOP (7-Azabenzotriazol-1 yloxytris (pyrrolidino)phosphonium-hexafluorophosphate) (Applied Biosystems, Foster City, Calif., U.S.A.) (0.6 mmole), HOAt (0.6 mmole), DMAP (0.1 g) and DIEA (1.8 mmole) for 10 minutes after which hexyl-NH$_2$(hexylamine) (Sigma-Aldrich Chemicals, St. Louis, Mo., U.S.A.) (2.0 mmole) was then added to the solution which was then shaken and allowed to stand overnight. The Fmoc protecting group was then removed using 25% piperidine in DMF. The peptide was cleaved off from the resin and purified on a HPLC system, as detailed above.

Using an HPLC assay, the purity of the resulting produce was found to be approximately 96.5%. Electro-spray ionization mass spectrometry (ESI-MS) analysis determined the molecular weight to 3435.00 which was in agreement with the calculated molecular weight of 3435.16.

The synthesis of peptidyl analogues according to formula IV, such as Ac(1-Apc$^1$, Aib$^{2,10}$, Glu(NH-hexyl)$^3$)hGhrelin(1-28)-NH$_2$ (SEQ ID: 402), (1-Apc$^1$, Aib$^{2,10}$, Glu(NH-hexyl)$^3$) hGhrelin(1-28)-NH$_2$ (SEQ ID: 385) and (Inp$^1$, Ser(n-octanoyl)$^{17}$)hGhrelin(1-28)-NH$_2$ (SEQ ID: 390), can be achieved by following the protocol as follows:

10: Ac-(1-Apc$^1$, Aib$^{2,10}$, Glu(NH-hexyl)$^3$)hGhrelin(1-28)-NH$_2$ (SEQ ID: 402)

Side chain protected Fmoc-(Aib$^{2,10}$,Glu$^3$) hGhrelin(2-28)-Rink amide-MBHA resin was synthesized on a 433A peptide synthesizer (Applied Biosystems, Foster City, Calif., U.S.A.) using Fluorenylmethyloxycarbonyl (Fmoc) chemistry. A Rink Amide-4-methylbenzylhydrylamine (MBHA) resin (Novabiochem, San Diego, Calif., U.S.A.) with substitution of 0.64 mmol/g was used. The Fmoc amino acids (AnaSpec, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-OH, Fmoc-His(Trt)-OH, Fmoc-Leu-OH, Fmoc-Lys(Boc)-OH, Fmoc-Phe-OH, Fmoc-Pro-OH, Fmoc-Ser (tBu)-OH, and Fmoc-Val-OH. In addition, Fmoc-Glu(O-2-PhiPr)-OH (Novabiochem, San Diego, Calif., U.S.A.) was used at A$^3$. The synthesis was carried out on a 0.1 mmol scale. The Fmoc groups were removed by treatment with 20% piperidine in N-methylpyrrolidone (NMP) for 30 minutes. In each coupling step, the Fmoc amino acid (3 eq, 0.3 mmol) was first pre-activated in a 2 mL solution of 0.45M 2-(1-H-benzotriazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added. The ABI 433A peptide synthesizer was programmed to perform the following:

(1) washing with NMP;
(2) removing Fmoc protecting group with 20% piperidine in NMP for 30 minutes;
(3) washing with NMP; and
(4) coupling with pre-activated Fmoc amino acid for one to three hours.

The resin was coupled successively according to the sequence of the title peptide. After the peptide chain was assembled, the resin was washed completely by using N,N-dimethylformamide (DMF) and dichloromethane (DCM).

At the end of the assembly of the peptide chain on the 433A, the peptide-resin was transferred to a reaction vessel on a shaker and the Fmoc was removed using 25% Pip/DMF for 30 min. The resin was washed with DMF. Fmoc-Apc-OH (0.4 mmole) was coupled using TFFH (tetramethylfluoroformamidinium hexafluorophosphate) (Perceptive Biosystems, Warrington, U.K) (0.4 mmole), HOAt (0.4 mmol), DMAP (dimethylaminopyridine) (0.1 g) and DIEA (1.2 mmole) once for a four hour cycle and then again overnight.

The Fmoc group was removed as above and the peptide was capped using Ac2O (acetic anhydride) (5 mmole) and DIEA (5 mmole) in DMF for 30 minutes. The PhiPr groups were removed from Glu$^3$ using 2×3% TFA in DCM for a 10 minute cycle. The Boc that was partially removed from the side chain of Lys was replaced using Boc2O (0.8 mmole) and DIEA (0.8 mmole) in DCM overnight. The resin was then treated with PyAOP (7-azabenzotriazol-1-yloxytris(pyrrolidino)phosphonium-hexafluorophosphate) (Applied Biosystems, Foster City, Calif., U.S.A.) (0.6 mmole), HOAt (0.6 mmole), DMAP (0.1 g) and DIEA (1.8 mmole) for a 10 minute cycle after which hexyl-NH$_2$, i.e., hexylamine (Sigma-Aldrich Chemicals, St. Louis, Mo., U.S.A.) (2.0 mmole) was added and the resulting resin was continuously shaken overnight.

To cleave the title peptide, the resin was treated with a mixture of TFA, H$_2$O and triisopropylsilane (TIS) (9.5 mL/0.85 mL/0.8 mL) for four hours. The resin was filtered off and the filtrate was poured into 200 mL of ether. The precipitate was collected by centrifugation. This crude product was dissolved in a mixture of acetonitrile and water and purified on a reverse-phase preparative HPLC system with a column (4×43 cm) of C$_{18}$ DYNAMAX-100 A$^0$ (Varian, Walnut Creek, Calif., U.S.A.). The column was eluted over approximately 1 hour using a linear gradient of 92% A:8% B to 72% A:28% B, where A was 0.1% TFA in water and B was 0.1% TFA in acetonitrile. The fractions were checked by analytical HPLC and those containing pure product were pooled and lyophilized to dryness to give 1.5 mg (0.5%) yield of a white solid.

Purity was assayed using HPLC and found to be approximately 97.5%. Electro-spray ionization mass spectrometry (ESI-MS) analysis gave the molecular weight at 3435.1 (in agreement with the calculated molecular weight of 3434.5).

11: (1-Apc$^1$, Aib$^{2,10}$, Glu(NH-hexyl)$^3$)hGhrelin(1-28)NH$_2$ (Example #2) (SEQ ID: 385)

Side chain protected Fmoc-(Aib$^{2,10}$, Glu$^3$) hGhrelin(2-28)-Rink amide-MBHA resin was synthesized on a 433A peptide synthesizer (Applied Biosystems, Foster City, Calif., U.S.A.) using Fluorenylmethyloxycarbonyl (Fmoc) chemistry. A Rink Amide-4-methylbenzylhydrylamine (MBHA) resin (Novabiochem, San Diego, Calif., U.S.A.) with substitution of 0.64 mmol/g was used. The Fmoc amino acids (AnaSpec, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-OH, Fmoc-His(Trt)-OH, Fmoc-Leu-OH, Fmoc-Lys(Boc)-OH, Fmoc-Phe-OH, Fmoc-Pro-OH, Fmoc-Ser(tBu)-OH, and Fmoc-Val-OH. In addition, Fmoc-Glu(O-2-PhiPr)-OH (Novabiochem, San Diego, Calif., U.S.A.) was used at A$^3$. The synthesis was carried out on a 0.1 mmol scale. The Fmoc groups were removed by treatment with 20% piperidine in N-methylpyrrolidone (NMP) for a 30 minute cycle. In each coupling step, the Fmoc amino acid (3 eq, 0.3 mmol) was first pre-activated in 2 mL solution of 0.45 M 2-(1-H-benzotriazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added to the resin. The ABI 433A peptide synthesizer was programmed to perform the following reaction:

(1) washing with NMP;
(2) removing Fmoc protecting group with 20% piperidine in NMP for 30 minutes;
(3) washing with NMP; and
(4) coupling with pre-activated Fmoc amino acid for one to four hours.

The resin was coupled successively according to the sequence of the title peptide. After the peptide chain was assembled, the resin was washed completely by using N,N-dimethylformamide (DMF) and dichloromethane (DCM).

At the end of the assembly of the peptide chain on the 433A, the peptide-resin was transferred to a reaction vessel on a shaker and the Fmoc was removed by immersing in a solution of 25% Pip/DMF for approximately 30 minutes. The resin was thereafter washed with DMF. Fmoc-Apc-OH (0.4 mmole) was coupled using TFFH (tetramethylfluoroformamidinium hexafluorophosphate) (Perceptive Biosystems, Warrington, U.K.) (0.4 mmole), HOAt (0.4 mmol), DMAP (dimethylaminopyridine) (0.1 g) and DIEA (1.2 mmole) for one four hour cycle and then again overnight.

The Fmoc group was removed as above. The PhiPr groups were removed from Glu$^3$ using two cycles of 3% TFA in DCM for a period of 10 minutes per cycle. The Boc that was partially removed from the side chain of Lys during the process was replaced using Boc2O (0.8 mmole) and DIEA (0.8 mmole) in DCM overnight. The resin was treated with PyAOP (7-Azabenzotriazol-1-yloxytris(pyrrolidino)phosphonium-hexafluorophosphate) (Applied Biosystems, Foster City, Calif., U.S.A.) (0.6 mmole), HOAt (0.6 mmole), DMAP (0.1 g) and DIEA (1.8 mmole) for 10 minutes after which hexyl-NH$_2$, i.e., hexylamine, (Sigma-Aldrich Chemicals, St. Louis, Mo., U.S.A.) (2.0 mmole) was added and the resin solution was shaken overnight.

The title peptide was cleaved from the resin by treating with a mixture of TFA, H$_2$O and triisopropylsilane (TIS) (9.5 mL/0.85 mL/0.8 mL) for a period of approximately 4 hours. The resin was filtered off and the filtrate was poured into 200 mL of ether. The precipitate was collected by centrifugation. The crude product was dissolved in a mixture of acetonitrile and water and purified on a reverse-phase preparative HPLC system with a column (4×43 cm) of C$_{18}$ DYNAMAX-100 A$^0$ (Varian, Walnut Creek, Calif., U.S.A.). The column was eluted over approximately one hour using a linear gradient of 92% A:8% B to 72% A:28% B, where A was 0.1% TFA in water and B was 0.1% TFA in acetonitrile.

The fractions were checked by analytical HPLC and those containing pure product were pooled and lyophilized to dryness to give 4.6 mg (1.4%) of a white solid. Purity was assayed using HPLC and found to be approximately 99.8%. Electro-spray ionization mass spectrometry (ESI-MS) analysis gave the molecular weight at 3393.5 (in agreement with the calculated molecular weight of 3393.1).

12: (Inp$^1$,Ser(n-octanoyl)$^{17}$)hGhrelin(1-28)-NH$_2$ (Example #28) (SEQ ID: 390)

Side chain protected Fmoc-(Ser$^{17}$) hGhrelin(2-28)-Rink amide-MBHA resin was synthesized on a model 433A peptide synthesizer (Applied Biosystems, Foster City, Calif., U.S.A.) using Fluorenylmethyloxycarbonyl (Fmoc) chemistry. A Rink Amide-4-methylbenzylhydrylamine (MBHA) resin (Novabiochem, San Diego, Calif., U.S.A.) with substitution of 0.64 mmol/g was used. The Fmoc amino acids (AnaSpec, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-OH, Fmoc-His(Trt)-OH, Fmoc-Leu-OH, Fmoc-Lys(Boc)-OH, Fmoc-Phe-OH, Fmoc-Pro-OH, Fmoc-Ser(tBu)-OH, and Fmoc-Val-OH. In addition, Fmoc-Ser(Trt)-OH (AnaSpec, San Jose, Calif., U.S.A.) was used at A$^3$ and A$^{17}$. The synthesis was carried out on a 0.2 mmol scale. The Fmoc groups were removed by treatment with 20% piperidine in N-methylpyrrolidone (NMP) for 30 minutes. In each coupling step, the Fmoc amino acid (3 eq, 0.3 mmol) was first pre-activated in 2 mL solution of 0.45M 2-(1-H-benzotriazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added. The ABI 433A® peptide synthesizer was programmed to perform the following:

(1) washing with NMP;
(2) removing Fmoc protecting group with 20% piperidine in NMP for 30 minutes;
(3) washing with NMP; and
(4) coupling with pre-activated Fmoc amino acid for 1 or 2 hours.

The resin was coupled successively according to the sequence of the title peptide. After the peptide chain was assembled, the resin was washed completely using N,N-dimethylformamide (DMF) and dichloromethane (DCM).

At the end of the assembly of the peptide chain on the 433A, the peptide-resin was transferred to a reaction vessel on a shaker and the Fmoc was removed using 25% Pip/DMF for a 30 minute cycle. The resin was washed with DMF. Fmoc-Inp-OH (1.0 mmole) was coupled using tetramethylfluoroformamidinium hexafluorophosphate (TFFH) (Perceptive Biosystems, Warrington, U.K.) (1.0 mmole), HOAt ((1.0 mmol), DMAP (dimethylaminopyridine) (0.1 g) and DIEA (3.0 mmole) once overnight.

The Trt groups were removed from $Ser^3$ and $Ser^{17}$ using two cycles of 3% TFA in DCM each cycle lasting approximately 10 minutes. The Boc that was partially removed from the side chain of Lys as indicate above, was replaced using Boc2O (0.8 mmole) and DIEA (0.8 mmole) in DCM overnight. Octanoic acid (10 mmole) was coupled to the $Ser^3$ and $Ser^{17}$ side chains using DIC (5 mmole), DMAP (0.2 mg) and DIEA (5 mmole) in DCM overnight.

The terminal Fmoc was removed by immersion in 25% Pip/DMF for 30 minutes. The resin was then washed with DMF. The title peptide was cleaved from the resin using a mixture of TFA, $H_2O$ and triisopropylsilane (TIS) (9.5 mL/0.85 mL/0.8 mL) for approximately 4 hours. The resin was filtered off and the filtrate was poured into 200 mL of ether. The precipitate was collected by centrifugation. The crude product was dissolved in a mixture of acetonitrile and water and purified on a reverse-phase preparative HPLC system with a column (4×43 cm) of $C_{18}$ DYNAMAX-100 $A^0$ (Varian, Walnut Creek, Calif., U.S.A.). The column was eluted over approximately 1 hour using a linear gradient of 85% A:15% B to 55% A:45% B, where A was 0.1% TFA in water and B was 0.1% TFA in acetonitrile.

The fractions were checked by analytical HPLC and those containing pure product were pooled and lyophilized to dryness resulting in a 41.7 mg (5.9%) yield of a white solid. Purity was assayed using HPLC and found to be approximately 96.6%. Electro-spray ionization mass spectrometry (ESI-MS) analysis gave the molecular weight at 3507.4 (in agreement with the calculated molecular weight of 3508.16).

E. Biological Testing

1. In Vitro Binding Assays

The activities of the compounds of the invention at the GHS receptor can be and were determined using techniques such as those described in the examples provided below. In different embodiments a ghrelin analogue has at least about 50%, at least about 60%, at least about 70%, at least about 80%, or at least about 90%, at least about 95%, at least about 98% or more, functional activity relative to ghrelin as determined using one or more of the functional activity assays described below; and/or has an $IC_{50}$ greater than about 1,000 nM, greater than about 100 nM, or greater than about 50 nM, using the receptor binding assay described below. With respect to $IC_{50}$, greater refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof.

A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in ghrelin binding can be readily identified using labeled ghrelin or ghrelin analogues and different receptor fragments. Different strategies can be employed to select fragments to be tested to narrow down the binding region. Examples of such strategies include testing consecutive fragments of about 15 amino acids in length starting at the N-terminus, and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally-occurring nucleic acid which is introduced into a different environment.

a Screening for GHS Receptor Active Compounds

Screening for GHS receptor active compounds is facilitated using a recombinantly expressed receptor. Using a recombinantly expressed GHS receptor offers several advantages such as the ability to express the receptor in a defined cell system so that a response to a compound at the GHS receptor can be more readily differentiated from responses at other receptors. For example, the GHS receptor can be expressed in a cell line such as HEK 293, COS 7 or CHO, not normally expressing the receptor by an expression vector, wherein the same cell line without the expression vector can act as a control.

Screening for compounds reducing GHS receptor activity is facilitated through the use of a ghrelin analogue in the assay. The use of a ghrelin analogue in a screening assay provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities, and/or in the intracellular messengers. Preferably, GHS receptor activity is measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17 (Button, D. et al., *Cell Calcium*, (1993), 14 (9):663-71; and Feighner, S. D. et al., *Science*, (1999), 284 (5423):2184-8).

Chimeric receptors containing a ghrelin binding region functionally coupled to a different G-protein can also be used to measure GHS receptor activity. A chimeric GHS receptor contains an N-terminal extracellular domain; a transmembrane domain made up of transmembrane regions, extracellular loop regions, and intracellular loop regions; and an intracellular carboxy terminus. Techniques for producing chimeric receptors and measuring G-protein coupled responses are provided in, for example, International Application Number WO 97/05252 and U.S. Pat. No. 5,264,565, both of which are hereby incorporated by reference herein.

Ghrelin analogues can be used to stimulate GHS receptor activity. Such stimulation can be used, for example, to study the effect of GHS receptor modulation, to study the effect of growth hormone secretion, to look for or study ghrelin antagonists, or to achieve a beneficial effect in a subject. It is contemplated that the ghrelin analogues of the instant invention are useful for stimulating gastrointestinal motility.

b. Preparation of CHO-K1 Cells Expressing the Human Recombinant GHS Receptor

The cDNA for human growth hormone secretagogue receptor (hGHS-R, or ghrelin receptor) was cloned by Polymerase Chain Reaction (PCR) using human brain RNA as a template (Clontech, Palo Alto, Calif., U.S.A.), gene specific primers flanking the full-length coding sequence of hGHS-R, (S: 5'-A T G T G G A A C G C G A C G C C C A G C G A A G A G-3' (SEQ ID: 403) and AS: 5'-T C A T G T A T T A A T A C T A G A T T C T G T C C A-3') (SEQ ID: 404), and Advantage 2 PCR Kit (Clontech, Palo Alto, Calif., U.S.A.). The PCR product was cloned into the pCR2.1® vector using Original TA® Cloning Kit (Invitrogen, Carlsbad, Calif., U.S.A.). The full length human GHS-R was subcloned into the mammalian expression vector pcDNA 3.1 (Invitrogen, Carlsbad, Calif., U.S.A.). The plasmid was transfected into the Chinese hamster ovary cell line, CHO-K1 (American Type Culture Collection, Rockville, Md., U.S.A.) by calcium phosphate method (Wigler, M. et al., *Cell*, (1977), 11 (1):223-32). Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (Gibco, Grand Island, N.Y., U.S.A.).

c. GHS-Receptor Binding Assay:

Membranes for radioligand binding studies can be and were prepared by homogenization of the foregoing CHO-K1 cells expressing the human recombinant GHS receptor. The cells were homogenized in 20 ml of ice-cold 50 mM Tris-HCl using a Brinkman Polytron® (Westbury, N.Y., U.S.A.; setting 6, 15 seconds). The homogenates were washed twice by centrifugation (39,000 g/10 minutes) and the final pellets were re-suspended in 50 mM Tris-HCl containing 2.5 mM $MgCl_2$ and 0.1% bovine serum albumin (BSA). For the assay, 0.4 ml aliquots were incubated with 0.05 nM ($^{125}$I)ghrelin (~2000 Ci/mmol, Perkin Elmer Life Sciences, Boston, Mass., U.S.A.) with and without 0.05 ml of unlabeled competing test peptide. After a 60 minute incubation at 4° C., the bound ($^{125}$I)ghrelin was separated from free ($^{125}$I)ghrelin by rapid filtration through GF/C filters (Brandel, Gaithersburg, Md., U.S.A.) which had been previously soaked in 0.5% polyethyleneimine/0.1% BSA. The filters were then washed three times with 5-ml aliquots of ice-cold 50 mM Tris-HCl and 0.1% BSA, and the bound radioactivity trapped on the filters was counted by gamma spectrometry (Wallac LKB, Gaithersburg, Md., U.S.A.). Specific binding was defined as the total ($^{125}$I)ghrelin bound minus that bound in the presence of 1000 nM ghrelin (Sachem, Torrence, Calif., U.S.A.).

A selection of the preferred embodiments was tested using the receptor binding assay discussed above and the results are reported in Table 1 presented below.

TABLE 1

Receptor Binding Ki Values for Selected Compounds

| Example # | COMPOUND | Ki (nM) |
|---|---|---|
| #1 | (Inp$^1$, Aib$^{2,10}$, Glu(NH-hexyl)$^3$)hGhrelin(1-28)-NH$_2$ (SEQ ID: 385) | 0.10 |
| #2 | (1-Apc$^1$, Aib$^{2,10}$, Glu(NH-hexyl)$^3$)-hGhrelin(1-28)NH$_2$ (SEQ ID: 385) | 0.12 |
| #3 | H-Apc-D-1-Nal-D-Trp-2-Thi-Lys-NH$_2$; (SEQ ID: 146) | 0.29 |
| #4 | Inp-D-2-Nal-D-Trp-Phe-Lys-NH$_2$ (SEQ ID: 407) | 0.30 |
| #5 | H-Inp-D-1-Nal-D-Trp-2-Thi-Lys-NH$_2$ (SEQ ID: 128) | 0.31 |
| #6 | H-Apc-D-Bal-D-Trp-Phe-Lys-NH$_2$ (SEQ ID: 153) | 0.32 |
| #7 | (Inp$^1$, Aib$^2$, Glu(NH-hexyl)$^3$)hGhrelin(1-28)-NH$_2$ (SEQ ID: 387) | 0.33 |
| #8 | H-Inp-D-Bal-D-Trp-Phe-Lys-NH$_2$ (SEQ ID: 144) | 0.33 |
| #9 | (Inp$^1$)hGhrelin(1-28)-NH$_2$ (SEQ ID: 386) | 0.36 |
| #10 | H-Inp-D-1-Nal-D-Trp-Phe-Apc-NH$_2$ (SEQ ID: 2) | 0.36 |
| #11 | H-Apc-D-Bal-D-Trp-2-Thi-Lys-NH$_2$ (SEQ ID: 153) | 0.36 |

TABLE 1-continued

Receptor Binding Ki Values for Selected Compounds

| Example # | COMPOUND | Ki (nM) |
|---|---|---|
| #12 | (Inp$^1$, Aib$^{2,8}$)hGhrelin(1-28)-NH$_2$ (SEQ ID: 389) | 0.37 |
| #13 | (Aib$^2$, Glu$^3$(NH-hexyl))hGhrelin(1-28)-NH$_2$ (SEQ ID: 92) | 0.38 |
| #14 | (Inp$^1$, Aib$^{2,10}$)hGhrelin(1-28)-NH$_2$ (SEQ ID: 388) | 0.40 |
| #15 | H-Inp-D-Bal-D-Trp-2-Thi-Apc-NH$_2$ (SEQ ID: 208) | 0.40 |
| #16 | (Inp$^1$, Aib$^2$)hGhrelin(1-28)-NH$_2$ (SEQ ID: 386) | 0.41 |
| #17 | (Aib$^8$)hGhrelin(1-28)-NH$_2$ (SEQ ID: 21) | 0.41 |
| #18 | H-Apc-D-2-Nal-D-Trp-Phe-Lys-NH$_2$ (SEQ ID: 145) | 0.42 |
| #19 | H-Inp-D-Bal-D-Trp-2-Thi-Lys-NH$_2$ (SEQ ID: 144) | 0.42 |
| #20 | H-Apc-D-1-Nal-D-Trp-Phe-Lys-NH$_2$ (SEQ ID: 145) | 0.42 |
| #21 | (Inp$^1$, Aib$^2$, Ser(n-octanoyl)$^{17}$)hGhrelin(1-28)-NH$_2$ (SEQ ID: 390) | 0.44 |
| #22 | H-Apc-D-1-Nal-D-Trp-Taz-Lys-NH$_2$ (SEQ ID: 152) | 0.45 |
| #23 | H-Inp-D-2-Nal-D-Trp-2-Thi-Lys-NH$_2$ (SEQ ID: 132) | 0.45 |
| #24 | (Aib$^{2,8}$, Glu(NH-hexyl)$^{3,17}$)hGhrelin(1-28)-NH$_2$ (SEQ ID: 249) | 0.45 |
| #25 | H-Apc-D-1-Nal-D-Trp-2-Thi-Apc-NH$_2$ (SEQ ID: 209) | 0.46 |
| #26 | H-Apc-D-1-Nal-D-Trp-Phe-Apc-NH$_2$ (SEQ ID: 154) | 0.46 |
| #27 | H-Inp-D-Bal-D-Trp-Phe-Apc-NH$_2$ (SEQ ID: 2) | 0.47 |
| #28 | (Inp$^1$, Ser(n-octanoyl)$^{17}$)hGhrelin(1-28)-NH$_2$ (SEQ ID: 390) | 0.49 |
| #29 | H-Apc-D-Bal-D-Trp-Taz-Lys-NH$_2$ (SEQ ID: 152) | 0.50 |
| #30 | (Glu$^3$(O-hexyl))hGhrelin(1-28)-NH$_2$ (SEQ ID: 91) | 0.50 |
| #31 | H-Apc-D-Bal-D-Trp-2-Thi-Apc-NH$_2$ (SEQ ID: 209) | 0.51 |
| #32 | H-Inp-D-Bal-D-Trp-Taz-Lys-NH$_2$; (SEQ ID: 151) | 0.52 |
| #33 | H-Inp-D-1-Nal-D-Trp-2-Thi-Apc-NH$_2$ (SEQ ID: 208) | 0.53 |
| #34 | (Aib$^2$)hGhrelin(1-28)-NH$_2$ (SEQ ID: 15) | 0.57 |
|  | rGhrelin (SEQ ID: 405) | 0.59 |
| #35 | (2-Thi$^9$)hGhrelin(1-28)-NH$_2$ (SEQ ID: 19) | 0.63 |

TABLE 1-continued

Receptor Binding Ki Values for Selected Compounds

| Example # | COMPOUND | Ki (nM) |
|---|---|---|
| #36 | (Aib$^2$, Taz$^9$)hGhrelin(1-28)-NH$_2$ (SEQ ID: 13) | 0.63 |
| #37 | H-Inp-D-2-Nal-D-Trp-Phe-Apc-NH$_2$ (SEQ ID: 2) | 0.64 |
| #38 | (Aib$^2$, 3-Pal$^9$)hGhrelin(1-28)-NH$_2$ (SEQ ID: 13) | 0.65 |
| #39 | H-Apc-D-Bal-D-2-Nal-Phe-Lys-NH$_2$ (SEQ ID: 158) | 0.68 |
| #40 | H-Apc-D-1-Nal-D-Trp-Phe-NH$_2$ (SEQ ID: 148) | 0.70 |
| #41 | (3-Pal$^9$)hGhrelin(1-28)-NH$_2$ (SEQ ID: 19) | 0.70 |
| #42 | H-Apc-D-Bal-D-Trp-Phe-Apc-NH$_2$ (SEQ ID: 154) | 0.71 |
| #43 | H-Apc-D-1-Nal-D-Trp-2-Thi-NH$_2$ (SEQ ID: 159) | 0.73 |
| #44 | (Glu$^3$(NH-hexyl), Aib$^8$)hGhrelin(1-28)-NH$_2$ (SEQ ID: 41) | 0.74 |
| #45 | (Aib$^2$, 4-Hyp$^7$)hGhrelin(1-28)-NH$_2$ (SEQ ID: 14) | 0.75 |
| #46 | H-Inp-D-2-Nal-D-Trp-Taz-Lys-NH$_2$ (SEQ ID: 132) | 0.80 |
| #47 | H-Inp-D-Bal-D-Trp-Taz-Apc-NH$_2$ (SEQ ID: 163) | 0.83 |
| #48 | H-Inp-D-1-Nal-D-Trp-2-Thi-NH$_2$ (SEQ ID: 147) | 0.87 |
| #49 | (Asp$^3$(O-hexyl))hGhrelin(1-28)-NH$_2$ (SEQ ID: 394) | 0.88 |
| #50 | H-Apc-D-Bal-D-Trp-Phe-NH$_2$ (SEQ ID: 160) | 0.89 |
| #51 | (Lys$^5$)hGhrelin(1-28)-NH$_2$ (SEQ ID: 406) | 0.89 |
| #52 | (Aib$^2$, Glu$^3$(NH-hexyl), Taz$^9$)hGhrelin(1-28)-NH$_2$ (SEQ ID: 70) | 0.90 |
| #53 | (Aib$^2$, Dhp$^7$)hGhrelin(1-28)-NH$_2$ (SEQ ID: 14) | 0.91 |
| #54 | H-Apc-D-2-Nal-D-Trp-2-Thi-NH$_2$ (SEQ ID: 162) | 0.95 |
| #55 | H-Apc-D-1-Nal-D-Trp-Taz-Apc-NH$_2$ (SEQ ID: 164) | 0.98 |
| #56 | H-Apc-D-Bal-D-Trp-2-Thi-NH$_2$ (SEQ ID: 161) | 0.98 |
| #57 | (Aib$^{2,10}$)hGhrelin(1-28)-NH$_2$ (SEQ ID: 17) | 1.02 |
| #58 | (Aib$^{2,8}$)hGhrelin(1-28)-NH$_2$ (SEQ ID: 16) | 1.02 |
| #59 | H-Inp-D-1-Nal-D-Trp-3-Pal-Lys-NH$_2$ (SEQ ID: 128) | 1.05 |
| #60 | (Aib$^2$, Glu$^3$(NH-hexyl), 2-Thi$^9$)hGhrelin(1-28)-NH$_2$ (SEQ ID: 70) | 1.06 |

TABLE 1-continued

Receptor Binding Ki Values for Selected Compounds

| Example # | COMPOUND | Ki (nM) |
|---|---|---|
| #61 | (A5c$^2$)hGhrelin(1-28)-NH$_2$ (SEQ ID: 15) | 1.07 |
| #62 | (Aib$^2$, Tic$^7$)hGhrelin(1-28)-NH$_2$ (SEQ ID: 14) | 1.08 |
| #63 | (Aib$^2$, Thz$^7$)hGhrelin(1-28)-NH$_2$ (SEQ ID: 14) | 1.08 |
| #64 | (Aib$^2$, 4-Pal$^9$)hGhrelin(1-28)-NH$_2$ (SEQ ID: 13) | 1.09 |
| #65 | (Aib$^{2,8}$, Glu$^3$(NH-hexyl))hGhrelin(1-28)-NH$_2$ (SEQ ID: 72) | 1.09 |
| #66 | H-Inp-D-1-Nal-D-Trp-Taz-Lys-NH$_2$ (SEQ ID: 151) | 1.11 |
| #67 | H-Apc-D-Bal-D-Trp-Taz-Apc-NH$_2$ (SEQ ID: 164) | 1.13 |
| #68 | (Aib$^{2,10}$, Glu$^3$(NH-hexyl))hGhrelin(1-28)-NH$_2$ (SEQ ID: 73) | 1.14 |
| #69 | H-Inp-D-1-Nal-D-Trp-Taz-Apc-NH$_2$ (SEQ ID: 163) | 1.19 |
| #70 | Cys$^3$(S(CH$_2$)$_9$CH$_3$)hGhrelin(1-28)-NH$_2$ (SEQ ID: 106) | 1.24 |
| #71 | (Aib$^1$)hGhrelin(1-28)-NH$_2$ (SEQ ID: 393) | 1.28 |
| #72 | (Ac-Gly$^1$, Aib$^2$)hGhrelin(1-28)-NH$_2$ (SEQ ID: 98) | 1.29 |
| #73 | H-Apc-D-1-Nal-D-1-Nal-Phe-Lys-NH$_2$ (SEQ ID: 156) | 1.32 |
| #74 | (Aib$^2$, Pip$^7$)hGhrelin(1-28)-NH$_2$ (SEQ ID: 14) | 1.34 |
| #75 | H-Inp-D-Bip-D-Trp-Phe-Lys-NH$_2$ (SEQ ID: 130) | 1.35 |
| #76 | H-Apc-D-1-Nal-D-Trp-Taz-NH$_2$ (SEQ ID: 159) | 1.41 |
| #77 | H-Apc-D-Bal-D-1-Nal-Phe-Lys-NH$_2$ (SEQ ID: 158) | 1.46 |
| #78 | H-Apc-D-Bal-D-2-Nal-Phe-Apc-NH$_2$ (SEQ ID: 157) | 1.49 |
| #79 | H-Inp-D-2-Nal-D-Trp-Thr(Bzl)-Lys-NH$_2$ (SEQ ID: 131) | 1.55 |
| #80 | H-Inp-D-2-Nal-D-Trp-3-Pal-Lys-NH$_2$ (SEQ ID: 143) | 1.58 |
| #81 | H-Apc-D-Bal-D-Trp-Taz-NH$_2$ (SEQ ID: 161) | 1.62 |
| #82 | H-Apc-D-1-Nal-D-2-Nal-Phe-Apc-NH$_2$ (SEQ ID: 155) | 1.71 |
| #83 | H-Apc-D-1-Nal-D-1-Nal-Phe-Apc-NH$_2$ (SEQ ID: 155) | 1.99 |
| #84 | (Dap$^3$(octanesulfonyl))hGhrelin(1-28)-NH$_2$ (SEQ ID: 6) | 2.00 |
| #85 | (Glu$^3$(NH-hexyl))hGhrelin(1-28)-NH$_2$ (SEQ ID: 91) | 2.03 |

TABLE 1-continued

Receptor Binding Ki Values for Selected Compounds

| Example # | COMPOUND | Ki (nM) |
|---|---|---|
| #86 | H-Apc-D-2-Nal-D-Trp-Taz-NH$_2$ (SEQ ID: 162) | 2.11 |
| #87 | H-Inp-D-Bal-D-Trp-Phe-NH$_2$ (SEQ ID: 141) | 2.30 |
| #88 | (Aib$^2$, Glu$^3$(NH-hexyl), 4-Hyp$^7$)hGhrelin(1-28)-NH$_2$ (SEQ ID: 71) | 2.34 |
| #89 | (Aib$^2$, Glu$^3$(NH-hexyl), 3-Pal$^9$)hGhrelin(1-28)-NH$_2$ (SEQ ID: 70) | 2.35 |
| #90 | (Aib$^2$, Cha$^5$)hGhrelin(1-28)-NH$_2$ (SEQ ID: 7) | 2.98 |
| #91 | (Glu$^3$(NH-hexyl), 4-Hyp$^7$)hGhrelin(1-28)-NH$_2$ (SEQ ID: 76) | 3.36 |
| #92 | H-Apc-D-Bal-D-1-Nal-Phe-Apc-NH$_2$ (SEQ ID: 157) | 3.48 |
| #93 | H-Inp-D-2-Nal-D-Trp-2-Thi-NH$_2$ (SEQ ID: 138) | 4.11 |
| #94 | (Aib$^2$, Glu$^3$(NH-hexyl), 4-Pal$^9$)hGhrelin(1-28)-NH$_2$ (SEQ ID: 70) | 4.15 |
| #95 | (Asp$^3$(NH-heptyl))hGhrelin(1-28)-NH$_2$ (SEQ ID: 391) | 4.27 |
| #96 | H-Inp-D-2-Nal-D-Trp-Thr(Bzl)-NH$_2$ (SEQ ID: 138) | 4.46 |
| #97 | (Aib$^2$, Abu$^6$)hGhrelin(1-28)-NH$_2$ (SEQ ID: 9) | 4.60 |
| #98 | (Aib$^{2,12}$, Glu$^3$(NH-hexyl), 4-Pal$^9$, Orn$^{15}$)hGhrelin(1-28)-NH$_2$ (SEQ ID: 125) | 4.83 |
| #99 | H-Inp-D-2-Nal-D-Trp-Taz-NH$_2$ (SEQ ID: 138) | 6.17 |
| #100 | H-Inp-D-2-Nal-D-Trp-4-Pal-Lys-NH$_2$ (SEQ ID: 129) | 7.35 |
| #101 | (n-octanoyl-Gly$^1$)hGhrelin(1-28)-NH$_2$ (SEQ ID: 104) | 10.19 |
| #102 | H-Inp-D-2-Nal-D-Trp-3-Pal-NH$_2$ (SEQ ID: 135) | 11.35 |
| #103 | (Act$^2$)hGhrelin(1-28)-NH$_2$ (SEQ ID: 15) | 12.72 |
| #104 | (n-butyryl-Gly$^1$)hGhrelin(1-28)-NH$_2$ (SEQ ID: 104) | 12.78 |
| #105 | (Aib$^2$, A6c$^5$)hGhrelin(1-28)-NH$_2$ (SEQ ID: 7) | 14.77 |
| #106 | H-Inp-D-1-Nal-D-Trp-3-Pal-NH$_2$ (SEQ ID: 136) | 16.10 |
| #107 | H-Inp-D-Bip-D-Trp-Phe-NH$_2$ (SEQ ID: 137) | 20.00 |
| #108 | (isobutyryl-Gly$^1$)hGhrelin(1-28)-NH$_2$ (SEQ ID: 104) | 21.85 |
| | hGhrelin(1-28)-NH$_2$ (SEQ ID: 1) | 24.16 |
| #109 | H-Inp-D-2-Nal-D-Trp-Pff-Lys-NH$_2$ (SEQ ID: 131) | 25.43 |

TABLE 1-continued

Receptor Binding Ki Values for Selected Compounds

| Example # | COMPOUND | Ki (nM) |
|---|---|---|
| #110 | H-Inp-D-2-Nal-D-Bal-Phe-NH$_2$ (SEQ ID: 142) | 27.40 |
| #111 | (A6c$^5$)hGhrelin(1-28)-NH$_2$ (SEQ ID: 8) | 35.82 |
| #112 | H-Inp-D-2-Nal-D-Trp-Pff-NH$_2$ (SEQ ID: 138) | 36.31 |
| #113 | (des-Ser$^2$)hGhrelin(1-28)-NH$_2$ (SEQ ID: 392) | 39.10 |
| #114 | H-Inp-D-Dip-D-Trp-Phe-Lys-NH$_2$ (SEQ ID: 133) | 46.78 |
| #115 | H-Inp-D-Bal-D-Trp(Ψ)-Pim (SEQ ID: 149) | 48.73 |
| #116 | H-Inp-D-1-Nal-D-Trp(Ψ)-Pim (SEQ ID: 149) | 50.55 |
| #117 | (Aib$^{2,6}$)hGhrelin(1-28)-NH$_2$ (SEQ ID: 9) | 71.55 |
| #118 | H-Inp-D-Bpa-D-Trp-Phe-Lys-NH$_2$ (SEQ ID: 133) | 93.75 |
| #119 | H-Inp-D-2-Nal-D-Dip-Phe-NH$_2$ (SEQ ID: 140) | 104.80 |
| #120 | H-Inp-D-Dip-D-Trp-Phe-NH$_2$ (SEQ ID: 139) | 104.83 |
| #121 | H-Inp-D-2-Nal-D-Trp-4-Pal-NH$_2$ (SEQ ID: 135) | 113.50 |
| #122 | H-Inp-D-2-Nal-D-Trp(Ψ)-Pim (SEQ ID: 149) | 116.68 |
| #123 | (Aib$^2$, Act$^6$)hGhrelin(1-28)-NH$_2$ (SEQ ID: 9) | 155.43 |
| #124 | H-Inp-D-Trp-D-2-Nal(Ψ)-Pim (SEQ ID: 127) | 182.00 |
| #125 | H-Inp-D-2-Nal-D-Trp-Orn-Lys-NH$_2$ (SEQ ID: 129) | 243.00 |
| #126 | (des-Gly$^1$, des-Ser$^2$)hGhrelin(1-28)-NH$_2$ (SEQ ID: 392) | 283.33 |
| #127 | H-Inp-D-2-Nal-D-Bpa-Phe-Lys-NH$_2$ (SEQ ID: 134) | 419.00 |
| #128 | H-Aib-D-Ser(Bzl)-D-Trp(Ψ)-Pim (SEQ ID: 150) | 753.33 |

2. In Vitro Cytokine Lipolysis Assay in 3T3-L1 Adipocytes

The claimed compounds were tested for their ability to ameliorate cytokine levels. The employed assay is based on the discovery that TNF-α has been shown to enhance lipolysis and decrease lipoprotein lipase activity in 3T3 adipocytes by a prostaglandin independent mechanism (Hardardóttir, I. et al., *Biochem. Biophys. Res. Commun.*, (1992), 186(1):237-43; and Souza, S. C. et al., *J. Cell Biochem.*, (2003), 89(6): 1077-86). It has been observed that TNF-α is overexpressed in the adipose tissue of obese insulin-resistant rodents and humans and that the neutralization of TNF-α in fa/fa Zucker rats resulted in a decrease level of plasma free fatty acids (Hotamisligil, G. S. and Spiegelman, B. M., *Diabetes*, (1994), 43 (11):1271-8). Infusion of TNF-α in humans has been shown to increase plasma levels of free fatty acids (Van der Poll, T. et al., *Am. J. Physiol.*, (1991), 261 (4 Pt 1):E457-65). In addition, it has been determined that extracellular glucose is required for TNF-α mediated adipocyte lipolysis (Green, A. et al., *Diabetes*, (2004), 53 (1):74-81). Glycerol, generated by triglyceride breakdown, is released into the extracellular space through aquaporin adipose. Extracellular glycerol is easily assayed by incubation with glycerol kinase (to produce glycerol phosphate), glycerol phosphate oxidase (to produce H$_2$O$_2$), and horseradish peroxidase in the presence of a calorimetric substrate. As such, free glycerol can be assayed as a marker for adipolysis.

It has been discovered that plasma ghrelin levels are altered in LPS-injected rats (Hataya, Y. et al., *Endocrinology*, (2003), 144 (12):5365-71) suggesting that such a model could be used to test the analogues of the instant application for their ability to inhibit cytokine production.

In the assay protocol, 3T3-L1 adipocytes were permeabilized and preincubated with the ghrelin analogues of the present invention. In particular, 3T3-L1 preadipocytes were obtained from 3T3-L1 fibroblasts (ATCC Deposit No. CL-173 described in U.S. Pat. No. 4,003,789). The preadipocytes were cultured in Dulbecco's Modified Eagle's Medium (DMEM) containing sterile 10% fetal calf serum (FCS) and induced to differentiate by treatment with a solution comprising 25 µM dexamethasone (DEX), 0.5 M isobutylmethyxanthin (IBMX) and 5 µg/ml insulin for a 72 hour period and thereafter maintained again in DMEM containing sterile 10% FCS for an addition 6-8 days using standard protocols (Kohanski, R. A. et al., *J. Biol. Chem.*, (1986), 261 (26):12272-81).

Figure 11:
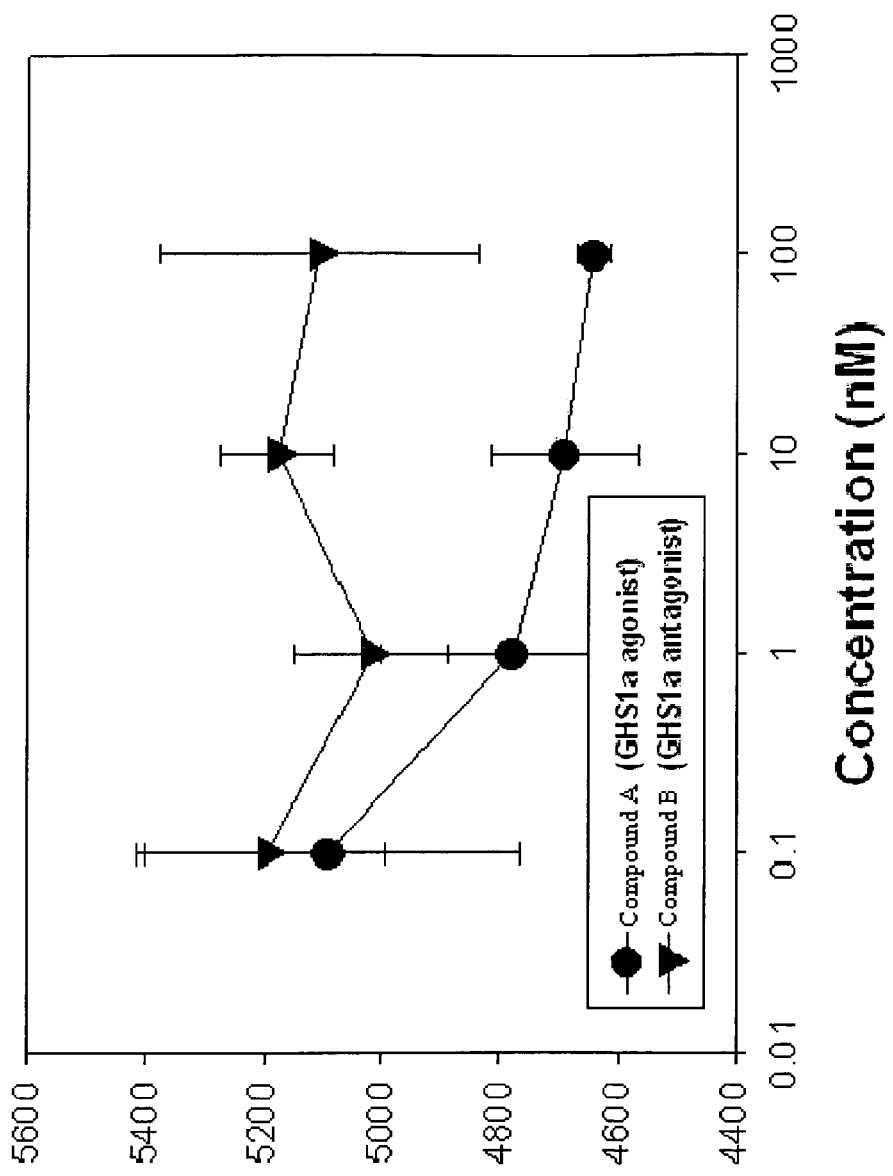
FIG. 11: shows the in vitro inhibition of LPS-stimulated IL-6 secretion from human peripheral blood monocytes by the ghrelin analogue H-Inp-D-Bal-D-Trp-Phe-Apc-NH$_2$ (SEQ ID: 2) (Compound A) and the ghrelin analogue (Aib$^2$, Glu$^3$(NH-hexyl)hGhrelin(1-28)-NH$_2$) (SEQ ID: 92) (Compound B)
Figure 13:
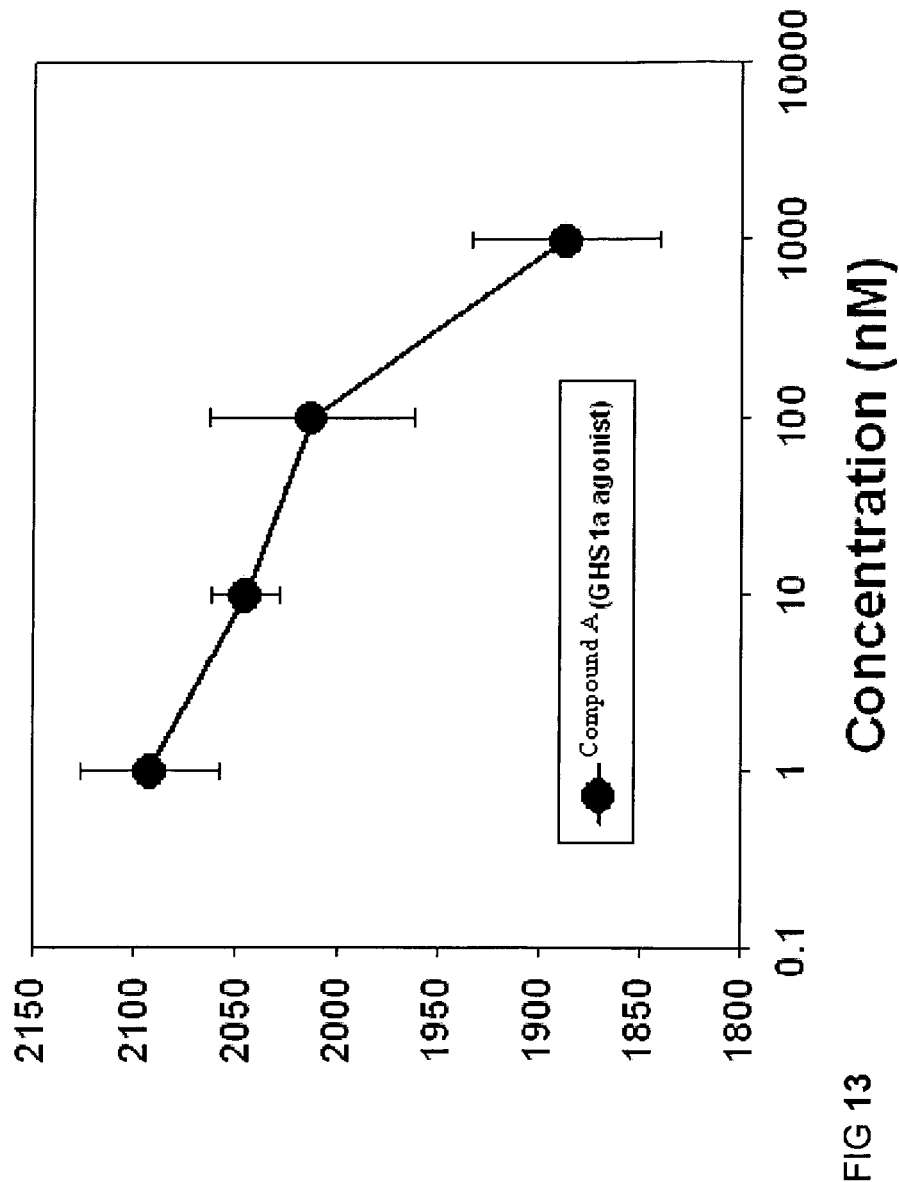
FIG. 13: shows the in vitro inhibition of LPS-stimulated TNF-α secretion from mouse peritoneal macrophages by ghrelin analogue H-Inp-D-Bal-D-Trp-Phe-Apc-NH$_2$; (SEQ ID: 2)
Figure 14:
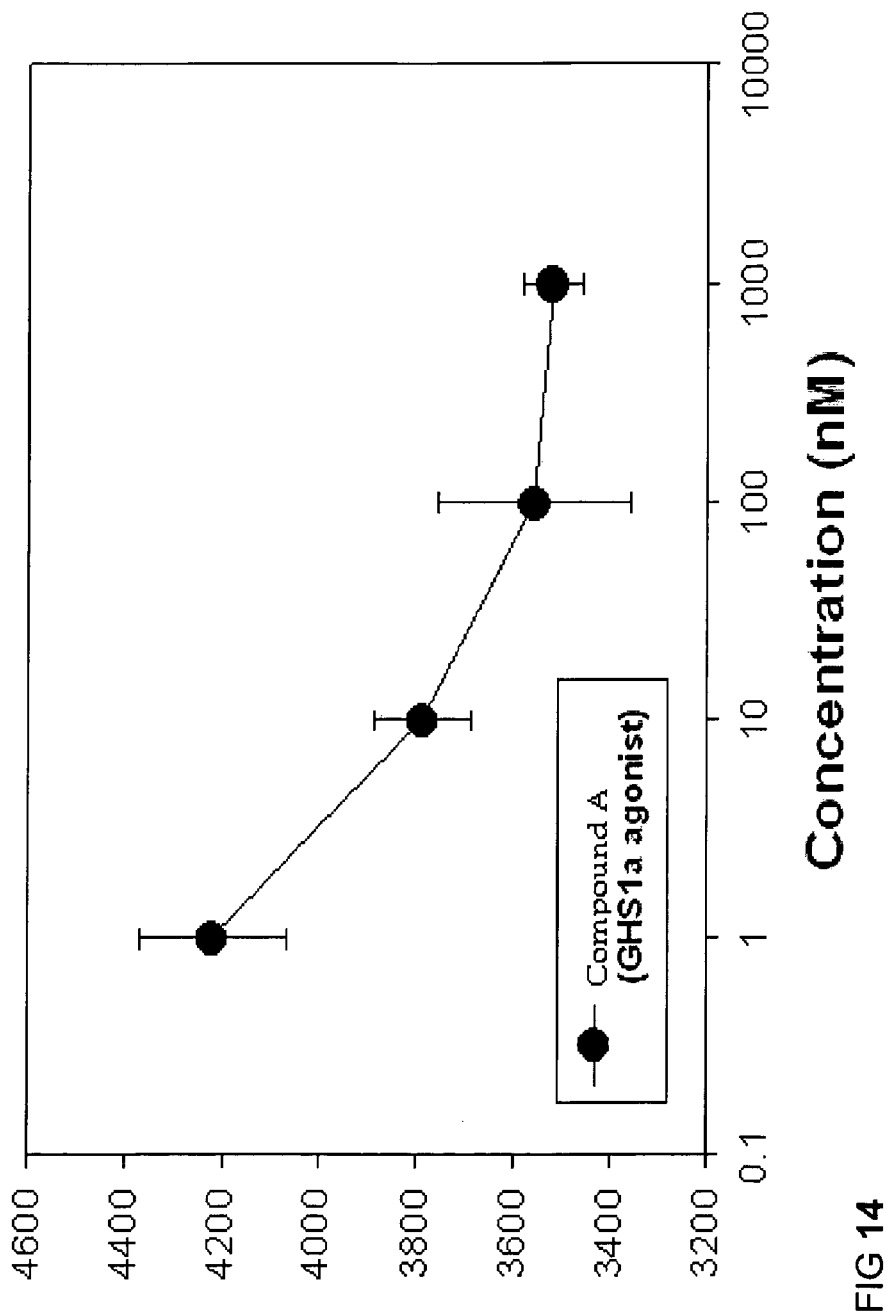
FIG. 14: shows the in vitro inhibition of LPS-stimulated IL-6 secretion from mouse peritoneal macrophages by ghrelin analogue H-Inp-D-Bal-D-Trp-Phe-Apc-NH$_2$; (SEQ ID: 2)

Differentiated 3T3-L1 adipocytes were pre-treated with 1, 10 or 100 ηM of H-Inp-D-Bal-D-Trp-Phe-Apc-NH$_2$ (Example #27) (SEQ ID: 2) for 10 minutes, treated with 20 ηg/ml of recombinant murine TNF-α (Genzyme, Cambridge, Mass., U.S.A.) and allowed to incubated for 24 hours. The glycerol content was determined using an Adipolysis Assay Kit (Millipore Corporation, Temecula, Calif., U.S.A.). The results, as shown in the figures attached to the instant application, indicate that the lipolysis in the adipocytes induced by 20 ηg/ml TNF-α is significantly inhibited by the addition of 1, 10 or 100 ηM of H-Inp-D-Bal-D-Trp-Phe-Apc-NH$_2$ (Example #27) (SEQ ID: 2) (FIGS. 11, 13 and 14)

3. In Vivo LPS/Cytokine Assay in a Mouse Model

Bacterial lipopolysaccharide (LPS), the principal component in the pathogenesis of endotoxic shock, acts primarily on monocytes and evokes an acute phase response in vivo resulting in excessive production of IL-1β, IL-6 and TNF-α. The amplification of these proximal cytokines has a broad array of pro-inflammatory and anorexigenic effects (Kotler, D. P., *Ann. Internal Med.*, (2000), 133 (8):622-34) contributing to pathogenesis of sepsis and multiple organ failure (Cohen, J., *Nature*, (2002), 420 (6917):885-91; and Riedemann, N. C. et al., *J. Clin. Invest.*, (2003), 112 (4):460-7). In an effort to examine the ability of the novel ligands of native ghrelin of the instant application to modulate inflammatory cytokine expression in vivo, mice were treated with ghrelin prior to an LPS administration. As shown in FIGS. 1, 2, 4, 5, 7, 8, 9 and 10, both 5 and 10 nmoles of the ghrelin analogue having the formula H-Inp-D-Bal-D-Trp-Phe-Apc-NH$_2$ (Example #27 (SEQ ID: 2)) exerted a potent anti-inflammatory effect on LPS-induced endotoxemia with inhibition of TNF-α, IL-6, IL-10 and IL-13 expression in vivo a. Test Subjects Male 22-24 g CD1 mice (Charles River Laboratories, Wilmington, Mass., U.S.A.) were used. The guidelines proposed by the committee for the Care of Laboratory Animal Resources Commission of Life Sciences-National Research Council were followed to minimize animal pain and distress. Each animal received rodent laboratory chow and ad libitum water.

b. LPS-Induced Inflammation

Endotoxin shock in mice was induced by intraperitoneal (i.p.) injection with 5 µg of lipopolysaccharide (LPS) (*E. coli* serotype 055:B5, Sigma-Aldrich, St. Louis, Mo., U.S.A.), an outer-membrane component of gram-negative bacteria which interacts with LPS-binding protein and CD14, which present LPS to toll-like receptor 4, activating inflammatory gene expression through nuclear factor κβ and mitogen-activated protein-kinase signaling (Bochkov, V. N. et al., *Nature*, (2002), 419 (6902):77-81). Animals first received a single 0.1 ml. i. p. injection of the claimed ghrelin analogue of the formula H-Inp-D-Bal-D-Trp-Phe-Apc-NH$_2$ (Example #27) (SEQ ID: 2) (5 ηM/ms) in phosphate-buffered saline for 10 minutes prior to LPS administration. Mice were sacrificed 2 hours post-LPS challenge and serum was collected via heart puncture and stored −80° C.

c. Cytokine Estimation

Figure 3:
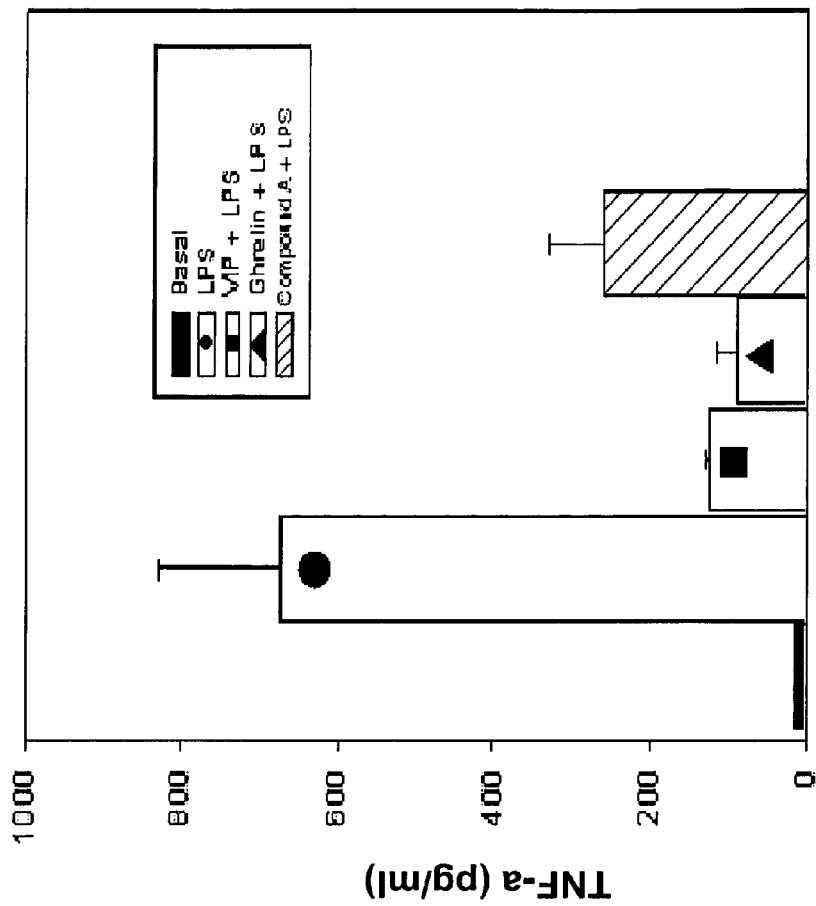
FIG. 3: shows the in vivo inhibition of LPS-stimulated cytokine secretion in mice in terms of TNF-α concentration for LPS alone and in combination with VIP, native ghrelin and the ghrelin analogue H-Inp-D-Bal-D-Trp-Phe-Apc-$NH_2$; (SEQ ID: 2)
Figure 4:
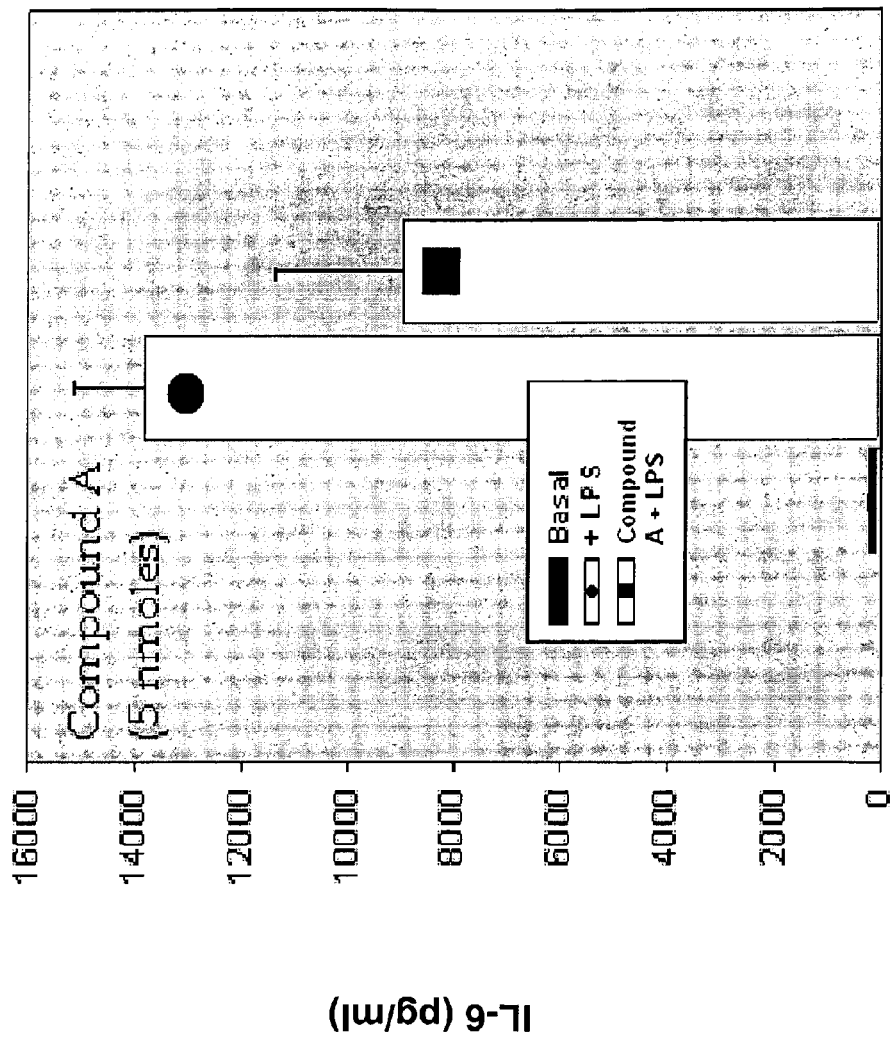
FIG. 4: shows the amount of IL-6 after an LPS challenge before and after injection of 5 nmoles of the ghrelin analogue H-Inp-D-Bal-D-Trp-Phe-Apc-$NH_2$; (SEQ ID: 2)
Figure 5:
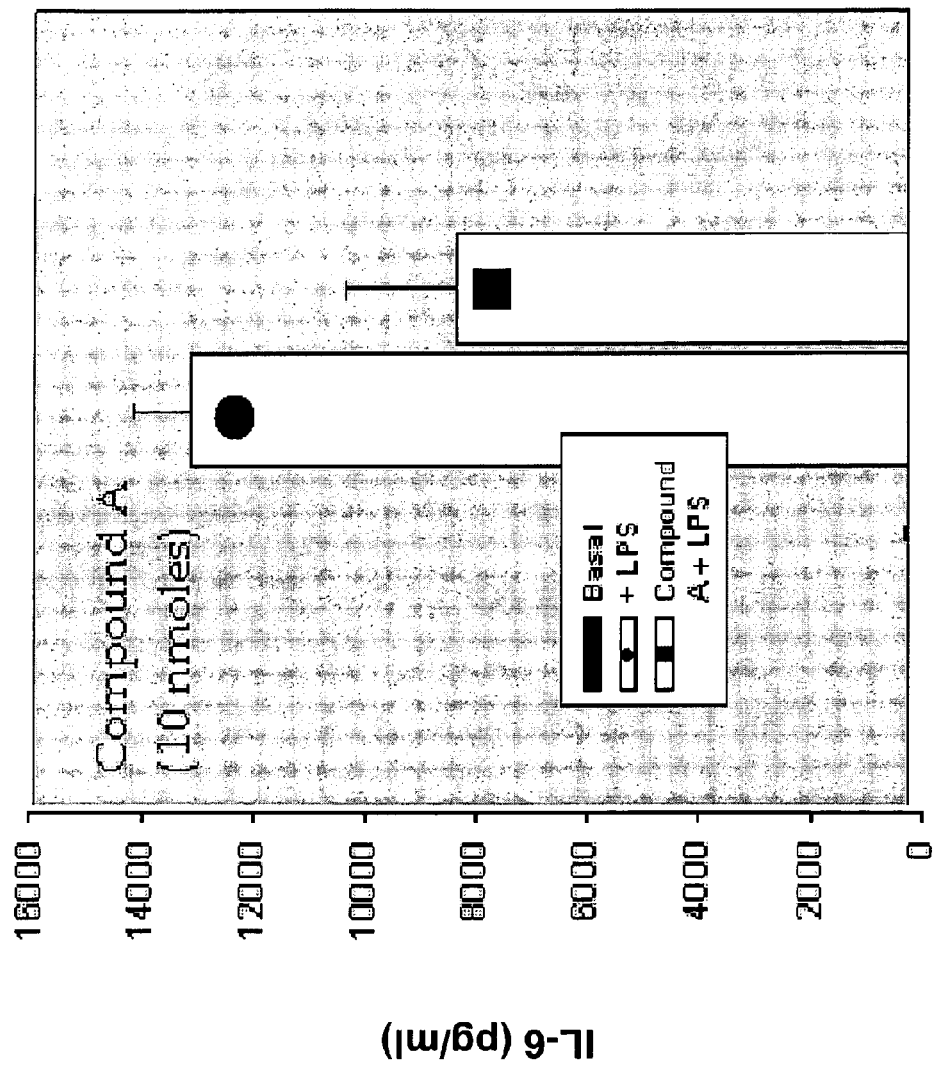
FIG. 5: shows the amount of IL-6 after an LPS challenge before and after injection of 10 nmoles of the ghrelin analogue H-Inp-D-Bal-D-Trp-Phe-Apc-$NH_2$; (SEQ ID: 2)
Figure 6:
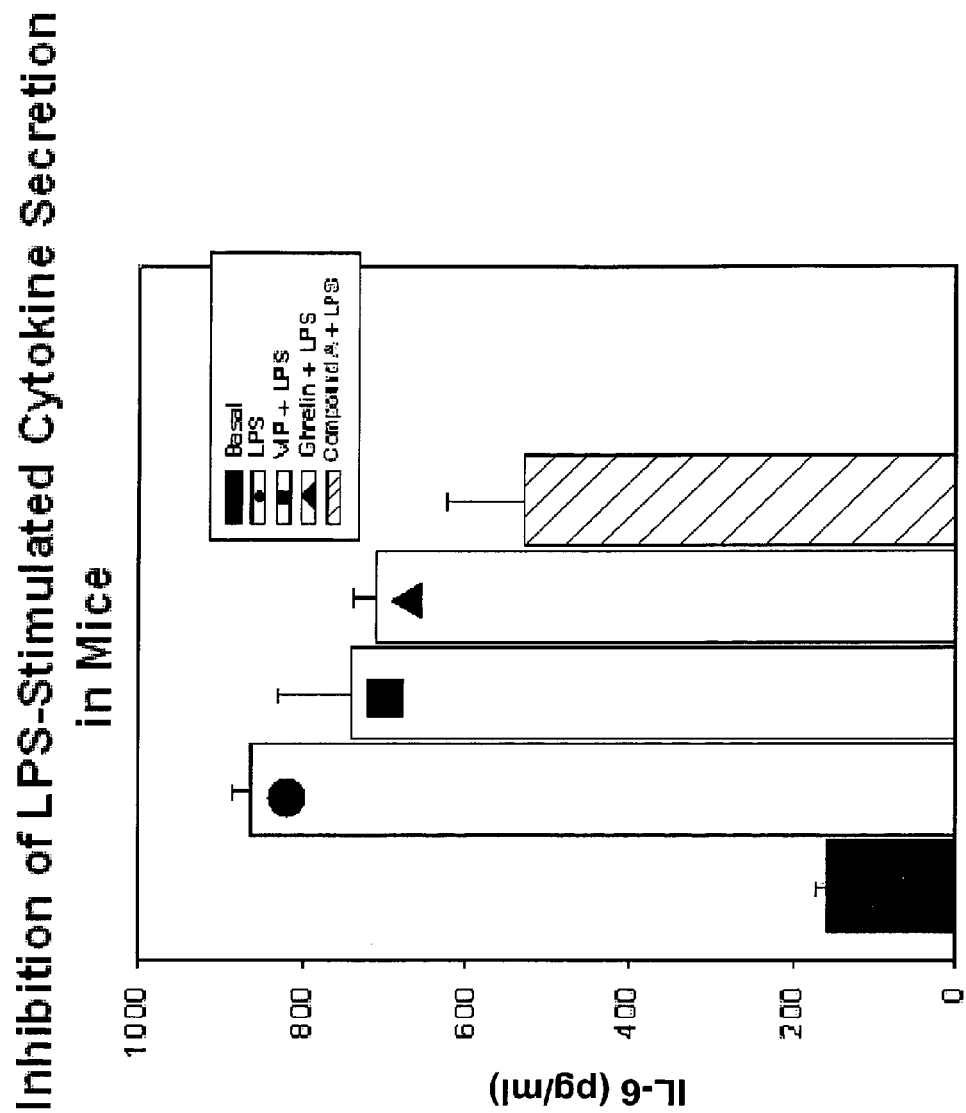
FIG. 6: shows the in vivo inhibition of LPS-stimulated cytokine secretion in mice in terms of IL-6 concentration for LPS alone and in combination with VIP, native ghrelin and the ghrelin analogue H-Inp-D-Bal-D-Trp-Phe-Apc-$NH_2$; (SEQ ID: 2)
Figure 7:
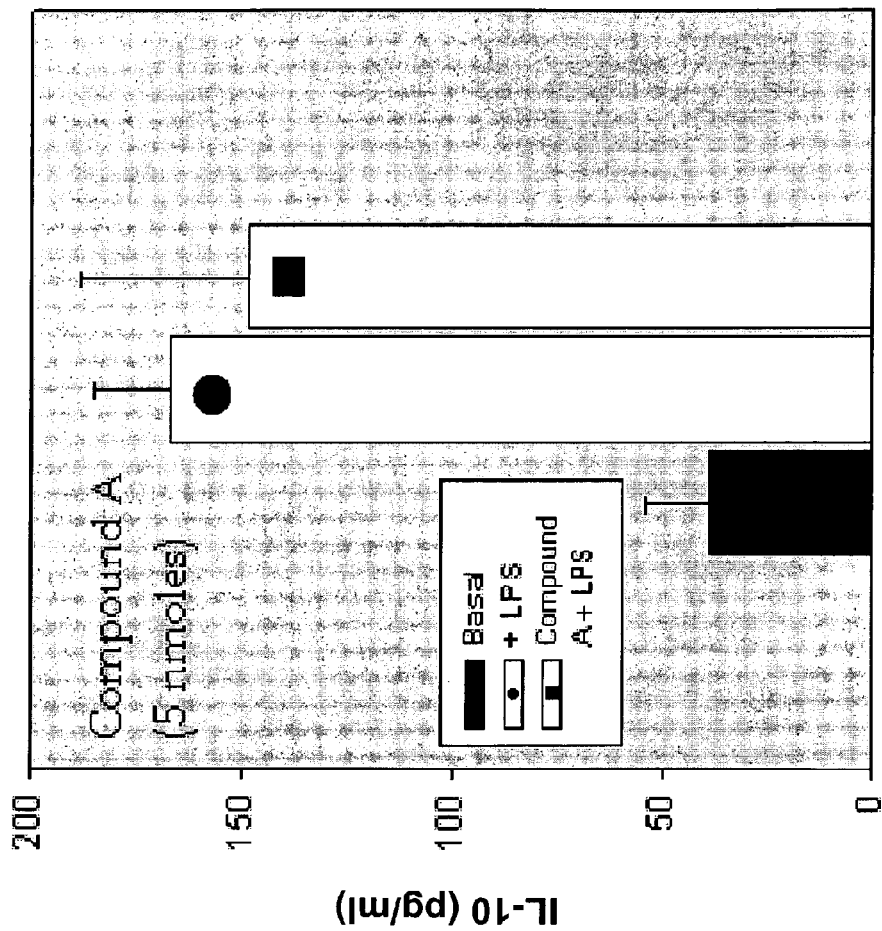
FIG. 7: shows the amount of IL-10 after an LPS challenge before and after injection of 5 nmoles of the ghrelin analogue H-Inp-D-Bal-D-Trp-Phe-Apc-$NH_2$; (SEQ ID: 2)
Figure 8:
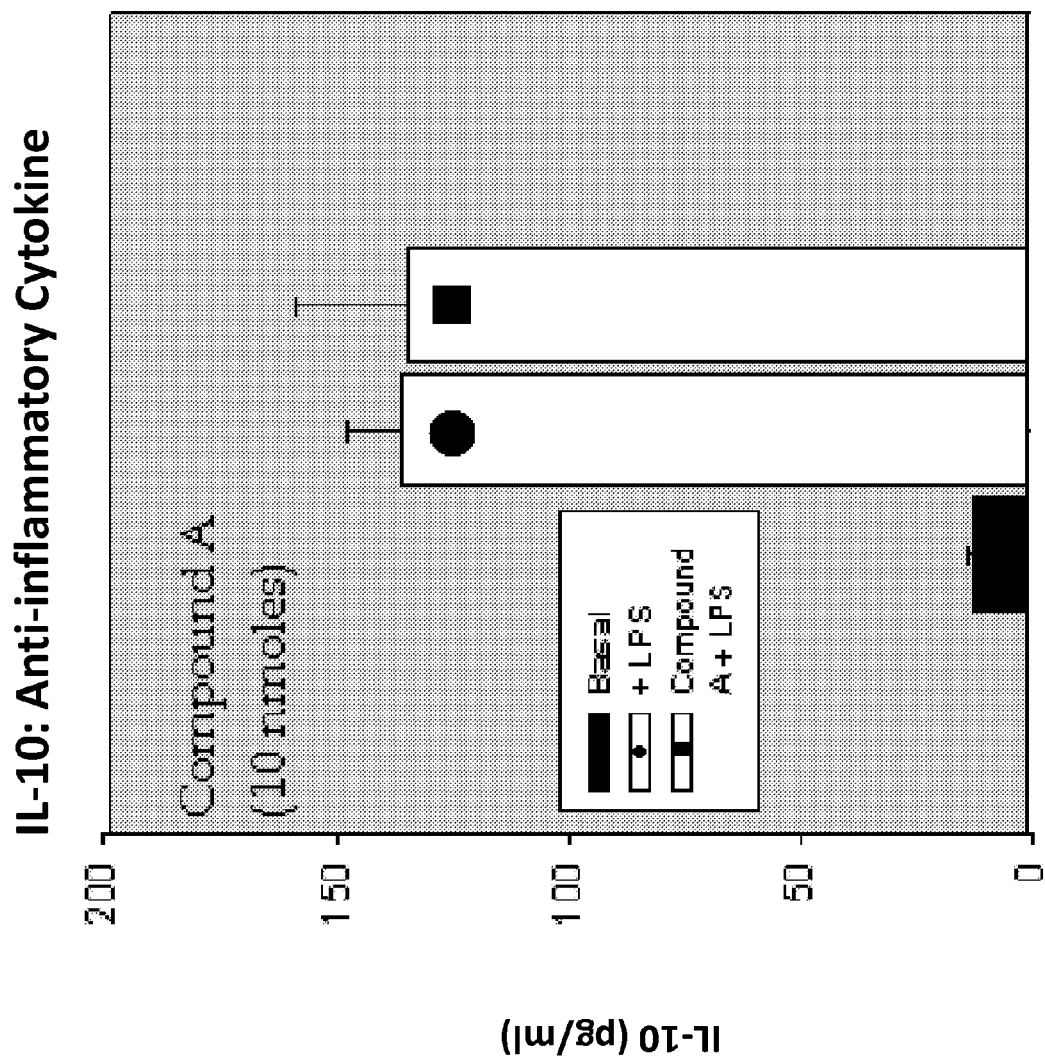
FIG. 8: shows the amount of IL-10 after an LPS challenge before and after injection of 10 nmoles of the ghrelin analogue H-Inp-D-Bal-D-Trp-Phe-Apc-NH$_2$; (SEQ ID: 2)
Figure 9:
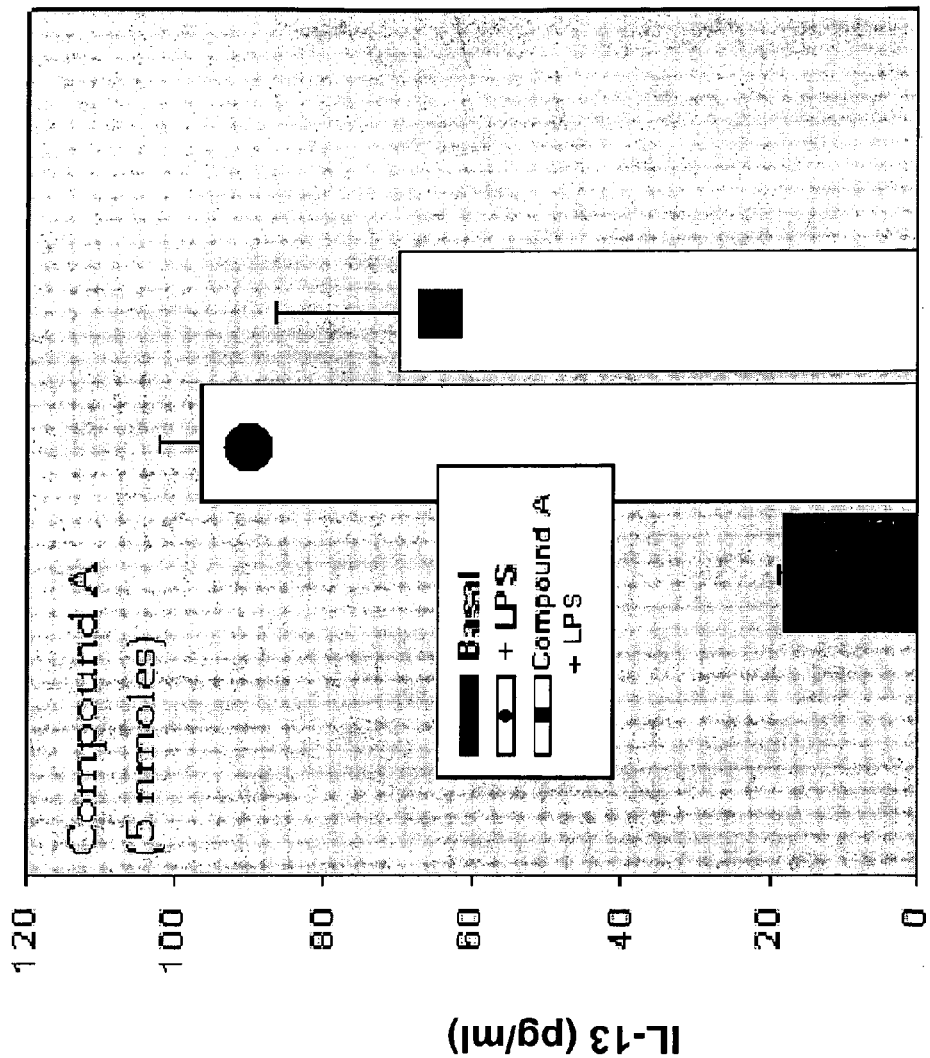
FIG. 9: shows the amount of IL-13 after an LPS challenge before and after injection of 5 nmoles of the ghrelin analogue H-Inp-D-Bal-D-Trp-Phe-Apc-NH$_2$; (SEQ ID: 2)
Figure 10:
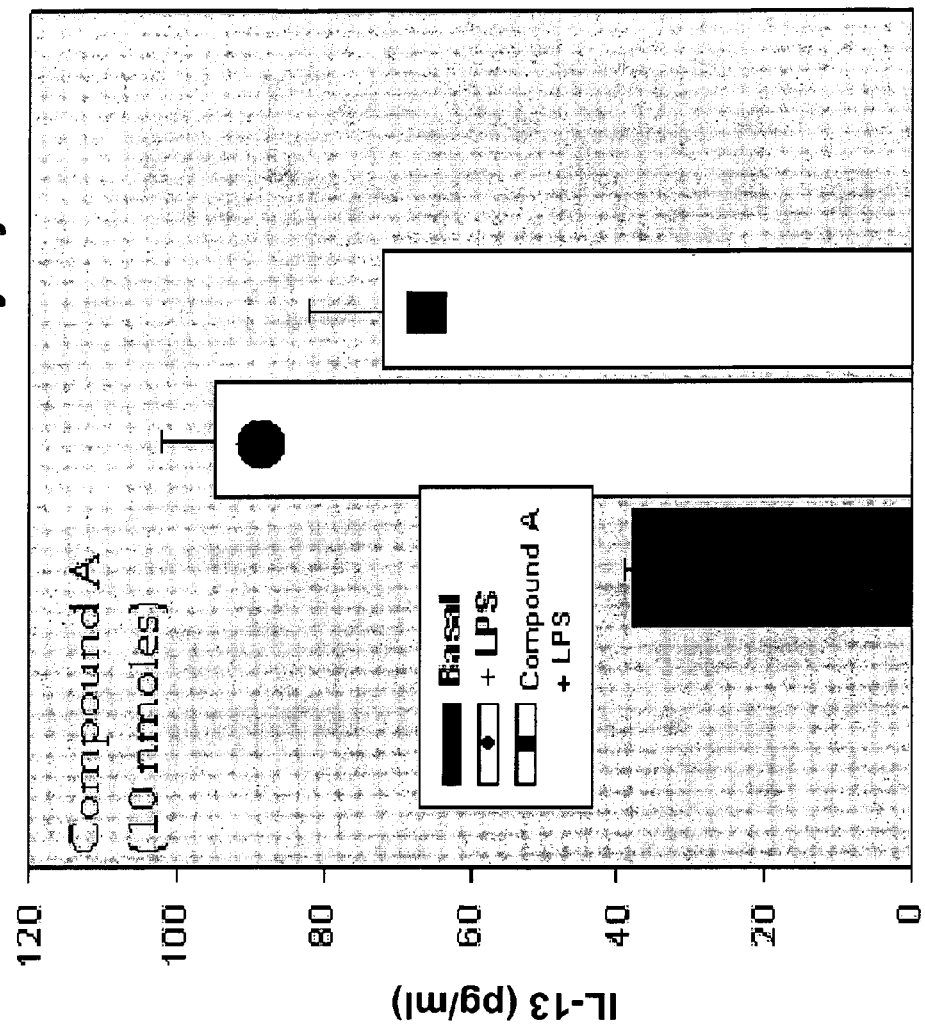
FIG. 10: shows the amount of IL-13 after an LPS challenge before and after injection of 10 nmoles of the ghrelin analogue H-Inp-D-Bal-D-Trp-Phe-Apc-NH$_2$; (SEQ ID: 2)

Mouse serum was used with Lincoplex™ custom 7-plex immunoassay for TNF-α (FIG. 3), IL-1β, IL-6 (FIG. 6), IL-10 and GM-CSF (Linco Research, Inc., St. Charles, Mo., U.S.A.). The assay was performed according to the manufacturer's instructions. Plates were run on a Luminex® 200 analyzer (Luminex, Austin, Tex., U.S.A.) using Masterplex CT™ v1.0 software for acquisition and Masterplex™ QT v2.5 software for analysis (MiraiBio, Hitachi Software Engineering Co., Yokohama, JP).

4. LPS/Cytokine Assay in a Human Model

Figure 12:
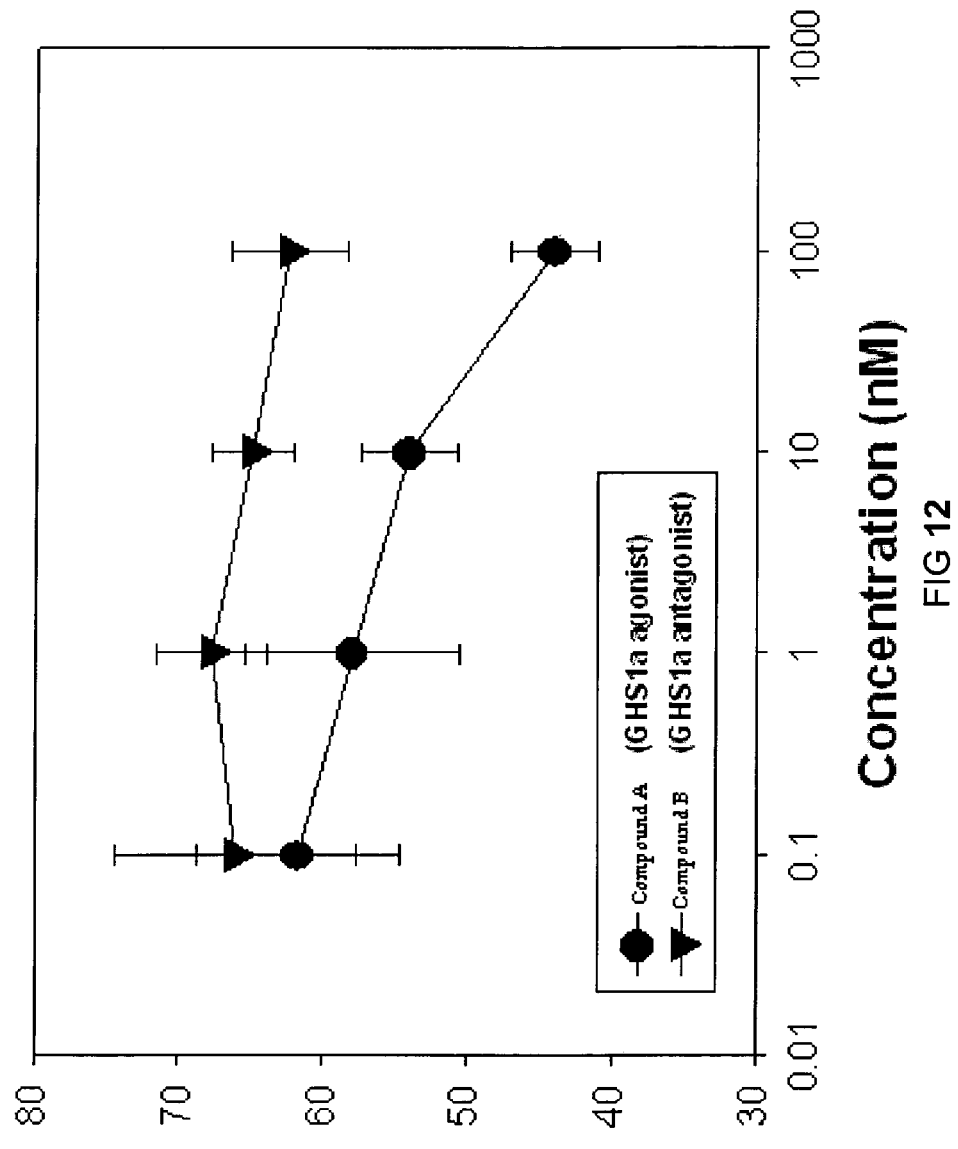
FIG. 12: shows the in vitro inhibition of LPS-stimulated IL-10 secretion from human peripheral blood monocytes by the ghrelin analogue H-Inp-D-Bal-D-Trp-Phe-Apc-NH$_2$ (SEQ ID: 2) (Compound A) and the ghrelin analogue (Aib$^2$, Glu$^3$(NH-hexyl)hGhrelin(1-28)-NH2) (SEQ ID: 92) (Compound B)
Figure 15:
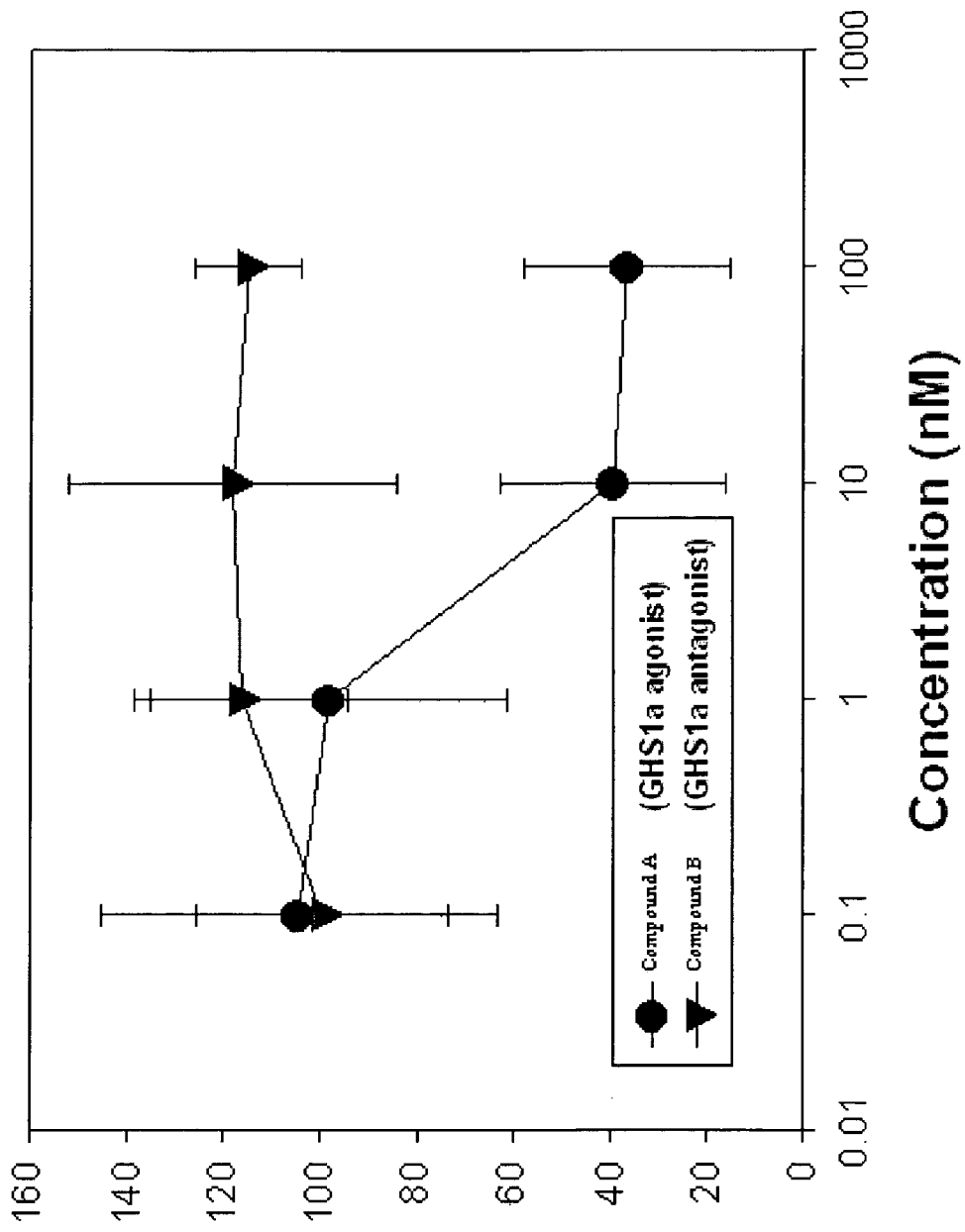
FIG. 15: shows the in vitro inhibition of LPS-stimulated TNF-α secretion from human peripheral blood monocytes by the ghrelin analogue H-Inp-D-Bal-D-Trp-Phe-Apc-NH$_2$ (SEQ ID: 2) (Compound A) and the ghrelin analogue (Aib$^2$, Glu$^3$(NH-hexyl)hGhrelin(1-28)-NH2) (SEQ ID: 92) (Compound B)

Human Peripheral Blood Mononuclear Cells (cat #7200) were procured for the assay (Seracare Diagnostics, Gaithersburg, Md., U.S.A.). Frozen vials were thawed and washed once with Phosphate Buffered Saline (Thermo Fisher Scientific, Inc., Waltham, Mass., U.S.A.). Cells were then counted and plated into 96-well dishes. Cells were incubated with H-Inp-D-Bal-D-Trp-Phe-Apc-NH$_2$ (Example #27) (SEQ ID: 2) and (Aib$^2$, Glu$^3$(NH-hexyl)hGhrelin(1-28)-NH$_2$ (Example #13) (SEQ ID: 92) for 30 minutes, stimulated with LPS at 100 ηg/ml, and then incubated a second time for 6 hours. When the incubation was complete, the well dishes were spun at 1000 rpm for 2 minutes. The supernatant that resulted from said procedure was collected and frozen at −80° C. At a later date, the frozen supernatant was thawed. An enzyme-linked immunoSorbent assay (ELISA) to measure TNF-a (FIG. 15), IL-6 (FIG. 11) and IL-10 (FIG. 12) levels was performed on the supernatant (cat #SMTA00, SM6000B and M1000, respectively obtained from R&D Systems, Minneapolis, Minn., U.S.A.). Plates were analyzed with a Spectramax® Reader using Softmax Pro software (Spectramax, Inc., Sunnyvale, Calif., U.S.A.).

5. In Vivo LPS/Chemokine Assay

Mouse peritoneal macrophages were elicited by intraperitoneal (i. p.) injection of 2 ml of 4% Brewer's thioglycollate medium (Difco, Detroit, Mich., U.S.A.) into male BALB/c mice aged 6 to 10 weeks (Ace Animals, Inc., Boyertown, Pa., U.S.A.). Peritoneal exudate cells were obtained 72 hours after injection by peritoneal lavage with ice-cold RPMI 1640 medium (Sigma-Aldrich, St. Louis, Mo., U.S.A.). Peritoneal exudate cells containing lymphocytes and macrophages were washed twice and re-suspended in ice-cold RPMI 1640 medium supplemented with 2% heat-inactivated fetal calf serum "FCS" (Life Technologies, Rockville, Md., U.S.A.) and were seeded in flat-bottomed 96-well microtiter plates (Corning Glass, Corning, N.Y., U.S.A.) at 8×104 cells per well in a final volume 200 µl. The cells were incubated at 37° C. for 2 hours to adhere. Those cells that did not adhere were removed by repeated washings with RPMI 1640 medium.

Figure 16:
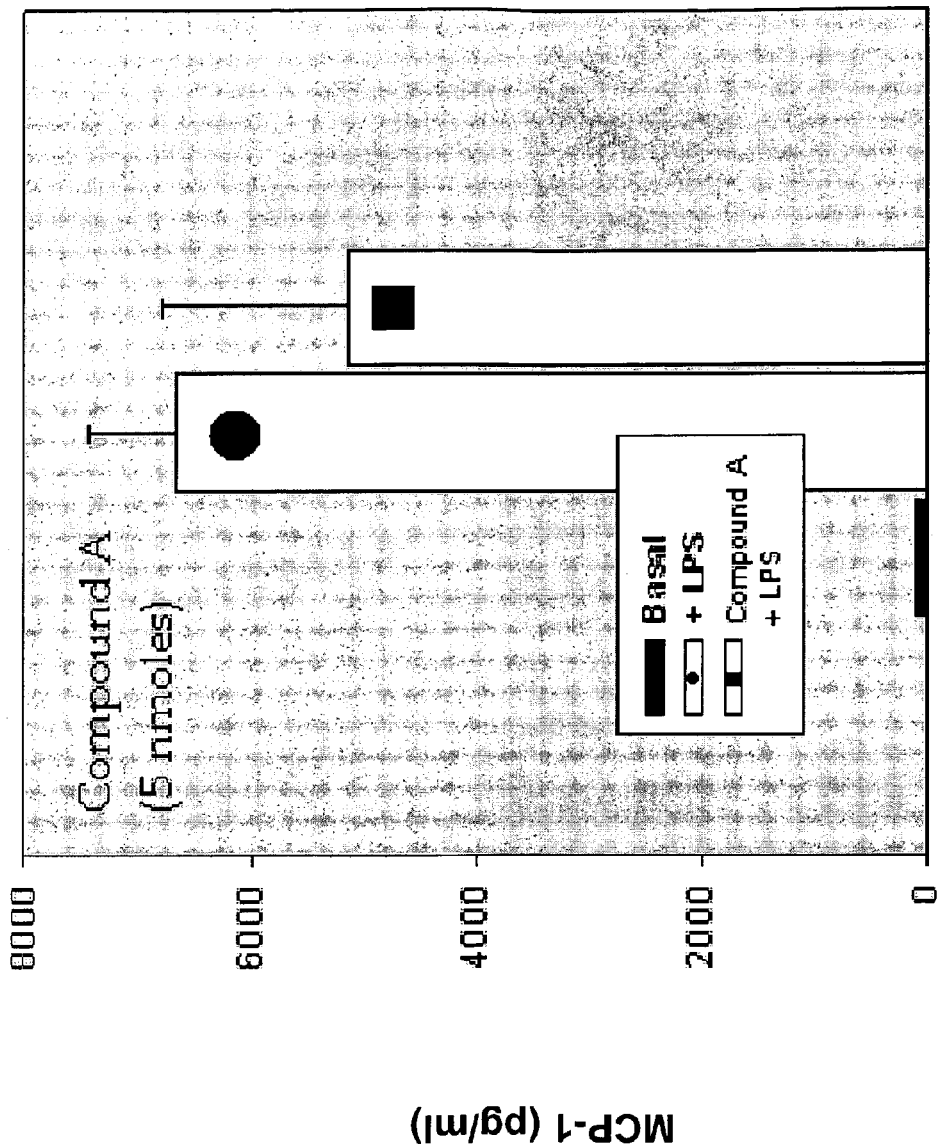
FIG. 16: shows the amount of MCP-1 chemokine after an LPS challenge before and after injection of 5 nmoles of the ghrelin analogue H-Inp-D-Bal-D-Trp-Phe-Apc-NH$_2$; (SEQ ID: 2)
Figure 17:
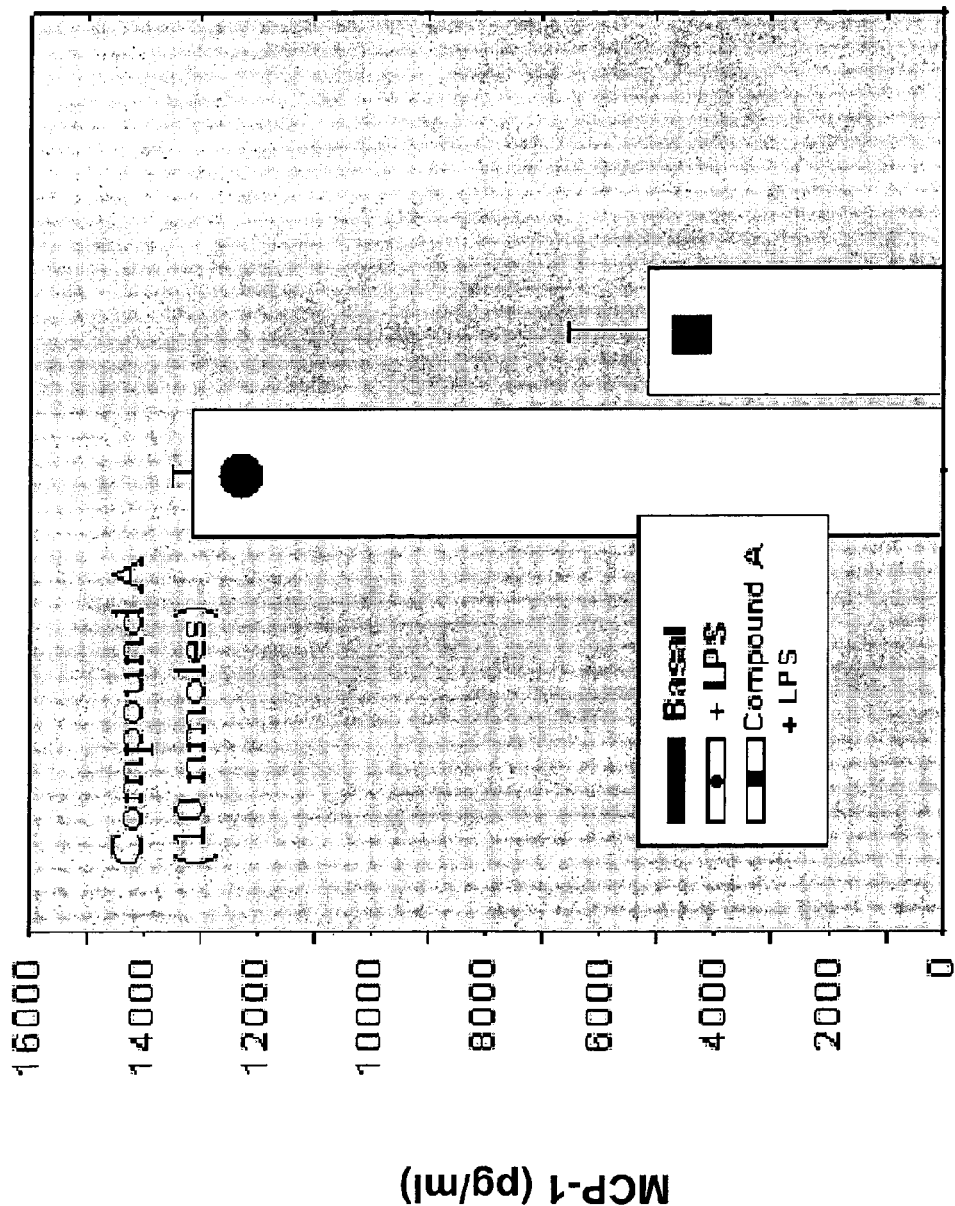
FIG. 17: shows the amount of MCP-1 chemokine after an LPS challenge before and after injection of 10 nmoles of the ghrelin analogue H-Inp-D-Bal-D-Trp-Phe-Apc-NH$_2$; (SEQ ID: 2)
Figure 18:
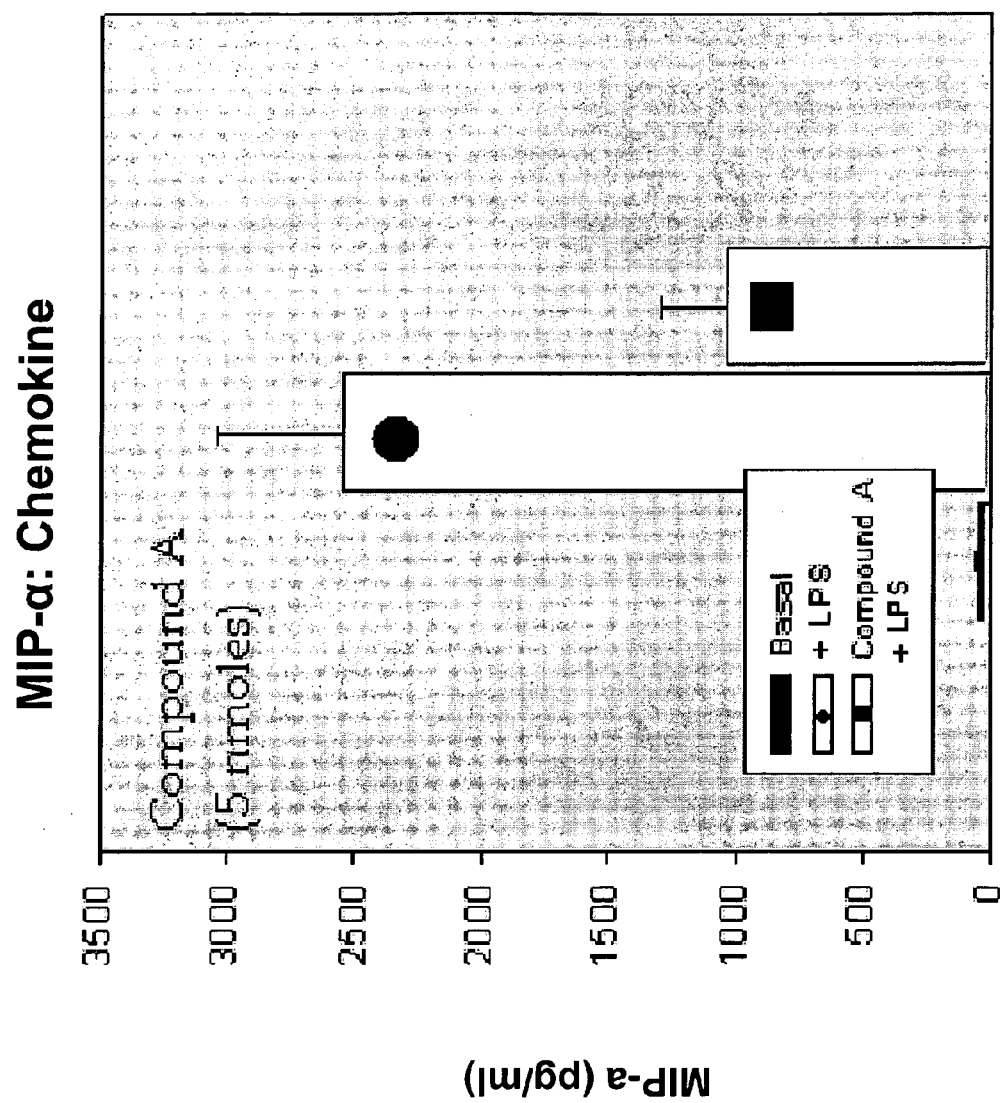
FIG. 18: shows the amount of MIP-α chemokine after an LPS challenge before and after injection of 5 nmoles of the ghrelin analogue H-Inp-D-Bal-D-Trp-Phe-Apc-NH$_2$; (SEQ ID: 2)
Figure 19:
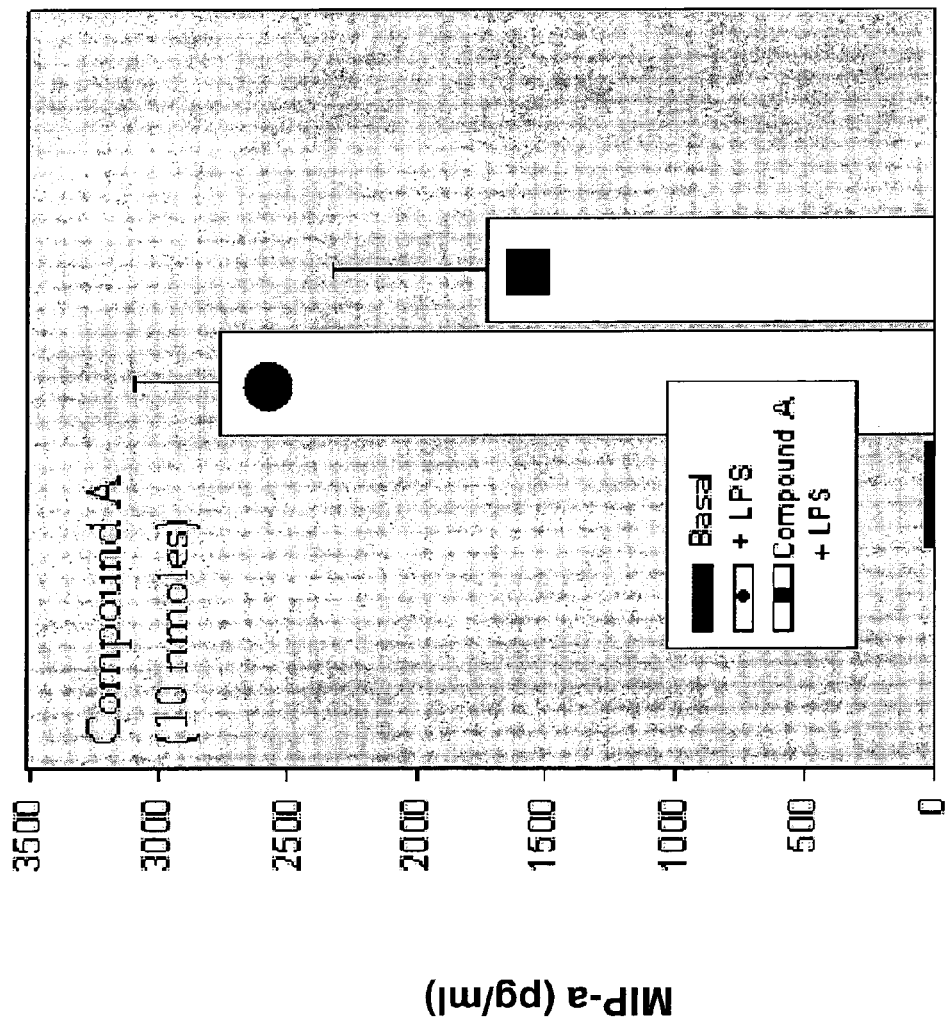
FIG. 19: shows the amount of MIP-α chemokine after an LPS challenge before and after injection of 10 nmoles of the ghrelin analogue H-Inp-D-Bal-D-Trp-Phe-Apc-NH$_2$; (SEQ ID: 2)
Figure 20:
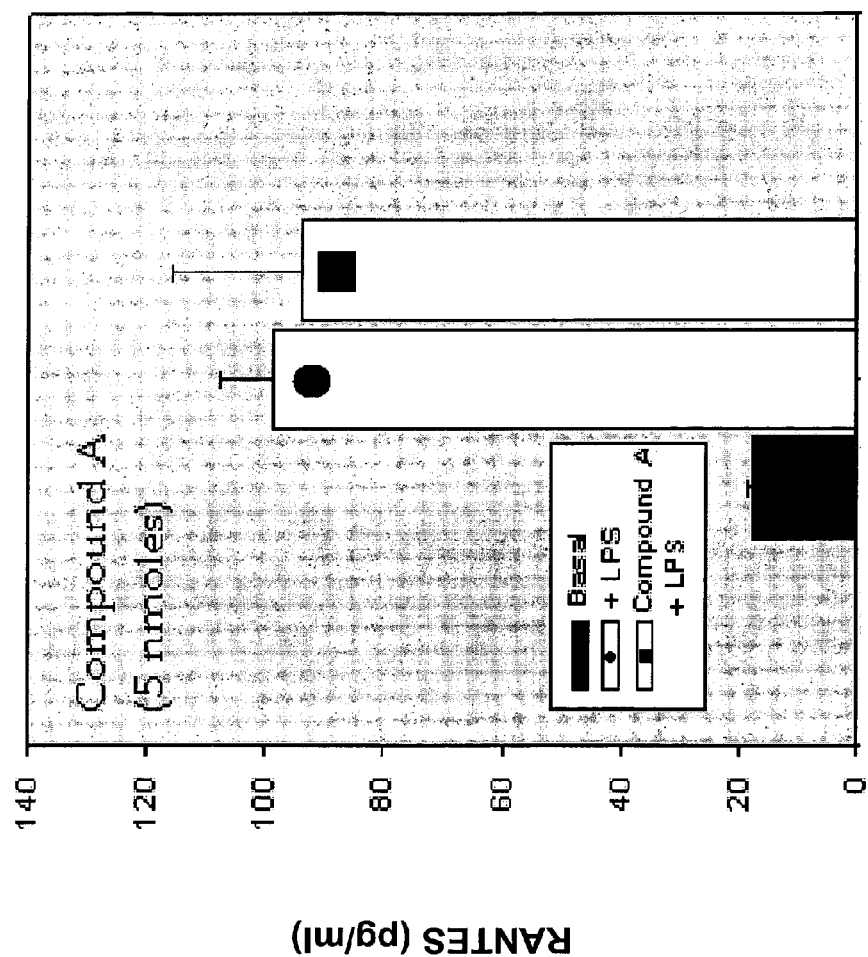
FIG. 20: shows the amount of RANTES chemokine after an LPS challenge before and after injection of 5 nmoles of the ghrelin analogue H-Inp-D-Bal-D-Trp-Phe-Apc-NH$_2$; (SEQ ID: 2)
Figure 21:
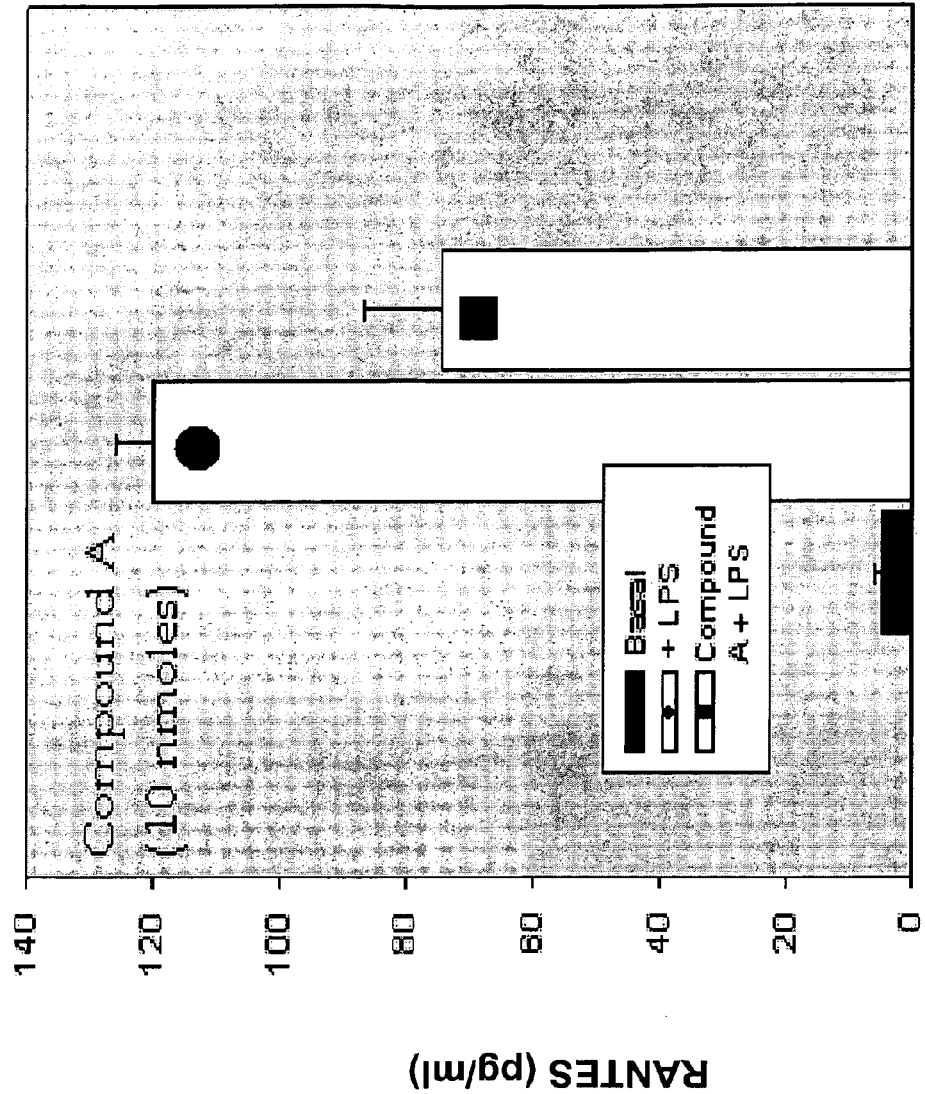
FIG. 21: shows the amount of RANTES chemokine after an LPS challenge before and after injection of 10 nmoles of the ghrelin analogue H-Inp-D-Bal-D-Trp-Phe-Apc-NH$_2$; (SEQ ID: 2)
Figure 22:
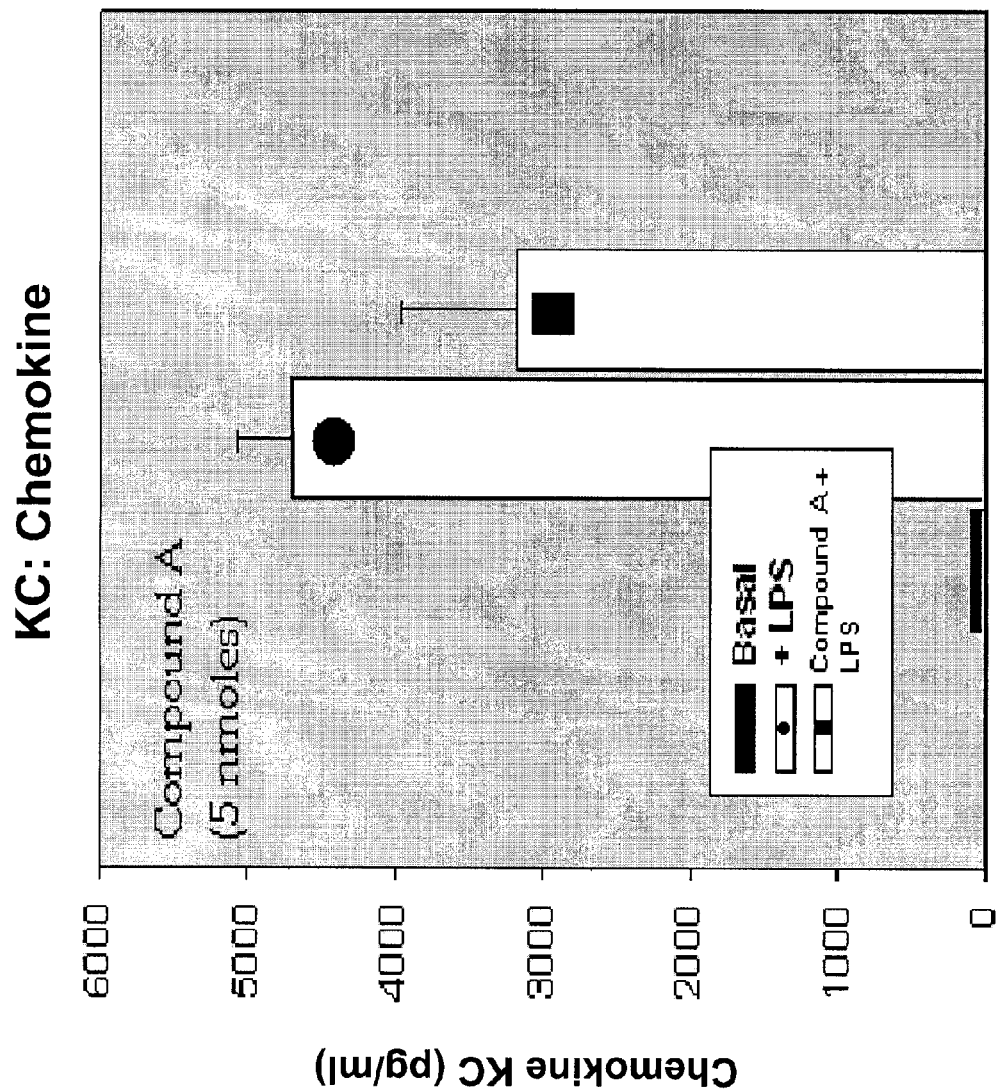
FIG. 22: shows the amount of KC chemokine after an LPS challenge before and after injection of 5 nmoles of the ghrelin analogue H-Inp-D-Bal-D-Trp-Phe-Apc-NH$_2$; (SEQ ID: 2)
Figure 23:
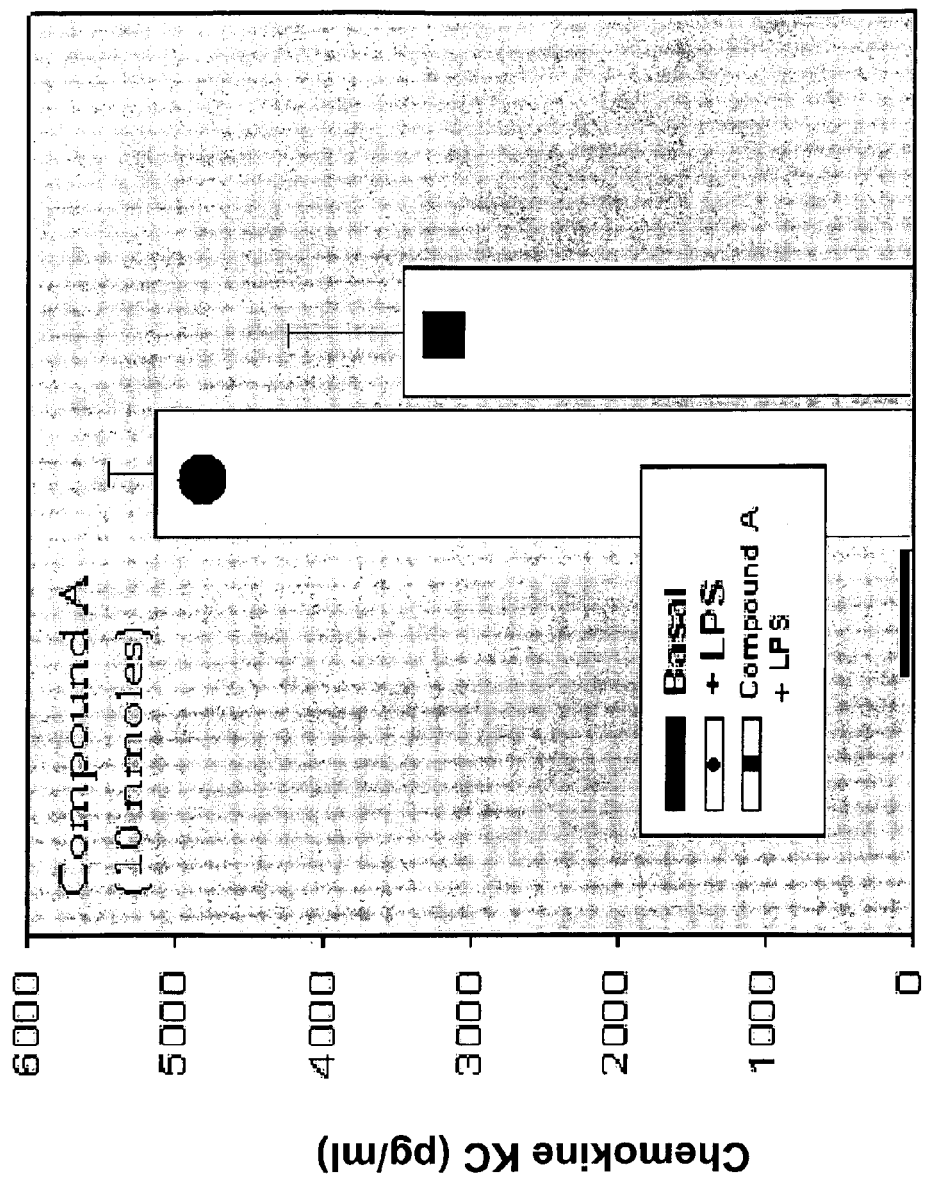
FIG. 23: shows the amount of KC chemokine after an LPS challenge before and after injection of 10 nmoles of the ghrelin analogue H-Inp-D-Bal-D-Trp-Phe-Apc-NH$_2$; (SEQ ID: 2)

Mouse serum was used with Lincoplex™ custom 7-plex immunoassay for MIP-1α (FIGS. 18 and 19), MCP-1 (FIGS. 16 and 17), RANTES (FIGS. 20 and 21) and KC (FIGS. 22 and 23) (cat #MCYTO-70K-07). The assay was performed according to the manufacturer's instructions. Plates were run on a Luminex® 200 analyzer using Masterplex CT™ v1.0 software for acquisition and Masterplex™ QT v2.5 software for analysis (MiraiBio).

6. Continuous Infusion of Ghrelin Analogues a. Test Subjects:

F344/NTacfBR male rats (Taconic Farms, Inc., Germantown, N.Y., U.S.A.) were housed two to a cage, fed rat chow (diet 5001, Purina Mills, Inc., St. Louis, Mo., U.S.A.) and acclimated for at least three days prior to use.

Studies were approved by the Institutional Animal Care and Use Committee of the Oregon Health and Science University and conducted according to NIH Guide for Care and Use of Laboratory Animals.

b. Nephrectomy Procedure

A 5/6 nephrectomy was performed in two stages. The test subjects were initially anesthetized with standard rat cocktail and placed prone in a clean environment. A 1 cm posterior incision was made on the right flank through which the right kidney was located. For animals undergoing nephrectomy, the renal capsule was removed and the upper and lower third of the kidney was transected and the resultant wound cauterized leaving the middle third of the kidney with the renal artery and vein intact. For animals receiving a sham operation, the renal capsule was opened up and cauterized to simulate the manipulations performed in the nephrectomy. The external surgical wounds were closed by suturing and the test subject was isolated to facilitate recovery.

Nine days following the initial surgery, the animals were again anesthetized and placed prone in the surgical area. A 1 cm incision was made on the left side of the subject's abdomen and the left kidney was isolated. For animals undergoing nephrectomy, the renal capsule was removed and the vasculature was tied off by suturing. The vascular bundle was then transected distal to the suture and the entire kidney removed. Any residual bleeding was cauterized. For animals in the sham group, the renal capsule was removed and cauterized. The external surgical wounds were closed with suture. While still under anesthesia, osmotic mini-pumps were placed in all test subjects. A 1 cm incision was made in the midline overlying the posterior thorax at the level of the forelimbs and the underlying sub-cutaneous space was opened via blunt dissection. The osmotic minipumps were placed inside and the incision and closed with suture. This procedure marked the first day ("Day 0") of treatment.

c. Continuous Administration of Ghrelin Analogues:

A continuous sterile infusion of one of two ghrelin analogues, i.e., H-Inp-D-Bal-D-Trp-Phe-Apc-$NH_2$ (Example #27) (SEQ ID: 2) and ($Aib^2$, $Glu^3$(NH-hexyl)hGhrelin(1-28)-$NH_2$ (Example #13) (SEQ ID: 92), native hGhrelin or saline were administered at a rate of 0.5 µl/h for five days subcutaneously using Alzet mini-osmotic pumps (Model 2002, Durect Corp., Cupertino, Calif., U.S.A.). The day before the implantation of the pumps, the mean body weight of each group was determined. To calculate the concentration required for the treatment group, the molecular weight of each administered compound, the dose given (150 ηmol/kg/day) and pump delivery rate, were taken into consideration. Each compound was dissolved in vehicle solution (2% inactivated rat serum, 5% Tween-80) sonicated and filtered through a 0.2 µl syringe filter.

d. Determination of Body Composition

Body composition was determined two days prior to the second stage of the nephrectomy or sham operation under anesthesia by dual-energy x-ray absorbtometry (DEXA, Discovery A—QDR Series, Hologic Corp., Waltham, Mass., U.S.A.) and on the $14^{th}$ day of compound treatment, prior to euthanasia with $CO_2$.

e. Tissue Collection

After sacrifice, blood, brain, stomach and muscle were collected. A subset of the rats had their hypothalami dissected out, preserved in RNAlater solution (Applied Biosystems, Inc., Foster City, Calif., U.S.A.) and stored at −70° C. for extraction of RNA and RT-PCR analysis. A subset of the rats had their hypothalami and brainstems dissected out, preserved in RNAlater solution and stored at −70° C. for extraction of RNA and RT-PCR analysis. Hypothalamic blocks were dissected by making coronal transections at the optic chiasm and at the intersection between the hypothalamus and the mammalary bodies and sagital transections along the optic tracks. Cortex was then removed at the level of the corpus callosom. Brainstem blocks were dissected by removal of the cerebellum and coronal transections at the rostral border of the pons and at the spinal cord.

f. Cytokine Estimation

Rat serum samples were collected and tested for cytokines IL-1α, IL-1β, IL-2, IL-4, IL-6, IL-10, GM-CSF, INF-γ and TNF-α using a Bio-Plex rat cytokine 9-Plex assay (Bio-Rad Laboratories, Hercules, Calif., U.S.A.) according to the manufacturer's instructions for use thereof.

The pre-mixed standards were reconstituted in 0.5 ml of a Bio-Plex human serum standard diluent generating a stock concentration of 50,000 pg/ml for each cytokine. The standard stock was serially diluted in the Bio-Plex rat serum standard diluent to generate eight points for a standard curve. The assay was performed in a 96 well filtration plate supplied with the assay kit. Pre-mixed beads (50 µl) coated with target capture antibodies were transferred to each well of the filtration plate and washed twice with Bio-Plex wash buffer. The samples were diluted (1:4) in the Bio-Plex serum sample diluent. Pre-mixed standards or diluted samples (50 µl) were added to each well containing washed beads. The plate was shaken and incubated at room temperature for thirty minutes at a low speed (300 rpm). After incubation and washing, pre-mixed biotin conjugated detection antibodies were added to each of the wells. The plate was thereafter incubated for approximately thirty minutes and shaken at a low speed (300 rpm). After incubation and washing, strepavidin-PE were added to each well. The incubation was terminated after shaking for ten minutes at room temperature. After washing, the beads were re-suspended in 125 µl of Bio-Plex assay buffer. Beads were read on the Bio-Plex suspension array system (Bio-Rad Laboratories, Hercules, Calif., U.S.A.). The accumulated data was analyzed using Bio-Plex Manager software version 3.0 with 5 PL curve fitting.

g. Statistical Analysis

One-way ANOVA was used to determine differences among the nephrectomy and sham groups using a Bonferoni post-hoc test; $P<0.05$ was considered significant. In the case of the serum cytokines, each individual set of data was considered by ANOVA and the composite of all of the cytokine levels were considered together after normalizing all levels to the Sham/Saline group using a mixed model analysis for a trend for cytokines values among the different groups. This model takes into account the propensity of some animals to have higher or lower cytokine levels across all of the different cytokines and accounts for within-sample variability.

Figure 24:
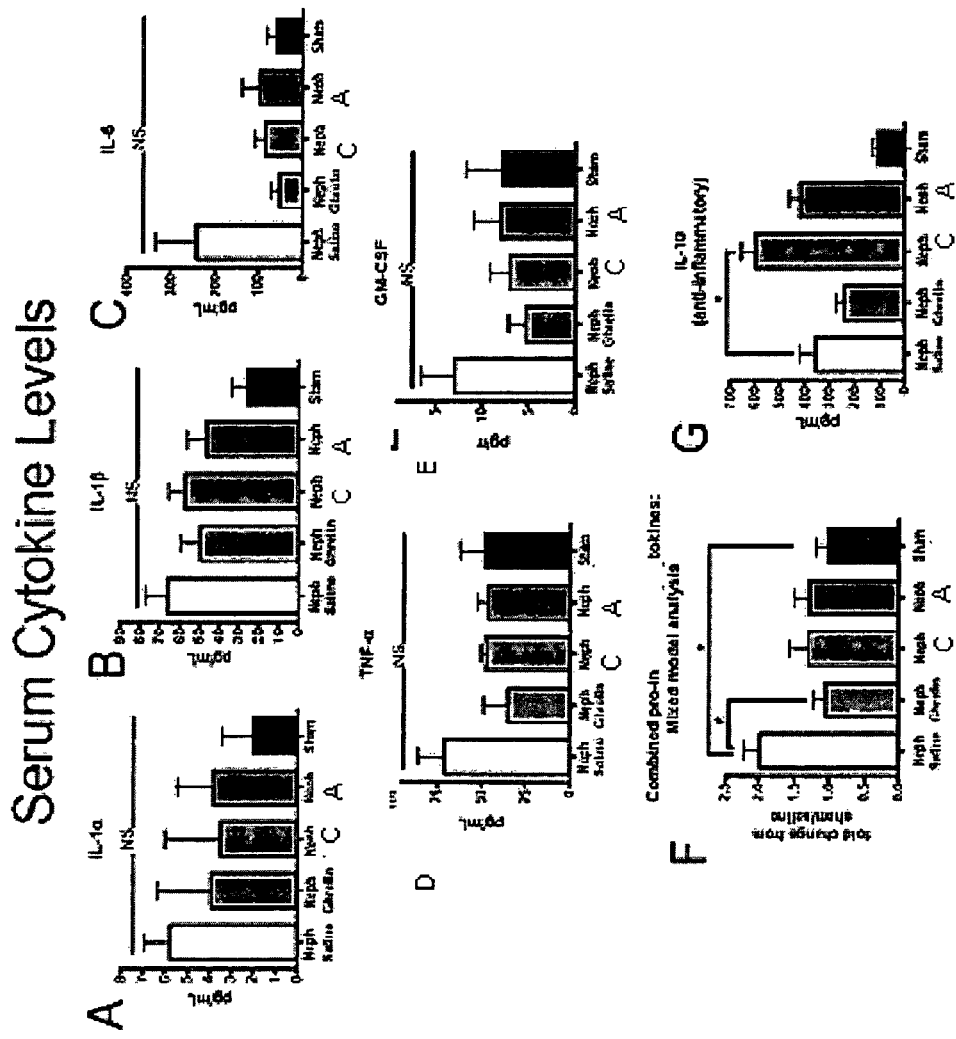
FIG. 24: shows serum cytokine levels after extended dosing with the ghrelin analogue H-Inp-D-Bal-D-Trp-Phe-Apc-NH$_2$; (SEQ ID: 2)

Among the pro-inflammatory cytokines measured, trends were found in all measured cytokines, but there was no significant difference in any single cytokine within the different treatment groups (IL-1α: Neph/Saline 5.75+/−1.14, N=10; Neph/Ghrelin(SEQ ID: 1) 3.92+/−2.39, N=11; Neph/($Aib^2$, $Glu^3$(NH-hexyl)hGhrelin(1-28)-$NH_2$ (Example #13) (SEQ ID: 92) 3.50+/−2.49, N=9; Neph/H-Inp-D-Bal-D-Trp-Phe-Apc-$NH_2$ (Example #27) (SEQ ID: 2) 3.84+/−1.62, N=11; Sham/Saline 2.00+/−1.39, N=5; IL-1-α: Neph/Saline 65.81+/−10.84, N=19; Neph/Ghrelin (SEQ ID: 1) 49.52+/−10.03, N=22; Neph/($Aib^2$, $Glu^3$(NH-hexyl)hGhrelin(1-28)-$NH_2$ (Example #13) (SEQ ID: 92) 57.37+/−7.48, N=9; Neph/H-Inp-D-Bal-D-Trp-Phe-Apc-$NH_2$ (Example #27) (SEQ ID: 2) 46.58+/−9.87, N=11; Sham/Saline 25.72+/−7.89, N=10; IL-6: Neph/Saline 241.00+/−90.87, N=20; Neph/Ghrelin (SEQ ID: 1) 52.42+/−18.68, N=22; Neph/(Aib$^2$, Glu$^3$(NH-hexyl)hGhrelin(1-28)-NH$_2$ (Example #13) (SEQ ID: 92) 83.65+/−21.71, N=9; Neph/H-Inp-D-Bal-D-Trp-Phe-Apc-NH$_2$ (Example #27) (SEQ ID: 2) 98.41+/−36.66, N=11; Sham/Saline 58.37+/−20.05, N=10; GM-CSF: Neph/Saline 12.85+/−3.60, N=19; Neph/Ghrelin (SEQ ID: 1) 5.24+/−1.93, N=22; Neph/(Aib$^2$, Glu$^3$(NH-hexyl)hGhrelin(1-28)-NH$_2$ (Example #13) (SEQ ID: 92) 7.01+/−2.05, N=9; Neph/H-Inp-D-Bal-D-Trp-Phe-Apc-NH$_2$ (Example #27) (SEQ ID: 2) 8.01+/−2.83, N=11; Sham/Saline 7.82+/−3.78, N=10; TNF-α: Neph/Saline 70.84+/−14.90, N=19; Neph/Ghrelin (SEQ ID: 1) 34.71+/−14.00, N=22; Neph/(Aib$^2$, Glu$^3$(NH-hexyl)hGhrelin(1-28)-NH$_2$ (Example #13) (SEQ ID: 92) 47.04+/−3.36, N=9; Neph/H-Inp-D-Bal-D-Trp-Phe-Apc-NH$_2$ (Example #27) (SEQ ID: 2) 45.81+/−6.23, N=11; Sham/Saline 47.83+/−13.73, N=10) (FIGS. 24A-24E). Using a mixed model ANOVA to detect significant trends among the pro-inflammatory cytokines for each treatment group, resulted in a significant decrease in pro-inflammatory cytokines in ghrelin-treated CKD rats and sham-operated rats relative to the nephrectomy/saline group (p<0.05) (FIG. 24F).

For the anti-inflammatory cytokine IL-10, there was a significant increase found in CKD rats receiving (Aib$^2$, Glu$^3$ (NH-hexyl)hGhrelin(1-28)-NH$_2$ (Example #13) (SEQ ID: 92) or H-Inp-D-Bal-D-Trp-Phe-Apc-NH$_2$ (Example #27) (SEQ ID: 2) relative to the nephrectomy/saline group (Neph/Saline 357.27+/−62.38, N=19; Neph/Ghrelin (SEQ ID: 1) 242.41+/−27.51, N=22; Neph/(Aib$^2$, Glu$^3$(NH-hexyl)hGhrelin(1-28)-NH$_2$ (Example #13) (SEQ ID: 92) 594.83+/−55.22, N=9 [p<0.05 vs. Neph/Saline]; Neph/H-Inp-D-Bal-D-Trp-Phe-Apc-NH$_2$ (Example #27) (SEQ ID: 2) 419.26+/−38.71, N=11; Sham/Saline 113.99+/−20.92, N=10) (FIG. 24G).

h. Central Inflammatory Transcripts

Figure 25:
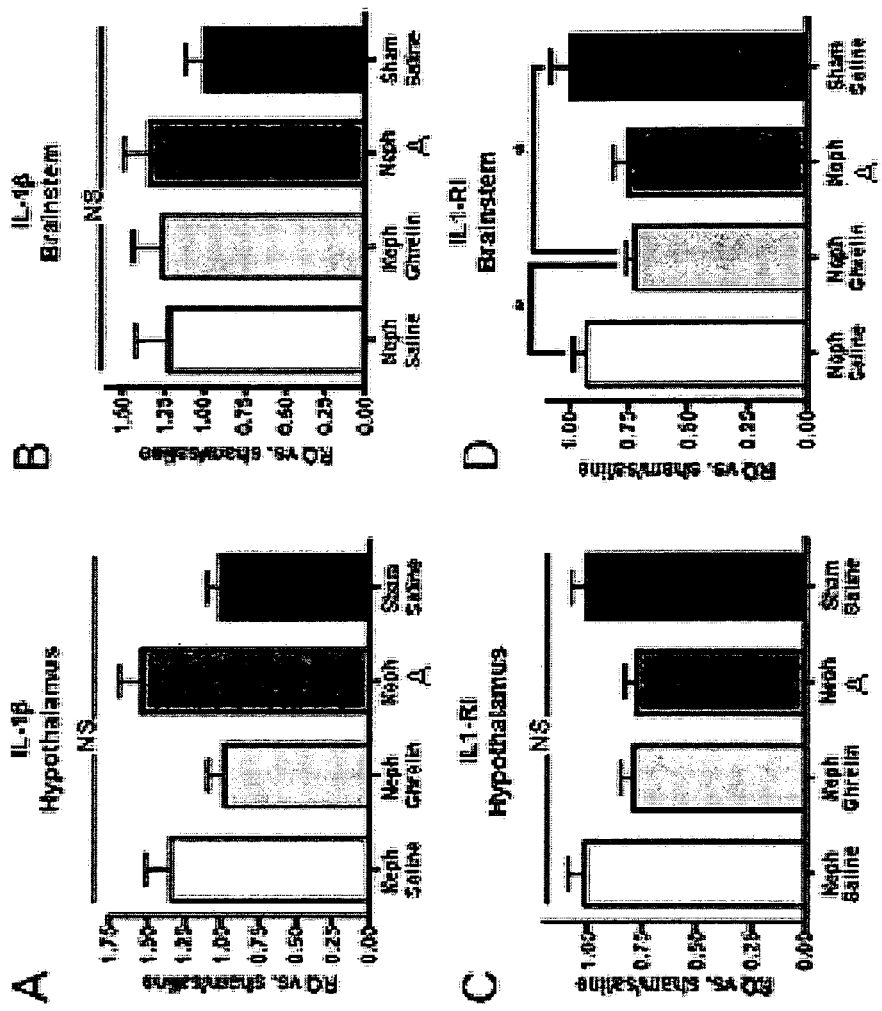
FIG. 25: shows expression levels for IL-1β and IL-1RI gene expression in the hypothalamus and brainstem for nephrectomized rats treated with saline, native ghrelin and the ghrelin analogue H-Inp-D-Bal-D-Trp-Phe-Apc-NH$_2$; (SEQ ID: 2)

There was no difference among the groups for transcript levels of IL-1β in the hypothalamus (Neph/Saline 1.34+/−0.74 n=18; Neph/Ghrelin (SEQ ID: 1) 0.98+/−0.46 n=19; Neph/H-Inp-D-Bal-D-Trp-Phe-Apc-NH$_2$ (Example #27) (SEQ ID: 2) 1.54+/−0.42 n=8; Sham/Saline 1.00+/−0.32 n=11) (FIG. 25A), IL-1R in the hypothalamus (Neph/Saline 1.01+/−0.31 n=17; Neph/Ghrelin(SEQ ID: 1) 0.78+/−0.26 n=19; Neph/H-Inp-D-Bal-D-Trp-Phe-Apc-NH$_2$ (Example #27) (SEQ ID: 2) 0.77+/−0.17 n=8; Sham/Saline 1.00+/−0.22 n=10) (FIG. 25B), or IL-1β in the brainstem (Neph/Saline 1.22+/−0.75 n=14 n=17; Neph/Ghrelin (SEQ ID: 1) 1.27+/−0.60 n=12; Neph/H-Inp-D-Bal-D-Trp-Phe-Apc-NH$_2$ (Example #27) (SEQ ID: 2) 1.34+/−0.46 n=8; Sham/Saline 1.00+/−0.33 n=8) (FIG. 25C), however, there was a significant decrease in expression of IL1-RI in the brainstem among ghrelin-treated animals relative to both the Neph/Saline group and the Sham/Saline group (Neph/Saline 0.93+/−0.21 n=14; Neph/Ghrelin (SEQ ID: 1) 0.72+/−0.12 n=12 [p<0.05 relative to both Neph/Saline and Sham/Saline]; Neph/H-Inp-D-Bal-D-Trp-Phe-Apc-NH$_2$ (Example #27) (SEQ ID: 2) 0.75+/−0.18 n=8; Sham/Saline 1.00+/−0.24 n=8) (FIG. 25D).

7. Studies in the Acute Colon Inflammation Model

In an effort to examine the ability of the novel ligands of native ghrelin of the instant application to ameliorate inflammation of the colon in vivo, inflammation was induced in a mouse model and thereafter said subjects were treated with a novel ghrelin analogue of the instant application. As shown in FIGS. 28-31, both a 5 nmolar and 50 nmolar dose of the ghrelin analogue, having the formula H-Inp-D-Bal-D-Trp-Phe-Apc-NH$_2$ (Example #27) (SEQ ID: 2), inhibited IFN-γ production in vivo.

a. Test Subjects

Male SJL mice (Charles River Laboratories, Wilmington, Mass., U.S.A.) approximately 5 to 6 weeks of age were employed. The guidelines proposed by the committee for the Care of Laboratory Animal Resources Commission of Life Sciences-National Research Council were followed to minimize animal pain and distress. Each animal received rodent laboratory chow and ad libitum water.

b. Colon Inflammation Induction

Acute colon inflammation was induced in the test subjects by administering 3 mg of 2,4,6-trinitrobenzene (Thermo Scientific Pierce Protein Research Products, Waltham, Mass., U.S.A.) (TNBS) in 50% ethanol via a catheter inserted intrarectally from the test subject's anus. Control mice received the same volume of 50% ethanol without the TNBS. Test subjects were treated intrapertoneally (ip) with the vehicle alone or with either a 5 nM or 50 nM dose of the ghrelin analogue H-Inp-D-Bal-D-Trp-Phe-Apc-NH$_2$ (Example #27) (SEQ ID: 2) approximately 12 hours after the TNBS administration. Five mice from both groups were sacrificed 4 days post-TNBS-induced challenge.

Figure 27:
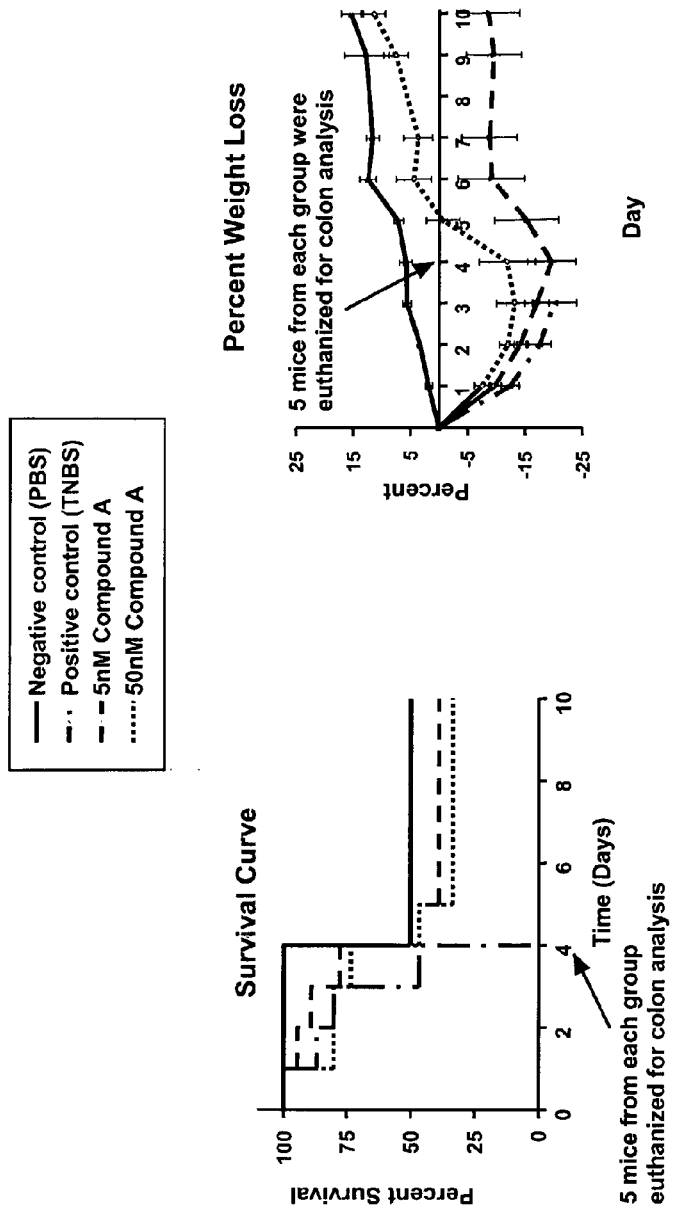
FIG. 27: shows comparative survival and weight loss percentages over time for ghrelin analogue H-Inp-D-Bal-D-Trp-Phe-Apc-NH$_2$ (SEQ ID: 2) in an acute colon inflammation mouse model.
Figure 28:
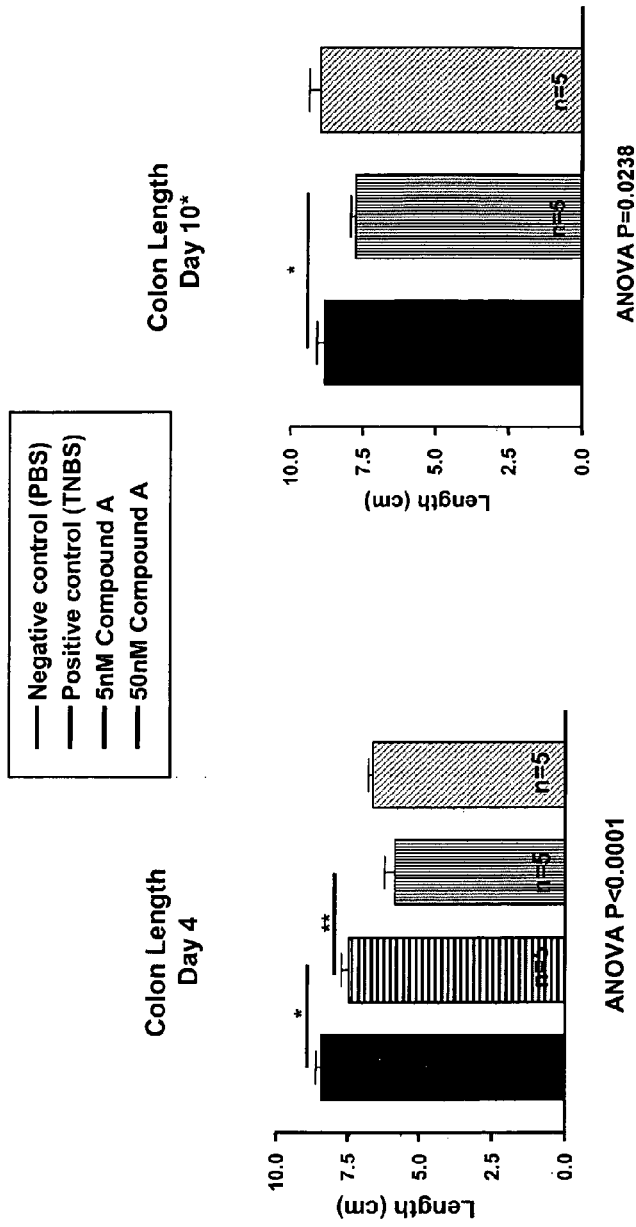
FIG. 28: shows the comparative length of an inflamed colon from mouse models treated with a negative control (shaded in bar), a positive control (horizontal lined bar), 5 nM of ghrelin analogue H-Inp-D-Bal-D-Trp-Phe-Apc-NH$_2$ (SEQ ID: 2) (vertical lined bar) and 50 nM of ghrelin analogue H-Inp-D-Bal-D-Trp-Phe-Apc-NH$_2$ (SEQ ID: 2) (diagonal lined bar) after 4 and 10 days of treatment.
Figure 29:
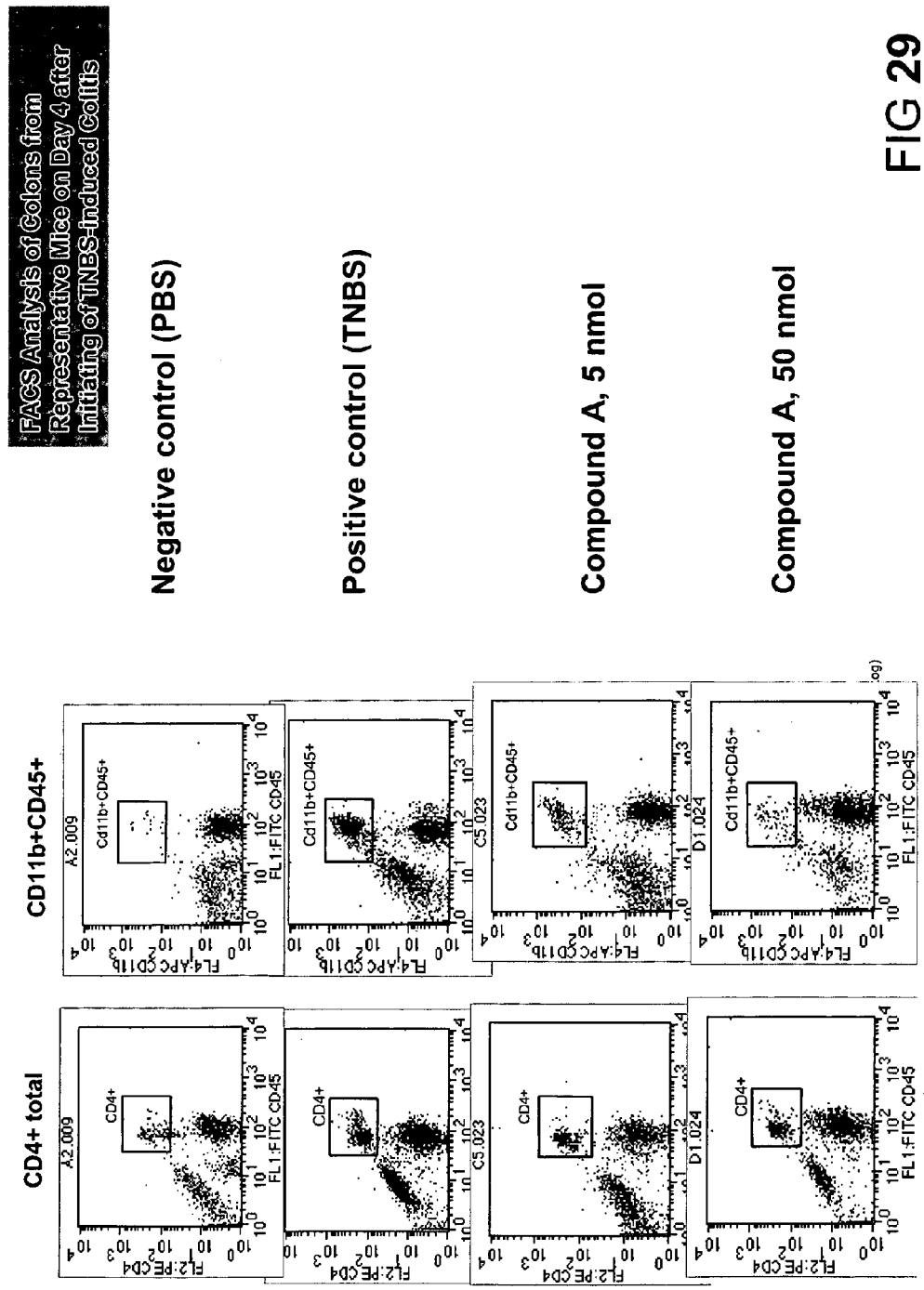
FIG. 29: shows the results of FACS analysis of colons from mouse models treated with a negative control, a positive control, 5 nM of ghrelin analogue H-Inp-D-Bal-D-Trp-Phe-Apc-NH$_2$ (SEQ ID: 2) and 50 nM of ghrelin analogue H-Inp-D-Bal-D-Trp-Phe-Apc-NH$_2$ (SEQ ID: 2) after 4 days of treatment after initiating TNBS-induced colitis.
Figure 30:
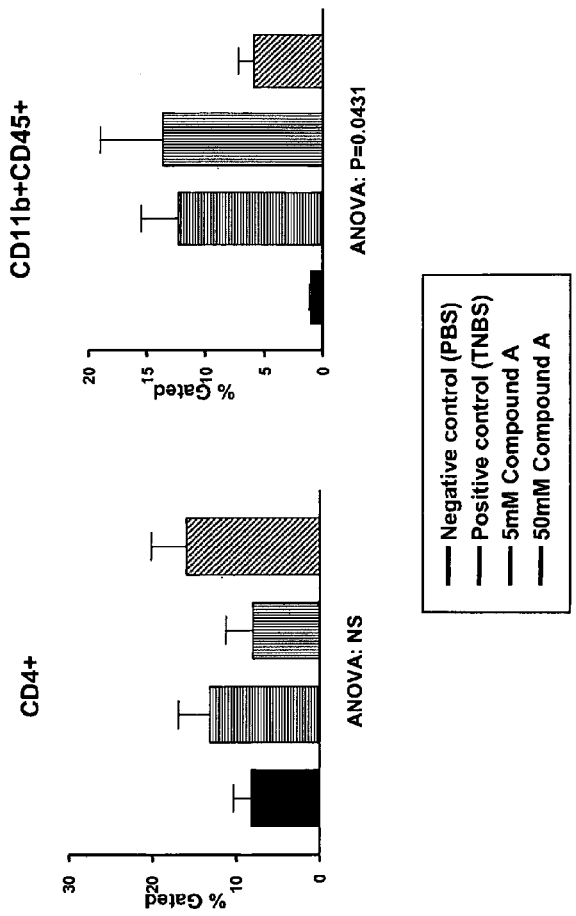
FIG. 30: shows the results of FACS analysis of colons from mouse models treated with a negative control (shaded in bar), a positive control (horizontal lined bar), 5 nM of ghrelin analogue H-Inp-D-Bal-D-Trp-Phe-Apc-NH$_2$ (SEQ ID: 2) (vertical lined bar) and 50 nM of ghrelin analogue H-Inp-D-Bal-D-Trp-Phe-Apc-NH$_2$ (SEQ ID: 2) (diagonal lined bar) after 4 days of treatment after initiating TNBS-induced colitis.
Figure 31:
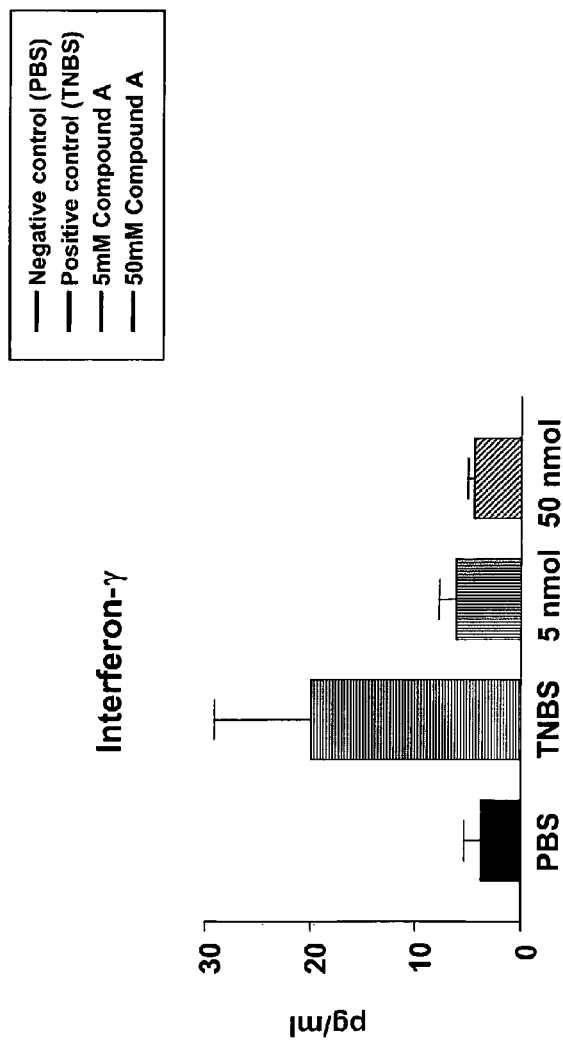
FIG. 31: shows the inhibition of INF-γ (measured in pg/ml) in mouse models treated with a negative control (shaded in bar), a positive control (horizontal lined bar), 5 nM of ghrelin analogue H-Inp-D-Bal-D-Trp-Phe-Apc-NH$_2$ (SEQ ID: 2) (vertical lined bar) and 50 nM of ghrelin analogue H-Inp-D-Bal-D-Trp-Phe-Apc-NH$_2$ (SEQ ID: 2) (diagonal line bar) after 4 days of treatment after initiating TNBS-induced colitis.

Body weight for all test subjects was measured every day. FIG. 27 Serum samples were tested for interferon-gamma by ELISA (Millipore, Inc., Billerica, Mass., U.S.A.). The results are reported in FIG. 31. Macroscopic evaluation and FACS analysis of colon inflammation was performed 4 day after inducing TNBS-induced colitis. The results are reported in FIGS. 29 and 30.

c. Reduction of Colon Inflammation

The colons of the sacrificed test subjects at day 4 and day 10 were removed and measured. As demonstrated in FIG. 28, the treated subjects had smaller colons thus evidencing the effectiveness of the ghrelin analogue H-Inp-D-Bal-D-Trp-Phe-Apc-NH$_2$ (Example #27) (SEQ ID: 2) on reducing the colon inflammation.

Figure 26:
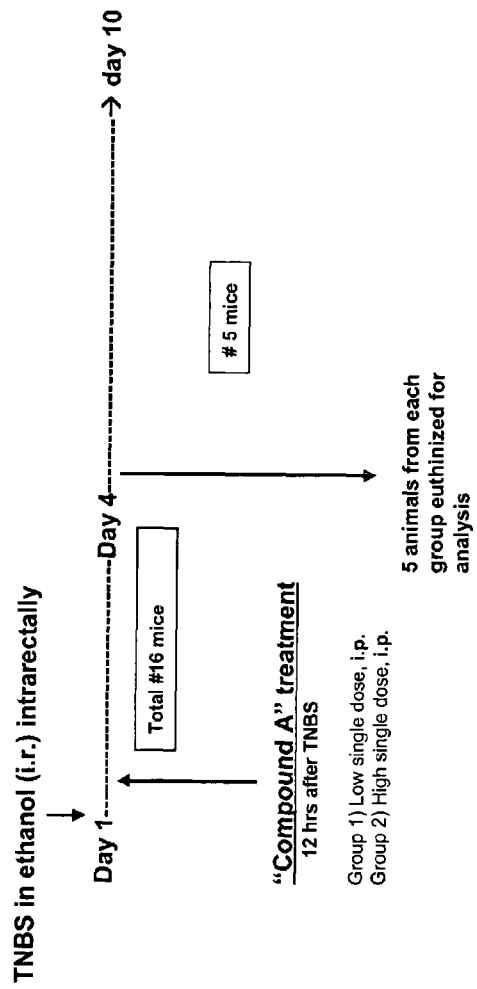
FIG. 26: shows the time frame for the study of ghrelin analogue H-Inp-D-Bal-D-Trp-Phe-Apc-NH$_2$ (SEQ ID: 2) in an acute colon inflammation mouse model.

A diagram of the protocol is depicted in FIG. 26.

8. Studies in the Established Colitis Model

In an effort to examine the ability of the novel ligands of native ghrelin of the instant application to reduce inflammation of the colon in vivo, inflammation was induced in a mouse model and thereafter said subjects were treated with a novel ghrelin analogue of the instant application. As shown in FIG. 33, the ghrelin analogue, having the formula H-Inp-D-Bal-D-Trp-Phe-Apc-NH$_2$ (Example #27) (SEQ ID: 2), effectively inhibited colitis in vivo.

a. Test Subjects

Male SJL mice (Charles River Laboratories, Wilmington, Mass., U.S.A.) approximately 5 to 6 weeks of age were employed. The guidelines proposed by the committee for the Care of Laboratory Animal Resources Commission of Life Sciences-National Research Council were followed to minimize animal pain and distress. Each animal received rodent laboratory chow and ad libitum water.

b. Colon Inflammation Induction

Acute colon inflammation was induced in the test subjects by administering 3 mg of 2,4,6-trinitrobenzene (Thermo Scientific Pierce Protein Research Products, Waltham, Mass., U.S.A.) (TNBS) in 50% ethanol via a catheter inserted intrarectally from the test subject's anus on the day the study commenced and then again approximately 7 days thereafter. Control mice received the same volume of 50% ethanol without the TNBS. Test subjects were treated intrapertoneally (ip) with a single 50 nM dose of the ghrelin analogue H-Inp-D-Bal-D-Trp-Phe-Apc-NH$_2$ (Example #27) (SEQ ID: 2) on days 6, 7 and 8 post-TNBS-induced challenge.

Body weight for all test subjects was measured every day. Macroscopic evaluation of colon inflammation was performed on the 9$^{th}$ day after inducing TNBS-induced colitis.

c. Reduction of Colon Inflammation

The colons of the sacrificed test subjects were removed and measured. As demonstrated in FIG. 33, the treated subjects had smaller colons thus evidencing the effectiveness of the ghrelin analogue H-Inp-D-Bal-D-Trp-Phe-Apc-NH$_2$ (Example #27) (SEQ ID: 2) on reducing the colon inflammation. A diagram of the protocol is depicted in FIG. 32.

E. Treatment

The agents and methods disclosed herein are of benefit to subjects who are experiencing inflammation or are at risk for inflammation and subjects who are experiencing loss of appetite. Because the agents and methods disclosed herein reduce the severity or duration of inflammation, any subject that can benefit from a reduction in inflammation can be treated with the methods and agents disclosed herein.

The compositions comprising an agent disclosed herein in a pharmaceutically acceptable carrier may be administered orally, parenterally (e.g., intravenously), by intramuscular injection, by intraperitoneal injection, transdermally, extracorporeally, topically or the like, or by topical intranasal administration, i.e., delivery of the compositions into the nose and nasal passages. Delivery can also be directly to any area of the respiratory system via intubation. The exact amount of the compositions required will vary from subject to subject, depending on the age, weight and general condition of the subject, the severity of the disorder being treated, the particular nucleic acid or vector used, its mode of administration and the like. It is not possible to specify an exact amount for every composition, however, an appropriate amount can be determined by one of ordinary skill in the art using only routine experimentation given the teachings herein.

Parenteral administration of the composition is generally characterized by injection. Injectables can be prepared in conventional forms, either as liquid solutions or suspensions, solid forms suitable for solution of suspension in liquid prior to injection, or as emulsions. Parenteral administration may also involve use of a slow-release or sustained-release system such that a constant dosage is maintained. The compositions may be in solution or in suspension (for example, incorporated into microparticles, liposomes or cells). These compositions may be targeted to a particular cell type via antibodies, receptors or receptor ligands. The following references are examples of the use of this technology to target specific proteins to given tissue (Senter, P. D. et al., *Bioconjug. Chem.*, (1991), 2 (6):447-51; Bagshawe, K. D., *Br. J. Cancer*, (1989), 60 (3):275-81; Bagshawe, K. D. et al., *Br. J. Cancer*, (1988), 58 (6):700-3; Senter, P. D. et al., *Bioconjug. Chem.*, (1993), 4 (1):3-9; Battelli, M. G. et al., *Cancer Immunol. Immunother.*, (1992), 35 (6):421-5; Pietersz, G. A. and McKenzie, I. F., *Immunolog. Rev.*, (1992), 129:57-80; and Roffler, S. R. et al., *Biochem. Pharmacol.*, (1991), 42 (10):2062-5). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency and ligand concentration. Molecular and cellular mechanisms of receptor-mediated endocytosis has been reviewed (Brown, V. I. and Greene, M. I., *DNA and Cell Biol.*, (1991), 10 (6):399-409).

1. Pharmaceutically Acceptable Salts

Ghrelin analogues may be potentially be administered as a pharmaceutically-acceptable acid- or base-addition salt (in the form of water- or oil-soluble or dispersible products), formed by reaction with inorganic acids such as hydrochloric acid, hydrobromic acid, hydroiodic acid, perchloric acid, nitric acid, thiocyanic acid, sulfuric acid and phosphoric acid, and with carboxylic acids or with organo-sulfonic acids. Organic acids such as formic acid, acetic acid, propionic acid, glycolic acid, lactic acid, pyruvic acid, oxalic acid, malonic acid, succinic acid, maleic acid and fumaric acid, or by reaction with an inorganic base such as sodium hydroxide, ammonium hydroxide, potassium hydroxide and organic bases such as mono-, di-, tri-alkyl and aryl amines and substituted ethanolamines are also possible. Examples of acid addition salts include acetate, adipate, alginate, aspartate, benzoate, benzenesulfonate, bisulfate, butyrate, citrate, camphorate, camphorsulfonate, camsylate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyehtanesulfonate, lactate, maleate, methanesulfonate, 2-naphthalenesulfonate, nicotinate, oxalate, pamoate, pectinate, persulfate, 3-phenylpropionate, picrate, pivalate, propionate, saccharate, succinate, tartrate, thiocyanate, p-toluenesulfonate, tosylate and undecanoate; and base salts such as ammonium salts (quaternary), non-toxic alkali metal salts such as sodium and potassium salts, non-toxic alkaline earth metal salts such as calcium and magnesium salts, as well as other metals such as aluminum, copper and zinc (Berge, S. M. et al., *J. Pharma. Sci.*, (1997), 66:1-19; Gould, P. L., *Int'l Pharmaceutics*, (1986), 33:201-17; and Bighley, L. D. et al., *Encyclo. Pharma. Tech.*, Marcel Dekker, Inc., New York, 13:453-97 (1996)) salts with organic bases such as dicyclohexylamine salts, N-methyl-D-glucamine and salts with amino acids such as arginine and lysine.

The analogues of the instant application may also be administered as solvates, including hydrates thereof. Also included within the scope of the invention are polymorphs. As such, use of the term "ghrelin analogues" or "compounds of the invention" as defined in any aspect of the invention (except intermediate compounds in chemical processes) encompasses the analogue and pharmaceutically-acceptable salts, solvates and polymorphs thereof.

2. Pharmaceutically Acceptable Carriers

Ghrelin analogues can be formulated and administered to a subject using the guidance provided herein along with techniques which are well-known in the art. The preferred route of administration ensures that an effective amount of compound reaches the target. Guidelines for pharmaceutical administration in general are provided for in, for example, Remington's Pharmaceutical Sciences 18$^{th}$ Edition, Ed. Gennaro, Mack Publishing, 1990, and Modem Pharmaceutics 2$^{nd}$ Edition, Eds. Banker and Rhodes, Marcel Dekker, Inc. 1990, both of which are hereby incorporated by reference herein.

While it is possible for the select peptidyl analogues of ghrelin to be administered as the pure or substantially pure compound, administration can occur in conjunction with other therapeutic agents in the form of a pharmaceutical formulation or preparation. For example, a subject can be treated with the disclosed agent alone, or in combination with chemotherapeutic agents, antibodies, antivirals, steroidal and non-steroidal anti-inflammatories, conventional immunotherapeutic agents, cytokines, chemokines and/or growth factors. Combinations may be administered either concomitantly (e. g., as an admixture), separately but simultaneously (e. g., via separate intravenous lines into the same subject), or sequentially (e.g., one of the compounds or agents is given first followed by the second). Thus, the term "combination" or "combined" is used to refer to either concomitant, simultaneous or sequential administration of two or more agents.

Delivery of the agents disclosed herein can be used therapeutically in combination with a pharmaceutically acceptable carrier. Pharmaceutical carriers are known to those skilled in the art. These most typically would be standard carriers for administration of drugs to humans, including solutions such as sterile water, saline and buffered solutions at physiological pH. The compositions can be administered intramuscularly or subcutaneously. Sustained released polymer compositions (e.g., a lactic acid polymer or copolymer microparticle or implant) are also possible. Other compounds will be administered according to standard procedures used by those skilled in the art.

Pharmaceutical compositions may include carriers, thickeners, diluents, buffers, preservatives, surface active agents and the like in addition to the molecule of choice. The carrier must be "acceptable" in the sense of being compatible with the active ingredient(s) of the formulation (e.g., capable of stabilizing peptides), are non-toxic and otherwise not deleterious to the subject to be treated. Desirably, the formulation should not include oxidizing agents or other substances with which peptides are known to be incompatible. Highly oxidative conditions can lead to the formation of cysteine sulfoxide and to the oxidation of tryptophan. Consequently, it is important to carefully select the excipient.

Pharmaceutical compositions may also include one or more active ingredients such as antimicrobial agents, anti-inflammatory agents, anesthetics, and the like.

3. Pharmaceutically Acceptable Modes of Administration

The pharmaceutical composition may be administered in a number of ways depending on whether local or systemic treatment is desired, and on the area to be treated by any method known in the art for administering gases, liquids, and/or solids to patients. The disclosed compounds can be administered intravenously (both bolus and infusion), intraperitoneally, intramuscularly, subcutaneously, enterally, intracavity, transmucously or transdermally (including opthamalically, vaginally, rectally and intranasally). It will be readily appreciated by those skilled in the art, that the route of administration will vary with the condition being treated and the activity and bioavailability of the peptidyl analogue of ghrelin being used.

Compositions for oral administration include powders or granules, suspensions or solutions in water or non-aqueous media, capsules, sachets or tablets. Thickeners such as microcrystalline cellulose, suspending agents such as alginic acid or sodium alginate, sweetening/flavoring agents, diluents, emulsifiers, dispersing aids or binders may be desirable. In general, the formulations for tablets or powders are prepared by uniformly and intimately blending the active ingredient with finely divided solid carriers, and then, if necessary, as in the case of tablets, forming the product into the desired shape and size.

Administration by nasal aerosol or inhalation formulations may be prepared, for example, as solutions in saline, employing benzyl alcohol or other suitable preservatives, absorption promoters to enhance bioavailability, employing fluorocarbons, and/or using other solubilizing or dispersing agents.

Preparations for parenteral administration include sterile aqueous or non-aqueous solutions, suspensions and emulsions. Examples of non-aqueous solvents are propylene glycol, polyethylene glycol, bland fixed oils including synthetic mono- or diglycerides, fatty acids including oleic acid and vegetable oils such as olive oil, and injectable organic esters such as ethyl oleate. Aqueous carriers include water, alcoholic/aqueous solutions, emulsions or suspensions, including saline and buffered media. Parenteral vehicles include isotonic sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents and inert gases and the like. Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

The pharmaceutical composition may be administered directly to the abdominal cavity of the patient.

For immediate release tablets, microcrystalline cellulose, dicalcium phosphate, starch, magnesium stearate and lactose and/or other excipients, binders, extenders, disintegrants, diluents and lubricants may be used. Formulations suitable for sustained release parenteral administrations (e.g., biodegradable polymer formulations such as polyesters containing lactic or glycolic acid residues) are also well known in the art (U.S. Pat. Nos. 3,773,919 and 4,767,628 and PCT Publication WO 94/15587).

4. Dosages

The formulations may conveniently be presented in unit dosage form and may be prepared by any of the methods well known in the art of pharmacy. All methods include the step of bringing the active ingredient(s) into association with the carrier which constitutes one or more accessory ingredients.

The substances of the present invention can be delivered at therapeutically effective amounts or concentrations. An effective concentration or amount of a substance is one that results in treatment or prevention of the inflammatory response and depends upon the condition being treated, the route of administration chosen, and the specific activity of the compound used and ultimately will be decided by the attending physician or veterinarian (e.g., between 5 g/day to 5 mg/day). One skilled in the art would know how to determine an effective concentration or amount according to methods known in the art, as well as provided herein. One of skill in the art can utilize in vitro assays to optimize the in vivo dosage of a particular substance, including concentration and time course of administration. In one embodiment, the peptidyl analogue of ghrelin is administered to the patient until the symptoms associated with inflammation, for example blanching of the skin or production of pus, often associated with inflammation, observed in patient have been alleviated or ceased.

Optimal precision in achieving concentrations of drug within the range that yields efficacy without toxicity requires a regimen based on the kinetics of the drug's availability to target sites. This involves a consideration of the distribution, equilibrium and elimination of the drug. The dosage ranges for the administration of the substances are those large enough to produce the desired effect in which the symptoms of the disorder are affected. For example, the dosage range can be from 0.1, 0.2, 0.3, 0.4, 0.5, 0.6, 0.7, 0.8, 0.9, 1, 2, 3, 4, 5, 6, 7, 8, 9, 10, 11, 12, 13, 14, 15,16, 17,18, 19 or 20 mg/kg body weight of the selected ghrelin analogue, for example, or any amount in between. The daily dose for a subject is expected to between 0.01 and 1,000 mg per subject per day.

The dosage should not be so large as to cause adverse side effects, such as unwanted cross-reactions, anaphylactic reactions, and the like. Generally, the dosage will vary with the particular compound selected for treatment, the route of administration, the age, condition, weight, sex, medical condition of the treated subject, the renal and hepatic function of the subject, the extent of the disease in the patient and the desired effect to be achieved; all of which can be determined by one of skill in the art. The dosage can be adjusted by the individual physician in the event of any contraindications. Dosage can vary, and can be administered in one or more dose administrations daily, for one or several days.

For example, to evaluate the efficacy of treatment of humans with a disorder characterized by inflammation with a substance that modulates cytokine activity, the following studies can be performed. Patients with active inflammation of, for example, the lung who have failed standard medical therapy, which can include prednisone and/or other immunomodulators known in the art (parenterally or orally) for control of the disorder, can be selected. Drug efficacy can be monitored. Patients can be randomized to two different protocols. In one protocol, subjects can remain on initial medication and in the second protocol, subjects can have their medication tapered after receiving the substance that modulates cytokine activity, such as a ghrelin analogue.

In one example, the ghrelin analogue can be infused over a two hour period or a weekly dosage of about 0.5 mg/kg of body weight infused each time over a two hour period until symptoms of inflammation or loss of appetite subside. The blood pressure, pulse and temperature of the subjects can be monitored prior to and at 30 minute intervals during the two hour infusion period. Subjects can also undergo routine inflammatory monitoring.

As described above, the agents disclosed herein can be administered together with other forms of therapy. For example, the molecules can be administered with antibodies, antibiotics or other cancer treatment protocols as described above, or viral vectors. When the agent is in a vector, as described above, the vector containing the nucleic acid for therapeutic purposes can also contain an analogue of ghrelin or a fragment thereof.

5. Nucleic Acid Approaches for Delivery

Those peptidyl analogues claimed in the instant application not having an unnatural amino acid substitution can be administered in vivo and/or ex vivo to patients or subjects as a nucleic acid preparation (e. g., DNA or RNA) that encodes a substance, such as a ghrelin analogue, such that the patient's or subject's own cells take up the nucleic acid and produce and secrete the encoded substances.

The nucleic acids of the present invention can be in the form of naked DNA or RNA, or the nucleic acids can be in a vector for delivering the nucleic acids to the cells, whereby the DNA fragment is under the transcriptional regulation of a promoter, as would be well understood by one of ordinary skill in the art. The vector can be a commercially available preparation, such as an adenovirus vector (Quantum Biotechnologies, Inc., Laval, Quebec, Calif.).

Delivery of the nucleic acid or vector to cells can be via a variety of mechanisms. As one example, delivery can be via a liposome using commercially available liposome preparations such as LIPOFECTIN, LIPOFECTAMINE (GIBCO-BRL, Inc., Gaithersburg, Md., U.S.A.), SUPERFECT (Qiagen, Inc. Hilden, Del.) and TRANSFECTAM (Promega Biotec, Inc., Madison, Wis., U.S.A.), as well as other liposomes developed according to procedures standard in the art. In addition, the nucleic acid or vector of this invention can be delivered in vivo by electroporation, the technology for which is available from Genetronics, Inc. (San Diego, Calif., U.S.A.) as well as by means of a SONOPORATION machine (ImaRx Pharmaceutical Corp., Tucson, Ariz., U.S.A.).

As one example, vector delivery can be via a viral system, such as a retroviral vector system which can package a recombinant retroviral genome (Pastan, I. et al., *Proc. Natl. Acad. Sci. U.S.A.*, (1988), 85 (12):4486-90; and Miller, A. D. et al., *Mol. Cell. Biol.*, (1986), 6 (8):2895-902). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors.

Other techniques are widely available for this procedure including the use of adenoviral vectors (Mitani, K. et al., *Hum. Gene Ther.*, (1994), 5 (8):941-8), adeno-associated viral (.AAV) vectors (Goodman, S. et al., *Blood*, (1994), 84 (5):1492-500), lentiviral vectors (Naldini, L. et al., *Science*, (1996), 272 (5259):263-7) and pseudo-typed retroviral vectors (Agrawal, Y. P. et al., *Exp. Hematol.*, (1996), 24 (6):738-47). Physical transduction techniques can also be used, such as, but not limited to, liposome delivery and receptor-mediated and other endocytosis mechanisms (Schwarzenberger, P. et al., *Blood*, (1996), 87 (2):472-8). This invention can be used in conjunction with any of these or other commonly used gene transfer methods.

As one example, if the antibody-encoding nucleic acid of the invention is delivered to the cells of a subject in an adenovirus vector, the dosage for administration of adenovirus to humans can range from about 107 to 109 plaque forming units (pfu) per injection but can be as high as $10^{12}$ pfu per injection (Crystal, R. G. et al., *Hum. Gene Ther.*, (1997), 8 (8):985-1001; and Alvarez, R. D. and Curiel, D. T., *Hum. Gene Ther.*, (1997), 8 (5):597-613). A subject can receive a single injection, or if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention is generally characterized by injection. Injectables can be prepared in conventional forms, either as liquid solutions or suspensions, solid forms suitable for solution of suspension in liquid prior to injection, or as emulsions. An example of an approach for parenteral administration involving the use of a slow release or sustained release system so that a constant dosage is maintained, is described in U.S. Pat. No. 3,610,795 (which is incorporated by reference herein). For additional discussion of suitable formulations and various routes of administration of therapeutic compounds, see, e.g., Remington: The Science and Practice of Pharmacy (19th ed.) ed. A. R. Gennaro, Mack Publishing Company, Easton, Pa. (1995).

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e. g., amounts, temperature, etc.), but some errors and deviations should be accounted for. Unless indicated otherwise, parts are parts by weight, temperature is in ° C. or is at ambient temperature, and pressure is at or near atmospheric.

6. Kits

The ghrelin analogues of the instant application may be provided in a kit. Such a kit typically contains an active compound in dosage forms for administration. A dosage form contains a sufficient amount of active compound such that a desirable effect may be obtained when administered to a subject during regular intervals, such as 1 to 6 times a day, during the course of 1 or more days. Preferably, a kit contains instructions indicating the use of the dosage form to achieve a desirable effect and the amount of dosage form to be taken over the specified time period.

Other Embodiments

The foregoing description has been limited to specific embodiments of this invention. It will be apparent however, that variations and modifications may be made to the invention, with the attainment of some or all of the advantages of the invention. Such embodiments are also within the scope of the following claims.

The patent and scientific literature referred to herein represents knowledge that is available to those with skill in the art. All patents, patent publications and other publications cited herein are hereby incorporated by reference in their entirety.

The invention claimed is:

1. A method of inhibiting the secretion of pro-inflammatory cytokines and stimulating the secretion of anti-inflammatory cytokines in a subject in need thereof, wherein said cytokine secretion is associated with an inflammatory disease of the gastrointestinal tract, which comprises administering to said subject an effective amount of the peptidyl analogue of ghrelin, H-Inp-D-Bal-D-Trp-Phe-Apc-NH$_2$ (SEQ ID: 2), or a pharmaceutically acceptable salt thereof, wherein said pro-inflammatory cytokine is IL-6, and wherein said anti-inflammatory cytokine is IL-10.

2. The method of claim 1, wherein said inflammatory disease of the gastrointestinal tract is selected from Crohn's disease, inflammatory bowel disease, ulcerative colitis, and celiac disease.

3. The method of claim 2, wherein said inflammatory disease of the gastrointestinal tract is Crohn's disease.

4. The method of claim 2, wherein said inflammatory disease of the gastrointestinal tract is inflammatory bowel disease.

5. The method of claim 2, wherein said inflammatory disease of the gastrointestinal tract is ulcerative colitis.

6. The method of claim 2, wherein said inflammatory disease of the gastrointestinal tract is celiac disease.

* * * * *

SEQUENCE LISTING

```
<160> NUMBER OF SEQ ID NOS: 407

<210> SEQ ID NO 1
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (28)..(28)
<223> OTHER INFORMATION: AMIDATION

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal),
      D-beta-(2-naphthyl)-L-Ala (D-2-Nal) or D-beta-(1-naphthyl)-L-Ala
      (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 2

Xaa Xaa Xaa Phe Xaa
```

-continued

```
<210> SEQ ID NO 3
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: Modified with Acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: Modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 3

Gly Xaa Glu Phe Leu Ser Pro Glu His Xaa Arg Val Gln Gln Arg Lys
 1               5                  10                  15

Glu Ser Lys Lys Pro Pro Ala Lys Leu Gln Pro Arg
            20                  25

<210> SEQ ID NO 4
<211> LENGTH: 7
<212> TYPE: PRT
<213> ORGANISM: Artificial Sequence
<220> FEATURE:
<223> OTHER INFORMATION: Example of designation in the specification
<220> FEATURE:
<221> NAME/KEY: MOD_RES
<222> LOCATION: (1)..(1)
<223> OTHER INFORMATION: Modified with Ac-Nle
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 4

Cys Xaa His Xaa Arg Trp Cys
 1               5

<210> SEQ ID NO 5
<211> LENGTH: 7
<212> TYPE: PRT
<213> ORGANISM: Artificial Sequence
<220> FEATURE:
<223> OTHER INFORMATION: Example of designation in the specification
<220> FEATURE:
```

```
<221> NAME/KEY: DOMAIN
<222> LOCATION: (1)..(7)
<223> OTHER INFORMATION: cyclic
<220> FEATURE:
<221> NAME/KEY: MOD_RES
<222> LOCATION: (1)..(1)
<223> OTHER INFORMATION: Modified with Ac-Nle
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: C-terminus is the free acid

<400> SEQUENCE: 5

Cys Xaa His Xaa Arg Trp Cys
1               5

<210> SEQ ID NO 6
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 6

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 7
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MOD_RES
<222> LOCATION: (28)..(28)
<223> OTHER INFORMATION: AMIDATION

<400> SEQUENCE: 7

Gly Xaa Ser Phe Xaa Ser Pro Glu His Gln Arg Val Gln Gln Arg Lys
1               5                   10                  15

Glu Ser Lys Lys Pro Pro Ala Lys Leu Gln Pro Arg
```

```
                    20                  25

<210> SEQ ID NO 8
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MOD_RES
<222> LOCATION: (28)..(28)
<223> OTHER INFORMATION: AMIDATION

<400> SEQUENCE: 8

Gly Ser Ser Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 9

Gly Xaa Ser Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION
```

```
<400> SEQUENCE: 10

Gly Xaa Ser Phe Leu Ser Pro Glu His Gln Arg Xaa Gln Gln Arg Lys
1               5                   10                  15

Glu Ser Lys Lys Pro Pro Ala Lys Leu Gln Pro Arg
            20                  25

<210> SEQ ID NO 11
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 11

Gly Xaa Ser Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 12

Gly Xaa Ser Phe Leu Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 13
<211> LENGTH: 28
<212> TYPE: PRT
```

```
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 13

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 14
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), 4-ketoPro
      (Ktp), or 1,2,3,4-tetrahydroisoquinoline-3-carboxylic acid (Tic)
<220> FEATURE:
<221> NAME/KEY: MOD_RES
<222> LOCATION: (28)..(28)
<223> OTHER INFORMATION: AMIDATION

<400> SEQUENCE: 14

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c), 4-amino-4-carboxytetrahydropyran (Act), or
      alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 15
```

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 16

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 17
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 17

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 18
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 18

Gly Ser Ser Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 19

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 20
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 20

Gly Ser Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 21

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 22
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 22

Gly Ser Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 23
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MOD_RES
<222> LOCATION: (28)..(28)
<223> OTHER INFORMATION: AMIDATION

<400> SEQUENCE: 23

Gly Xaa Xaa Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 24
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl

```
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MOD_RES
<222> LOCATION: (28)..(28)
<223> OTHER INFORMATION: AMIDATION

<400> SEQUENCE: 24

Gly Ser Xaa Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 25
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 25

Gly Xaa Xaa Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 26
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
```

<223> OTHER INFORMATION: AMIDATION

<400> SEQUENCE: 26

Gly Xaa Xaa Phe Leu Ser Pro Glu His Gln Arg Xaa Gln Gln Arg Lys
1               5                   10                  15

Glu Ser Lys Lys Pro Pro Ala Lys Leu Gln Pro Arg
            20                  25

<210> SEQ ID NO 27
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 27

Gly Xaa Xaa Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 28

```
Gly Xaa Xaa Phe Leu Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 29

Gly Xaa Xaa Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 30

Gly Xaa Xaa Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 31
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c), or 4-amino-4-carboxytetrahydropyran (Act)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 31

Gly Xaa Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 32
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c), alpha-aminoisobutyric acid (Aib), homoLeu, or
      beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 32

Gly Xaa Xaa Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 33
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
```

```
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 33

Gly Xaa Xaa Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 34

Gly Xaa Xaa Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 35
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 35

Gly Ser Xaa Phe Leu Xaa Pro Glu His Gln Arg Val Gln Gln Arg Lys
```

```
1               5                   10                  15
Glu Ser Lys Lys Pro Pro Ala Lys Leu Gln Pro Arg
            20                  25

<210> SEQ ID NO 36
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 36

Gly Ser Xaa Phe Leu Ser Pro Glu His Gln Arg Xaa Gln Gln Arg Lys
1               5                   10                  15

Glu Ser Lys Lys Pro Pro Ala Lys Leu Gln Pro Arg
            20                  25

<210> SEQ ID NO 37
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) or
      2,4-diaminobutyric acid (Dab), both modified with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 37

Gly Ser Xaa Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 38
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
```

```
<223> OTHER INFORMATION: Xaa = 2,3-diaminopropionic acid (Dap) or
      2,4-diaminobutyric acid (Dab), both modified with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 38

Gly Ser Xaa Phe Leu Ser Pro Glu His Gln Arg Xaa Gln Gln Arg Xaa
1               5                   10                  15
Glu Ser Lys Lys Pro Pro Ala Lys Leu Gln Pro Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 39

Gly Ser Xaa Phe Leu Ser Pro Glu Xaa Gln Arg Val Gln Gln Arg Lys
1               5                   10                  15
Glu Ser Lys Lys Pro Pro Ala Lys Leu Gln Pro Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
```

<223> OTHER INFORMATION: AMIDATION

<400> SEQUENCE: 40

Gly Ser Xaa Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 41
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 41

Gly Ser Xaa Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 42
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 42

Gly Ser Xaa Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 43
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)

```
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 43

Gly Xaa Ser Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 44
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 44

Gly Ser Ser Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 45
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
```

```
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 45

Gly Xaa Ser Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 46
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 46

Gly Xaa Ser Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 47
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
```

```
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 47

Gly Xaa Ser Phe Leu Ser Xaa Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 48
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 48

Gly Xaa Ser Phe Leu Ser Pro Xaa His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 49
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
```

```
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 49

Gly Xaa Ser Phe Leu Ser Pro Glu His Xaa Arg Xaa Gln Gln Xaa Lys
1               5                   10                  15

Glu Ser Lys Lys Pro Pro Ala Lys Leu Gln Pro Arg
            20                  25

<210> SEQ ID NO 50
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 50

Gly Xaa Ser Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 51
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MISC_FEATURE
<222> LOCATION: (12)..(12)
```

```
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 51

Gly Ser Ser Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 52

Gly Xaa Ser Phe Leu Xaa Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MISC_FEATURE
```

```
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 53

Gly Xaa Ser Phe Leu Ser Pro Glu Xaa Gln Arg Xaa Gln Gln Arg Xaa
1               5                  10                  15

Glu Ser Lys Lys Pro Pro Ala Lys Leu Gln Pro Arg
            20                  25

<210> SEQ ID NO 54
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 54

Gly Xaa Ser Phe Leu Ser Xaa Glu His Gln Arg Xaa Gln Gln Arg Xaa
1               5                  10                  15

Glu Ser Lys Lys Pro Pro Ala Lys Leu Gln Pro Arg
            20                  25

<210> SEQ ID NO 55
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
```

```
            (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 55

Gly Xaa Ser Phe Leu Ser Pro Xaa His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 56
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 56

Gly Xaa Ser Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25

<210> SEQ ID NO 57
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
```

```
<222> LOCATION: (28)..(28)
<223> OTHER INFORMATION: AMIDATION

<400> SEQUENCE: 57

Gly Ser Ser Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 58
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = beta-(3-pyridinyl)Ala (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 58

Gly Ser Ser Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 59
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 59

Gly Ser Ser Phe Leu Ser Xaa Glu His Gln Arg Xaa Gln Gln Xaa Lys
1               5                   10                  15
```

```
Glu Ser Lys Lys Pro Pro Ala Lys Leu Gln Pro Arg
            20                  25

<210> SEQ ID NO 60
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 60

Gly Ser Ser Phe Leu Ser Pro Xaa His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 61
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 61

Gly Ser Ser Phe Leu Ser Pro Glu His Xaa Arg Xaa Gln Gln Xaa Lys
1               5                   10                  15

Glu Ser Lys Lys Pro Pro Ala Lys Leu Gln Pro Arg
            20                  25

<210> SEQ ID NO 62
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
```

<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 62

Gly Ser Ser Phe Leu Xaa Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 63
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      beta-(2-furyl)-Ala (2Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 63

Gly Ser Ser Phe Leu Ser Pro Glu Xaa Gln Arg Xaa Gln Gln Arg Xaa
1               5                   10                  15

Glu Ser Lys Lys Pro Pro Ala Lys Leu Gln Pro Arg
            20                  25

<210> SEQ ID NO 64
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE -continued

```
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 64

Gly Ser Ser Phe Leu Ser Xaa Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 65
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 65

Gly Ser Ser Phe Leu Ser Pro Xaa His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 66
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 66
```

```
Gly Ser Ser Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25
```

```
<210> SEQ ID NO 67
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), or homoLeu
<220> FEATURE:
<221> NAME/KEY: MOD_RES
<222> LOCATION: (28)..(28)
<223> OTHER INFORMATION: AMIDATION

<400> SEQUENCE: 67

Gly Xaa Glu Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 68
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MOD_RES
<222> LOCATION: (28)..(28)
<223> OTHER INFORMATION: AMIDATION

<400> SEQUENCE: 68

Gly Ser Glu Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 69
<211> LENGTH: 28
<212> TYPE: PRT
<213> ORGANISM: Artificial Sequence
<220> FEATURE:
<223> OTHER INFORMATION: Ghrelin Analogue
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
     4-amino-4-carboxytetrahydropyran (Act), Thr, or
     alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 69

Gly Xaa Glu Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 70
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
     beta-(2-pyridinyl)Ala (2Pal), beta-(4-pyridinyl)Ala (4Pal),
     beta-(4-thiazolyl)Ala (Taz), beta-(2-thienyl)Ala (2Thi),
     alpha-aminoisobutyric acid (2Fua), Apc, or alpha-aminoisobutyric
     acid (Aib)
<220> FEATURE:
<221> NAME/KEY: MOD_RES
<222> LOCATION: (28)..(28)
<223> OTHER INFORMATION: AMIDATION

<400> SEQUENCE: 70

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 71
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 71

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 72
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 72

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 73
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 73

Gly Xaa Glu Phe Leu Ser Pro Glu His Xaa Arg Val Gln Gln Arg Lys
1               5                   10                  15
```

```
Glu Ser Lys Lys Pro Pro Ala Lys Leu Gln Pro Arg
            20                  25
```

```
<210> SEQ ID NO 74
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 74

Gly Ser Glu Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 75
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      alpha-aminoisobutyric acid (2Fua), Apc, or alpha-aminoisobutyric
      acid (Aib)
<220> FEATURE:
<221> NAME/KEY: MOD_RES
<222> LOCATION: (28)..(28)
<223> OTHER INFORMATION: AMIDATION

<400> SEQUENCE: 75

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 76
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
```

```
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 76

Gly Ser Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 77
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), or beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 77

Gly Xaa Glu Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 78
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MISC_FEATURE
```

```
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 78

Gly Ser Glu Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 79
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 79

Gly Xaa Glu Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 80
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      alpha-aminoisobutyric acid (2Fua), (Apc), or alpha-aminoisobutyric
      acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 80

Gly Xaa Glu Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 81
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 81

Gly Xaa Glu Phe Leu Ser Xaa Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 82
<211> LENGTH: 28
<212> TYPE: PRT
<213> ORGANISM: Artificial Sequence
<220> FEATURE:
```

<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 82

Gly Xaa Glu Phe Leu Ser Pro Xaa His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 83
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 83

Gly Xaa Glu Phe Leu Ser Pro Glu His Xaa Arg Xaa Gln Gln Xaa Lys
1               5                   10                  15

Glu Ser Lys Lys Pro Pro Ala Lys Leu Gln Pro Arg
            20                  25

<210> SEQ ID NO 84
<211> LENGTH: 28

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu, or beta-cyclohexylAla
      (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 84

Gly Xaa Glu Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 85
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 85

Gly Ser Glu Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25
```

```
<210> SEQ ID NO 86
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 86

Gly Xaa Glu Phe Leu Xaa Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 87
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(2-pyridinyl)Ala (2Pal), beta-(4-pyridinyl)Ala (4Pal),
      beta-(4-thiazolyl)Ala (Taz), beta-(2-thienyl)Ala (2Thi),
      alpha-aminoisobutyric acid (2Fua), Apc, or alpha-aminoisobutyric
      acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION
```

-continued

```
<400> SEQUENCE: 87

Gly Xaa Glu Phe Leu Ser Pro Glu Xaa Gln Arg Xaa Gln Gln Arg Xaa
1               5                   10                  15

Glu Ser Lys Lys Pro Pro Ala Lys Leu Gln Pro Arg
            20                  25

<210> SEQ ID NO 88
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 88

Gly Xaa Glu Phe Leu Ser Xaa Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 89
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
```

```
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 89

Gly Xaa Glu Phe Leu Ser Pro Xaa His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 90
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 90

Gly Xaa Glu Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25

<210> SEQ ID NO 91
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with O-hexyl, or NH-hexyl
<220> FEATURE:
<221> NAME/KEY: MOD_RES
<222> LOCATION: (28)..(28)
<223> OTHER INFORMATION: AMIDATION

<400> SEQUENCE: 91

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 92
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with O-hexyl, or NH-hexyl
<220> FEATURE:
<221> NAME/KEY: MOD_RES
<222> LOCATION: (28)..(28)
<223> OTHER INFORMATION: AMIDATION

<400> SEQUENCE: 92

Gly Xaa Glu Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 93
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Glu modified with NH-hexyl, or Dap
      (2,3-diaminopropionic acid) modified with 1-octanesulfonyl
<220> FEATURE:
<221> NAME/KEY: MOD_RES
<222> LOCATION: (28)..(28)
<223> OTHER INFORMATION: AMIDATION

<400> SEQUENCE: 93

Xaa Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 94
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Dap (2,3-diaminopropionic acid) modified
      with 1-octanesulfonyl
<220> FEATURE:
<221> NAME/KEY: MOD_RES
<222> LOCATION: (28)..(28)
<223> OTHER INFORMATION: AMIDATION
```

<400> SEQUENCE: 94

Gly Xaa Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 95
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (5)..(5)
<223> OTHER INFORMATION: AMIDATION

<400> SEQUENCE: 95

Gly Ser Ser Phe Leu
1               5

<210> SEQ ID NO 96
<211> LENGTH: 6
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (6)..(6)
<223> OTHER INFORMATION: AMIDATION

<400> SEQUENCE: 96

Gly Ser Ser Phe Leu Ser
1               5

<210> SEQ ID NO 97
<211> LENGTH: 7
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (7)..(7)
<223> OTHER INFORMATION: AMIDATION

<400> SEQUENCE: 97

Gly Ser Ser Phe Leu Ser Pro
1               5

<210> SEQ ID NO 98
<211> LENGTH: 28
<212> TYPE: PRT
<213> ORGANISM: Artificial Sequence
<220> FEATURE:
<223> OTHER INFORMATION: Ghrelin Analogue
<220> FEATURE:

<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 98

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 99
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (5)..(5)
<223> OTHER INFORMATION: AMIDATION

<400> SEQUENCE: 99

Gly Xaa Glu Phe Leu
1               5

<210> SEQ ID NO 100
<211> LENGTH: 6
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (6)..(6)
<223> OTHER INFORMATION: AMIDATION

<400> SEQUENCE: 100

Gly Xaa Glu Phe Leu Ser
1               5

```
<210> SEQ ID NO 101
<211> LENGTH: 7
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (7)..(7)
<223> OTHER INFORMATION: AMIDATION

<400> SEQUENCE: 101

Gly Xaa Glu Phe Leu Ser Pro
1               5

<210> SEQ ID NO 102
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 102

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 103
<211> LENGTH: 8
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (8)..(8)
<223> OTHER INFORMATION: Xaa = Arg or Lys
<220> FEATURE:
<221> NAME/KEY: MOD_RES
<222> LOCATION: (8)..(8)
<223> OTHER INFORMATION: AMIDATION

<400> SEQUENCE: 103

Gly Xaa Glu Phe Leu Ser Pro Xaa
1               5

<210> SEQ ID NO 104
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-butyryl, isobutyryl, or
      n-octanoyl
<220> FEATURE:
<221> NAME/KEY: MOD_RES
<222> LOCATION: (28)..(28)
<223> OTHER INFORMATION: AMIDATION

<400> SEQUENCE: 104

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 105
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-butyryl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 105

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 106
<211> LENGTH: 28
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MOD_RES
<222> LOCATION: (3)..(3)
<223> OTHER INFORMATION: modified with S(CH2)9CH3, or S-decyl
<220> FEATURE:
<221> NAME/KEY: MOD_RES
<222> LOCATION: (28)..(28)
<223> OTHER INFORMATION: AMIDATION

<400> SEQUENCE: 106

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 107
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 107

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 108
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-butyryl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 108

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 109
<211> LENGTH: 8
```

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (8)..(8)
<223> OTHER INFORMATION: AMIDATION

<400> SEQUENCE: 109

Gly Xaa Ser Phe Leu Ser Pro Arg
1               5

<210> SEQ ID NO 110
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 110

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 111
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 111

Gly Xaa Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 112
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
```

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib), or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 112

Gly Xaa Thr Phe Leu Xaa Pro Glu His Gln Arg Val Gln Gln Arg Lys
1               5                  10                  15

Glu Ser Lys Lys Pro Pro Ala Lys Leu Gln Pro Arg
            20                  25

<210> SEQ ID NO 113
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 113

Gly Ser Thr Phe Xaa Ser Pro Glu His Gln Arg Val Gln Gln Arg Lys
1               5                  10                  15

Glu Ser Lys Lys Pro Pro Ala Lys Leu Gln Pro Arg
            20                  25

<210> SEQ ID NO 114
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)Ala (3Pal),
      beta-(4-thiazolyl)Ala (Taz), or beta-(2-thienyl)Ala (2Thi)
<220> FEATURE:
<221> NAME/KEY: MOD_RES
<222> LOCATION: (28)..(28)
<223> OTHER INFORMATION: AMIDATION

<400> SEQUENCE: 114

Gly Xaa Thr Phe Leu Ser Pro Glu Xaa Gln Arg Val Gln Gln Arg Lys
1               5                  10                  15

Glu Ser Lys Lys Pro Pro Ala Lys Leu Gln Pro Arg
            20                  25

<210> SEQ ID NO 115
<211> LENGTH: 28
<212> TYPE: PRT
<213> ORGANISM: Artificial Sequence
```

```
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid (Thz),
      4-hydroxyPro (4Hyp), 3,4-dehydroPro (Dhp), pipecolic acid (Pip),
      or 1,2,3,4-tetrahydroisoquinoline-3-carboxylic acid (Tic)
<220> FEATURE:
<221> NAME/KEY: MOD_RES
<222> LOCATION: (28)..(28)
<223> OTHER INFORMATION: AMIDATION

<400> SEQUENCE: 115

Gly Xaa Thr Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 116
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 116

Gly Xaa Thr Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 117
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 117

Gly Xaa Thr Phe Leu Ser Pro Xaa His Gln Arg Val Gln Gln Arg Lys
1               5                   10                  15

Glu Ser Lys Lys Pro Pro Ala Lys Leu Gln Pro Arg
```

20                  25

<210> SEQ ID NO 118
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Gly or Gly modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 118

Xaa Xaa Thr Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 119
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-butyryl, or acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 119

Gly Xaa Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 120
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES

```
<222> LOCATION: (8)..(8)
<223> OTHER INFORMATION: AMIDATION

<400> SEQUENCE: 120

Gly Xaa Thr Phe Leu Ser Pro Arg His Gln Arg Val Gln Gln Arg Lys
1               5                   10                  15

Glu Ser Lys Lys Pro Pro Ala Lys Leu Gln Pro Arg
            20                  25

<210> SEQ ID NO 121
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 121

Gly Ser Thr Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 122
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(4-thiazolyl)Ala (Taz),
      beta-(3-pyridinyl)Ala (3Pal), beta-(4-pyridinyl)Ala (4Pal), or
      beta-(2-thienyl)Ala (2Thi)
<220> FEATURE:
<221> NAME/KEY: MOD_RES
<222> LOCATION: (28)..(28)
<223> OTHER INFORMATION: AMIDATION

<400> SEQUENCE: 122

Gly Ser Thr Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 123
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (7)..(7)
<223> OTHER INFORMATION: Xaa = 4-hydroxyPro (4Hyp)
<220> FEATURE:
<221> NAME/KEY: MOD_RES
<222> LOCATION: (28)..(28)
<223> OTHER INFORMATION: AMIDATION

<400> SEQUENCE: 123
```

-continued

```
Gly Ser Thr Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 124
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 124

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 125
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-pyridinyl)Ala (4Pal)
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 125

Gly Xaa Glu Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 126
<211> LENGTH: 28
<212> TYPE: PRT
<213> ORGANISM: Artificial Sequence
```

```
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = Ava
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with 1-octanesulfonyl
<220> FEATURE:
<221> NAME/KEY: MOD_RES
<222> LOCATION: (27)..(27)
<223> OTHER INFORMATION: AMIDATION

<400> SEQUENCE: 126

Gly Xaa Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 127
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (3)..(3)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (4)..(4)
<223> OTHER INFORMATION: Xaa = 2'-(4-phenyl)imidazolyl (psi-Pim)

<400> SEQUENCE: 127

Xaa Xaa Xaa Xaa
1

<210> SEQ ID NO 128
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal) or
      beta-(2-thienyl)Ala (2-Thi)
<220> FEATURE:
<221> NAME/KEY: MOD_RES
```

<222> LOCATION: (5)..(5)
<223> OTHER INFORMATION: AMIDATION

<400> SEQUENCE: 128

Xaa Xaa Xaa Xaa Lys
1               5

<210> SEQ ID NO 129
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-pyridiyl)Ala (4-Pal) or ornithine
      (Orn)
<220> FEATURE:
<221> NAME/KEY: MOD_RES
<222> LOCATION: (5)..(5)
<223> OTHER INFORMATION: AMIDATION

<400> SEQUENCE: 129

Xaa Xaa Xaa Xaa Lys
1               5

<210> SEQ ID NO 130
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 130

Xaa Xaa Xaa Phe Lys
1               5

<210> SEQ ID NO 131
<211> LENGTH: 5
<212> TYPE: PRT
<213> ORGANISM: Artificial Sequence
<220> FEATURE:
<223> OTHER INFORMATION: Ghrelin Analogue
<220> FEATURE:

```
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = O-bezyl-threonine (Thr(Bzl)) or
      pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 131

Xaa Xaa Xaa Xaa Lys
1               5

<210> SEQ ID NO 132
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or
      beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 132

Xaa Xaa Xaa Xaa Lys
1               5

<210> SEQ ID NO 133
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta,beta-diphenylAla (D-Dip) or
      D-4-benzoylphenylAla (D-Bpa)
<220> FEATURE:
<221> NAME/KEY: MISC_FEATURE
<222> LOCATION: (3)..(3)
```

```
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 133

Xaa Xaa Xaa Phe Lys
1               5

<210> SEQ ID NO 134
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-4-benzoylphenylAla (D-Bpa)
<220> FEATURE:
<221> NAME/KEY: MOD_RES
<222> LOCATION: (5)..(5)
<223> OTHER INFORMATION: AMIDATION

<400> SEQUENCE: 134

Xaa Xaa Xaa Phe Lys
1               5

<210> SEQ ID NO 135
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal) or
      beta-(4-pyridiyl)Ala (4-Pal)

<400> SEQUENCE: 135

Xaa Xaa Xaa Xaa
1

<210> SEQ ID NO 136
<211> LENGTH: 4
<212> TYPE: PRT
<213> ORGANISM: Artificial Sequence
```

```
-continued

<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)

<400> SEQUENCE: 136

Xaa Xaa Xaa Xaa
1

<210> SEQ ID NO 137
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 137

Xaa Xaa Xaa Phe
1

<210> SEQ ID NO 138
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
```

```
<223> OTHER INFORMATION: AMIDATION
<220> FEATURE:
<221> NAME/KEY: MISC_FEATURE
<222> LOCATION: (4)..(4)
<223> OTHER INFORMATION: Xaa = O-bezyl-threonine (Thr(Bzl),
      pentafluorophenylAla (Pff), beta-(2-thienyl)Ala (2-Thi) or
      beta-(4-thiazolyl)Ala (Taz)

<400> SEQUENCE: 138

Xaa Xaa Xaa Xaa
1

<210> SEQ ID NO 139
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta,beta-diphenylAla (D-Dip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 139

Xaa Xaa Xaa Phe
1

<210> SEQ ID NO 140
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-beta,beta-diphenylAla (D-Dip)
<220> FEATURE:
<221> NAME/KEY: MOD_RES
<222> LOCATION: (4)..(4)
<223> OTHER INFORMATION: AMIDATION

<400> SEQUENCE: 140

Xaa Xaa Xaa Phe
1

<210> SEQ ID NO 141
<211> LENGTH: 4
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 141

Xaa Xaa Xaa Phe
1

<210> SEQ ID NO 142
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION

<400> SEQUENCE: 142

Xaa Xaa Xaa Phe
1

<210> SEQ ID NO 143
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)
<220> FEATURE:
<221> NAME/KEY: MOD_RES
<222> LOCATION: (5)..(5)
<223> OTHER INFORMATION: AMIDATION

<400> SEQUENCE: 143
```

```
Xaa Xaa Xaa Xaa Lys
1               5

<210> SEQ ID NO 144
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or Phe
<220> FEATURE:
<221> NAME/KEY: MOD_RES
<222> LOCATION: (5)..(5)
<223> OTHER INFORMATION: AMIDATION

<400> SEQUENCE: 144

Xaa Xaa Xaa Xaa Lys
1               5

<210> SEQ ID NO 145
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal) or
      D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 145

Xaa Xaa Xaa Phe Lys
1               5

<210> SEQ ID NO 146
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
```

```
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 146

Xaa Xaa Xaa Xaa Lys
1               5

<210> SEQ ID NO 147
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 147

Xaa Xaa Xaa Xaa
1

<210> SEQ ID NO 148
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 148
```

```
Xaa Xaa Xaa Phe
1

<210> SEQ ID NO 149
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal),
      D-beta-(1-naphthyl)-L-Ala (D-1-Nal) or D-3-benzothienylAla
      (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)

<400> SEQUENCE: 149

Xaa Xaa Xaa Xaa
1

<210> SEQ ID NO 150
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (H-Aib)
<220> FEATURE:
<221> NAME/KEY: MISC_FEATURE
<222> LOCATION: (2)..(2)
<223> OTHER INFORMATION: Xaa = D-O-bezyl-serine (D-Ser(Bzl))
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)

<400> SEQUENCE: 150

Xaa Xaa Xaa Xaa
1

<210> SEQ ID NO 151
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
```

```
                D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)

<400> SEQUENCE: 151

Xaa Xaa Xaa Xaa Lys
1               5

<210> SEQ ID NO 152
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
      D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 152

Xaa Xaa Xaa Xaa Lys
1               5

<210> SEQ ID NO 153
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or Phe
<220> FEATURE:
<221> NAME/KEY: MOD_RES
<222> LOCATION: (5)..(5)
```

<223> OTHER INFORMATION: AMIDATION

<400> SEQUENCE: 153

Xaa Xaa Xaa Xaa Lys
1               5

<210> SEQ ID NO 154
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
      D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 154

Xaa Xaa Xaa Phe Xaa
1               5

<210> SEQ ID NO 155
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal) or
      D-beta-(2-naphthyl)-L-Ala (D-2-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 155

Xaa Xaa Xaa Phe Xaa
1               5

<210> SEQ ID NO 156
<211> LENGTH: 5
<212> TYPE: PRT

```
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal)
<220> FEATURE:
<221> NAME/KEY: MOD_RES
<222> LOCATION: (5)..(5)
<223> OTHER INFORMATION: AMIDATION

<400> SEQUENCE: 156

Xaa Xaa Xaa Phe Lys
1               5

<210> SEQ ID NO 157
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal) or
      D-beta-(2-naphthyl)-L-Ala (D-2-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 157

Xaa Xaa Xaa Phe Xaa
1               5

<210> SEQ ID NO 158
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal) or
      D-beta-(2-naphthyl)-L-Ala (D-2-Nal)
```

```
<220> FEATURE:
<221> NAME/KEY: MOD_RES
<222> LOCATION: (5)..(5)
<223> OTHER INFORMATION: AMIDATION

<400> SEQUENCE: 158

Xaa Xaa Xaa Phe Lys
1               5

<210> SEQ ID NO 159
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or
      beta-(4-thiazolyl)Ala (Taz)

<400> SEQUENCE: 159

Xaa Xaa Xaa Xaa
1

<210> SEQ ID NO 160
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 160

Xaa Xaa Xaa Phe
1

<210> SEQ ID NO 161
<211> LENGTH: 4
<212> TYPE: PRT
<213> ORGANISM: Artificial Sequence
<220> FEATURE:
```

```
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or
      beta-(4-thiazolyl)Ala (Taz)

<400> SEQUENCE: 161

Xaa Xaa Xaa Xaa
1

<210> SEQ ID NO 162
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi) or
      beta-(4-thiazolyl)Ala (Taz)

<400> SEQUENCE: 162

Xaa Xaa Xaa Xaa
1

<210> SEQ ID NO 163
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
      D-3-benzothienylAla (D-Bal)
<220> FEATURE:
```

```
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 163

Xaa Xaa Xaa Xaa Xaa
1               5

<210> SEQ ID NO 164
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
     D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 164

Xaa Xaa Xaa Xaa Xaa
1               5

<210> SEQ ID NO 165
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
```

```
<221> NAME/KEY: MISC_FEATURE
<222> LOCATION: (4)..(4)
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc, Lys or absent

<400> SEQUENCE: 165

Xaa Xaa Xaa Xaa Xaa
1               5

<210> SEQ ID NO 166
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-pyridiyl)Ala (2-Pal) or
      beta-(3-pyridiyl)Ala (3-Pal)

<400> SEQUENCE: 166

Xaa Xaa Xaa Xaa
1

<210> SEQ ID NO 167
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (3)..(3)
<223> OTHER INFORMATION: Xaa = beta-(3-thienyl)Ala (3-Thi)
<220> FEATURE:
<221> NAME/KEY: MISC_FEATURE
<222> LOCATION: (4)..(4)
<223> OTHER INFORMATION: Xaa = Apc or Lys
<220> FEATURE:
```

```
<221> NAME/KEY: MOD_RES
<222> LOCATION: (5)..(5)
<223> OTHER INFORMATION: AMIDATION

<400> SEQUENCE: 167

Xaa Xaa Xaa Xaa Xaa
1               5

<210> SEQ ID NO 168
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(3-thienyl)Ala (3-Thi),
      beta-(4-pyridiyl)Ala (4-Pal) or pentafluorophenylAla (Pff)

<400> SEQUENCE: 168

Xaa Xaa Xaa Xaa
1

<210> SEQ ID NO 169
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 169

Xaa Xaa Xaa Xaa Xaa
1               5
```

```
<210> SEQ ID NO 170
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 170

Xaa Xaa Xaa Xaa Xaa
1               5

<210> SEQ ID NO 171
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
     beta-(2-pyridiyl)Ala (2-Pal), beta-(3-pyridiyl)Ala (3-Pal),
     beta-(3-thienyl)Ala (3-Thi), beta-(4-pyridiyl)Ala (4-Pal) or
     pentafluorophenylAla (Pff)

<400> SEQUENCE: 171

Xaa Xaa Xaa Xaa
1

<210> SEQ ID NO 172
<211> LENGTH: 5
<212> TYPE: PRT
<213> ORGANISM: Artificial Sequence
```

```
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 172

Xaa Xaa Xaa Xaa Xaa
1               5

<210> SEQ ID NO 173
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 173

Xaa Xaa Xaa Xaa Xaa
1               5

<210> SEQ ID NO 174
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
```

```
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 174

Xaa Xaa Xaa Xaa Xaa
1               5

<210> SEQ ID NO 175
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MISC_FEATURE
<222> LOCATION: (5)..(5)
<223> OTHER INFORMATION: Xaa = Apc or Lys

<400> SEQUENCE: 175

Xaa Xaa Xaa Xaa Xaa
1               5

<210> SEQ ID NO 176
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
```

```
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 176

Xaa Xaa Xaa Xaa Xaa
1               5

<210> SEQ ID NO 177
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa= H-Apc
<220> FEATURE:
<221> NAME/KEY: MISC_FEATURE
<222> LOCATION: (2)..(2)
<223> OTHER INFORMATION: Xaa= D-3-benzothienylAla (D-Bal)
<220> FEATURE:
<221> NAME/KEY: MISC_FEATURE
<222> LOCATION: (3)..(3)
<223> OTHER INFORMATION: Xaa= D-3-benzothienylAla (D-Bal)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa= beta-(2-furyl)-Ala (2-Fua),
     beta-(2-pyridiyl)Ala (2-Pal), beta-(2-thienyl)Ala (2-Thi),
     beta-(3-pyridiyl)Ala (3-Pal), beta-(3-thienyl)Ala (3-Thi),
     beta-(4-pyridiyl)Ala (4-Pal), pentafluorophenylAla (Pff), Phe or
     beta-(4-thiazolyl)Ala (Taz)

<400> SEQUENCE: 177

Xaa Xaa Xaa Xaa
1

<210> SEQ ID NO 178
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
```

```
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 178

Xaa Xaa Xaa Xaa Xaa
1               5

<210> SEQ ID NO 179
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = beta-(3-thienyl)Ala (3-Thi)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = Apc or Lys

<400> SEQUENCE: 179

Xaa Xaa Xaa Xaa
1

<210> SEQ ID NO 180
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
```

```
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 180

Xaa Xaa Xaa Xaa Xaa
1               5

<210> SEQ ID NO 181
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 181

Xaa Xaa Xaa Phe Xaa
1               5

<210> SEQ ID NO 182
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 182
```

Xaa Xaa Xaa Xaa Xaa
1               5

<210> SEQ ID NO 183
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 183

Xaa Xaa Xaa Xaa Xaa
1               5

<210> SEQ ID NO 184
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(3-thienyl)Ala (3-Thi), beta-(4-pyridiyl)Ala (4-Pal)
      pentafluorophenylAla (Pff), beta-(2-pyridiyl)Ala (2-Pal) or
      beta-(3-pyridiyl)Ala (3-Pal)

<400> SEQUENCE: 184

Xaa Xaa Xaa Xaa
1

<210> SEQ ID NO 185
<211> LENGTH: 5
<212> TYPE: PRT
<213> ORGANISM: Artificial Sequence
<220> FEATURE:
<223> OTHER INFORMATION: Ghrelin Analogue

```
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 185

Xaa Xaa Xaa Xaa Xaa
1               5

<210> SEQ ID NO 186
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 186

Xaa Xaa Xaa Xaa Xaa
1               5

<210> SEQ ID NO 187
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
```

```
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(2-thienyl)Ala (2-Thi), beta-(3-thienyl)Ala (3-Thi),
      pentafluorophenylAla (Pff), Phe or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 187

Xaa Xaa Xaa Xaa Lys
1               5

<210> SEQ ID NO 188
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      pentafluorophenylAla (Pff) or beta-(4-thiazolyl)Ala (Taz)

<400> SEQUENCE: 188

Xaa Xaa Xaa Xaa
1

<210> SEQ ID NO 189
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
```

```
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc, Lys or absent

<400> SEQUENCE: 189

Xaa Xaa Xaa Xaa Xaa
1               5

<210> SEQ ID NO 190
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 190

Xaa Xaa Xaa Xaa Xaa
1               5

<210> SEQ ID NO 191
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION
```

```
<220> FEATURE:
<221> NAME/KEY: MISC_FEATURE
<222> LOCATION: (5)..(5)
<223> OTHER INFORMATION: Xaa = Apc or Lys

<400> SEQUENCE: 191

Xaa Xaa Xaa Xaa Xaa
1               5

<210> SEQ ID NO 192
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = pentafluorophenylAla (Pff) or
      beta-(4-thiazolyl)Ala (Taz)

<400> SEQUENCE: 192

Xaa Xaa Xaa Xaa
1

<210> SEQ ID NO 193
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(2-thienyl)Ala (2-Thi), beta-(3-thienyl)Ala (3-Thi),
      pentafluorophenylAla (Pff) or beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 193
```

```
Xaa Xaa Xaa Xaa Xaa
1               5

<210> SEQ ID NO 194
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(3-thienyl)Ala (3-Thi), pentafluorophenylAla (Pff) or
      beta-(4-thiazolyl)Ala (Taz)

<400> SEQUENCE: 194

Xaa Xaa Xaa Xaa
1

<210> SEQ ID NO 195
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi)
<220> FEATURE:
<221> NAME/KEY: MOD_RES
<222> LOCATION: (5)..(5)
<223> OTHER INFORMATION: AMIDATION

<400> SEQUENCE: 195

Xaa Xaa Xaa Xaa Lys
1               5

<210> SEQ ID NO 196
<211> LENGTH: 5
<212> TYPE: PRT
<213> ORGANISM: Artificial Sequence
<220> FEATURE:
<223> OTHER INFORMATION: Ghrelin Analogue
```

```
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(2-thienyl)Ala (2-Thi), beta-(3-thienyl)Ala (3-Thi),
      pentafluorophenylAla (Pff), Phe, or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 196

Xaa Xaa Xaa Xaa Lys
1               5

<210> SEQ ID NO 197
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      pentafluorophenylAla (Pff) or beta-(4-thiazolyl)Ala (Taz)

<400> SEQUENCE: 197

Xaa Xaa Xaa Xaa
1

<210> SEQ ID NO 198
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
```

```
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 198

Xaa Xaa Xaa Xaa Xaa
1               5

<210> SEQ ID NO 199
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      pentafluorophenylAla (Pff) or beta-(4-thiazolyl)Ala (Taz)

<400> SEQUENCE: 199

Xaa Xaa Xaa Xaa
1

<210> SEQ ID NO 200
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi)
<220> FEATURE:
<221> NAME/KEY: MOD_RES
```

```
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 200

Xaa Xaa Xaa Xaa Xaa
1               5

<210> SEQ ID NO 201
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc or Lys

<400> SEQUENCE: 201

Xaa Xaa Xaa Xaa Xaa
1               5

<210> SEQ ID NO 202
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      beta-(2-thienyl)Ala (2-Thi), beta-(3-thienyl)Ala (3-Thi) or
      pentafluorophenylAla (Pff)
<220> FEATURE:
<221> NAME/KEY: MOD_RES
<222> LOCATION: (5)..(5)
<223> OTHER INFORMATION: AMIDATION
```

```
<400> SEQUENCE: 202

Xaa Xaa Xaa Xaa Lys
1               5

<210> SEQ ID NO 203
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua) or
      pentafluorophenylAla (Pff)

<400> SEQUENCE: 203

Xaa Xaa Xaa Xaa
1

<210> SEQ ID NO 204
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 204

Xaa Xaa Xaa Xaa Lys
1               5

<210> SEQ ID NO 205
<211> LENGTH: 4
<212> TYPE: PRT
<213> ORGANISM: Artificial Sequence
<220> FEATURE:
<223> OTHER INFORMATION: Ghrelin Analogue
```

```
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)

<400> SEQUENCE: 205

Xaa Xaa Xaa Xaa
1

<210> SEQ ID NO 206
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
     beta-(2-thienyl)Ala (2-Thi), beta-(3-thienyl)Ala (3-Thi),
     pentafluorophenylAla (Pff), or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 206

Xaa Xaa Xaa Xaa Lys
1               5

<210> SEQ ID NO 207
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
```

```
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-furyl)-Ala (2-Fua),
      pentafluorophenylAla (Pff), or beta-(4-thiazolyl)Ala (Taz)

<400> SEQUENCE: 207

Xaa Xaa Xaa Xaa
1

<210> SEQ ID NO 208
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
      D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 208

Xaa Xaa Xaa Xaa Xaa
1               5

<210> SEQ ID NO 209
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal) or
      D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
```

```
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 209

Xaa Xaa Xaa Xaa Xaa
1               5

<210> SEQ ID NO 210
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 210

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 211
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 211

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 212
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
```

<223> OTHER INFORMATION: AMIDATION

<400> SEQUENCE: 212

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 213
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 213

Gly Ser Glu Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 214
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 214

Gly Xaa Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 215
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES

```
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 215

Gly Xaa Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 216
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 216

Gly Xaa Ser Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 217
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

-continued

<400> SEQUENCE: 217

Gly Xaa Glu Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 218
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 218

Gly Xaa Ser Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 219
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 219

Gly Xaa Glu Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 220
<211> LENGTH: 28

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 220

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 221
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 221

Gly Ser Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 222
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 222

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 223
<211> LENGTH: 28
<212> TYPE: PRT
<213> ORGANISM: Artificial Sequence
<220> FEATURE:
```

<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 223

Gly Ser Glu Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 224
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 224

Gly Xaa Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 225
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 225

Gly Xaa Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 226
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 226

Gly Xaa Ser Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 227
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 227

Gly Xaa Glu Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 228
<211> LENGTH: 28
<212> TYPE: PRT
<213> ORGANISM: Artificial Sequence
<220> FEATURE:
<223> OTHER INFORMATION: Ghrelin Analogue
<220> FEATURE:

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 228

Gly Xaa Ser Phe Leu Ser Pro Glu His Xaa Arg Val Gln Gln Arg Glu
 1               5                  10                  15

Glu Ser Lys Lys Pro Pro Ala Lys Leu Gln Pro Arg
            20                  25

<210> SEQ ID NO 229
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 229

Gly Xaa Glu Phe Leu Ser Pro Glu His Xaa Arg Val Gln Gln Arg Glu
 1               5                  10                  15

Glu Ser Lys Lys Pro Pro Ala Lys Leu Gln Pro Arg
            20                  25

<210> SEQ ID NO 230
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 230

Gly Ser Ser Phe Leu Ser Pro Glu His Gln Arg Val Gln Gln Arg Lys
```

```
  1               5                   10                  15
Ser Ser Lys Lys Pro Pro Ala Lys Leu Gln Pro Arg
            20                  25

<210> SEQ ID NO 231
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 231

Gly Ser Ser Phe Leu Ser Pro Glu His Gln Arg Val Gln Gln Arg Lys
  1               5                   10                  15
Glu Ser Lys Lys Pro Pro Ala Lys Leu Gln Pro Arg
            20                  25

<210> SEQ ID NO 232
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 232

Gly Ser Glu Phe Leu Ser Pro Glu His Gln Arg Val Gln Gln Arg Lys
  1               5                   10                  15
Glu Ser Lys Lys Pro Pro Ala Lys Leu Gln Pro Arg
            20                  25

<210> SEQ ID NO 233
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 233
```

Gly Ser Glu Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 234
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 234

Gly Ser Ser Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 235
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 235

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 236
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES

<222> LOCATION: (28)..(28)
<223> OTHER INFORMATION: AMIDATION

<400> SEQUENCE: 236

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 237
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 237

Gly Ser Xaa Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 238
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 238

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 239
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (17)..(17)

<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 239

Gly Ser Ser Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 240
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 240

Gly Ser Cys Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 241
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 241

Gly Ser Glu Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 242
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES

```
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 242

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 243
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 243

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 244
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 244

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 245
<211> LENGTH: 28
<212> TYPE: PRT
```

```
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 245

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 246
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid,
      4-hydroxyproline, i.e., (2S, 4R)-4-hydroxypyrrolidine-2-carboxylic
      acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 246

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 247
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MISC_FEATURE
<222> LOCATION: (7)..(7)
<223> OTHER INFORMATION: Xaa = thiazolidine-4-carboxylic acid,
      4-hydroxyproline, i.e., (2S, 4R)-4-hydroxypyrrolidine-2-carboxylic
      acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 247

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 248
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 248

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 249
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modfied with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modfied with NH-hexyl
<220> FEATURE:
```

```
<221> NAME/KEY: MOD_RES
<222> LOCATION: (28)..(28)
<223> OTHER INFORMATION: AMIDATION

<400> SEQUENCE: 249

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 250
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)alanine,
      beta-(4-pyridinyl)alanine, beta-(4-thiazolyl)alanine or
      beta-(2-thienyl)alanine
<220> FEATURE:
<221> NAME/KEY: MOD_RES
<222> LOCATION: (17)..(17)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 250

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 251
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MISC_FEATURE
<222> LOCATION: (9)..(9)
<223> OTHER INFORMATION: Xaa = beta-(3-pyridinyl)alanine,
      beta-(4-pyridinyl)alanine, beta-(4-thiazolyl)alanine or
      beta-(2-thienyl)alanine
<220> FEATURE:
<221> NAME/KEY: MOD_RES
<222> LOCATION: (17)..(17)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 251

Gly Xaa Glu Phe Leu Ser Pro Glu Xaa Gln Arg Val Gln Gln Arg Lys
```

```
1               5                   10                  15
Glu Ser Lys Lys Pro Pro Ala Lys Leu Gln Pro Arg
            20                  25

<210> SEQ ID NO 252
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 252

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 253
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 253

Gly Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 254
<211> LENGTH: 28
<212> TYPE: PRT
<213> ORGANISM: Artificial Sequence
<220> FEATURE:
```

<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 254

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 255
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(4-thiazolyl)alanine,
      beta-(3-pyridinyl)alanine, beta-(4-pyridinyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 255

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 256
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 256

Gly Ser Glu Phe Leu Ser Pro Xaa His Gln Arg Val Gln Gln Arg Lys

```
                1               5                  10                  15

Glu Ser Lys Lys Pro Pro Ala Lys Leu Gln Pro Arg
            20                  25

<210> SEQ ID NO 257
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)alanine,
      beta-(3-pyridinyl)alanine, beta-(4-pyridinyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 257

Gly Ser Glu Phe Leu Ser Pro Glu Xaa Gln Arg Val Gln Gln Arg Lys
1               5                  10                  15

Glu Ser Lys Lys Pro Pro Ala Lys Leu Gln Pro Arg
            20                  25

<210> SEQ ID NO 258
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 258

Xaa Xaa Ser Phe Leu Ser Pro Glu His Xaa Arg Val Gln Gln Arg Lys
1               5                  10                  15

Glu Ser Lys Lys Pro Pro Ala Lys Leu Gln Pro Arg
            20                  25

<210> SEQ ID NO 259
<211> LENGTH: 28
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (1)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 259

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 260
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5C)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 260

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 261
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5C)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 261

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 262
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 262

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 263
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 263

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 264
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 264

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 265
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 265

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 266
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 266

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 267
<211> LENGTH: 28
```

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 267

Gly Ser Ser Phe Leu Ser Pro Glu His Gln Arg Val Gln Gln Arg Lys
1               5                   10                  15

Lys Ser Lys Lys Pro Pro Ala Lys Leu Gln Pro Arg
            20                  25

<210> SEQ ID NO 268
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 268

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 269
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 269

Gly Ser Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 270
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
```

<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 270

Gly Ser Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 271
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 271

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 272
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 272

Gly Xaa Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 273
<211> LENGTH: 28
<212> TYPE: PRT
<213> ORGANISM: Artificial Sequence

```
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 273

Gly Xaa Glu Phe Leu Ser Pro Glu His Gln Arg Val Gln Gln Arg Lys
 1               5                  10                  15

Glu Glu Lys Lys Pro Pro Ala Lys Leu Gln Pro Arg
            20                  25

<210> SEQ ID NO 274
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 274

Gly Xaa Ser Phe Leu Ser Pro Xaa His Gln Arg Val Gln Gln Arg Lys
 1               5                  10                  15

Glu Glu Lys Lys Pro Pro Ala Lys Leu Gln Pro Arg
            20                  25

<210> SEQ ID NO 275
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
```

```
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 275

Gly Xaa Glu Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 276
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 276

Gly Xaa Ser Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 277
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 277

Gly Xaa Glu Phe Leu Ser Pro Glu His Xaa Arg Val Gln Gln Arg Lys
```

```
                1               5                  10                 15
Glu Glu Lys Lys Pro Pro Ala Lys Leu Gln Pro Arg
            20                  25

<210> SEQ ID NO 278
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 278

Gly Ser Ser Phe Leu Ser Pro Glu His Gln Arg Val Gln Gln Arg Lys
1               5                   10                  15
Glu Ser Ser Lys Pro Pro Ala Lys Leu Gln Pro Arg
            20                  25

<210> SEQ ID NO 279
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 279

Gly Ser Ser Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 280
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 280

Gly Ser Glu Phe Leu Ser Pro Glu His Gln Arg Val Gln Gln Arg Lys
1               5                   10                  15
Glu Ser Glu Lys Pro Pro Ala Lys Leu Gln Pro Arg
```

```
                        20                  25

<210> SEQ ID NO 281
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 281

Gly Ser Glu Phe Leu Ser Pro Glu His Gln Arg Val Gln Gln Arg Lys
1               5                   10                  15

Glu Ser Ser Lys Pro Pro Ala Lys Leu Gln Pro Arg
                20                  25

<210> SEQ ID NO 282
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 282

Gly Xaa Ser Phe Leu Ser Pro Glu His Gln Arg Val Gln Gln Arg Lys
1               5                   10                  15

Glu Ser Glu Lys Pro Pro Ala Lys Leu Gln Pro Arg
                20                  25

<210> SEQ ID NO 283
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 283

Gly Xaa Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 284
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 284

Gly Xaa Ser Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 285
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 285

Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25
```

```
<210> SEQ ID NO 286
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 286

Gly Xaa Ser Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 287
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 287

Gly Xaa Glu Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 288
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (20)..(20)
<223> OTHER INFORMATION: modified with n-octanoyl
```

<220> FEATURE:
<221> NAME/KEY: MOD_RES
<222> LOCATION: (28)..(28)
<223> OTHER INFORMATION: AMIDATION

<400> SEQUENCE: 288

Gly Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 289
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 289

Gly Ser Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 290
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 290

Gly Ser Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 291
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)

<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 291

Gly Ser Glu Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 292
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 292

Gly Xaa Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 293
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 293

Gly Xaa Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 294
<211> LENGTH: 28
<212> TYPE: PRT
<213> ORGANISM: Artificial Sequence

```
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 294

Gly Xaa Ser Phe Leu Ser Pro Xaa His Gln Arg Val Gln Gln Arg Lys
 1               5                  10                  15

Glu Ser Lys Glu Pro Pro Ala Lys Leu Gln Pro Arg
            20                  25

<210> SEQ ID NO 295
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 295

Gly Xaa Glu Phe Leu Ser Pro Xaa His Gln Arg Val Gln Gln Arg Lys
 1               5                  10                  15

Glu Ser Lys Glu Pro Pro Ala Lys Leu Gln Pro Arg
            20                  25

<210> SEQ ID NO 296
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
```

```
<221> NAME/KEY: MOD_RES
<222> LOCATION: (20)..(20)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 296

Gly Xaa Ser Phe Leu Ser Pro Glu His Xaa Arg Val Gln Gln Arg Lys
1               5                   10                  15

Glu Ser Lys Glu Pro Pro Ala Lys Leu Gln Pro Arg
            20                  25

<210> SEQ ID NO 297
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 297

Gly Xaa Glu Phe Leu Ser Pro Glu His Xaa Arg Val Gln Gln Arg Lys
1               5                   10                  15

Glu Ser Lys Glu Pro Pro Ala Lys Leu Gln Pro Arg
            20                  25

<210> SEQ ID NO 298
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 298

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 299
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 299

Gly Ser Ser Phe Leu Ser Pro Glu His Gln Arg Val Gln Gln Arg Lys
 1               5                  10                  15

Ser Ser Lys Lys Pro Pro Ala Lys Leu Gln Pro Arg
            20                  25

<210> SEQ ID NO 300
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 300

Gly Ser Glu Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 301
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
```

<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 301

Gly Ser Glu Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 302
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 302

Gly Ser Ser Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 303
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 303

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 304

```
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 304

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 305
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 305

Gly Ser Xaa Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 306
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (17)..(17)
<223> OTHER INFORMATION: Xaa = 2,3-diaminopropionic acid (Aib) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 306

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 307
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 307

Gly Ser Ser Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 308
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 308

Gly Ser Cys Phe Leu Ser Pro Glu His Gln Arg Val Gln Gln Arg Lys
1               5                   10                  15

Cys Ser Lys Lys Pro Pro Ala Lys Leu Gln Pro Arg
            20                  25
```

```
<210> SEQ ID NO 309
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 309

Gly Ser Glu Phe Leu Ser Pro Glu His Gln Arg Val Gln Gln Arg Lys
 1               5                  10                  15

Cys Ser Lys Lys Pro Pro Ala Lys Leu Gln Pro Arg
            20                  25

<210> SEQ ID NO 310
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modifed with acyl
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 310

Gly Ser Cys Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 311
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with S-(CH2)9CH3
<220> FEATURE:
```

```
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 311

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 312
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 312

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 313
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid,
    4-hydroxyproline, i.e., (2S, 4R)-4-hydroxypyrrolidine-2-carboxylic
    acid, 3,4-dehydroproline, pipecolic acid, or
    1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

-continued

<400> SEQUENCE: 313

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 314
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = thiazolidine-4-carboxylic acid,
      4-hydroxyproline, i.e., (2S, 4R)-4-hydroxypyrrolidine-2-carboxylic
      acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 314

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 315
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

```
<400> SEQUENCE: 315

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 316
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)alanine,
      beta-(4-pyridinyl)alanine, beta-(4-thiazolyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 316

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 317
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridinyl)alanine,
      beta-(4-pyridinyl)alanine, beta-(4-thiazolyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

<400> SEQUENCE: 317

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 318
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 318

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 319
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 319

```
Gly Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25
```

<210> SEQ ID NO 320
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 320

```
Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25
```

<210> SEQ ID NO 321
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (9)..(9)
<223> OTHER INFORMATION: Xaa = beta-(4-thiazolyl)alanine,
      beta-(3-pyridinyl)alanine, beta-(4-pyridinyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 321

```
Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

<210> SEQ ID NO 322
<211> LENGTH: 28
<212> TYPE: PRT
<213> ORGANISM: Artificial Sequence
<220> FEATURE:
<223> OTHER INFORMATION: Ghrelin Analogue

```
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 322

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 323
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)alanine,
      beta-(3-pyridinyl)alanine, beta-(4-pyridinyl)alanine or
      beta-(2-thienyl)alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 323

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 324
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib) modified
      with acyl group
```

<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 324

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 325
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib) modified
      with acyl group
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 325

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 326
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl group
<220> FEATURE:
<221> NAME/KEY: MISC_FEATURE

```
<222> LOCATION: (2)..(2)
<223> OTHER INFORMATION: Xaa = 1-amino-1-cyclopentanecarboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 326

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 327
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl group
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 327

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 328
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION
```

<400> SEQUENCE: 328

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 329
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 329

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 330
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 330

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 331
<211> LENGTH: 28
<212> TYPE: PRT
<213> ORGANISM: Artificial Sequence
<220> FEATURE:

```
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 331

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 332
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 332

Gly Xaa Glu Phe Leu Ser Pro Glu His Xaa Arg Val Gln Gln Arg Lys
1               5                   10                  15

Lys Ser Lys Lys Pro Pro Ala Lys Leu Gln Pro Arg
            20                  25

<210> SEQ ID NO 333
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: is modified with acyl
<220> FEATURE:
<221> NAME/KEY: MOD_RES
```

```
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 333

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 334
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 334

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 335
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 335

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 336
<211> LENGTH: 28
<212> TYPE: PRT
```

```
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 336

Gly Ser Glu Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 337
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 337

Gly Xaa Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 338
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 338

Gly Xaa Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 339
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 339

Gly Xaa Ser Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 340
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
```

```
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 340

Gly Xaa Glu Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 341
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 341

Gly Xaa Ser Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 342
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 342

Gly Xaa Glu Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 343
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 343

Gly Ser Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 344
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 344

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 345
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
```

```
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 345

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 346
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 346

Gly Ser Glu Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 347
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 347

Gly Xaa Ser Phe Leu Ser Pro Glu His Gln Arg Val Gln Gln Arg Glu
```

```
1               5                   10                  15
Glu Ser Lys Lys Pro Pro Ala Lys Leu Gln Pro Arg
            20                  25

<210> SEQ ID NO 348
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 348

Gly Xaa Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 349
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 349

Gly Xaa Ser Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 350
```

```
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 350

Gly Xaa Glu Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 351
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 351

Gly Xaa Ser Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 352
<211> LENGTH: 28
<212> TYPE: PRT
<213> ORGANISM: Artificial Sequence
```

```
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified by acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 352

Gly Xaa Glu Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 353
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (18)..(18)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 353

Gly Ser Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 354
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (18)..(18)
<223> OTHER INFORMATION: modified by n-octanoyl
<220> FEATURE:
```

```
<221> NAME/KEY: MOD_RES
<222> LOCATION: (28)..(28)
<223> OTHER INFORMATION: AMIDATION

<400> SEQUENCE: 354

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 355
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MOD_RES
<222> LOCATION: (18)..(18)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 355

Gly Ser Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 356
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 356

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 357
<211> LENGTH: 28
```

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 357

Gly Xaa Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 358
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 358

Gly Xaa Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 359
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 359

Gly Xaa Ser Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 360
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 360

Gly Xaa Glu Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 361
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
```

```
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 361

Gly Xaa Ser Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 362
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 362

Gly Xaa Glu Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 363
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

<400> SEQUENCE: 363

Gly Ser Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 364
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 364

Gly Ser Ser Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 365
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 365

Gly Ser Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 366
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 366

Gly Ser Glu Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 367
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 367

Gly Xaa Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 368
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
```

<223> OTHER INFORMATION: AMIDATION

<400> SEQUENCE: 368

Gly Xaa Glu Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 369
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 369

Gly Xaa Ser Phe Leu Ser Pro Xaa His Gln Arg Val Gln Gln Arg Lys
1               5                   10                  15
Glu Ser Glu Lys Pro Pro Ala Lys Leu Gln Pro Arg
            20                  25

<210> SEQ ID NO 370
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 370

```
Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25
```

<210> SEQ ID NO 371
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 371

```
Gly Xaa Ser Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25
```

<210> SEQ ID NO 372
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 372

```
Gly Xaa Glu Phe Leu Ser Pro Glu His Xaa Arg Val Gln Gln Arg Lys
1               5                   10                  15
```

```
Glu Ser Glu Lys Pro Pro Ala Lys Leu Gln Pro Arg
            20                  25

<210> SEQ ID NO 373
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 373

Gly Ser Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 374
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 374

Gly Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 375
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 375

Gly Ser Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 376
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 376

Gly Ser Glu Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 377
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 377

Gly Xaa Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 378
```

```
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 378

Gly Xaa Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 379
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 379

Gly Xaa Ser Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 380
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
```

<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 380

Gly Xaa Glu Phe Leu Ser Pro Xaa His Gln Arg Val Gln Gln Arg Lys
 1               5                  10                  15

Glu Ser Lys Glu Pro Pro Ala Lys Leu Gln Pro Arg
            20                  25

<210> SEQ ID NO 381
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 381

Gly Xaa Ser Phe Leu Ser Pro Glu His Xaa Arg Val Gln Gln Arg Lys
 1               5                  10                  15

Glu Ser Lys Glu Pro Pro Ala Lys Leu Gln Pro Arg
            20                  25

<210> SEQ ID NO 382
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl
<220> FEATURE:

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 382

Gly Xaa Glu Phe Leu Ser Pro Glu His Xaa Arg Val Gln Gln Arg Lys
 1               5                  10                  15

Glu Ser Lys Glu Pro Pro Ala Lys Leu Gln Pro Arg
             20                  25

<210> SEQ ID NO 383
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION

<400> SEQUENCE: 383

Gly Xaa Ser Phe Leu Ser Pro Glu His Gln Arg Val Gln Gln Arg Lys
 1               5                  10                  15

Lys Ser Lys Lys Pro Pro Ala Lys Leu Gln Pro Arg
             20                  25

<210> SEQ ID NO 384
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with myristyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION
```

```
<400> SEQUENCE: 384

Gly Xaa Ser Phe Leu Ser Pro Glu His Gln Arg Val Gln Gln Arg Lys
1               5                   10                  15

Lys Ser Lys Lys Pro Pro Ala Lys Leu Gln Pro Arg
            20                  25

<210> SEQ ID NO 385
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp or 1-Apc or acyl-Inp or acyl-1-Apc
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 385

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 386
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = Ser or alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 386

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 387
<211> LENGTH: 28
<212> TYPE: PRT
<213> ORGANISM: Artificial Sequence
<220> FEATURE:
```

```
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 387

Xaa Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 388
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 388

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 389
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
```

```
<222> LOCATION: (17)..(17)
<223> OTHER INFORMATION: Xaa = Ser, or Ser modified with n-octanoyl
<220> FEATURE:
<221> NAME/KEY: MOD_RES
<222> LOCATION: (28)..(28)
<223> OTHER INFORMATION: AMIDATION

<400> SEQUENCE: 389

Xaa Xaa Ser Phe Leu Ser Pro Xaa His Gln Arg Val Gln Gln Arg Lys
1               5                   10                  15

Xaa Ser Lys Lys Pro Pro Ala Lys Leu Gln Pro Arg
            20                  25

<210> SEQ ID NO 390
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = Ser, or alpha-aminoisobutyric acid (Aib)
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 390

Xaa Xaa Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 391
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-heptyl
<220> FEATURE:
<221> NAME/KEY: MOD_RES
<222> LOCATION: (28)..(28)
<223> OTHER INFORMATION: AMIDATION

<400> SEQUENCE: 391

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 392
<211> LENGTH: 28
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (1)..(1)
<223> OTHER INFORMATION: Xaa = Gly or des-Gly
<220> FEATURE:
<221> NAME/KEY: MISC_FEATURE
<222> LOCATION: (2)..(2)
<223> OTHER INFORMATION: Xaa = des-Ser
<220> FEATURE:
<221> NAME/KEY: MOD_RES
<222> LOCATION: (28)..(28)
<223> OTHER INFORMATION: AMIDATION

<400> SEQUENCE: 392

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 393
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 393

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 394
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with o-hexyl
<220> FEATURE:
<221> NAME/KEY: MOD_RES
<222> LOCATION: (28)..(28)
<223> OTHER INFORMATION: AMIDATION

<400> SEQUENCE: 394

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 395
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib)
```

```
<220> FEATURE:
<221> NAME/KEY: MISC_FEATURE
<222> LOCATION: (3)..(3)
<223> OTHER INFORMATION: Xaa = Ser or Thr
<220> FEATURE:
<221> NAME/KEY: MOD_RES
<222> LOCATION: (28)..(28)
<223> OTHER INFORMATION: AMIDATION

<400> SEQUENCE: 395

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 396
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 396

Gly Ser Ser Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 397
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Ser or Thr
<220> FEATURE:
<221> NAME/KEY: MISC_FEATURE
<222> LOCATION: (4)..(4)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(4-pyridiyl)Ala (4-Pal)
<220> FEATURE:
<221> NAME/KEY: MOD_RES
<222> LOCATION: (28)..(28)
<223> OTHER INFORMATION: AMIDATION

<400> SEQUENCE: 397

Gly Xaa Xaa Xaa Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 398
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-octanoyl, isobutyryl or
      n-butyryl
<220> FEATURE:
<221> NAME/KEY: MOD_RES
<222> LOCATION: (28)..(28)
<223> OTHER INFORMATION: AMIDATION

<400> SEQUENCE: 398

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 399
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-octanoyl, isobutyryl or
      n-butyryl
<220> FEATURE:
<221> NAME/KEY: MOD_RES
<222> LOCATION: (28)..(28)
<223> OTHER INFORMATION: AMIDATION

<400> SEQUENCE: 399

Gly Ser Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 400
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (28)..(28)
<223> OTHER INFORMATION: AMIDATION

<400> SEQUENCE: 400

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 401
<211> LENGTH: 8
<212> TYPE: PRT
<213> ORGANISM: Artificial Sequence
<220> FEATURE:
```

```
<223> OTHER INFORMATION: Ghrelin Analogue
<220> FEATURE:
<221> NAME/KEY: MOD_RES
<222> LOCATION: (8)..(8)
<223> OTHER INFORMATION: AMIDATION
<220> FEATURE:
<221> NAME/KEY: MISC_FEATURE
<222> LOCATION: (8)..(8)
<223> OTHER INFORMATION: Xaa = Lys or Arg

<400> SEQUENCE: 401

Gly Ser Ser Phe Leu Ser Pro Xaa
1               5

<210> SEQ ID NO 402
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: Modified with acyl (Ac)
<220> FEATURE:
<221> NAME/KEY: MISC_FEATURE
<222> LOCATION: (1)..(1)
<223> OTHER INFORMATION: Xaa = 1-Apc
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: Modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 402

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 403
<211> LENGTH: 27
<212> TYPE: DNA
<213> ORGANISM: Artificial Sequence
<220> FEATURE:
<223> OTHER INFORMATION: DNP primer flanking the full length coding
      sequence of hGHS-R

<400> SEQUENCE: 403
atgtggaacg cgacgcccag cgaagag                                      27

<210> SEQ ID NO 404
<211> LENGTH: 27
<212> TYPE: DNA
<213> ORGANISM: Artificial Sequence
<220> FEATURE:
<223> OTHER INFORMATION: DNA primer flanking the full length coding
      sequence of hGHS-R

<400> SEQUENCE: 404
```

```
tcatgtatta atactagatt ctgtcca                                           27
```

<210> SEQ ID NO 405
<211> LENGTH: 28
<212> TYPE: PRT
<213> ORGANISM: Artificial Sequence
<220> FEATURE:
<223> OTHER INFORMATION: rGhrelin

<400> SEQUENCE: 405

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 406
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (28)..(28)
<223> OTHER INFORMATION: AMIDATION

<400> SEQUENCE: 406

Gly Ser Ser Phe Lys Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 407
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 407

Xaa Xaa Xaa Phe Lys
1               5